(12) United States Patent
Gray et al.

(10) Patent No.: US 10,870,651 B2
(45) Date of Patent: Dec. 22, 2020

(54) INHIBITORS OF CYCLIN-DEPENDENT KINASE 7 (CDK7)

(71) Applicant: Dana-Farber Cancer Institute, Inc., Boston, MA (US)

(72) Inventors: Nathanael S. Gray, Boston, MA (US); Yanke Liang, Brookline, MA (US); Tinghu Zhang, Brookline, MA (US); Nicholas Paul Kwiatkowski, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 156 days.

(21) Appl. No.: 15/538,763

(22) PCT Filed: Dec. 23, 2015

(86) PCT No.: PCT/US2015/000297
§ 371 (c)(1),
(2) Date: Jun. 22, 2017

(87) PCT Pub. No.: WO2016/105528
PCT Pub. Date: Jun. 30, 2016

(65) Prior Publication Data
US 2019/0055248 A1   Feb. 21, 2019

Related U.S. Application Data

(60) Provisional application No. 62/096,040, filed on Dec. 23, 2014.

(51) Int. Cl.
| | | |
|---|---|---|
| C07D 487/04 | (2006.01) | |
| C07D 487/10 | (2006.01) | |
| A61P 35/00 | (2006.01) | |
| A61K 31/454 | (2006.01) | |
| A61K 31/4162 | (2006.01) | |
| A61K 45/06 | (2006.01) | |

(52) U.S. Cl.
CPC ........ *C07D 487/04* (2013.01); *A61K 31/4162* (2013.01); *A61K 31/454* (2013.01); *A61K 45/06* (2013.01); *A61P 35/00* (2018.01); *C07D 487/10* (2013.01)

(58) Field of Classification Search
CPC   C07D 487/04; C07D 487/10; A61K 31/4162; A61K 31/454; A61K 45/06; A61P 35/00
USPC .......................................................... 514/407
See application file for complete search history.

(56) References Cited

U.S. PATENT DOCUMENTS

| | | |
|---|---|---|
| 4,231,938 A | 11/1980 | Monaghan et al. |
| 4,270,537 A | 6/1981 | Romaine et al. |
| 4,596,556 A | 6/1986 | Morrow et al. |
| 4,782,084 A | 11/1988 | Vyas et al. |

(Continued)

FOREIGN PATENT DOCUMENTS

| | | |
|---|---|---|
| CA | 2486101 A1 | 11/2003 |
| CA | 2503646 A1 | 5/2004 |

(Continued)

OTHER PUBLICATIONS

International Search Report and Written Opinion for PCT/US2012/065618, dated Mar. 19, 2013.

(Continued)

*Primary Examiner* — Yong L Chu

(74) *Attorney, Agent, or Firm* — Wolf, Greenfield & Sacks, P.C.

(57) ABSTRACT

The present invention provides novel compounds of Formula (I), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating and/or preventing proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject. Treatment of a subject with a proliferative disease using a compound or composition of the invention may inhibit the aberrant activity of a kinase, such as a cyclin-dependent kinase (CDK) (e.g., cyclin-dependent kinase 7 (CDK7)), and therefore, induce cellular apoptosis and/or inhibit transcription in the subject.

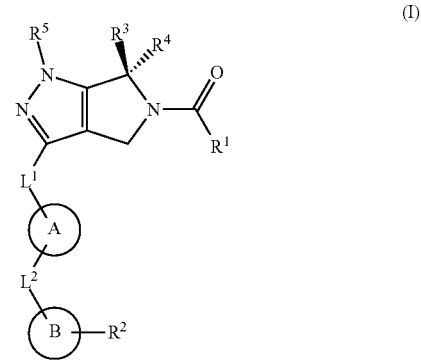

36 Claims, 2 Drawing Sheets

Specification includes a Sequence Listing.

(56) References Cited

U.S. PATENT DOCUMENTS

| | | |
|---|---|---|
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,214,852 B1 | 4/2001 | Kim et al. |
| 6,921,763 B2 | 7/2005 | Hirst et al. |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,884,117 B2 | 2/2011 | Zhang et al. |
| 7,928,140 B2 | 4/2011 | Booker et al. |
| 8,273,765 B2 * | 9/2012 | Fancelli .............. C07D 471/04 514/303 |
| 8,394,818 B2 | 3/2013 | Gray et al. |
| 8,765,747 B2 | 7/2014 | Choi et al. |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 9,670,165 B2 | 6/2017 | Cohen et al. |
| 9,758,522 B2 | 9/2017 | Gray et al. |
| 9,814,709 B2 | 11/2017 | Liu et al. |
| 9,862,688 B2 | 1/2018 | Gray et al. |
| 9,879,003 B2 | 1/2018 | Gray et al. |
| 10,000,483 B2 | 6/2018 | Gray et al. |
| 10,017,477 B2 | 7/2018 | Gray et al. |
| 10,047,070 B2 | 8/2018 | Gray et al. |
| 10,112,927 B2 | 10/2018 | Gray et al. |
| 10,144,730 B2 | 12/2018 | Gray et al. |
| 10,550,121 B2 | 2/2020 | Gray et al. |
| 2003/0139416 A1 | 7/2003 | Buchanan et al. |
| 2004/0106634 A1 | 6/2004 | Satoh et al. |
| 2004/0126359 A1 | 7/2004 | Lamb et al. |
| 2004/0209878 A1 | 10/2004 | Guzi et al. |
| 2005/0026914 A1 | 2/2005 | Buchanan et al. |
| 2005/0197338 A1 | 9/2005 | Huang et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2007/0060546 A1 | 3/2007 | Ruat et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0275963 A1 | 11/2007 | Guzi et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0105250 A1 | 4/2009 | Sim et al. |
| 2009/0156582 A1 | 6/2009 | Tsukamoto et al. |
| 2010/0056524 A1 | 3/2010 | Mciver et al. |
| 2010/0197688 A1 | 8/2010 | Nantermet et al. |
| 2010/0254905 A1 | 10/2010 | Honigberg et al. |
| 2011/0039873 A1 | 2/2011 | Gaeta et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0207711 A1 | 8/2011 | Katz et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0196865 A1 | 8/2012 | Ruat et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2013/0184287 A1 | 7/2013 | Gray et al. |
| 2014/0187772 A1 | 7/2014 | Bebbington et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0246913 A1 | 9/2015 | Gray et al. |
| 2015/0274728 A1 | 10/2015 | Gray et al. |
| 2016/0046636 A1 | 2/2016 | Gray et al. |
| 2016/0122323 A1 | 5/2016 | Gray et al. |
| 2016/0264551 A1 | 9/2016 | Ciblat et al. |
| 2016/0264554 A1 | 9/2016 | Gray et al. |
| 2016/0368910 A1 | 12/2016 | Gray et al. |
| 2017/0044111 A1 | 2/2017 | Gray et al. |
| 2017/0044112 A1 | 2/2017 | Gray et al. |
| 2017/0204096 A1 | 7/2017 | Gelin et al. |
| 2018/0093990 A1 | 4/2018 | Gray et al. |
| 2018/0169097 A1 | 6/2018 | Hammerman et al. |
| 2018/0319801 A1 | 11/2018 | Gray et al. |
| 2018/0362483 A1 | 12/2018 | Gray et al. |
| 2019/0015411 A9 | 1/2019 | Hammerman et al. |
| 2019/0031642 A1 | 1/2019 | Gray et al. |
| 2019/0100511 A1 | 4/2019 | Gray et al. |
| 2019/0112305 A1 | 4/2019 | Gray et al. |
| 2019/0241541 A1 | 8/2019 | Ciblat et al. |
| 2019/0248778 A1 | 8/2019 | Gray et al. |
| 2019/0315747 A9 | 10/2019 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| CN | 1701073 | 11/2005 |
| CN | 1735614 | 2/2006 |
| CN | 100482665 | 5/2006 |
| CN | 1784410 | 6/2006 |
| EP | 0604181 A1 | 12/1993 |
| EP | 0618221 A2 | 3/1994 |

(56) References Cited

FOREIGN PATENT DOCUMENTS

| | | |
|---|---|---|
| EP | 0675112 A1 | 3/1995 |
| EP | 0696593 A2 | 8/1995 |
| EP | 1 935 890 A1 | 6/2008 |
| EP | 2 311 842 A2 | 4/2011 |
| GB | 796524 A | 6/1958 |
| JP | H11-514336 | 12/1999 |
| JP | 2000-515550 | 11/2000 |
| JP | 2002-537300 | 11/2002 |
| JP | 2003-503481 A | 1/2003 |
| JP | 2004-505977 | 2/2004 |
| JP | 2004-516326 | 6/2004 |
| JP | 2004-517075 | 6/2004 |
| JP | 2004-529140 A | 9/2004 |
| JP | 2005-501860 A | 1/2005 |
| JP | 2005-505535 A | 2/2005 |
| JP | 2005-530711 A | 10/2005 |
| JP | 2005-534635 A | 11/2005 |
| JP | 2005-538100 A | 12/2005 |
| JP | 2006-502163 | 1/2006 |
| JP | 2006-502184 | 1/2006 |
| JP | 2006-514026 | 4/2006 |
| JP | 2006-521394 A | 9/2006 |
| JP | 2007-500226 A | 1/2007 |
| JP | 2007-500725 A | 1/2007 |
| JP | 2007-522220 | 8/2007 |
| JP | 2008-500320 A | 1/2008 |
| JP | 2008-501669 A | 1/2008 |
| JP | 2008-502610 A | 1/2008 |
| JP | 2009-510110 A | 3/2009 |
| JP | 2009-511483 | 3/2009 |
| JP | 2009-520805 | 5/2009 |
| JP | 2009-538304 | 11/2009 |
| JP | 2010-505905 | 2/2010 |
| JP | 2010-511655 A | 4/2010 |
| JP | 2010-518069 | 5/2010 |
| JP | 2010-521487 A | 6/2010 |
| JP | 2010-523643 | 7/2010 |
| JP | 2010-529140 | 8/2010 |
| JP | 2011-516533 A | 5/2011 |
| JP | 2012-530071 A | 11/2012 |
| JP | 2016-533379 A | 10/2016 |
| JP | 2017-504651 A | 2/2017 |
| MX | 2016-009974 A | 10/2016 |
| MX | 2016-009975 A | 10/2016 |
| MX | 2016-009976 A | 11/2016 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/25086 A1 | 9/1995 |
| WO | WO 95/26412 A1 | 10/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/17861 A1 | 6/1996 |
| WO | WO 96/21456 A1 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 00/44777 A1 | 8/2000 |
| WO | WO 2000/50032 A1 | 8/2000 |
| WO | WO 00/61186 A1 | 10/2000 |
| WO | WO 2001/02369 A2 | 1/2001 |
| WO | WO 2001/019829 A2 | 3/2001 |
| WO | WO 02/076986 A1 | 10/2002 |
| WO | WO 02/079197 A1 | 10/2002 |
| WO | WO 02/080926 A1 | 10/2002 |
| WO | WO 2002/083653 A1 | 10/2002 |
| WO | WO 02/096905 A1 | 12/2002 |
| WO | WO 02/102800 A1 | 12/2002 |
| WO | WO 2003/018021 A1 | 3/2003 |
| WO | WO 2003/018022 A1 | 3/2003 |
| WO | WO 03/026664 A1 | 4/2003 |
| WO | WO 2003/051847 A1 | 6/2003 |
| WO | WO 2003/078403 A2 | 9/2003 |
| WO | WO 2003/097610 A2 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/022561 A1 | 3/2004 |
| WO | WO 2004/026229 A2 | 4/2004 |
| WO | WO 2004/039796 A1 | 5/2004 |
| WO | WO 2004/046118 A2 | 6/2004 |
| WO | WO 2004/074283 A1 | 9/2004 |
| WO | WO 2004/076458 A1 | 9/2004 |
| WO | WO 2004/078757 A2 | 9/2004 |
| WO | WO 2004/081013 A1 | 9/2004 |
| WO | WO 2004/087699 A2 | 10/2004 |
| WO | WO 2004/087707 A1 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/012256 A1 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2006/124731 A2 | 11/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/044420 A1 | 4/2007 |
| WO | WO 2007/048070 A2 | 4/2007 |
| WO | WO 2007/075869 A2 | 7/2007 |
| WO | WO 2007/129195 A2 | 11/2007 |
| WO | WO 2007/138277 A1 | 12/2007 |
| WO | WO 2008/049856 A1 | 5/2008 |
| WO | WO 2008/063888 A2 | 5/2008 |
| WO | WO 2008/068171 A1 | 6/2008 |
| WO | WO 2008/074749 A1 | 6/2008 |
| WO | WO 2008/080015 A2 | 7/2008 |
| WO | WO 2008/112913 A1 | 9/2008 |

(56) References Cited

FOREIGN PATENT DOCUMENTS

| | | |
|---|---|---|
| WO | WO 2008/124393 A1 | 10/2008 |
| WO | WO 2008/144253 A1 | 11/2008 |
| WO | WO 2008/151183 A1 | 12/2008 |
| WO | WO 2008/151304 A1 | 12/2008 |
| WO | WO 2009/017822 A2 | 2/2009 |
| WO | WO 2009/028655 A1 | 3/2009 |
| WO | WO 2009/032694 A1 | 3/2009 |
| WO | WO 2009/145360 A1 | 12/2009 |
| WO | WO 2009/152027 A1 | 12/2009 |
| WO | WO 2009/155017 A2 | 12/2009 |
| WO | WO 2010/008847 A2 | 1/2010 |
| WO | WO 2010/044885 A2 | 4/2010 |
| WO | WO 2010/051781 A1 | 5/2010 |
| WO | WO 2010/125799 A1 | 11/2010 |
| WO | WO 2010/144909 A1 | 12/2010 |
| WO | WO 2011/079231 A1 | 6/2011 |
| WO | WO 2011/115725 A2 | 9/2011 |
| WO | WO 2012/066061 A1 | 5/2012 |
| WO | WO 2013/014162 A1 | 1/2013 |
| WO | WO 2013/040436 A2 | 3/2013 |
| WO | WO 2013/074986 A1 | 5/2013 |
| WO | WO 2013/154778 A1 | 10/2013 |
| WO | WO 2014/063061 A1 | 4/2014 |
| WO | WO 2014/063068 A1 | 4/2014 |
| WO | WO 2015/013635 A2 | 1/2015 |
| WO | WO 2015/058126 A1 | 4/2015 |
| WO | WO 2015/058140 A1 | 4/2015 |
| WO | WO 2015/117087 A1 | 8/2015 |
| WO | WO 2015/154022 A1 | 10/2015 |
| WO | WO 2015/154038 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/058544 A1 | 4/2016 |
| WO | WO 2016/105528 A2 | 6/2016 |
| WO | WO 2016/142855 A2 | 9/2016 |
| WO | WO 2016/201370 A1 | 12/2016 |
| WO | WO 2017/037576 A1 | 3/2017 |

OTHER PUBLICATIONS

International Preliminary Report on Patentability for PCT/US2012/065618, dated May 30, 2014.
International Search Report and Written Opinion for PCT/US2013/065708, dated Feb. 4, 2014.
International Preliminary Report on Patentability for PCT/US2013/065708, dated Apr. 30, 2015.
International Search Report and Written Opinion for PCT/US2013/065689, dated Mar. 4, 2014.
International Preliminary Report on Patentability for PCT/US2013/065689, dated Apr. 30, 2015.
International Search Report and Written Opinion for PCT/US2013/065698, dated Feb. 20, 2014.
International Preliminary Report on Patentability for PCT/US2013/065698, dated Apr. 30, 2015.
International Search Report and Written Opinion for PCT/US2014/061232, dated Dec. 23, 2014.
International Search Report and Written Opinion for PCT/US2015/027312, dated Jul. 10, 2015.
International Preliminary Report on Patentability for PCT/US2015/027312, dated Nov. 3, 2016.
International Search Report and Written Opinion for PCT/US2015/027294, dated Jul. 10, 2015.
Extended European Search Report for EP 10786967.9, dated Oct. 23, 2012.
International Search Report and Written Opinion for PCT/US2010/038518, dated Aug. 6, 2010.
International Preliminary Report on Patentability for PCT/US2010/038518, dated Dec. 22, 2011.
Extended European Search Report for EP 10844280.7, dated Apr. 17, 2013.
Partial European Search Report for EP 15160591.2, dated Jul. 14, 2015.
Extended European Search Report for EP 15160591.2, dated Nov. 2, 2015.
International Search Report and Written Opinion for PCT/US2010/062310, dated Oct. 4, 2011.
International Preliminary Report on Patentability for PCT/US2010/062310, dated Jul. 12, 2012.
International Search Report and Written Opinion for PCT/US2015/000297, dated Mar. 4, 2016.
International Preliminary Report on Patentability PCT/US2015/000297, dated Jul. 6, 2017.
International Search Report and Written Opinion for PCT/US2016/037086, dated Sep. 2, 2016.
Invitation to Pay Additional Fees for PCT/US2016/024345, dated Aug. 9, 2016.
International Search Report and Written Opinion for PCT/US2016/024345, dated Oct. 6, 2016.
Invitation to Pay Additional Fees for PCT/US2016/051118, dated Dec. 1, 2016.
International Search Report and Written Opinion for PCT/US2016/051118, dated Mar. 13, 2017.
Invitation to Pay Additional Fees for PCT/US2011/025423, dated May 31, 2011.
International Search Report and Written Opinion from PCT/US2011/025423, dated Nov. 5, 2012.
International Preliminary Report on Patentability PCT/US2011/025423, dated Nov. 29, 2012.
CAS Registry No. 916173-61-0, STN Entry Date Dec. 21, 2006.
CAS Registry CAS No. 769961-42-4, STN Entry Date Oct. 27, 2004.
CAS Registry No. 769961-59-3, STN Entry Date Oct. 27, 2004.
CAS Registry No. 1334419-59-8, STN Entry Date Dec. 30, 2013.
GenBank Accession No. M80629. Lapidot-Lifson et al., Dec. 31, 1994. 2 pages.
GenBank Accession No. NP_001790. Yang et al., Oct. 6, 2016. 4 pages.
PubChem-CID-68365059. Available at https://pubchem.ncbi.nlm.nih.gov/compound/68365059. Accessed Jun. 17, 2016.
Uniprot No. Q9NYV4. Last modified Mar. 15, 2017. 14 pages.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990;108:573.
Berge et al., Pharmaceutical salts. J. Pharmaceutical Sciences 1977 66:1-19.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bosken et al., The structure and substrate specificity of human Cdk12/Cyclin K. Nat Commun. Mar. 24, 2014;5:3505. doi: 10.1038/ncomms4505.
Brower et al., Tumor Angiogenesis: New drugs on the block. Nature Biotechnology 1999;17:963-8.

(56) References Cited

OTHER PUBLICATIONS

Brunton et al., eds., Chemotherapy of Neoplastic Diseases. In Goodman & Gilman's the Pharmacological Basis of Therapeutics. 2008; 11th edition:853-908.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chiarugi et al., Cox-2, iNOS and p53 as play-makers of tumor angiogenesis. International Journal of Molecular Medicine 1998;2:715-9.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials. 16 pages.
Chong et al., Positive and negative regulation of Raf kinase activity and function by phosphorylation EMBO J. Jul. 16, 2001;20(14):3716-27.
Christensen et al., Targeting transcriptional addictions in small cell lung cancer with a covalent CDK7 inhibitor. Cancer Cell. Dec. 8, 2014;26(6):909-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Downward, Targeting RAS signalling pathways in cancer therapy Nat Rev Cancer. Jan. 2003;3(1):11-22.
Drapkin et al., Human cyclin-dependent kinase-activating kinase exists in three distinct complexes. Proc Natl Acad Sci U S A. Jun. 25, 1996;93(13):6488-93.
Ercan et al., Reactivation of ERK signaling causes resistance to EGFR kinase inhibitors. Cancer Discov. Oct. 2012;2(10):934-47.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fernandez et al., Neovascularization produced by angiotensin I.Journal of Laboratory and Clinical Medicine 1985;105(2):141-5.
Filippakopoulos et al., Selective inhibition of BET bromodomains. Nature. Dec. 23, 2010;468(7327):1067-73.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fizazi, The role of Src in prostate cancer. Ann Oncol. Nov. 2007;18(11):1765-73. Epub Apr. 10, 2007.
Fleisher et al., Improved oral drug delivery: solubility limitations overcome by the use of prodrugs. Advanced Drug Delivery Reviews 1996;19:115-30.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hla et al., Human cyclooxygenase-2 cDNA. Proceedings of the National Academy of Sciences 1992;89(16):7384-8.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kaldis et al., Analysis of CAK activities from human cells. Eur J Biochem. Jul. 2000;267(13):4213-21.
Kantarjian et al., Dasatinib versus imatinib in newly diagnosed chronic-phase chronic myeloid leukemia. N Engl J Med. Jun. 17, 2010;362(24):2260-70.
Kauraniemi et al., New amplified and highly expressed genes discovered in the ERBB2 amplicon in breast cancer by cDNA microarrays. Cancer Res. Nov. 15, 2001;61(22):8235-40.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.

(56) References Cited

OTHER PUBLICATIONS

Ko et al., CrkRS: a novel conserved Cdc2-related protein kinase that colocalises with SC35 speckles. J Cell Sci. Jul. 2001;114(Pt 14):2591-603.

Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.

Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.

Kwiatkowski et al., Targeting transcription regulation in cancer with a covalent CDK7 inhibitor. Nature. Jul. 31, 2014;511(7511):616-20.

Kwong et al., Targeted therapy for melanoma: rational combinatorial approaches. Oncogene. Jan. 2, 2014;33(1):1-9. doi: 10.1038/onc.2013.34. Epub Feb. 18, 2013.

Larochelle et al., Requirements for Cdk7 in the assembly of Cdk1/cyclin B and activation of Cdk2 revealed by chemical genetics in human cells. Mol Cell. Mar. 23, 2007;25(6):839-50.

Lavis et al., Bright ideas for chemical biology. ACS Chem Biol. Mar. 20, 2008;3(3):142-55. doi: 10.1021/cb700248m.

Lee et al., BRAF mutations in non-Hodgkin's lymphoma. Br J Cancer. Nov. 17, 2003;89(10):1958-60.

Lin et al., Phase II study of flavopiridol in relapsed chronic lymphocytic leukemia demonstrating high response rates in genetically high-risk disease. J Clin Oncol. Dec. 10, 2009;27(35):6012-8.

Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.

Liu et al., Discovery of 1-(4-(4-propionylpiperazin-1-y1)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.

Liu et al., Two cyclin-dependent kinases promote RNA polymerase II transcription and formation of the scaffold complex. Mol Cell Biol. Feb. 2004;24(4):1721-35.

Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.

Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.

Majima et al., Significant Roles of Inducible Cyclooxygenase (COX)-2 in Angiogenesis in Rat Sponge Implants. Japanese Journal of Pharmacology 1997;75;105-14.

Mallinson et al., Macrocycles in new drug discovery. Future Med Chem. Jul. 2012;4(11):1409-38. doi: 10.4155/fmc.12.93.

March, Advanced Organic Chemistry Reactions, Mechanisms and Structure. 4th ed. 1992:383-386.

Marques et al., A new subfamily of high molecular mass CDC2-related kinases with PITAI/VRE motifs. Biochem Biophys Res Commun. Dec. 29, 2000;279(3):832-7.

Mukaiyama et al., The unexpected and the unpredictable in organic synthesis. Tetrahedron Jul. 1999;55(29):8609-70.

Neklesa et al., Small-molecule hydrophobic tagging-induced degradation of HaloTag fusion proteins. Nat Chem Biol. Jul. 3, 2011;7(8):538-43. doi: 10.1038/nchembio.597.

Obenauf et al., Therapy-induced tumour secretomes promote resistance and tumour progression. Nature. Apr. 16, 2015;520(7547):368-72. doi: 10.1038/nature14336. Epub Mar. 25, 2015.

Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.

Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.

Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.

Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.

Seed et al., The Inhibition of colon-26 Adenocarcinoma Development and Angiogenesis by Topical Diclofenac in 2.5% Hyaluronan. Cancer Research 1997;57:1625-9.

Serizawa et al., Association of Cdk-activating kinase subunits with transcription factor TFIIH. Nature. Mar. 16, 1995;374(6519):280-2.

Sharma et al., A chromatin-mediated reversible drug-tolerant state in cancer cell subpopulations. Cell. Apr. 2, 2010;141(1):69-80.

Shiekhattar et al., Cdk-activating kinase complex is a component of human transcription factor TFIIH. Nature. Mar. 16, 1995;374(6519):283-7.

Smith et al., Recent advances in the research and development of RAF kinase inhibitors. Curr. Top Med. Chem. 2006; 6(11):1071-89.

Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.

Stanovnik et al., The Tautomerism of Heterocycles: Substituent Tautomerism of Six-Membered Ring Heterocycles. Advances in Heterocyclic Chemistry. 2006;91:1-134.

Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.

Terai et al., Activation of the FGF2-FGFR1 autocrine pathway: a novel mechanism of acquired resistance to gefitinib in NSCLC. Mol Cancer Res. Jul. 2013;11(7):759-67.

Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.

Tsujii et al., Cyclooxygenase regulates angiogenesis induced by colon cancer cells. Cell. May 29, 1998;93(5):705-16.

Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.

Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.

Wellbrock et al., The RAF proteins take centre stage Nat Rev Mol Cell Biol. Nov. 2004;5(11):875-85.

Xin et al., Peroxisome proliferator-activated receptor gamma ligands are potent inhibitors of angiogenesis in vitro and in vivo. Journal of Biological Chemistry 1996;274(13):9116-21.

Yalpani, Cholesterol Lowering Drugs. Chemistry and Industry Feb. 1996;3:85-89.

Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.

Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.

Zebisch et al., Back to the roots: the remarkable RAF oncogene story Cell Mol Life Sci. Jun. 2006;63(11):1314-30.

Zhang et al., Discovery of potent and selective covalent inhibitors of JNK. Chem Biol. Jan. 27, 2012;19(1):140-54. doi: 10.1016/j.chembiol.2011.11.010.

Zhou et al., Novel mutant-selective EGFR kinase inhibitors against EGFR T790M. Nature. Dec. 24, 2009;462(7276):1070-4.

(56) References Cited

OTHER PUBLICATIONS

Ziche et al., Role of prostaglandin E1 and copper in angiogenesis. Journal of the National Cancer Institute 1982;69(2):475.
Extended European Search Report for EP 15773870.7, dated Oct. 17, 2018.
Partial Supplementary Search Report for EP 16808476.2, dated Mar. 7, 2019.
Extended European Search Report for EP 16845194.6, dated Mar. 1, 2019.
Dent et al., Coding categorical and coordinate spatial relations in visual-spatial short-term memory. Q J Exp Psychol (Hove). Dec. 2009;62(12):2372-87. doi: 10.1080/17470210902853548. Epub May 11, 2009.
Fiskus et al., BET protein antagonist JQ1 is synergistically lethal with FLT3 tyrosine kinase inhibitor (TKI) and overcomes resistance to FLT3-TKI in AML cells expressing FLT-ITD. Mol Cancer Ther. Oct. 2014; 13(10): 2315-2327. Published online Jul. 22, 2014. doi: 10.1158/1535-7163.MCT-14-0258.
Fleming et al., Synergistic inhibition of ErbB signaling by combined treatment with seliciclib and ErbB-targeting agents. Clin Cancer Res. Jul. 1, 2008;14(13):4326-35. doi: 10.1158/1078-0432.CCR-07-4633.
Girotti et al., No longer an untreatable disease: How targeted and immunotherapies have changed the management of melanoma patients. Mol Oncol. Sep. 2014; 8(6): 1140-1158. Published online Aug. 15, 2014. doi: 10.1016/j.molonc.2014.07.027.
Orzaez et al., Intrinsic caspase-8 activation mediates sensitization of erlotinib-resistant tumor cells to erlotinib/cell-cycle inhibitors combination treatment. Cell Death Dis. Oct. 25, 2012;3:e415. doi: 10.1038/cddis.2012.155.
Vora et al., CDK 4/6 inhibitors sensitize PIK3CA Mutant Breast Cancer to PI3K inhibitors. Cancer Cell. Jul. 14, 2014;26(1):136-149. Published online Jul. 4, 2014. doi: 10.1016/j.ccr.2014.05.020.
U.S. Appl. No. 14/358,606, filed May 15, 2014, Gray et al.
U.S. Appl. No. 15/188,545, filed Jun. 21, 2016, Gray et al.
U.S. Appl. No. 14/436,496, filed Apr. 17, 2015, Gray et al.
U.S. Appl. No. 14/436,387, filed Apr. 16, 2015, Gray et al.
U.S. Appl. No. 14/436,657, filed Apr. 17, 2015, Gray et al.
U.S. Appl. No. 15/305,801, filed Oct. 21, 2016, Gray et al.
U.S. Appl. No. 15/305,845, filed Oct. 21, 2016, Gray et al.
U.S. Appl. No. 13/376,539, filed Dec. 6, 2011, Choi et al.
U.S. Appl. No. 14/321,242, filed Jul. 1, 2014, Gray et al.
U.S. Appl. No. 13/519,826, filed Nov. 1, 2012, Gray et al.
U.S. Appl. No. 14/552,229, filed Nov. 24, 2014, Gray et al.
U.S. Appl. No. 14/921,894, filed Oct. 23, 2015, Gray et al.
U.S. Appl. No. 13/583,974, filed Dec. 5, 2012, Gray et al.
PCT/US2012/065618, Mar. 19, 2013, International Search Report and Written Opinion.
PCT/US2012/065618, May 30, 2014, International Preliminary Report on Patentability.
PCT/US2013/065708, Feb. 4, 2014, International Search Report and Written Opinion.
PCT/US2013/065708, Apr. 30, 2015, International Preliminary Report on Patentability.
PCT/US2013/065689, Mar. 4, 2014, International Search Report and Written Opinion.
PCT/US2013/065689, Apr. 30, 2015, International Preliminary Report on Patentability.
PCT/US2013/065698, Feb. 20, 2014, International Search Report and Written Opinion.
PCT/US2013/065698, Apr. 30, 2015, International Preliminary Report on Patentability.
PCT/US2014/061232, Dec. 23, 2014, International Search Report and Written Opinion.
PCT/US2015/027312, Jul. 10, 2015, International Search Report and Written Opinion.
PCT/US2015/027312, Nov. 3, 2016, International Preliminary Report on Patentability.
PCT/US2015/027294, Jul. 10, 2015, International Search Report and Written Opinion.
PCT/US2015/027294, Nov. 3, 2016, International Preliminary Report on Patentability.
PCT/US2010/038518, Dec. 22, 2011, International Preliminary Report on Patentability.
PCT/US2010/038518, Aug. 6, 2010, International Search Report and Written Opinion.
EP 10786967.9, Oct. 23, 2012, Extended European Search Report.
EP 10844280.7, Apr. 17, 2013, Extended European Search Report.
EP15160591.2, Jul. 14, 2015, Partial European Search Report.
EP15160591.2, Nov. 2, 2015, Partial European Search Report.
PCT/US2010/062310, Oct. 4, 2011, International Search Report and Written Opinion.
PCT/US2010/062310, Jul. 12, 2012, International Preliminary Report on Patentability.
PCT/US2015/000297, Mar. 4, 2016, International Search Report and Written Opinion.
PCT/US2015/000297, Jul. 6, 2017, International Preliminary Report on Patentability.
PCT/US2016/037086, Sep. 2, 2016, International Search Report and Written Opinion.
PCT/US2016/024345, Aug. 9, 2016, Invitation to Pay Additional Fees.
PCT/US2016/024345, Oct. 6, 2016, International Search Report and Written Opinion.
PCT/US2016/051118, Dec. 1, 2016, Invitation to Pay Additional Fees.
PCT/US2016/051118, Mar. 13, 2017, International Search Report and Written Opinion.
PCT/US2011/025423, May 31, 2011, Invitation to Pay Additional Fees.
PCT/US2011/025423, Nov. 5, 2012, International Search Report and Written Opinion.
PCT/US2011/025423, Nov. 29, 2012, International Preliminary Report on Patentability.
International Preliminary Report on Patentability for PCT/US2016/024345, dated Oct. 12, 2017.
International Preliminary Report on Patentability for PCT/US/2016/037086, dated Dec. 21, 2017.
International Preliminary Report on Patentability for PCT/US2016/051118, dated Mar. 22, 2018.
Partial European Search Report for EP 16773870.7, dated Jul. 12, 2018.
Akira et al., Toll-like receptor signalling. Nat Rev Immunol. Jul. 2004;4(7):499-511.
Attoub et al., The c-kit tyrosine kinase inhibitor STI571 for colorectal cancer therapy. Cancer Res. Sep. 1, 2002;62(17):4879-83.
Beeler et al., Role of the JNK-interacting protein 1/islet brain 1 in cell degeneration in Alzheimer disease and diabetes. Brain Res Bull. Oct. 28, 2009;80(4-5):274-81. doi:.10.1016/j.brainresbull.2009.07.006. Epub Jul. 16, 2009.
Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.
Carvajal et al., KIT as a therapeutic target in metastatic melanoma. JAMA. Jun. 8, 2011;305(22):2327-34. doi: 10.1001/jama.2011.746.
Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.
Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Fan et al., Dual leucine zipper-bearing kinase (DLK) activates p46SAPK and p38mapk but not ERK2. J Biol Chem. Oct. 4, 1996;271(40):24788-93.
Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.

(56) References Cited

OTHER PUBLICATIONS

Hirai et al., The c-Jun N-terminal kinase activator dual leucine zipper kinase regulates axon growth and neuronal migration in the developing cerebral cortex. J Neurosci. Nov. 15, 2006;26(46):11992-2002.
Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Kanakaraj et al., Interleukin (IL)-1 receptor-associated kinase (IRAK) requirement for optimal induction of multiple IL-1 signaling pathways and IL-6 production. J Exp Med. Jun. 15, 1998;187(12):2073-9.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Lorenzo et al., Expression of proto-oncogene c-kit in high risk prostate cancer. Eur J Surg Oncol. Nov. 2004;30(9):987-92.
Marelli et al., Tumor targeting via integrin ligands. Front. Oncol., Aug. 30, 2013. https://doi.org/10.3389/fonc.2013.00222.
Matsuyama et al., Activation of Discoidin Domain Receptor 1 Isoform b with Collagen Up-Regulates Chemokine Production in Human Macrophages: Role of p38 Mitogen-Activated Protein Kinase and NF-κB. J Immunol Feb. 15, 2004, 172 (4) 2332-2340; DOI: https://doi.org/10.4049/jimmunol.172.4.2332.
Peifer et al., Small-molecule inhibitors of PDK1. ChemMedChem. Dec. 2008;3(12):1810-38. doi: 10.1002/cmdc.200800195.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
Roberts et al., Antiangiogenic and antitumor activity of a selective PDGFR tyrosine kinase inhibitor, CP-673,451. Cancer Res. Feb. 1, 2005;65(3):957-66.
Rubin et al., KIT activation is a ubiquitous feature of gastrointestinal stromal tumors. Cancer Res. Nov. 15, 2001;61(22):8118-21.
Sengupta et al., DLK induces developmental neuronal degeneration via selective regulation of proapoptotic JNK activity. Journal of Cell Biology 2011;194(5):751-764. DOI https://doi.org/10.1083/jcb.201103153.
Shin et al., Dual leucine zipper kinase is required for retrograde injury signaling and axonal regeneration. Neuron. Jun. 21, 2012;74(6):1015-22. doi: 10.1016/j.neuron.2012.04.028.
Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.
Takemori et al., Inactivation of HDAC5 by SIK1 in AICAR-treated C2C12 myoblasts. Endocr J. 2009;56(1):121-30. Epub Oct. 22, 2008.
Wang et al., IRAK-4 inhibitors for inflammation. Curr Top Med Chem. 2009;9(8):724-37.
Wietek et al., IRAK-4: a new drug target in inflammation, sepsis, and autoimmunity. Mol Interv. Jul. 2002;2(4):212-5.
Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
Yasuda et al., The stem cell factor/c-kit receptor pathway enhances proliferation and invasion of pancreatic cancer cells. Mol Cancer. Oct. 18, 2006;5:46.
U.S. Appl. No. 16/202,961, filed Nov. 28, 2018, Gray et al.
U.S. Appl. No. 16/130,975, filed Sep. 13, 2018, Gray et al.
U.S. Appl. No. 16/179,833, filed Nov. 2, 2018, Gray et al.
EP 16773870.7, Oct. 17, 2018, Extended European Search Report.
EP 16808476.2, Mar. 7, 2019, Partial supplementary European Search Report.
EP16845194.6, Mar. 1, 2019, Extended European Search Report.
U.S. Appl. No. 15/699,948, filed Sep. 8, 2017, Gray et al.
U.S. Appl. No. 15/735,532, filed Dec. 11, 2017, Hammerman et al.
U.S. Appl. No. 15/561,729, filed Sep. 26, 2017, Gray et al.
U.S. Appl. No. 15/758,982, filed Mar. 9, 2018, Gray et al.
PCT/US2016/024345, Oct. 12, 2017, International Preliminary Report on Patentability.
PCT/US2016/037086, Dec. 21, 2017, International Preliminary Report on Patentability.
PCT/US2016/051118, Mar. 22, 2018, International Preliminary Report on Patentability.
EP 16773870.7, Jul. 12, 2018, Partial Supplementary European Search Report.
Extended European Search Report for EP19168422.4, dated Aug. 13, 2019.
Extended European Search Report for EP 16808476.2, dated Jun. 14, 2019.
Bai et al., Design, synthesis and anticancer activity of 1-acyl-3-amino-1,4,5,6-tetrahydropyrrolo[3,4-c]pyrazole derivatives. Bioorg Med Chem Lett. Nov. 15, 2012;22(22):6947-51. Suppl. Info, 46 pages. doi: 10.1016/j.bmcl.2012.08.117. Epub Sep. 8, 2012.
Blachly et al., Emerging drug profile: cyclin-dependent kinase inhibitors. Leuk Lymphoma. Oct. 2013;54(10):2133-43. doi: 10.3109/10428194.2013.783911. Epub Jul. 29, 2013. Author manuscript.
Fancelli et al., Potent and selective Aurora inhibitors identified by the expansion of a novel scaffold for protein kinase inhibition. J Med Chem. Apr. 21, 2005;48(8):3080-4.
Katt et al., Dissemination from a Solid Tumor: Examining the Multiple Parallel Pathways. Trends Cancer. Jan. 2018;4(1):20-37. doi: 10.1016/j.trecan.2017.12.002. Epub Jan. 10, 2018. Author manuscript.
McAuley et al., CARMA3 Is a Critical Mediator of G Protein-Coupled Receptor and Receptor Tyrosine Kinase-Driven Solid Tumor Pathogenesis. Front Immunol. Aug. 15, 2018;9:1887. doi: 10.3389/fimmu.2018.01887. eCollection 2018.
Ochiana et al., The human Aurora kinase inhibitor danusertib is a lead compound for anti-trypanosomal drug discovery via target repurposing. Eur J Med Chem. Apr. 2013;62:777-84. doi: 10.1016/j.ejmech.2012.07.038. Epub Jul. 31, 2012.
Pevarello et al., 3-Amino-1,4,5,6-tetrahydropyrrolo[3,4-c]pyrazoles: A new class of CDK2 inhibitors. Bioorg Med Chem Lett. Feb. 15, 2006;16(4):1084-90.
Sidow et al., Concepts in solid tumor evolution. Trends Genet. Apr. 2015;31(4):208-14. doi: 10.1016/j.tig.2015.02.001. Epub Feb. 27, 2015. Author manuscript.
Tian et al., mTOR Signaling in Cancer and mTOR Inhibitors in Solid Tumor Targeting Therapy. Int J Mol Sci. Feb. 11, 2019;20(3). pii: E755. doi: 10.3390/ijms20030755.
International Preliminary Report on Patentability for Application No. PCT/US2017/063132 dated Jun. 6, 2019.
International Search Report and Written Opinion for Application No. PCT/US2017/063132 dated Jan. 29, 2018.
Bogoyevitch et al., c-Jun N-terminal kinase (JNK) signaling: recent advances and challenges. Biochim Biophys Acta. Mar. 2010;1804(3):463-75. doi: 10.1016/j.bbapap.2009.11.002. Epub Nov. 10, 2009.
Brasca et al., 6-Substituted pyrrolo[3,4-c]pyrazoles: an improved class of CDK2 inhibitors. ChemMedChem. Jun. 2007;2(6):841-52.
Chène, Challenges in design of biochemical assays for the identification of small molecules to target multiple conformations of protein kinases. Drug Discov Today. Jun. 2008;13(11-12):522-9. doi: 10.1016/j.drudis.2008.03.023. Epub May 5, 2008.
Database Registry [Online] Retrieved from STN, Dec. 4, 2011, search date :Oct. 7, 2019; RN 1350102-23-6, 1349782-05-3, 1349471-31-3, 1349357-86-3, 1349106-33-7, 1348397-56-7, 1348192-23-3, 1348088-42-5.
Kooistra et al., Kinase-Centric Computational Drug Development, in 50 Annual Reports in Medicinal Chemistry. 2017;197-236.
Li et al., Identification of novel pyrrolopyrazoles as protein kinase C β II inhibitors. Bioorg Med Chem Lett. Jan. 1, 2011;21(1):584-7. doi: 10.1016/j.bmcl.2010.10.032. Epub Oct. 13, 2010.

(56) References Cited

OTHER PUBLICATIONS

Patel et al., Discovery of dual leucine zipper kinase (DLK, MAP3K12) inhibitors with activity in neurodegeneration models. J Med Chem. Jan. 8, 2015;58(1):401-18. doi: 10.1021/jm5013984. Epub Oct. 23, 2014.

Sánchez-Martínez et al., Cyclin dependent kinase (CDK) inhibitors as anticancer drugs. Bioorg Med Chem Lett. Sep. 1, 2015;25(17):3420-35. doi: 10.1016/j.bmcl.2015.05.100. Epub Jun. 6, 2015.

Wu et al., FDA-approved small-molecule kinase inhibitors. Trends Pharmacol Sci. Jul. 2015;36(7):422-39. doi: 10.1016/j.tips.2015.04.005. Epub May 12, 2015.

Patani et al., Bioisosterism: A Rational Approach in Drug Design. Chem Rev. 1996;96:3147-3176.

Powell et al., Regulation of immune responses by mTOR. Annu Rev Immunol. 2012;30:39-68. doi:10.1146/annurev-immunol-020711-075024. Epub Nov. 29, 2011.

Zeng et al. Targeting MYC dependency in ovarian cancer through inhibition of CDK7 and CDK12/13. Elife. 2018;7:e39030. Published Nov. 13, 2018. doi:10.7554/eLife.39030.

Zhang et al. CDK7 Inhibition Potentiates Genome Instability Triggering Anti-tumor Immunity in Small Cell Lung Cancer. Cancer Cell. 2020;37(1):37-54.e9. doi:10.1016/j.ccell.2019.11.003.

Zhang et al., Etk/Bmx transactivates vascular endothelial growth factor 2 and recruits phosphatidylinositol 3-kinase to mediate the tumor necrosis factor-induced angiogenic pathway. J Biol Chem. Dec. 19, 2003;278(51):51267-76. Epub Oct. 7, 2003.

Zompi et al., Animal models of dengue virus infection. Viruses. Jan. 2012;4(1):62-82. doi: 10.3390/v4010062. Epub Jan. 9, 2012.

\* cited by examiner

INHIBITORS OF CYCLIN-DEPENDENT KINASE 7 (CDK7)

RELATED APPLICATIONS

This application is a national stage filing under 35 U.S.C. § 371 of international PCT application, PCT/US2015/000297, filed Dec. 23, 2015, which claims priority under 35 U.S.C. § 119(e) to U.S. Provisional Application, U.S. Ser. No. 62/096,040, filed Dec. 23, 2014, the entire contents of each of which is incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jul. 31, 2020, is named D050470082US01-SEQ-JBR and is 5 kilobytes in size.

GOVERNMENT SUPPORT

This invention was made with government support under grant number 1 R01 CA 179483-01A1 awarded by the National Institutes of Health. The government has certain rights in the invention.

BACKGROUND OF THE INVENTION

The members of the cyclin-dependent kinase (CDK) family play critical regulatory roles in cell proliferation. There are currently 20 known mammalian CDKs. While CDK7-CDK13 have been linked to transcription, only CDK1, 2, 4, and 6 show demonstrable association with the cell cycle. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., "Effects of phosphorylation by CAK on cyclin binding by CDC2 and CDK2." Mol. Cell Biol. 15, 345-350 (1995); Kaldis et al., "Analysis of CAK activities from human cells." Eur. J. Biochem. 267, 4213-4221 (2000); Larochelle et al., "Requirements for CDK7 in the assembly of CDK1/cyclin B and activation of CDK2 revealed by chemical genetics in human cells." Mol. Cell 25, 839-850 (2007)). In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation (Serizawa. et al., "Association of CDK-activating kinase subunits with transcription factor TFIIH." Nature 374, 280-282 (1995); Shiekhattar et al., "CDK-activating kinase complex is a component of human transcription factor TFIIH." Nature 374, 283-287 (1995); Drapkin et al., "Human cyclin-dependent kinase-activating kinase exists in three distinct complexes." Proc. Natl. Acad. Sci. U.S.A. 93, 6488-6493 (1996); Liu. et al., "Two cyclin-dependent kinases promote RNA polymerase II transcription and formation of the scaffold complex." Mol. Cell Biol. 24, 1721-1735 (2004); Akhtar et al., "TFIIH kinase places bivalent marks on the carboxy-terminal domain of RNA polymerase II." Mol. Cell 34, 387-393 (2009); Glover-Cutter et al., "TFIIH-associated CDK7 kinase functions in phosphorylation of C-terminal domain Ser7 residues, promoter-proximal pausing, and termination by RNA polymerase II." Mol. Cell Biol. 29, 5455-5464 (2009)). Together, the two functions of CDK7, i.e., CAK and CTD phosphorylation, support critical facets of cellular proliferation, cell cycling, and transcription.

Disruption of RNAP II CTD phosphorylation has been shown to preferentially affect proteins with short half-lives, including those of the anti-apoptotic BCL-2 family (Konig et al., "The novel cyclin-dependent kinase inhibitor flavopiridol downregulates Bcl-2 and induces growth arrest and apoptosis in chronic B-cell leukemia lines." Blood 1, 4307-4312 (1997); Gojo et al., "The cyclin-dependent kinase inhibitor flavopiridol induces apoptosis in multiple myeloma cells through transcriptional repression and down-regulation of Mcl-1." Clin. Cancer Res. 8, 3527-3538 (2002)). Cancer cells have demonstrated ability to circumvent pro-cell death signaling through up-regulation of BCL-2 family members (Llambi et al., "Apoptosis and oncogenesis: give and take in the BCL-2 family." Curr. Opin. Genet. Dev. 21, 12-20 (2011)). Therefore, inhibition of human CDK7 kinase activity is likely to result in antiproliferative activity, and pharmacological inhibition is thought to be useful in treating proliferative disorders, including cancer. Indeed, flavopiridol, a non-selective pan-CDK inhibitor that targets CTD kinases, has demonstrated efficacy for the treatment of chronic lymphocytic leukemia (CLL) but suffers from a poor toxicity profile (Lin et al., "Phase II study of flavopiridol in relapsed chronic lymphocytic leukemia demonstrating high response rates in genetically high-risk disease." J. Clin. Oncol. 27, 6012-6018 (2009); Christian et al., "Flavopiridol in chronic lymphocytic leukemia: a concise review." Clin. Lymphoma Myeloma 9 Suppl. 3, S179-S185 (2009)). A selective CDK7 inhibitor may hold promise as a therapeutic agent for the treatment of CLL and other cancers.

SUMMARY OF THE INVENTION

The present invention provides compounds of Formula (I), and pharmaceutically acceptable salts, solvates, hydrates, polymorphs, co-crystals, tautomers, stereoisomers, isotopically labeled derivatives, prodrugs, and compositions thereof. The compounds of Formula (I), and pharmaceutically acceptable salts, solvates, hydrates, polymorphs, co-crystals, tautomers, stereoisomers, isotopically labeled derivatives, prodrugs, and compositions thereof, may inhibit the activity of a kinase. In certain embodiments, the inhibited kinase is a CDK. In certain embodiments, the kinase is CDK7. In certain embodiments, the compound of Formula (I) is selective for CDK7 compared to other kinases (e.g., CDK12 and CDK13). The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., CDK7) and as therapeutics for the prevention and/or treatment of diseases associated with the overexpression and/or aberrant activity of a kinase (e.g., CDK7). In certain embodiments, the inventive compounds are used for the prevention and/or treatment of proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject.

In certain embodiments, the compounds of Formula (I) may selectively inhibit the activity of CDK7 compared to CDK13. Since the discovery of selective inhibitors of CDK7 has been hampered by the high sequence and structural similarities of the kinase domain of CDK family members, the development of selective inhibitors of the transcriptional cyclin-dependent kinases (tCDKs) will allow dissection of their individual contributions to the regulation of transcription and evaluation of their therapeutic potential. Without wishing to be bound by any particular theory, the inventive compounds' selectivity for CDK7 may be due to the compounds' ability to covalently modify the cysteine residue (Cys312) of CDK7. Cys312 of CDK7 is largely unique among the CDKs and other kinases.

In one aspect, the present invention provides compounds of Formula (I):

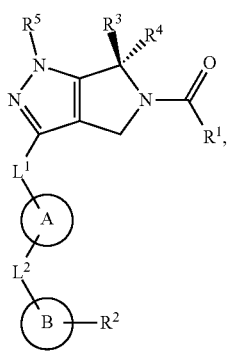

(I)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, $R^5$, linker $L^1$, linker $L^2$, Ring A, and Ring B are as defined herein.

In certain embodiments, a compound of Formula (I) is of Formula (II):

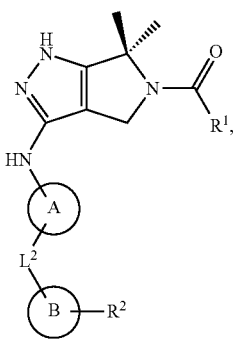

(II)

or a pharmaceutically acceptable salt, solvate, hydrate, polymorph, co-crystal, tautomer, stereoisomer, isotopically labeled derivative, or prodrug thereof, wherein $R^1$, $R^2$, linker $L^2$, Ring A, and Ring B are as defined herein.

In certain embodiments, a compound of Formula (I) is of Formula (III):

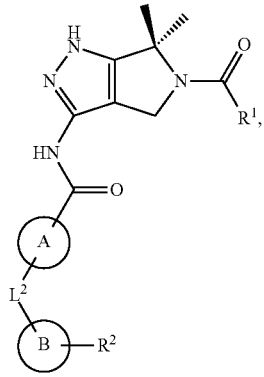

(III)

or a pharmaceutically acceptable salt, solvate, hydrate, polymorph, co-crystal, tautomer, stereoisomer, isotopically labeled derivative, or prodrug thereof, wherein $R^1$, $R^2$, linker $L^2$, Ring A, and Ring B are as defined herein.

In certain embodiments, a compound of Formula (I) is of Formula (V-a), (V-b), (V-c), or (V-d):

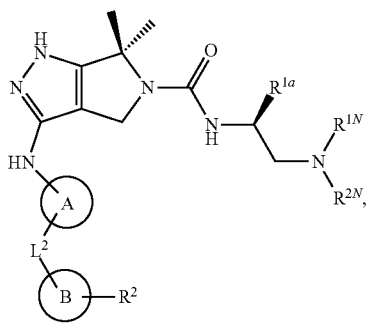

(V-a)

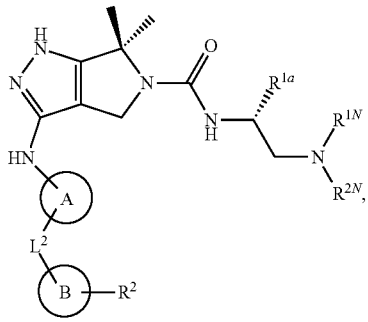

(V-b)

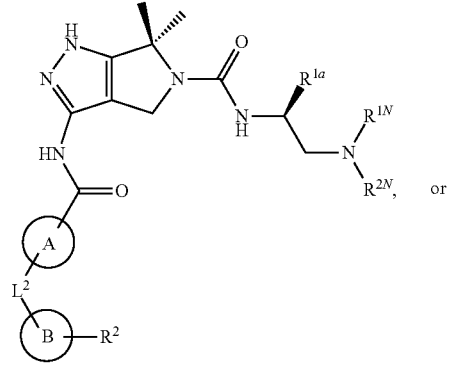

(V-c)

or (V-d)

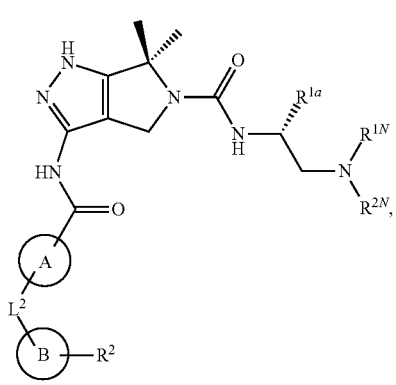

or a pharmaceutically acceptable salt, solvate, hydrate, polymorph, co-crystal, tautomer, stereoisomer, isotopically labeled derivative, or prodrug thereof, wherein $R^2$, $R^{1a}$, $R^{1N}$, $R^{2N}$, linker $L^2$, Ring A, and Ring B are as defined herein.

In certain embodiments, a compound of Formula (I) is of Formula (IX-a), (IX-b), (IX-C), or (IX-d):

(IX-a)

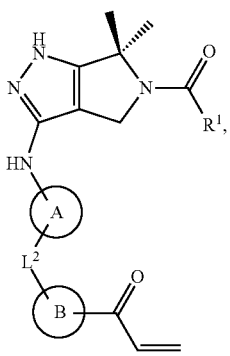

(IX-b)

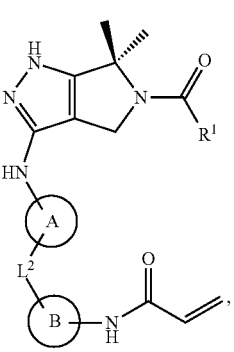

(IX-c)

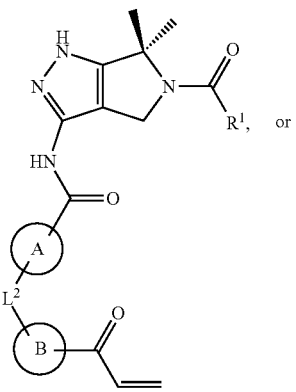

or (IX-d)

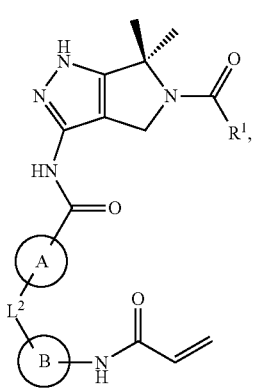

or a pharmaceutically acceptable salt, solvate, hydrate, polymorph, co-crystal, tautomer, stereoisomer, isotopically labeled derivative, or prodrug thereof, wherein $R^1$, linker $L^2$, Ring A, and Ring B are as defined herein.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating a proliferative disease in a subject in need thereof, preventing a proliferative disease in a subject in need thereof, inhibiting the activity of a protein kinase in a subject, biological sample, tissue, or cell, and/or inducing apoptosis in a cell.

In another aspect, the present invention provides methods for treating and/or preventing a proliferative disease. Exemplary proliferative diseases which may be treated include cancer (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasm, diseases associated with angiogenesis, inflammatory diseases, autoinflammatory diseases, and autoimmune diseases.

Another aspect of the invention relates to methods of inhibiting the activity of a kinase (e.g., CDK (e.g., CDK7)) in a biological sample or subject. In certain embodiments, the method involves the selective inhibition of CDK7.

Also provided by the present invention are methods of inhibiting transcription in a biological sample or subject. The transcription of genes affected by the activity of CDK7 may be inhibited by the compounds of the invention.

The present invention also provides methods of inhibiting cell growth in a biological sample or subject. In still another aspect, the present invention provides methods of inducing apoptosis of a cell in a biological sample or a subject.

In yet another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment of a proliferative disease (e.g., cancer) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency such as the U.S. Food and Drug Administration (FDA).

The present invention describes methods for administering to the subject an effective amount of a compound, or pharmaceutical composition thereof, as described herein. Also described are methods for a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent. A method described herein may further include performing radiotherapy, immunotherapy, and/or transplantation on the subject.

In yet another aspect, the present disclosure provides compounds, and pharmaceutical compositions thereof, as described herein for use in a method of the disclosure.

The details of one or more embodiments of the invention are set forth herein. Other features, objects, and advantages of the invention will be apparent from the Detailed Description, the Examples, and the Claims.

BRIEF DESCRIPTION OF THE DRAWINGS

The accompanying drawing, which are incorporated in and constitute a part of this specification, illustrate several embodiments of the invention and together with the description, serve to explain the principles of the invention.

FIG. 1 shows the total ion chromatograms (TIC; A,E) and extracted ion chromatograms (XIC; B-D, F-H) for CDK7 peptides recorded during analysis of CAK complexes treated with DMSO (A-D) or Compound 101 (E-H). FIGS. 1B and 1F, 1C and 1G, and 1D and 1H depict SEQ ID NOs: 1 through 3, respectively.

DEFINITIONS

Figure 1A:
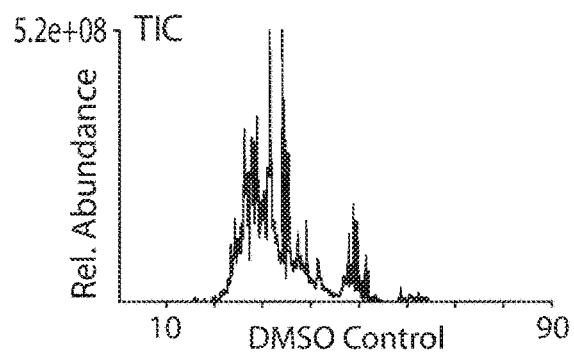
FIG. 1A: TIC; DMSO.
Figure 1E:
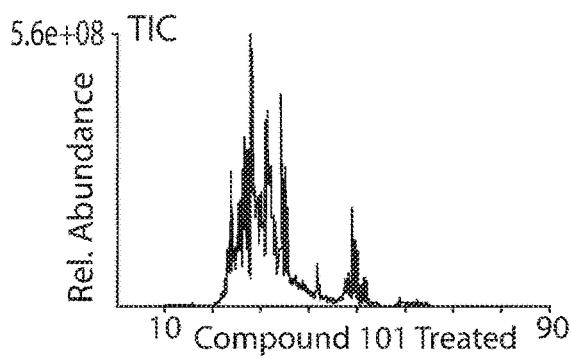
FIG. 1E: TIC; compound 101.
Figure 1B:
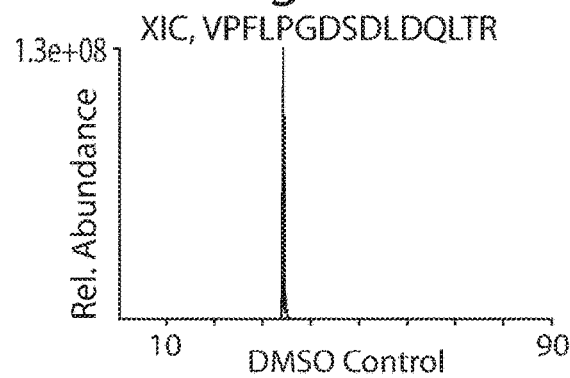
FIG. 1B: XIC; DMSO.
Figure 1F:
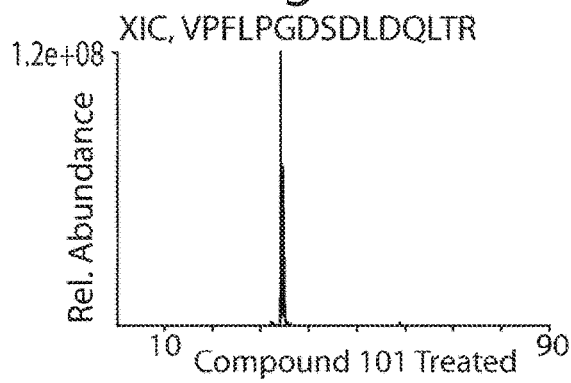
FIG. 1F: XIC; compound 101.
Figure 1C:
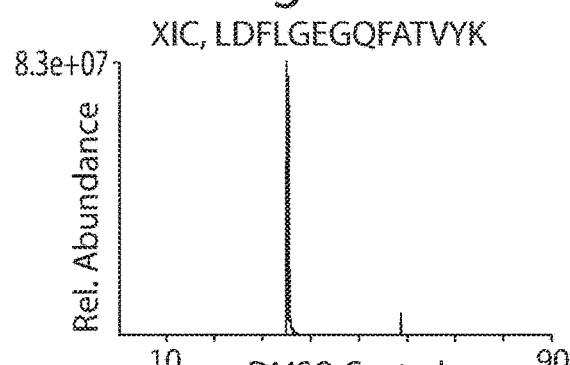
FIG. 1C: XIC; DMSO.
Figure 1G:
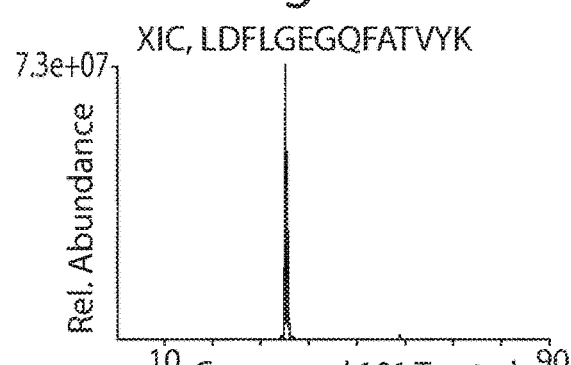
FIG. 1G: XIC; compound 101.
Figure 1D:
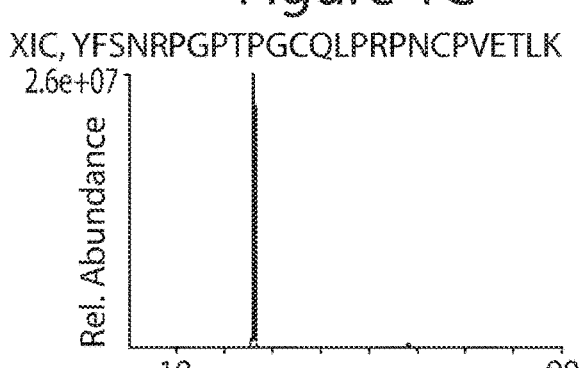
FIG. 1D: XIC; DMSO.
Figure 1H:
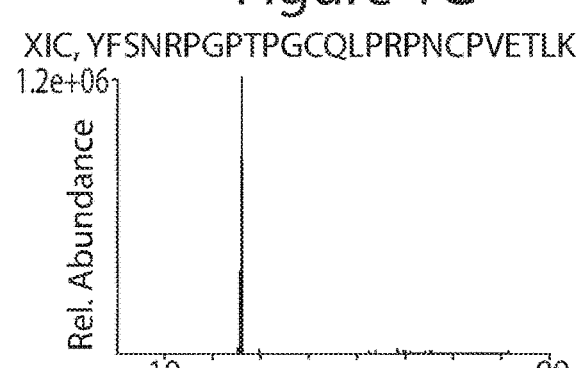
FIG. 1H: XIC; compound 101.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$). In certain embodiments, the alkyl group is a substituted $C_{1-10}$ alkyl (such as substituted $C_{1-6}$ alkyl, e.g., —$CF_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or Spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or Spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered, non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydropyranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thicpanyl. Exemplary 8-membered heterocyclyl groups containing one heteroatom include, without limitation, azocanyl, oxetanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups, wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered, monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent linking groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NRC(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)

NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=NR$^{bb}$)$R^{aa}$, —C(=NR$^{bb}$)O$R^{aa}$, —C(=NR$^{bb}$)N($R^{bb}$)$_2$, —C(=O)NR$^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=NR$^{bb}$)$R^{aa}$, —C(=NR$^{cc}$)O$R^{aa}$, —C(=NR$^{cc}$)N($R^{cc}$)$_2$, —SO$_2$N($R^{cc}$)$_2$, —SO$_2$$R^{cc}$, —SO$_2$O$R^{cc}$, —SOR$^{aa}$a, —C(=S)N($R^{cc}$)$_2$, —C(=O)S$R^{cc}$, —C(=S)S$R^{cc}$, —P(=O) (O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=NR$^{cc}$)$R^{aa}$, —C(=NR$^{cc}$)O$R^{aa}$, —C(=NR$^{cc}$)N($R^{cc}$)$_2$, —SO$_2$N($R^{cc}$)$_2$, —SO$_2$$R^{cc}$, —SO$_2$O$R^{cc}$, —SOR$^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=$NR^{bb}$)$R^{aa}$, —C(=$NR^{bb}$)$OR^{aa}$, —C(=$NR^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3^+$X$^-$, —P($OR^{cc}$)$_2$, —P($OR^{cc}$)$_3^+$X$^-$, —P(=O)($R^{aa}$)$_2$, —P(=O)($OR^{cc}$)$_2$, and —P(=O)(N($R^{bb}$)$_2$)$_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —($C^BH_2C^CH_3$). The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH($C_2H_5$)— is a $C_1$ hydrocarbon chain, and

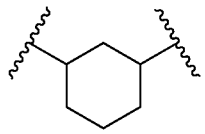 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

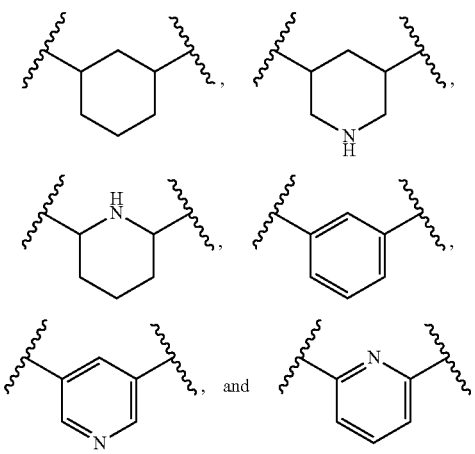

are all examples of a hydrocarbon chain. In contrast, in certain embodiments,

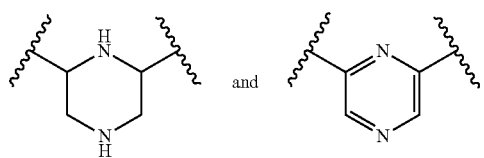 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

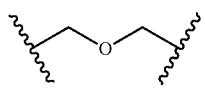 [SMILES: *COC*]

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. Exemplary leaving groups include, but are not limited to, activated substituted hydroxyl groups (e.g., $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OP(R^{cc})_2$, $-OP(R^{cc})_3$, $-OP(=O)_2R^{aa}$, $-OP(=O)(R^{aa})_2$, $-OP(=O)(OR^{cc})_2$, $-OP(=O)_2N(R^{bb})_2$, and $-OP(=O)(NR^{bb})_2$, wherein $R^{aa}$, $R^{bb}$, and $R^{cc}$ are as defined herein). In some cases, the leaving group is a sulfonic acid ester, such as toluenesulfonate (tosylate, -OTs), methanesulfonate (mesylate, -OMs), p-bromobenzenesulfonyloxy (brosylate, -OBs), $-OS(=O)_2(CF_2)_3CF_3$ (nonaflate, -ONf), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

Other Definitions

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4} alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5\ H_2O$)), and polyhydrates (x is a number greater than 1, e.g., dihydrates ($R.2H_2O$) and hexahydrates ($R.6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal may contain a compound of the present invention and one or more other component, including but not limited to, atoms, ions, molecules, or solvent molecules. In certain embodiments, a co-crystal may contain a compound of the present invention and one or more components related to said compound, including not limited to, an isomer, tautomer, salt, solvate, hydrate, synthetic precursor, synthetic derivative, fragment or impurity of said compound.

The term "isotopically labeled derivative" or "isotopically labeled" refers to a compound wherein one or more atoms in the compound (or in an associated ion or molecule of a salt, hydrate, or solvate) has been replaced with an isotope of the same element. For the given element or position in the molecule the isotope will be enriched, or present in a higher percentage of all atoms of the element or of all atoms at the position in the molecule in a sample, relative to an unlabeled variant. In certain embodiments, the enriched isotope will be a stable isotope. In certain embodiments, the enriched isotope will be an unstable or radioactive isotope (e.g., a radionuclide). In certain embodiments, the enriched isotope may be detected by a measurement technique, including but not limited to nuclear magnetic resonance, mass spectrometry, infrared spectroscopy, or a technique that measures radioactive decay.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process (e.g., activity of a bromodomain and/or a bromodomain-containing protein) in a cell relative to vehicle.

When a compound, pharmaceutical composition, method, use, or kit is referred to as "selectively," "specifically," or "competitively" binding a first protein or a first chromatin, the compound, pharmaceutical composition, method, use, or kit binds the first protein or the first chromatin with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or second chromatin that is different from the first protein and the first chromatin. When a compound, pharmaceutical composition, method, use, or kit is referred to as "selectively," "specifically," or "competitively" modulating (e.g., increasing or inhibiting) the activity of a bromodomain-containing protein, the compound, pharmaceutical composition, method, use, or kit modulates the activity of the bromodomain-containing protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the bromodomain-containing protein.

The term "aberrant activity" refers to activity deviating from normal activity, that is, abnormal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from another biological sample.

The terms "administer," "administering," or "administration" refers to implanting, absorbing, ingesting, injecting, inhaling, or otherwise introducing a compound described herein, or a composition thereof, into, in, or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated as in the growth of normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC)); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "hematological malignancy" refers to tumors that affect blood, bone marrow, and/or lymph nodes. Exemplary hematological malignancies include, but are not limited to, leukemia, such as acute lymphoblastic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hay fever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. Exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wec1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "SRC family kinase" refers to a family of non-receptor tyrosine protein kinases that includes nine members: SRCA subfamily that includes c-SRC (proto-oncogene tyrosine-protein kinase SRC), YES (proto-oncogene tyrosine-protein kinase Yes), FYN (proto-oncogene tyrosine-protein kinase FYN), and FGR (Gardner-Rasheed feline sarcoma viral (v-FGR) oncogene homolog); SRCB subfamily that includes LCK (lymphocyte-specific protein tyrosine kinase), HCK (tyrosine-protein kinase HCK, hemopoietic cell kinase), BLK (tyrosine-protein kinase BLK), and LYN (tyrosine-protein kinase LYN); and FRK (Fyn-related kinase).

The term "CDK" refers to a cyclin-dependent kinase. A CDK binds a cyclin (e.g., Cyclin H), which is a regulatory protein. CDKs phosphorylate their substrates at serines and threonines. The consensus sequence for the phosphorylation site in the amino acid sequence of a CDK substrate is [S/T*]PX[K/R], where S/T* is the phosphorylated serine or threonine, P is proline, X is any amino acid, K is lysine, and R is arginine. CDKs include CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19 and CDK20.

CDK7, cyclin-dependent kinase 7, is a CDK, wherein the substrate is Cyclin H, MAT1 (e.g., MNAT1), or Cyclin H and MAT1. CDK7 is alternatively referred to as CAK1, HCAK, MO15, STK1, CDKN7, and p39MO15. Non-limiting examples of the nucleotide and protein sequences for human CDK7 are described in GenBank Accession Number NP_001790, incorporated herein by reference. The amino acid sequence of this CDK7 is as follows:

MALDVKSRAKRYEKLDFLGEGQFATVYKARDKNTNQIVAIKKIKLGHRS

EAKDGINRTALREIKLLQELSHPNIIGLLDAFGHKSNISLVFDFMETDLE

-continued

VIIKDNSLVLTPSHIKAYMLMTLQGLEYLHQHWILHRDLKPNNLLLDENG

VLKLADFGLAKSFGSPNRAYTHQVVTRWYRAPELLFGARMYGVGVDMW

AVGCILAELLLRVPFLPGDSDLDQLTRIFETLGTPTEEQWPDMCSLPDY

VTFKSFPGIPLHHIFSAAGDDLLDLIQGLFLFNPCARITATQALKMKYFS

NRPGPTPGCQLPRPNCPVETLKEQSNPALAIKRKRTEALEQGGLPKKL

IF

DETAILED DESCRIPTION OF CERTAIN EMBODIMENTS OF THE INVENTION

Cyclin dependent kinases (CDKs) are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. Cyclin-dependent kinase 7 (CDK7) plays a critical role in the regulation of RNA polymerase II-mediated transcription of protein-encoding genes. Disruption of CDK7 signaling causes defects in transcription; however, a complete understanding of how CDK7 disruption affects global transcription is lacking. Furthermore, the absence of selective inhibitors of CDK7 has hindered investigation of the transcriptional and functional consequences of acute and long-term inhibition of CDK7 under normal and pathological conditions. The present invention describes a cellular screen and conventional proteomics target discovery approach that resulted in the identification of highly selective CDK7 inhibitors and analogs, which have the ability to covalently modify a cysteine residue located outside of the canonical kinase domain (i.e., Cys312 of CDK7). This cysteine is exclusively found in CDK7 and provides an unanticipated means of overcoming the daunting challenge of achieving selectivity amongst the 19 CDKs reported to date. Irreversible inhibition of CDK7 using an inhibitor of the present invention results in the prolonged disruption of transcription and the induction of apoptosis of a diverse subset of cancer cell lines. Genome-wide transcript analysis following inhibitor treatment delineates CDK7-responsive genes as important in the maintenance of the cancer cell state, in particular MYC and MCL-1 genes. Selective covalent inhibition of CDK7 may be a viable cancer therapeutic strategy.

The present invention provides compounds, which inhibit the activity of a kinase, for the prevention and/or treatment of a subject with a proliferative disease. In certain embodiments, the inventive compounds inhibit the activity of cyclin-dependent kinase (CDK). In certain embodiments, the inventive compounds inhibit the activity of a cyclin-dependent kinase 7 (CDK7). The present invention also provides methods of using the compounds described herein, e.g., as biological probes to study the inhibition of the activity of a kinase (e.g., CDK (e.g., CDK7)), and as therapeutics, e.g., in the prevention and/or treatment of diseases associated with the overexpression and/or aberrant activity of a kinase (e.g., CDK (e.g., CDK7)). In certain embodiments, the diseases are proliferative diseases. The proliferative diseases that may be treated and/or prevented include, but are not limited to, cancers (e.g., leukemia, melanoma, multiple myeloma), benign neoplasms, diseases associated with angiogenesis, inflammatory diseases, auto-inflammatory diseases, and autoimmune diseases. Also provided by the present disclosure are pharmaceutical compositions, kits, methods, and uses including a compound of Formula (I) as described herein.

In addition to inhibiting the activity of CDK7, compounds of the present invention are selective for CDK7 relative to other CDKs. The present invention addresses potential deficiencies of some previous CDK7 inhibitors which also have the ability to inhibit CDK12 or CDK13 (Kwiatowski et al., "Targeting transcription regulation in cancer with a covalent CDK7 inhibitor." *Nature* 511, 616-620 (2014)). This affords the opportunity to more clearly differentiate pharmacological effects that are derived from CDK7 inhibition relative to CDK12 and/or CDK13 inhibition and provides new compounds, and compositions thereof, for drug development and therapeutic use.

Compounds

Aspects of the present disclosure relate to the compounds described herein. The compounds described herein are pyrrolo-pyrazole containing compounds that may be useful in treating and/or preventing proliferative diseases in a subject, inhibiting the activity of a protein kinase (e.g., CDK) in a subject or biological sample, and inducing apoptosis of a cell. In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt thereof.

Provided herein are compounds of Formula (I):

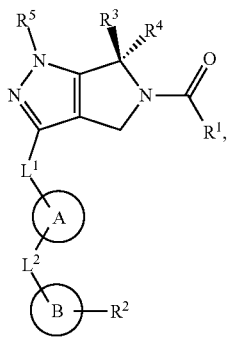

(I)

and pharmaceutically acceptable salts, solvates, hydrates, polymorphs, co-crystals, tautomers, stereoisomers, isotopically labeled derivatives, and prodrugs thereof, wherein:

$R^1$ is —$NR^aR^b$, —$CHR^aR^b$ or —$OR^a$, wherein each of $R^a$ and $R^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or $R^a$ and $R^b$ are joined to form an optionally substituted carbocyclic, optionally substituted heterocyclic, optionally substituted aryl, or optionally substituted heteroaryl ring;

each of $R^3$ and $R^4$ is independently hydrogen, halogen, optionally substituted $C_1$-$C_6$ alkyl, or optionally substituted aryl, or $R^3$ and $R^4$ are joined to form an optionally substituted $C_3$-$C_6$ carbocyclyl ring;

$R^5$ is independently hydrogen, optionally substituted $C_1$-$C_6$ alkyl, or a nitrogen protecting group;

$L^1$ is —$NR^{L1}$—, —$NR^{L1}C(=O)$—, —$C(=O)NR^{L1}$—, —O—, or —S—, wherein $R^{L1}$ is hydrogen, optionally substituted $C_1$-$C_6$ alkyl, or a nitrogen protecting group;

Ring A is optionally substituted carbocyclyl, optionally substituted heterocyclyl, optionally substituted aryl, or optionally substituted heteroaryl;

$L^2$ is a bond, —$C(=O)$—, —$NR^{L2}$—, —$C(=O)NR^{L2}$—, —$NR^{L2}C(=O)$—, —O—, or —S—, wherein $R^{L2}$ is hydrogen, optionally substituted $C_1$-$C_6$ alkyl, or a nitrogen protecting group;

Ring B is absent, optionally substituted carbocyclyl, optionally substituted heterocyclyl, optionally substituted aryl, or optionally substituted heteroaryl; and $R^2$ is any of Formulae (i-1)-(i-42) as defined herein:

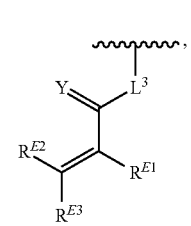

(i-1)

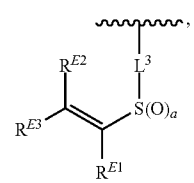

(i-2)

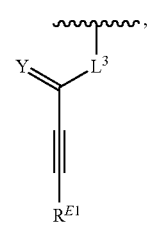

(i-3)

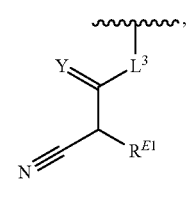

(i-4)

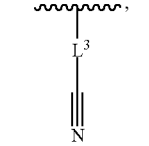

(i-5)

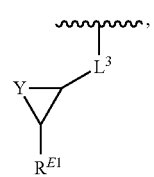

(i-6)

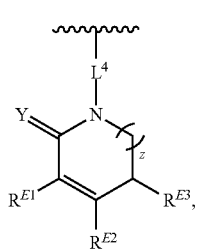
(i-7)
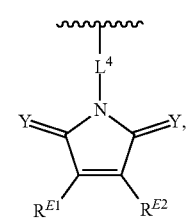
(i-8)
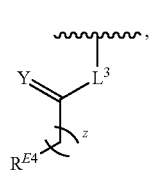
(i-9)
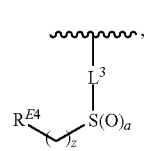
(i-10)
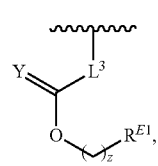
(i-11)
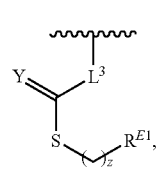
(i-12)
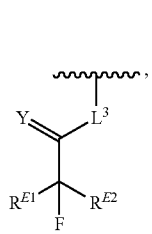
(i-13)
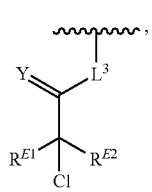
(i-14)
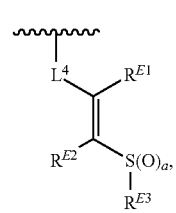
(i-15)
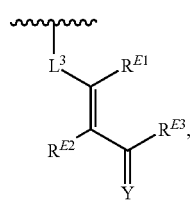
(i-16)
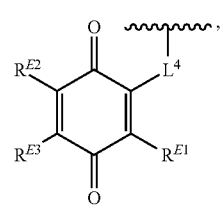
(i-17)
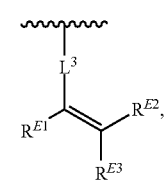
(i-18)
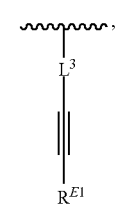
(i-19)
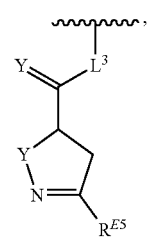
(i-20)
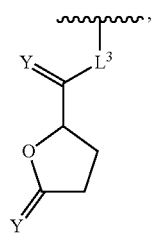
(i-21)

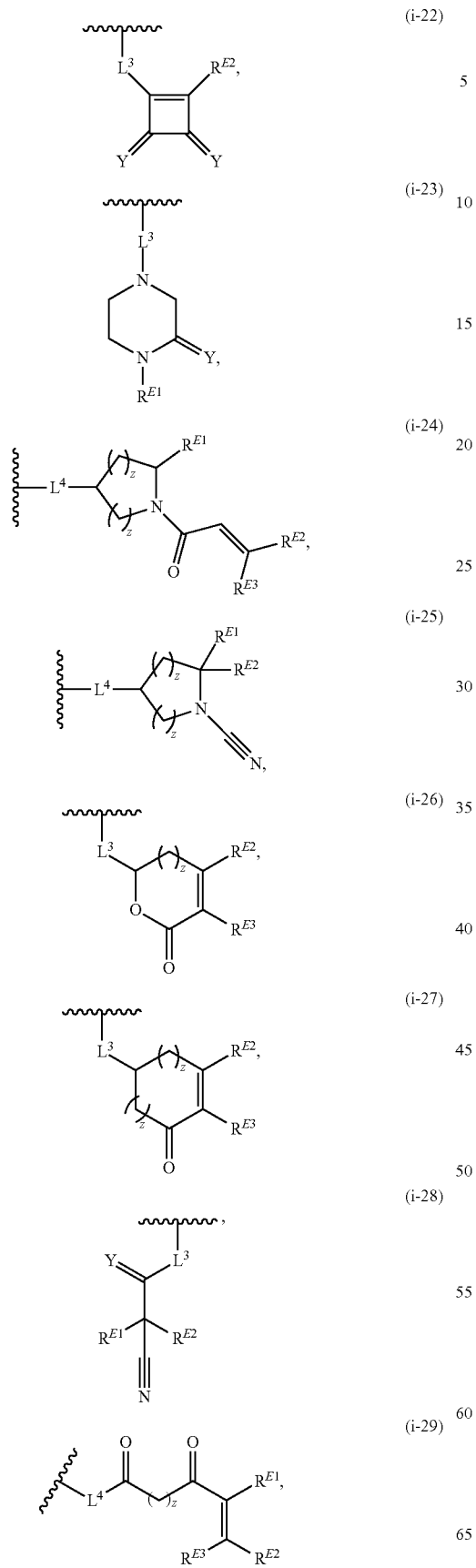
(i-22)
(i-23)
(i-24)
(i-25)
(i-26)
(i-27)
(i-28)
(i-29)
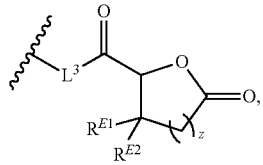
(i-30)
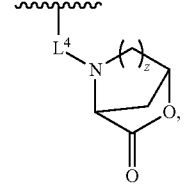
(i-31)
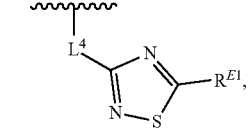
(i-32)
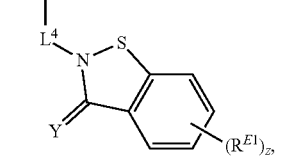
(i-33)
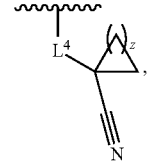
(i-34)
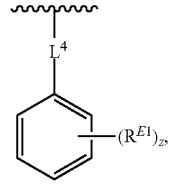
(i-35)
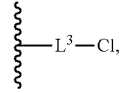
(i-36)
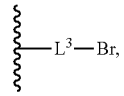
(i-37)
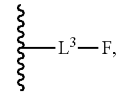
(i-38)
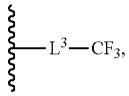
(i-39)

-continued

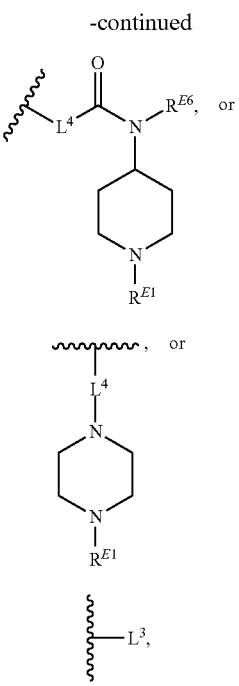

wherein:

L³ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L⁴ is a bond or an optionally substituted, branched or unbranched $C_{1-6}$ hydrocarbon chain; each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;
R$^{E5}$ is halogen;
R$^{E6}$ is hydrogen, substituted or unsubstituted $C_{1-6}$ alkyl, or a nitrogen protecting group;
each instance of Y is independently O, S, or NR$^{E7}$, wherein R$^{E7}$ is hydrogen, substituted or unsubstituted $C_{1-6}$ alkyl, or a nitrogen protecting group;
a is 1 or 2; and
each instance of z is independently 0, 1, 2, 3, 4, 5, or 6, as valency permits.

In certain embodiments, a compound described herein is of Formula (I):

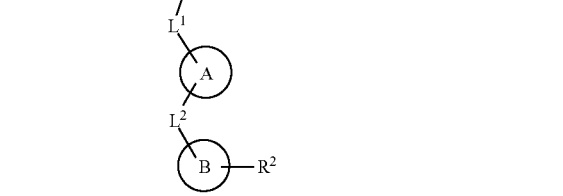

(I)

and pharmaceutically acceptable salts, solvates, hydrates, polymorphs, co-crystals, tautomers, stereoisomers, isotopically labeled derivatives, and prodrugs thereof, wherein:

R¹ is —NR$^a$R$^b$, —CHR$^a$R$^b$ or —OR$^a$, wherein each of R$^a$ and R$^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or R$^a$ and R$^b$ are joined to form an optionally substituted carbocyclic, optionally substituted heterocyclic, optionally substituted aryl, or optionally substituted heteroaryl ring;

each of R³ and R⁴ is independently hydrogen, halogen, or optionally substituted $C_1$-$C_6$ alkyl, or R³ and R⁴ are joined to form an optionally substituted $C_3$-$C_6$ carbocyclyl ring;

R⁵ is hydrogen, optionally substituted $C_1$-$C_6$ alkyl, or a nitrogen protecting group;

L¹ is —NR$^{L1}$—, —NR$^{L1}$C(=O)—, —C(=O)NR$^{L1}$—, —O—, or —S—, wherein R$^{L1}$ is hydrogen, optionally substituted $C_1$-$C_6$ alkyl, or a nitrogen protecting group;

Ring A is optionally substituted carbocyclyl, optionally substituted heterocyclyl, optionally substituted aryl, or optionally substituted heteroaryl;

L² is a bond, —C(=O)—, —NR$^{L2}$—, —C(=O)NR$^{L2}$—, —NR$^{L2}$C(=O)—, —O—, or —S—, wherein R$^{L2}$ is hydrogen, optionally substituted $C_1$-$C_6$ alkyl, or a nitrogen protecting group;

Ring B is absent, optionally substituted carbocyclyl, optionally substituted heterocyclyl, optionally substituted aryl, or optionally substituted heteroaryl; and $R^2$ is any of Formulae (i-1)-(i-41) as defined herein:
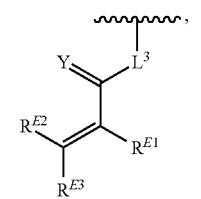 (i-1)
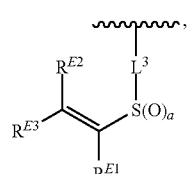 (i-2)
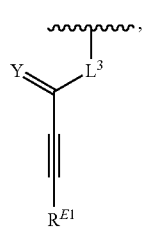 (i-3)
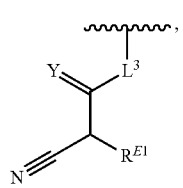 (i-4)
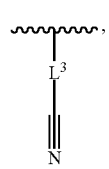 (i-5)
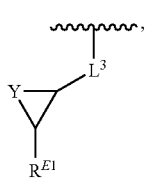 (i-6)
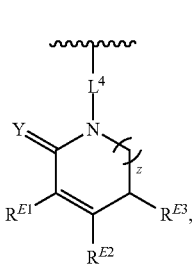 (i-7)
-continued
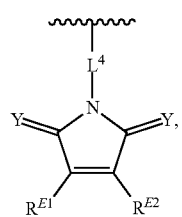 (i-8)
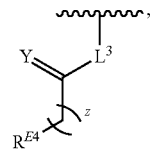 (i-9)
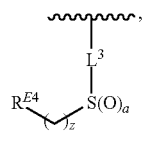 (i-10)
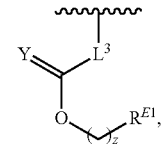 (i-11)
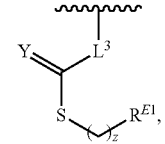 (i-12)
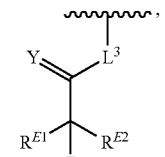 (i-13)
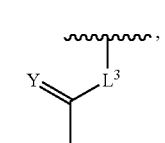 (i-14)
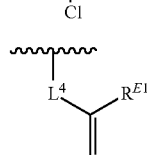 (i-15)
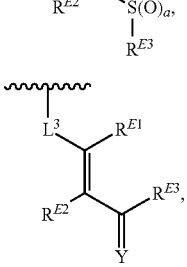 (i-16)

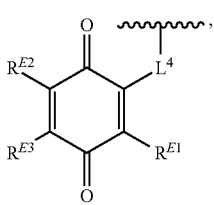 (i-17)
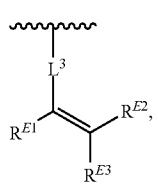 (i-18)
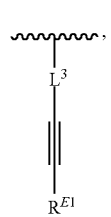 (i-19)
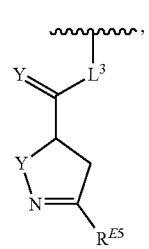 (i-20)
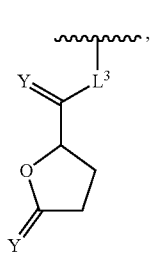 (i-21)
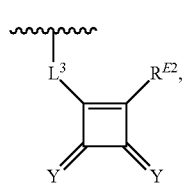 (i-22)
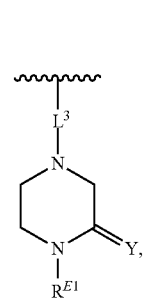 (i-23)
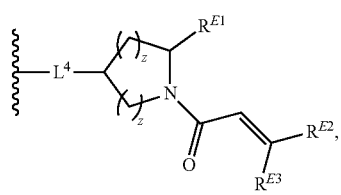 (i-24)
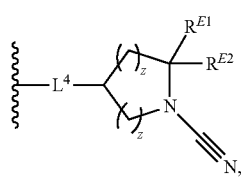 (i-25)
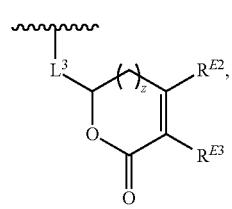 (i-26)
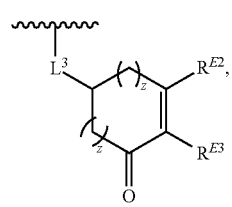 (i-27)
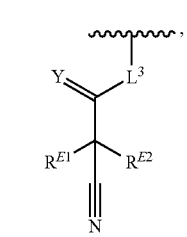 (i-28)
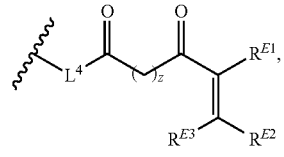 (i-29)
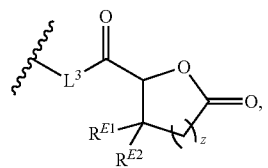 (i-30)
(i-31)

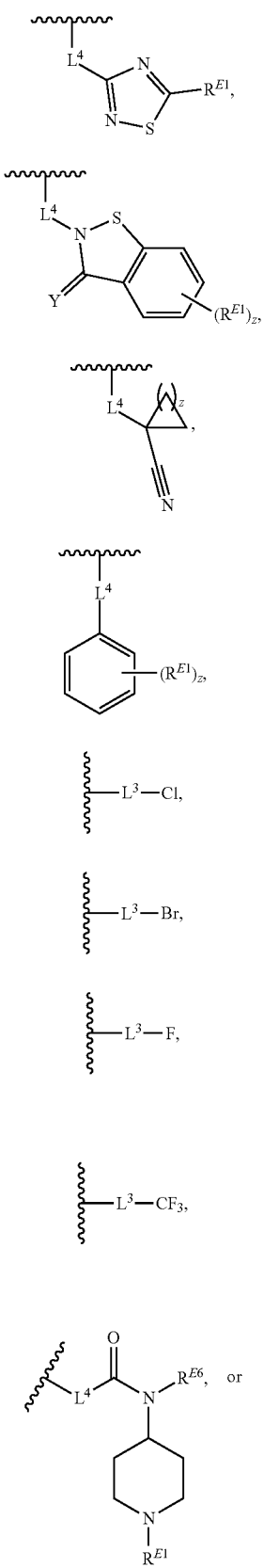

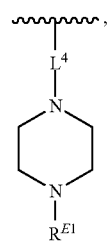

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=C$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of $R^{E1}$, $R^{E2}$, and $R^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, and —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

$R^{E4}$ is a leaving group;

$R^{E5}$ is halogen;

$R^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits.

Compounds of Formula (I) include R$^1$ attached to the carbonyl substituent of the pyrrolopyrazole bicyclic ring. R$^1$ may be —NR$^a$R$^b$, —CHR$^a$R$^b$ or —OR$^a$, wherein each of R$^a$ and R$^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or R$^a$ and R$^b$ are joined to form an optionally substituted carbocyclic, optionally substituted heterocyclic, optionally substituted aryl, or optionally substituted heteroaryl ring. In certain embodiments, R$^1$ is —NR$^a$R$^b$. In certain embodiments, R$^1$ is —CHR$^a$R$^b$. In certain embodiments, R$^1$ is —OR$^a$.

In certain embodiments, R$^1$ is

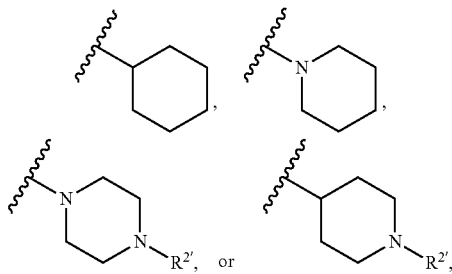

wherein R$^{2'}$ is hydrogen, optionally substituted C$_1$-C$_6$ alkyl, or a nitrogen protecting group, and each ring atom is optionally substituted. In certain embodiments, R$^1$ is

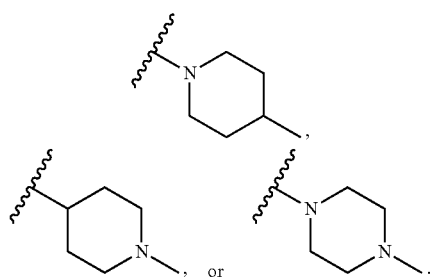

In certain embodiments, R$^1$ is of Formula (ii-1):

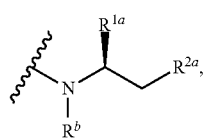

(ii-1)

wherein:
R$^b$ is hydrogen, optionally substituted C$_1$-C$_6$ alkyl, or a nitrogen protecting group;
R$^{1a}$ is hydrogen, C$_1$-C$_6$ alkyl, or optionally substituted aryl; and
R$^{2a}$ is hydrogen, —OR$^{1N}$, or —NR$^{1N}$R$^{2N}$, wherein each of R$^{1N}$ and R$^{2N}$ is independently hydrogen, C$_1$-C$_6$ alkyl, a nitrogen protecting group when attached to a nitrogen atom, or an oxygen protecting group when attached to an oxygen atom.

In certain embodiments, R$^1$ is of Formula (ii-2):

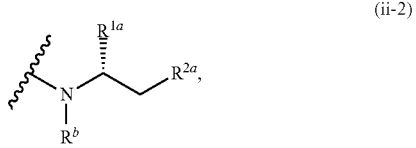

(ii-2)

wherein:
R$^b$ is hydrogen, optionally substituted C$_1$-C$_6$ alkyl, or a nitrogen protecting group;
R$^{1a}$ is hydrogen, C$_1$-C$_6$ alkyl, or optionally substituted aryl; and
R$^{2a}$ is hydrogen, —OR$^{1N}$, or —NR$^{1N}$R$^{2N}$, wherein each of R$^{1N}$ and R$^{2N}$ is independently hydrogen, C$_1$-C$_6$ alkyl, a nitrogen protecting group when attached to a nitrogen atom, or an oxygen protecting group when attached to an oxygen atom.

In certain embodiments, R$^b$ is hydrogen. In certain embodiments, R$^b$ is optionally substituted C$_1$-C$_6$ alkyl. In certain embodiments, R$^b$ is unsubstituted C$_1$-C$_6$ alkyl. In certain embodiments, R$^b$ is a nitrogen protecting group. In certain embodiments, R$^b$ is Bn, BOC, Cbz, Fmoc, trifluoroacetyl, triphenylmethyl, acetyl, or Ts.

In certain embodiments, R$^{1a}$ is hydrogen. In certain embodiments, R$^{1a}$ is methyl. In certain embodiments, R$^{1a}$ is ethyl. In certain embodiments, R$^{1a}$ is propyl. In certain embodiments, R$^{1a}$ is optionally substituted phenyl. In certain embodiments, R$^{1a}$ is phenyl.

In certain embodiments, R$^{2a}$ is hydrogen. In certain embodiments, R$^{2a}$ is —OR$^{1N}$, wherein R$^{1N}$ is hydrogen, C$_1$-C$_6$ alkyl, or an oxygen protecting group. In certain embodiments, R$^{2a}$ is —OH. In certain embodiments, R$^{2a}$ is —NR$^{1N}$R$^{2N}$, wherein each of R$^{1N}$ and R$^{2N}$ is independently hydrogen, C$_1$-C$_6$ alkyl, or a nitrogen protecting group. In certain embodiments, R$^{1N}$ and R$^{2N}$ are the same. In certain embodiments, R$^{1N}$ and R$^{2N}$ are distinct. In certain embodiments, R$^{1N}$ and R$^{2N}$ are both methyl. In certain embodiments, R$^{1N}$ and R$^{2N}$ are both ethyl. In certain embodiments, R$^{1N}$ and R$^{2N}$ are both propyl. In certain embodiments, R$^{1N}$ and R$^{2N}$ are both hydrogen. In certain embodiments, R$^{1N}$ and R$^{2N}$ are both nitrogen protecting groups. In certain embodiments, at least one of R$^{1N}$ and R$^{2N}$ is methyl. In certain embodiments, at least one of R$^{1N}$ and R$^{2N}$ is ethyl. In certain embodiments, at least one of R$^{1N}$ and R$^{2N}$ is propyl. In certain embodiments, at least one of R$^{1N}$ and R$^{2N}$ is hydrogen. In certain embodiments, at least one of R$^{1N}$ and R$^{2N}$ is a nitrogen protecting group. In certain embodiments, R$^{1N}$ is methyl, and R$^{2N}$ is hydrogen. In certain embodiments, R$^{1N}$ is ethyl, and R$^{2N}$ is hydrogen. In certain embodiments, R$^{1N}$ is propyl, and R$^{2N}$ is hydrogen. In certain embodiments, R$^{1N}$ is a nitrogen protecting group, and R$^{2N}$ is hydrogen. In certain embodiments, R$^{1N}$ is methyl, and R$^{2N}$ is a nitrogen protecting group. In certain embodiments, R$^{1N}$ is ethyl, and R$^{2N}$ is a nitrogen protecting group. In certain embodiments, R$^{1N}$ is propyl, and R$^{2N}$ is a nitrogen protecting group.

In certain embodiments, R$^1$ is of Formula (ii-1a):

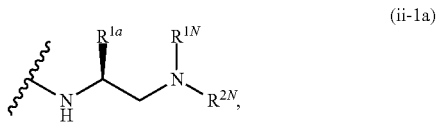

(ii-1a)

wherein:
R$^{1a}$ is hydrogen, C$_1$-C$_6$ alkyl, or optionally substituted aryl; and
each of R$^{1N}$ and R$^{2N}$ is independently hydrogen, C$_1$-C$_6$ alkyl, or a nitrogen protecting group.

In certain embodiments, R$^1$ is of Formula (ii-2a):

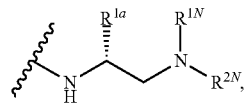
(ii-2a)

wherein:
R$^{1a}$ is hydrogen, C$_1$-C$_6$ alkyl, or optionally substituted aryl; and
each of R$^{1N}$ and R$^{2N}$ is independently hydrogen, C$_1$-C$_6$ alkyl, or a nitrogen protecting group.

In certain embodiments, R$^{1a}$ is hydrogen. In certain embodiments, R$^{1a}$ is methyl. In certain embodiments, R$^{1a}$ is ethyl. In certain embodiments, R$^{1a}$ is propyl. In certain embodiments, R$^{1a}$ is optionally substituted phenyl. In certain embodiments, R$^{1a}$ is phenyl. In certain embodiments, R$^{1N}$ and R$^{2N}$ are the same.

In certain embodiments, R$^{1N}$ and R$^{2N}$ are distinct. In certain embodiments, R$^{1N}$ and R$^{2N}$ are both methyl. In certain embodiments, R$^{1N}$ and R$^{2N}$ are both ethyl. In certain embodiments, R$^{1N}$ and R$^{2N}$ are both propyl. In certain embodiments, R$^{1N}$ and R$^{2N}$ are both hydrogen. In certain embodiments, R$^{1N}$ and R$^{2N}$ are both nitrogen protecting groups. In certain embodiments, at least one of R$^{1N}$ and R$^{2N}$ is methyl. In certain embodiments, at least one of R$^{1N}$ and R$^{2N}$ is ethyl. In certain embodiments, at least one of R$^{1N}$ and R$^{2N}$ is propyl. In certain embodiments, at least one of R$^{1N}$ and R$^{2N}$ is hydrogen. In certain embodiments, at least one of R$^{1N}$ and R$^{2N}$ is a nitrogen protecting group. In certain embodiments, R$^{1N}$ is methyl, and R$^{2N}$ is hydrogen. In certain embodiments, R$^{1N}$ is ethyl, and R$^{2N}$ is hydrogen. In certain embodiments, R$^{1N}$ is propyl, and R$^{2N}$ is hydrogen. In certain embodiments, R$^{1N}$ is a nitrogen protecting group, and R$^{2N}$ is hydrogen. In certain embodiments, R$^{1N}$ is methyl, and R$^{2N}$ is a nitrogen protecting group. In certain embodiments, R$^{1N}$ is ethyl, and R$^{2N}$ is a nitrogen protecting group. In certain embodiments, R$^{1N}$ is propyl, and R$^{2N}$ is a nitrogen protecting group.

In certain embodiments, R$^1$ is of Formula (ii-1b):

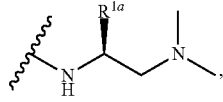
(ii-1b)

wherein R$^{1a}$ is hydrogen, C$_1$-C$_6$ alkyl, or optionally substituted aryl.

In certain embodiments, R$^1$ is of Formula (ii-2b):

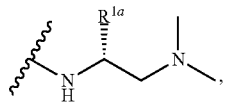
(ii-2b)

wherein R$^{1a}$ is hydrogen, C$_1$-C$_6$ alkyl, or optionally substituted aryl.

In certain embodiments, R$^{1a}$ is hydrogen. In certain embodiments, R$^{1a}$ is methyl. In certain embodiments, R$^{1a}$ is ethyl. In certain embodiments, R$^{1a}$ is propyl. In certain embodiments, R$^{1a}$ is optionally substituted phenyl. In certain embodiments, R$^{1a}$ is phenyl.

In certain embodiments, R$^1$ is:

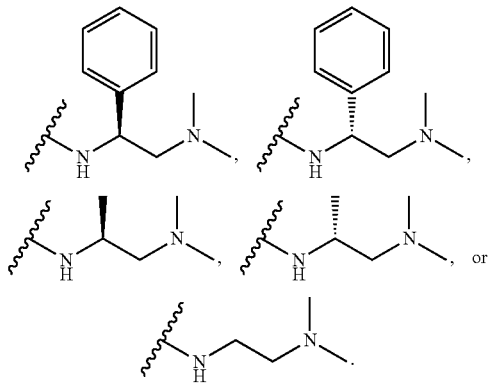

In certain embodiments, R$^1$ is:

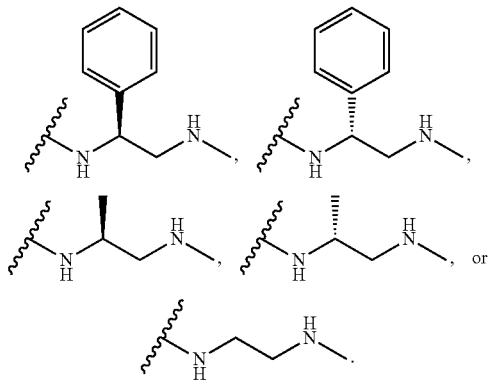

In certain embodiments, R$^1$ is:

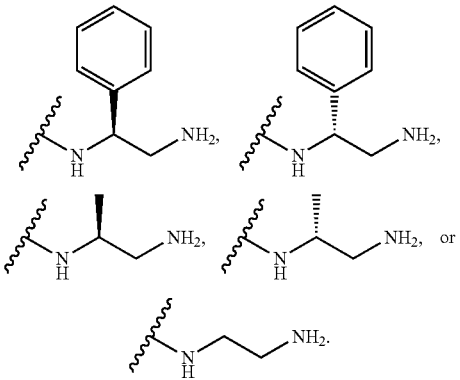

In certain embodiments, $R^1$ is:

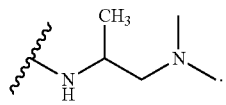

In certain embodiments, $R^1$ is of Formula (ii-1c):

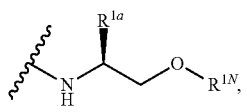

(ii-1c)

wherein:
$R^{1a}$ is hydrogen, $C_1$-$C_6$ alkyl, or optionally substituted aryl; and
each of $R^{1N}$ and $R^{2N}$ is independently hydrogen, $C_1$-$C_6$ alkyl, or an oxygen protecting group.

In certain embodiments, $R^1$ is of Formula (ii-2c):

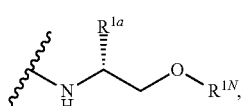

(ii-2c)

wherein:
$R^{1a}$ is hydrogen, $C_1$-$C_6$ alkyl, or optionally substituted aryl; and
each of $R^{1N}$ and $R^{2N}$ is independently hydrogen, $C_1$-$C_6$ alkyl, or an oxygen protecting group.

In certain embodiments, $R^{1a}$ is hydrogen. In certain embodiments, $R^{1a}$ is methyl. In certain embodiments, $R^{1a}$ is ethyl. In certain embodiments, $R^{1a}$ is propyl. In certain embodiments, $R^{1a}$ is optionally substituted phenyl. In certain embodiments, $R^{1a}$ is phenyl. In certain embodiments, $R^{1N}$ is hydrogen. In certain embodiments, $R^{1N}$ is methyl. In certain embodiments, $R^{1N}$ is ethyl. In certain embodiments, $R^{1N}$ is propyl. In certain embodiments, $R^{1N}$ is an oxygen protecting group.

In certain embodiments, $R^1$ is of Formula (ii-1d):

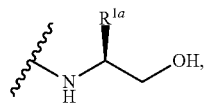

(ii-1d)

wherein $R^{1a}$ is hydrogen, $C_1$-$C_6$ alkyl, or optionally substituted aryl.

In certain embodiments, $R^1$ is of Formula (ii-2d):

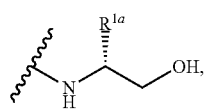

(ii-2d)

wherein $R^{1a}$ is hydrogen, $C_1$-$C_6$ alkyl, or optionally substituted aryl.

In certain embodiments, $R^{1a}$ is hydrogen. In certain embodiments, $R^{1a}$ is methyl. In certain embodiments, $R^{1a}$ is ethyl. In certain embodiments, $R^{1a}$ is propyl. In certain embodiments, $R^{1a}$ is optionally substituted phenyl. In certain embodiments, $R^{1a}$ is phenyl.

In certain embodiments, $R^1$ is

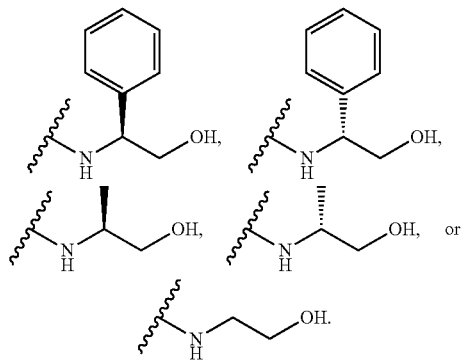

In certain embodiments, $R^1$ is —$NR^aR^b$, wherein $R^a$ is optionally substituted aryl, and $R^b$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^1$ is —$NR^aR^b$, wherein $R^a$ is optionally substituted heteroaryl, and $R^b$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^1$ is —$NR^aR^b$, wherein $R^a$ is optionally substituted heterocyclyl, and $R^b$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^1$ is —$NR^aR^b$, wherein $R^a$ is optionally substituted carbocyclyl, and $R^b$ is selected from hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^1$ is —$NR^aR^b$, wherein $R^a$ is optionally substituted aryl, and $R^b$ is hydrogen. In certain embodiments, $R^1$ is —$NR^aR^b$ wherein $R^a$ is optionally substituted heteroaryl, and $R^b$ is hydrogen. In certain embodiments, $R^1$ is —$NR^aR^b$, wherein $R^a$ is optionally substituted heterocyclyl, and $R^b$ is hydrogen. In certain embodiments, $R^1$ is —$NR^aR^b$, wherein $R^a$ is optionally substituted carbocyclyl, and $R^b$ is hydrogen. In certain embodiments, $R^1$ is —$NR^aR^b$, wherein $R^a$ is optionally substituted pyrazolyl, and $R^b$ is hydrogen. In certain embodiments, $R^1$ is —$NR^aR^b$, wherein $R^a$ is 1-methyl-1H-pyrazol-4-yl, and $R^b$ is hydrogen. In certain embodiments, $R^1$ is

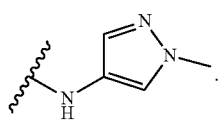 [SMILES: *Nc1cnn(C)c1]

Compounds of Formula (I) include linker $L^1$ joining the pyrrolopyrazole bicyclic ring and Ring A. Linker $L^1$ may be $-NR^{L1}-$, $-NR^{L1}C(=O)-$, $-C(=O)NR^{L1}-$, $-O-$, or $-S-$, wherein $R^{L1}$ is hydrogen, optionally substituted $C_1$-$C_6$ alkyl, or a nitrogen protecting group. In certain embodiments, $L^1$ is $-NR^{L1}-$, wherein $R^{L1}$ is hydrogen, optionally substituted $C_1$-$C_6$ alkyl, or a nitrogen protecting group. In certain embodiments, $L^1$ is $-NR^{L1}C(=O)-$, wherein $R^{L1}$ is hydrogen, optionally substituted $C_1$-$C_6$ alkyl, or a nitrogen protecting group. In certain embodiments, $L^1$ is $-C(=O)NR^{L1}-$, wherein $R^{L1}$ is hydrogen, optionally substituted $C_1$-$C_6$ alkyl, or a nitrogen protecting group. In certain embodiments, $R^{L1}$ is hydrogen. In certain embodiments, $L^1$ is $-NH-$. In certain embodiments, $L^1$ is $-NH(C=O)-$. In certain embodiments, $L^1$ is $-(C=O)NH-$. In certain embodiments, $L^1$ is $-O-$. In certain embodiments, $L^1$ is $-S-$.

Compounds of Formula (I) include $R^3$ and $R^4$ attached to the pyrrolopyrazole bicyclic ring. Each of $R^3$ and $R^4$ is independently hydrogen, halogen, optionally substituted aryl, or optionally substituted $C_1$-$C_6$ alkyl, or $R^3$ and $R^4$ are joined to form an optionally substituted $C_3$-$C_6$ carbocyclyl ring. In certain embodiments, $R^3$ is a substituted or unsubstituted aryl (e.g., substituted or unsubstituted phenyl). In certain embodiments, $R^4$ is a substituted or unsubstituted aryl (e.g., substituted or unsubstituted phenyl). In certain embodiments, $R^3$ and $R^4$ are joined to form an optionally substituted $C_3$-$C_6$ carbocyclyl. In certain embodiments, $R^3$ and $R^4$ are joined to form an optionally substituted cyclopropane. In certain embodiments, $R^3$ and $R^4$ are joined to form an unsubstituted cyclopropane. In certain embodiments, $R^3$ and $R^4$ are joined to form an optionally substituted cyclohexane. In certain embodiments, $R^3$ and $R^4$ are joined to form an unsubstituted cyclohexane. In certain embodiments, $R^3$ and $R^4$ are the same. In certain embodiments, $R^3$ and $R^4$ are distinct. In certain embodiments, $R^3$ and $R^4$ are optionally substituted $C_1$-$C_6$ alkyl. In certain embodiments, $R^3$ and $R^4$ are unsubstituted $C_1$-$C_6$ alkyl. In certain embodiments, $R^3$ and $R^4$ are both methyl. In certain embodiments, $R^3$ and $R^4$ are both ethyl. In certain embodiments, $R^3$ and $R^4$ are both propyl. In certain embodiments, $R^3$ and $R^4$ are both hydrogen. In certain embodiments, $R^3$ and $R^4$ are both halogen. In certain embodiments, each of $R^3$ and $R^4$ is independently $-Cl$, $-Br$, or $-I$. In certain embodiments, $R^3$ and $R^4$ are both $-F$. In certain embodiments, $R^3$ and $R^4$ are joined as $-CH_2CH_2-$.

In certain embodiments, $R^3$ is optionally substituted $C_1$-$C_6$ alkyl (e.g., isopropyl). In certain embodiments, $R^3$ is unsubstituted $C_1$-$C_6$ alkyl. In certain embodiments, $R^3$ is methyl. In certain embodiments, $R^3$ is ethyl. In certain embodiments, $R^3$ is propyl. In certain embodiments, $R^3$ is hydrogen. In certain embodiments, $R^3$ is halogen. In certain embodiment, $R^3$ is $-Cl$, $-Br$, or $-I$. In certain embodiment, $R^3$ is $-F$. In certain embodiments, $R^4$ is optionally substituted $C_1$-$C_6$ alkyl (e.g., isopropyl). In certain embodiments, $R^4$ is unsubstituted $C_1$-$C_6$ alkyl. In certain embodiments, $R^4$ is methyl. In certain embodiments, $R^4$ is ethyl. In certain embodiments, $R^4$ is propyl. In certain embodiments, $R^4$ is hydrogen. In certain embodiments, $R^4$ is halogen. In certain embodiment, $R^4$ is $-Cl$, $-Br$, or $-I$. In certain embodiment, $R^4$ is $-F$.

In certain embodiments, $R^3$ is hydrogen, and $R^4$ is methyl. In certain embodiments, $R^3$ is methyl, and $R^4$ is hydrogen. In certain embodiments, $R^3$ is hydrogen, and $R^4$ is ethyl. In certain embodiments, $R^3$ is ethyl, and $R^4$ is hydrogen. In certain embodiments, $R^3$ is hydrogen, and $R^4$ is propyl. In certain embodiments, $R^3$ is propyl, and $R^4$ is hydrogen. In certain embodiments, $R^3$ is hydrogen, and $R^4$ is $-Cl$, $-Br$, or $-I$. In certain embodiments, $R^3$ is $-Cl$, Br, or $-I$, and $R^4$ is hydrogen. In certain embodiments, $R^3$ is hydrogen, and $R^4$ is $-F$. In certain embodiments, $R^3$ is $-F$, and $R^4$ is hydrogen. In certain embodiments, $R^3$ is methyl, and $R^4$ is $-F$. In certain embodiments, $R^3$ is $-F$, and $R^4$ is methyl. In certain embodiments, $R^3$ is ethyl, and $R^4$ is $-F$. In certain embodiments, $R^3$ is $-F$, and $R^4$ is ethyl. In certain embodiments, $R^3$ is propyl, and $R^4$ is $-F$. In certain embodiments, $R^3$ is $-F$, and $R^4$ is propyl. In certain embodiments, $R^3$ is methyl, and $R^4$ is $-Cl$, $-Br$, or $-I$. In certain embodiments, $R^3$ is $-Cl$, $-Br$, or $-I$, and $R^4$ is methyl. In certain embodiments, $R^3$ is ethyl, and $R^4$ is $-Cl$, $-Br$, or $-I$. In certain embodiments, $R^3$ is $-Cl$, $-Br$, or $-I$, and $R^4$ is ethyl. In certain embodiments, $R^3$ is propyl, and $R^4$ is $-Cl$, $-Br$, or $-I$. In certain embodiments, $R^3$ is $-Cl$, $-Br$, or $-I$, and $R^4$ is propyl.

Compounds of Formula (I) include $R^5$ attached to a pyrazole nitrogen. $R^5$ may be hydrogen, optionally substituted $C_1$-$C_6$ alkyl, or a nitrogen protecting group. In certain embodiments, $R^5$ is optionally substituted $C_1$-$C_6$ alkyl. In certain embodiments, $R^5$ is unsubstituted $C_1$-$C_6$ alkyl. In certain embodiments, $R^5$ is substituted methyl. In certain embodiments, $R^5$ is unsubstituted methyl. In certain embodiments, $R^5$ is hydrogen. In certain embodiments, $R^5$ is a nitrogen protecting group. In certain embodiments, $R^5$ is Bn, BOC, Cbz, Fmoc, trifluoroacetyl, triphenylmethyl, acetyl, or Ts.

Compounds of Formula (I) may exist as tautomers or mixtures thereof of Formulae (I-a) and (I-b):

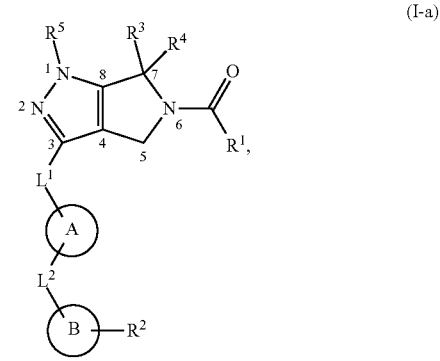

(I-a)

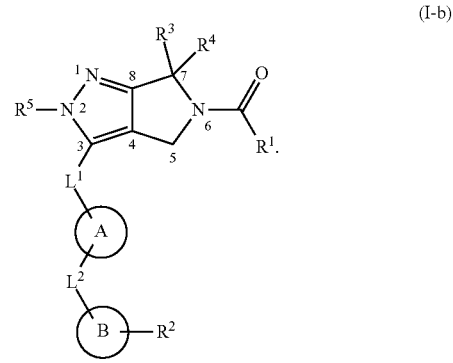

(I-b)

In each tautomer, $R^5$ is attached to different pyrazole nitrogens in compounds of each formula. In certain embodiments, $R^5$ is attached to the nitrogen at the position labeled 1, as in Formula (I-a). In certain embodiments, $R^5$ is attached to the nitrogen at the position labeled 2, as in Formula (I-b). In certain embodiments, compounds of Formula (I) may exist as a mixture of compounds of Formulae (I-a) and (I-b), in which case $R^5$ is attached to the nitrogen at the position labeled 1 for components of the mixture corresponding to Formula (I-a), and $R^5$ is the nitrogen at the position labeled 2 for components of the mixture corresponding to Formula (I-b).

Compounds of Formula (I) include Ring A between linker $L^1$ and linker $L^2$. Ring A may be optionally substituted carbocyclyl, optionally substituted heterocyclyl, optionally substituted aryl, or optionally substituted heteroaryl. In certain embodiments, Ring A is optionally substituted carbocyclyl. In certain embodiments, Ring A is optionally substituted heterocyclyl. In certain embodiments, Ring A is optionally substituted aryl. In certain embodiments, Ring A is optionally substituted heteroaryl. In certain embodiments, Ring A is optionally substituted phenyl. In certain embodiments, Ring A is phenyl substituted with only $L^1$ and $L^2$. In certain embodiments, Ring A is optionally substituted cyclohexyl. In certain embodiments, Ring A is optionally substituted piperidinyl. In certain embodiments, Ring A is optionally substituted piperizinyl. In certain embodiments, Ring A is optionally substituted pyridinyl. In certain embodiments, Ring A is optionally substituted pyrimidinyl.

In certain embodiments, linkers $L^1$ and $L^2$ are attached "ortho" or 1,2 to Ring A. In certain embodiments, linkers $L^1$ and $L^2$ are attached "meta" or 1,3 to Ring A. In certain embodiments, linkers $L^1$ and $L^2$ are attached "para" or 1,4 to ring A.

In certain embodiments, Ring A is

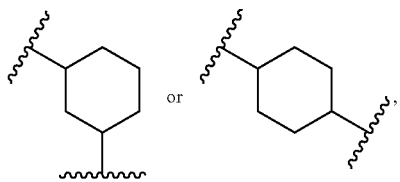 [SMILES: *C1CCCC(*)C1 ; *C1CCC(*)CC1]

wherein each ring atom is optionally substituted. In certain embodiments, Ring A is

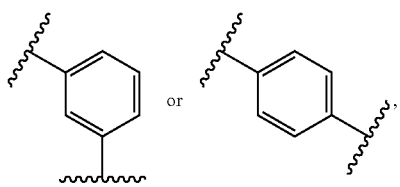 [SMILES: *c1cccc(*)c1 ; *c1ccc(*)cc1]

wherein each ring atom is optionally substituted. In certain embodiments, Ring A is

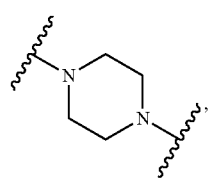 [SMILES: *N1CCN(*)CC1]

wherein each ring atom is optionally substituted. In certain embodiments, Ring A is

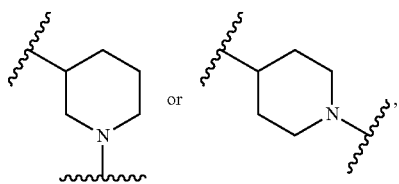 [SMILES: *C1CCCN(*)C1 ; *C1CCN(*)CC1]

wherein each ring atom is optionally substituted, and $L^1$ and $L^2$ may attach to ring A at either indicated position. In certain embodiments, Ring A is

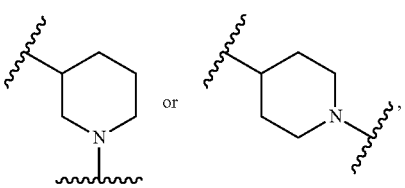 [SMILES: *C1CCCN(*)C1 ; *C1CCN(*)CC1]

wherein each ring atom is optionally substituted, and $L^1$ and $L^2$ may attach to ring A at either indicated position. In certain embodiments, Ring A is

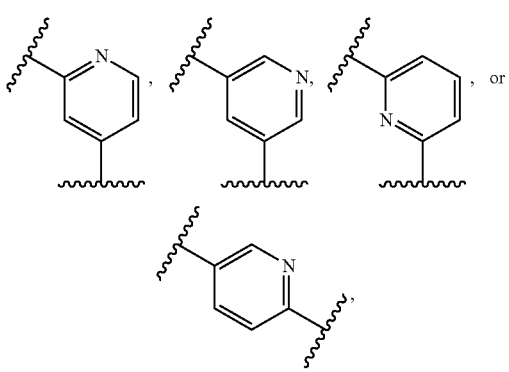

wherein each ring atom is optionally substituted, and $L^1$ and $L^2$ may attach to ring A at either indicated position. In certain embodiments, Ring A is

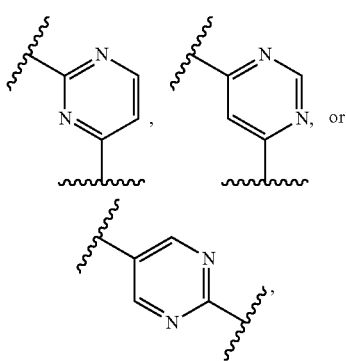

wherein each ring atom is optionally substituted, and $L^1$ and $L^2$ may attach to ring A at either indicated position.

In certain embodiments, Ring A is

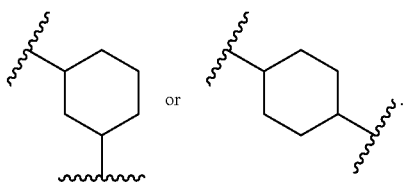

In certain embodiments, Ring A is

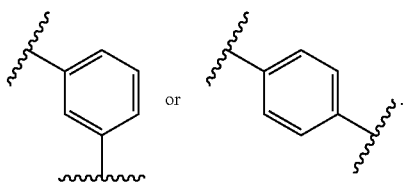 [SMILES: *c1cccc(*)c1 ; *c1ccc(*)cc1]

In certain embodiments, Ring A is

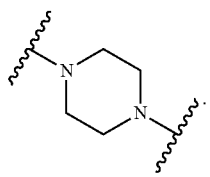 [SMILES: *N1CCN(*)CC1]

In certain embodiments, Ring A is

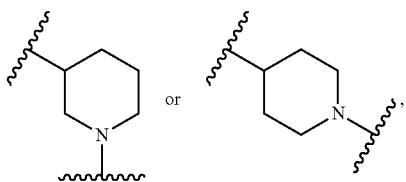 [SMILES: *C1CCCN(*)C1 ; *C1CCN(*)CC1]

$L^1$ and $L^2$ may attach to ring A at either indicated position. In certain embodiments, Ring A is

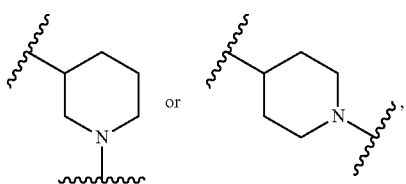

wherein $L^1$ and $L^2$ may attach to ring A at either indicated position. In certain embodiments, Ring A is

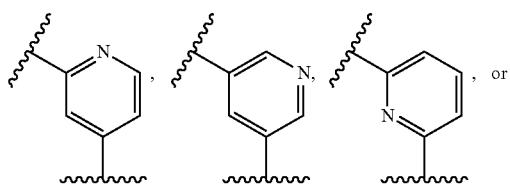

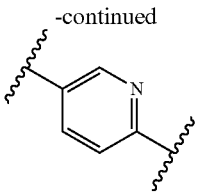

wherein $L^1$ and $L^2$ may attach to ring A at either indicated position. In certain embodiments, Ring A is

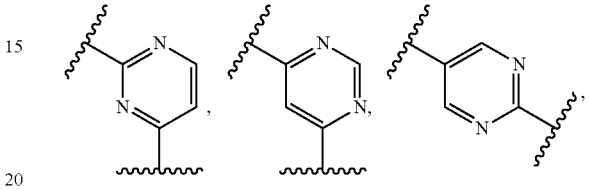

wherein $L^1$ and $L^2$ may attach to ring A at either indicated position.

Compounds of Formula (I) include linker $L^2$ joining Ring A to Ring B. Linker $L^2$ may be a bond, —C(=O)—, —NR$^{L2}$—, —C(=O)NR$^{L2}$—, —NR$^{L2}$C(=O)—, —O—, or —S— wherein R$^{L2}$ is hydrogen, optionally substituted $C_1$-$C_6$ alkyl, or a nitrogen protection group. In certain embodiments, $L^2$ is a bond, such that Ring B or $R^2$ is directly attached to Ring A. In certain embodiments, $L^2$ is —NR$^{L2}$—, wherein R$^{L2}$ is hydrogen, optionally substituted $C_1$-$C_6$ alkyl, or a nitrogen protection group. In certain embodiments, $L^2$ is —C(=O)NR$^{L2}$—, wherein R$^{L2}$ is hydrogen, optionally substituted $C_1$-$C_6$ alkyl, or a nitrogen protection group. In certain embodiments, $L^2$ is —NR$^{L2}$C(=O)—, wherein R$^{L2}$ is hydrogen, optionally substituted $C_1$-$C_6$ alkyl, or a nitrogen protection group. In certain embodiments, $L^2$ is —O—. In certain embodiments, $L^2$ is —S—. In certain embodiments, R$^{L2}$ is hydrogen. In certain embodiments, $L^2$ is —C(=O)—. In certain embodiments, $L^2$ is —NH—. In certain embodiments, $L^2$ is —NHC(=O)—. In certain embodiments, $L^2$ is —C(=O)NH—. In certain embodiments, $L^2$ is —O—. In certain embodiments, $L^2$ is —S—.

Compounds of Formula (I) include Ring B between linker $L^2$ and group $R^2$. In certain embodiments, linker $L^2$ is a bond, such that Ring B is directly attached to Ring A. Ring B may absent, optionally substituted carbocyclyl, optionally substituted heterocyclyl, optionally substituted aryl, or optionally substituted heteroaryl. In certain embodiments, Ring B is absent, such that $L^2$ is directly attached to $R^2$. In certain embodiments, Ring B is absent and linker $L^2$ is a bond, such that Ring A is directly attached to $R^2$. In certain embodiments, Ring B is optionally substituted carbocyclyl. In certain embodiments, Ring B is optionally substituted heterocyclyl. In certain embodiments, Ring B is optionally substituted aryl. In certain embodiments, Ring B is optionally substituted heteroaryl. In certain embodiments, Ring B is optionally substituted phenyl. In certain embodiments, Ring B is optionally substituted cyclohexyl. In certain embodiments, Ring B is optionally substituted piperidinyl. In certain embodiments, Ring B is optionally substituted piperizinyl. In certain embodiments, Ring B is optionally substituted pyridinyl. In certain embodiments, Ring B is optionally substituted pyrimidinyl.

In certain embodiments, linker $L^2$ and group $R^2$ are attached "ortho" or 1,2 to each other on Ring B. In certain embodiments, linkers L² and group R² are attached "meta" or 1,2 to each other on Ring B. In certain embodiments, linkers L² and R² are attached "para" or 1,4 to each other on Ring B.

In certain embodiments, Ring B is

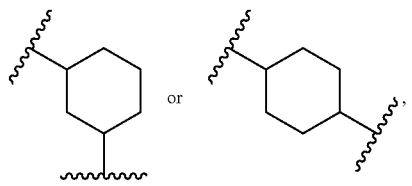 [SMILES: *C1CCCC(*)C1 ; *C1CCC(*)CC1]

wherein each ring atom is optionally substituted. In certain embodiments, Ring B is

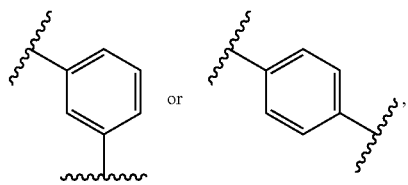 [SMILES: *c1cccc(*)c1 ; *c1ccc(*)cc1]

wherein each ring atom is optionally substituted. In certain embodiments, Ring B is

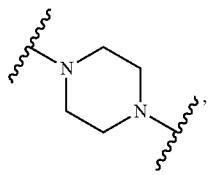 [SMILES: *N1CCN(*)CC1]

wherein each ring atom is optionally substituted. In certain embodiments, Ring B is

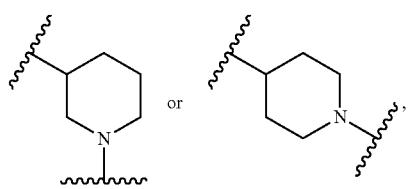 [SMILES: *C1CCCN(*)C1 ; *C1CCN(*)CC1]

wherein each ring atom is optionally substituted, and L² and R² may attach to Ring B at either indicated position. In certain embodiments, Ring B is

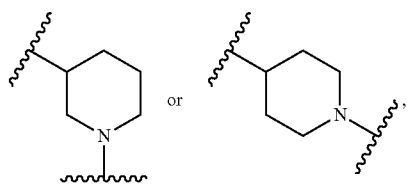 [SMILES: *C1CCCN(*)C1 ; *C1CCN(*)CC1]

wherein each ring atom is optionally substituted, and L² and R² may attach to Ring B at either indicated position. In certain embodiments, Ring B is

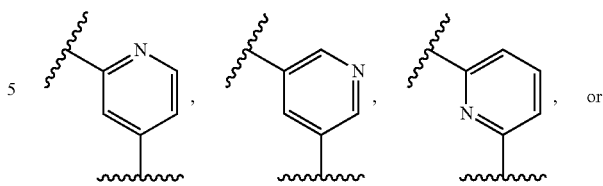

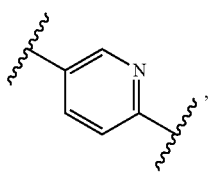

wherein each ring atom is optionally substituted, and L² and R² may attach to Ring B at either indicated position. In certain embodiments, Ring B is

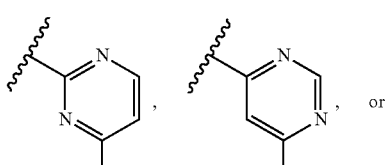

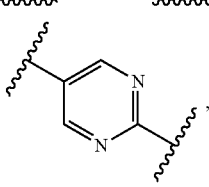

wherein each ring atom is optionally substituted, and L² and R² may attach to Ring B at either indicated position.

In certain embodiments, Ring B is

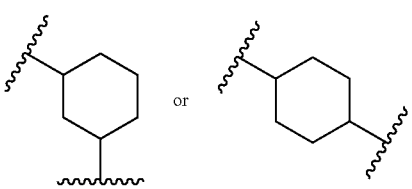

In certain embodiments, Ring B is

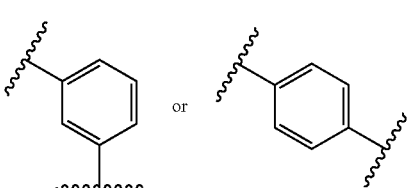

In certain embodiments, Ring B is

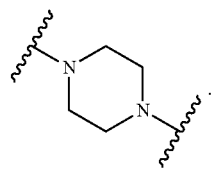 [SMILES: *N1CCN(*)CC1]

In certain embodiments, Ring B is

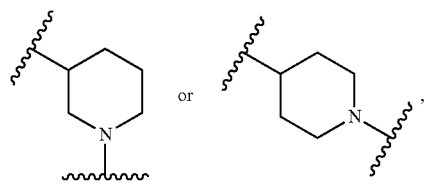 [SMILES: *C1CCCN(*)C1 ; *C1CCN(*)CC1]

$L^1$ and $L^2$ may attach to Ring B at either indicated position. In certain embodiments, Ring B is

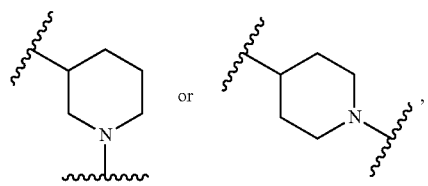

wherein $L^2$ and $R^2$ may attach to Ring B at either indicated position. In certain embodiments, Ring B is

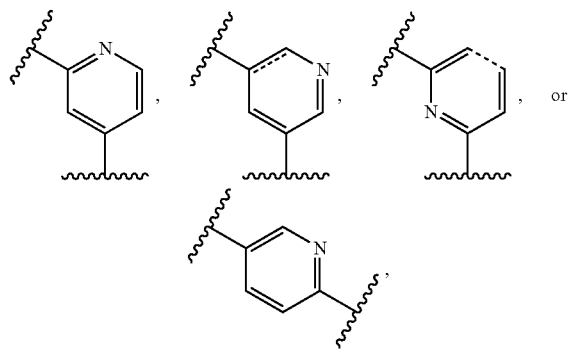

wherein $L^2$ and $R^2$ may attach to Ring B at either indicated position. In certain embodiments, Ring B is

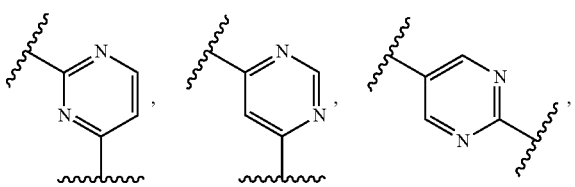

wherein $L^2$ and $R^2$ may attach to Ring B at either indicated position.

Compounds of Formula (I) include $R^2$ attached to Ring B. In certain embodiments, Ring B is absent, such that $R^2$ is directly attached to linker $L^2$. In certain embodiments, Ring B is absent and $L^2$ is a bond, such that $R^2$ is directly attached to Ring A. In certain embodiments, $R^2$ comprises an electrophilic moiety. In certain embodiments, $R^2$ comprises a Michael acceptor moiety. The electrophilic moiety (e.g., Michael acceptor moiety) may react with a cysteine residue of a kinase (e.g., CDK (e.g., CDK7)) to allow for covalent attachment of the compound to the kinase. In certain embodiments, the electrophilic moiety (e.g., Michael acceptor moiety) may react with a cysteine residue of a kinase (e.g., CDK (e.g., CDK7)). In certain embodiments, the electrophilic moiety (e.g., Michael acceptor moiety) may react with the Cys312 residue of CDK7. In certain embodiments, the covalent attachment is irreversible. In certain embodiments, the covalent attachment is reversible.

$R^2$ may be any one of Formulae (i-1)-(i-42). In certain embodiments, $R^2$ is of Formula (i-1):

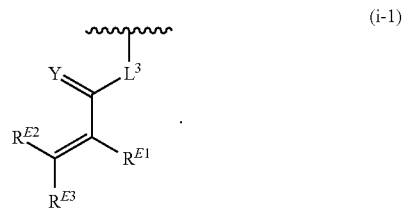

(i-1)

In certain embodiments, $R^2$ is of Formula (i-2):

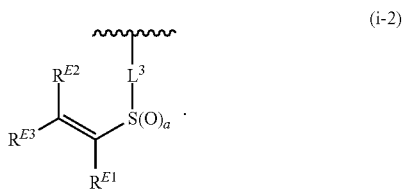

(i-2)

In certain embodiments, $R^2$ is of Formula (i-3):

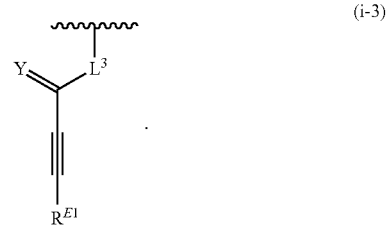

(i-3)

In certain embodiments, $R^2$ is of Formula (i-4):

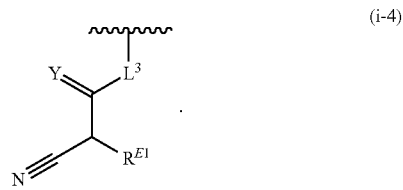

(i-4)

In certain embodiments, R² is of Formula (i-5):

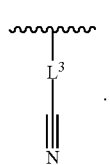
(i-5)

In certain embodiments, R² is of Formula (i-6):

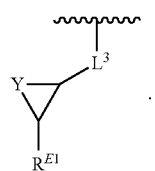
(i-6)

In certain embodiments, R² is of Formula (i-7):

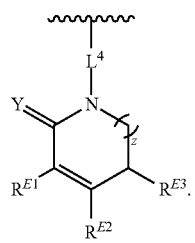
(i-7)

In certain embodiments, R² is of Formula (i-8):

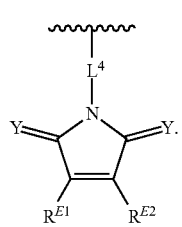
(i-8)

In certain embodiments, R² is of Formula (i-9):

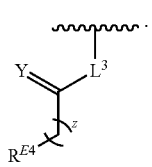
(i-9)

In certain embodiments, R² is of Formula (i-10):

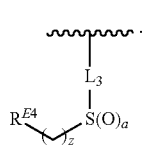
(i-10)

In certain embodiments, R² is of Formula (i-11):

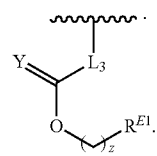
(i-11)

In certain embodiments, R² is of Formula (i-12):

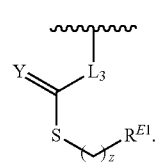
(i-12)

In certain embodiments, R² is of Formula (i-13):

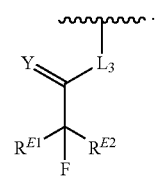
(i-13)

In certain embodiments, R² is of Formula (i-14):

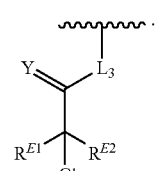
(i-14)

In certain embodiments, R² is of Formula (i-15):

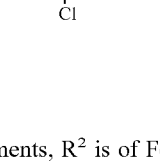
(i-15)

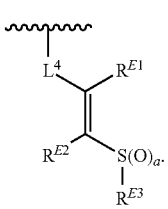

In certain embodiments, R² is of Formula (i-16):

(i-16)

In certain embodiments, R² is of Formula (i-17):

(i-17)

In certain embodiments, R² is of Formula (i-18):

(i-18)

In certain embodiments, R² is of Formula (i-19):

(i-19)

In certain embodiments, R² is of Formula (i-20):

(i-20)

In certain embodiments, R² is of Formula (i-21):

(i-21)

In certain embodiments, R² is of Formula (i-22):

(i-22)

In certain embodiments, R² is of Formula (i-23):

(i-23)

In certain embodiments, R² is of Formula (i-24):

(i-24)

In certain embodiments, R² is of Formula (i-25):

(i-25)

In certain embodiments, $R^2$ is of Formula (i-26):

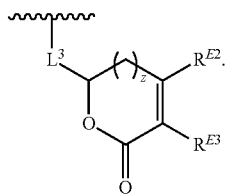

(i-26). In certain embodiments, $R^2$ is of Formula (i 27):

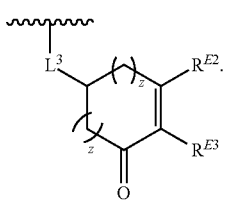

In certain embodiments, $R^2$ is of Formula (i-28):

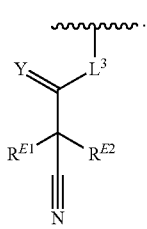

In certain embodiments, $R^2$ is of Formula (i-29):

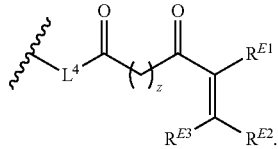

In certain embodiments, $R^2$ is of Formula (i-30):

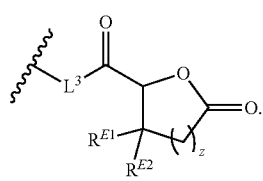

In certain embodiments, $R^2$ is of Formula (i-31):

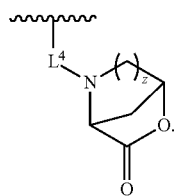

In certain embodiments, $R^2$ is of Formula (i-32):

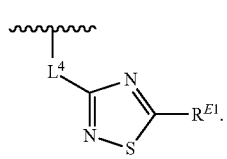

In certain embodiments, $R^2$ is of Formula (i-33):

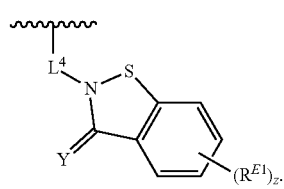

In certain embodiments, $R^2$ is of Formula (i-34):

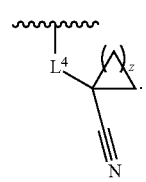

In certain embodiments, $R^2$ is of Formula (i-35):

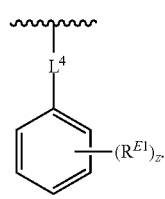

In certain embodiments, $R^2$ is of Formula (i-36):

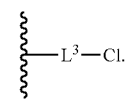

In certain embodiments, $R^2$ is of Formula (i-37):

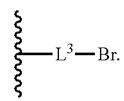

In certain embodiments, $R^2$ is of Formula (i-38):

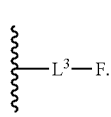 (i-38)

In certain embodiments, $R^2$ is of Formula (i-39):

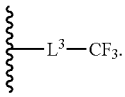 (i-39)

In certain embodiments, $R^2$ is of Formula (i-40):

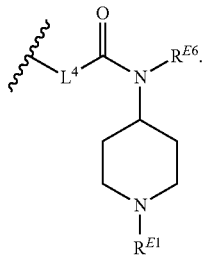 (i-40)

In certain embodiments, $R^2$ is of Formula (i-41):

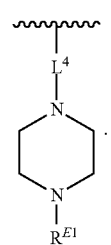 (i-41)

In certain embodiments, $R^2$ is of Formula (i-42):

 (i-42)

In certain embodiments, $R^2$ is of Formula (i-1a):

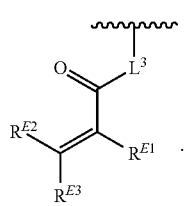 (i-1a)

In certain embodiments, $R^2$ is of Formula (i-1b):

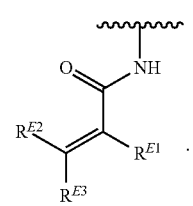 (i-1b)

In certain embodiments, $R^2$ is of Formula (i-1c):

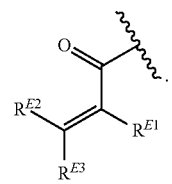 (i-1c)

In certain embodiments, $R^2$ is of Formula (i-1d)

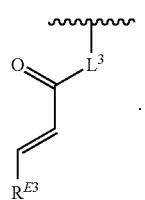 (i-1d)

In certain embodiments, $R^2$ is of Formula (i-1e):

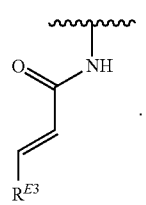 (i-1e)

In certain embodiments, $R^2$ is of Formula (i-1f):

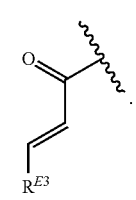 (i-1f)

In certain embodiments, $R^2$ is of Formula (i-1g):

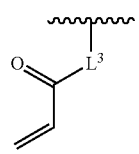

(i-1g)

In certain embodiments, $R^2$ is of Formula (i-1g):

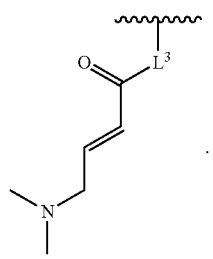

(i-1g)

In certain embodiments, $R^2$ is

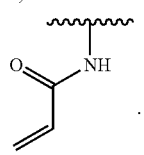

In certain embodiments, $R^2$ is

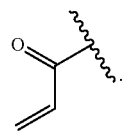 [SMILES: *C(=O)C=C]

In certain embodiments, $R^2$ is

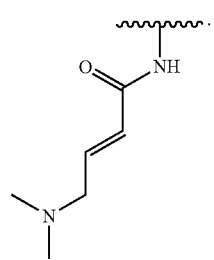 [SMILES: *NC(=O)/C=C/CN(C)C]

In certain embodiments, $R^2$ is

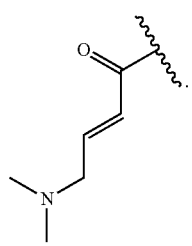 [SMILES: *C(=O)/C=C/CN(C)C]

In certain embodiments, $R^2$ is of Formula (i-1a):

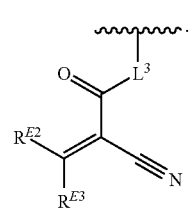

(i-1a)

In certain embodiments, $R^2$ is of Formula (i-1b):

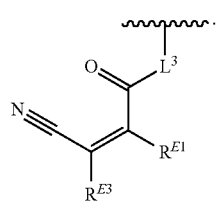

(i-1b)

In certain embodiments, $R^2$ is of Formula (i-1c):

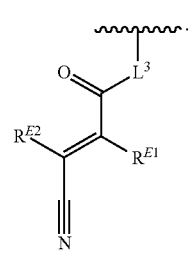

(i-1c)

In certain embodiments, $R^2$ is
In certain embodiments, $R^2$ is of Formula (i-18a):

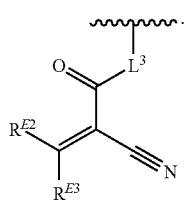

(i-18a)

In certain embodiments, $R^2$ is of Formula (i-18b):

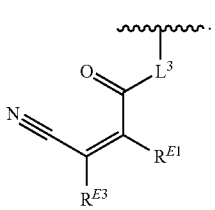

(i-18b)

In certain embodiments, $R^2$ is of Formula (i-18c):

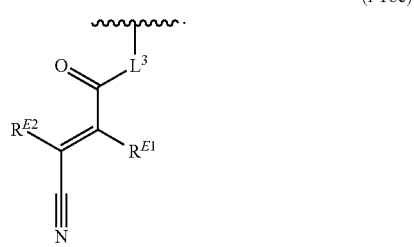

(i-18c)

In certain embodiments, $R^2$ is of Formula (i-15a):

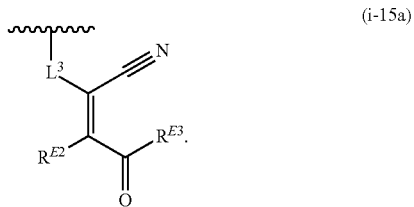

(i-15a)

In certain embodiments, $R^2$ is of Formula (i-15b):

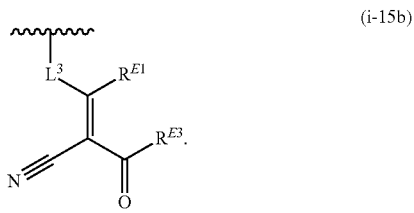

(i-15b)

In certain embodiments, $R^2$ is of Formula (i-15c):

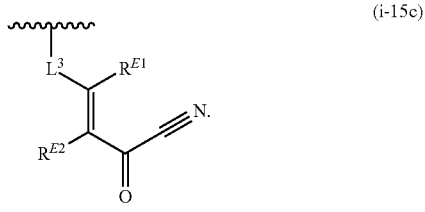

(i-15c)

$R^2$ may contain linker $L^3$ or $L^4$. In certain embodiments, $L^3$ is a bond. $L^3$ is an optionally substituted $C_{1-4}$ hydrocarbon chain. In certain embodiments, $L^3$ is optionally substituted ethyl. In certain embodiments, $L^3$ is optionally substituted alkenyl. In certain embodiments, $L^3$ is an optionally substituted $C_{1-4}$ hydrocarbon chain, wherein one or more carbon units of the hydrocarbon chain are independently replaced with —C(=O)—, —O—, —S—, —NR$^{L3a}$—, —NR$^{L3a}$C(=)-, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—. In certain embodiments, $L^3$ is an optionally substituted $C_{1-4}$ hydrocarbon chain, wherein one carbon unit of the hydrocarbon chain is replaced with —NR$^{L3a}$— (e.g., —NH—). In certain embodiments, $L^3$ is of the formula: —(CH$_2$)$_{1-4}$—NR$^{L3a}$— (e.g., —(CH$_2$)$_{1-4}$—NH—) or —NR$^{L3a}$—(CH$_2$)$_{1-4}$— (e.g., —NH—CH$_2$)$_{1-4}$—). In certain embodiments, $L^3$ is —NR$^{L3a}$—. In certain embodiments, $L^3$ is —NR$^{L3a}$(C=O)—. In certain embodiments, $L^3$ is —(C=O)NR$^{L3a}$—. In certain embodiments, $L^3$ is —NH—. In certain embodiments, $L^3$ is —(C=O)—. In certain embodiments, $L^3$ is —NH(C=O)—. In certain embodiments, $L^3$ is —(C=O)NH—. In certain embodiments, $L^3$ is —O—. In certain embodiments, $L^3$ is —S—. In certain embodiments, $L^4$ is a bond. In certain embodiments, $L^4$ is an optionally substituted $C_{1-4}$ hydrocarbon chain.

Linker $L^3$ may contain groups $R^{L3a}$ or $R^{L3b}$. In certain embodiments, $R^{L3}$a is hydrogen. In certain embodiments, at least one instance of $R^{L3b}$ is hydrogen. In certain embodiments, each instance of $R^{L3b}$ is hydrogen. In certain embodiments, at least one instance of $R^{L3b}$ is —Cl, —Br, or —I. In certain embodiments, each instance of $R^{L3b}$ is —Cl, —Br, or —I. In certain embodiments, at least one instance of $R^{L3b}$ is —F. In certain embodiments, each instance of $R^{L3b}$ is —F. In certain embodiments, at least one instance of $R^{L3b}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, two $R^{L3b}$ groups are joined to form an optionally substituted carbocyclic or optionally substituted heterocyclic ring.

$R^2$ may contain groups $R^{E1}$, $R^{E2}$, and/or $R^{E3}$. In certain embodiments, $R^{E1}$ is hydrogen. In certain embodiments, $R^{E2}$ is hydrogen. In certain embodiments, $R^{E3}$ is hydrogen. In certain embodiments, $R^{E1}$ is —Cl, —Br, or —I. In certain embodiments, $R^{E2}$ is —Cl, —Br, or —I. In certain embodiments, $R^{E3}$ is —Cl, —Br, or —I. In certain embodiments, $R^{E1}$ is —F. In certain embodiments, $R^{E2}$ is —F. In certain embodiments, $R^{E3}$ is —F. In certain embodiments, $R^{E1}$ is optionally substituted alkyl (e.g., substituted or unsubstituted $C_{1-6}$ alkyl). In certain embodiments, $R^{E2}$ is optionally substituted alkyl (e.g., substituted or unsubstituted $C_{1-6}$ alkyl). In certain embodiments, $R^{E3}$ is optionally substituted alkyl (e.g., substituted or unsubstituted $C_{1-6}$ alkyl). In certain embodiments, $R^{E1}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$. In certain embodiments, $R^{E2}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$. In certain embodiments, $R^{E3}$ is optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$. In certain embodiments, $R^{E1}$ is —N(R$^{EE}$)$_2$. In certain embodiments, $R^{E2}$ is —N(R$^{EE}$)$_2$. In certain embodiments, $R^{E3}$ is —N(R$^{EE}$)$_2$. In certain embodiments, $R^{E1}$ is —N(CH$_3$)$_2$. In certain embodiments, $R^{E2}$ is —N(CH$_3$)$_2$. In certain embodiments, $R^{E3}$ is —N(CH$_3$)$_2$. In certain embodiments, $R^{E1}$ is —CH$_2$N(R$^{EE}$)$_2$. In certain embodiments, $R^{E2}$ is —CH$_2$N(R$^{EE}$)$_2$. In certain embodiments, $R^{E3}$ is —CH$_2$N(R$^{EE}$)$_2$. In certain embodiments, $R^{E1}$ is —CH$_2$N(CH$_3$)$_2$. In certain embodiments, $R^{E2}$ is —CH$_2$N(CH$_3$)$_2$. In certain embodiments, $R^{E3}$ is —CH$_2$N (CH$_3$)$_2$. In certain embodiments, R$^{E1}$ is —CN. In certain embodiments, R$^{E2}$ is —CN. In certain embodiments, R$^{E3}$ is —CN.

In certain embodiments, R$^{E1}$ and R$^{E3}$ are joined to form an optionally substituted carbocyclic ring. In certain embodiments, R$^{E1}$ and R$^{E3}$ are joined to form an optionally substituted heterocyclic ring. In certain embodiments, R$^{E2}$ and R$^{E3}$ are joined to form an optionally substituted carbocyclic ring. In certain embodiments, R$^{E2}$ and R$^{E3}$ are joined to form an optionally substituted heterocyclic ring. In certain embodiments, R$^{E1}$ and R$^{E2}$ are joined to form an optionally substituted carbocyclic ring. In certain embodiments, R$^{E1}$ and R$^{E2}$ are joined to form an optionally substituted heterocyclic ring.

R$^2$ may contain group R$^{E4}$, where R$^{E4}$ is a leaving group. In certain embodiments, R$^{E4}$ is —Cl, —Br, or —I. In certain embodiments, R$^{E4}$ is —F. In certain embodiments, R$^{E4}$ is —OS(=O)R$^{E4a}$ or —OS(=O)$_2$R$^{E4a}$, wherein R$^{E4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, R$^{E4}$ is —OR$^{E4a}$. In certain embodiments, R$^{E4}$ is -OMs, -OTf, -OTs, -OBs, or 2-nitrobenzenesulfonyloxy. In certain embodiments, R$^{E4}$ is —OR$^{E4a}$. In certain embodiments, R$^{E4}$ is —OMe, —OCF$_3$, or —OPh. In certain embodiments, R$^{E4}$ is —OC(=O)R$^{E4a}$. In certain embodiments, R$^{E4}$ is —OC(=O)Me, —OC(=O)CF$_3$, —OC(=O)Ph, or —OC(=O)Cl. In certain embodiments, R$^{E4}$ is —OC(=O)OR$^{E4a}$. In certain embodiments, R$^{E4}$ is —OC(=O)OMe or —OC(=O)O(t-Bu).

R$^2$ may contain group R$^{E5}$, where R$^{E5}$ is a halogen. In certain embodiments, R$^{E5}$ is —Cl, —Br, or —I. In certain embodiments, R$^{E5}$ is —F.

R$^2$ may contain group R$^{E6}$. In certain embodiments, R$^{E6}$ is hydrogen. In certain embodiments, R$^{E6}$ is substituted or unsubstituted C$_1$-C$_6$ alkyl. In certain embodiments, R$^{E6}$ is a nitrogen protecting group.

In certain embodiments, a is 1. In certain embodiments, a is 2.

In certain embodiments, z is 0. In certain embodiments, z is 1. In certain embodiments, z is 2. In certain embodiments, z is 3, 4, 5, or 6.

R$^2$ may contain group Y. In certain embodiments, Y is O. In certain embodiments, Y is S. In certain embodiments, Y is NR$^{E7}$. In certain embodiments, Y is NH.

In certain embodiments, a compound described herein is of Formula (II):

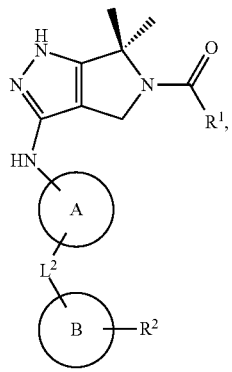

(II)

or a pharmaceutically acceptable salt, solvate, hydrate, polymorph, co-crystal, tautomer, stereoisomer, isotopically labeled derivative, or prodrug thereof, wherein R$^1$, R$^2$, linker L$^2$, Ring A, and Ring B are as defined for Formula (I).

In certain embodiments, a compound of Formula (I) is of Formula (III):

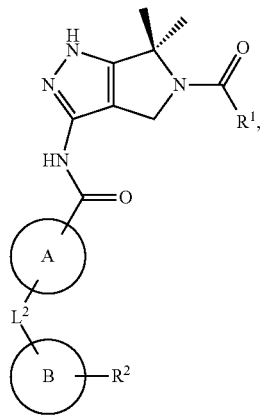

(III)

or a pharmaceutically acceptable salt, solvate, hydrate, polymorph, co-crystal, tautomer, stereoisomer, isotopically labeled derivative, or prodrug thereof, wherein R$^1$, R$^2$, linker L$^2$, Ring A, and Ring B are as defined for Formula (I).

In certain embodiments, a compound of Formula (I) is of Formula (IV-a):

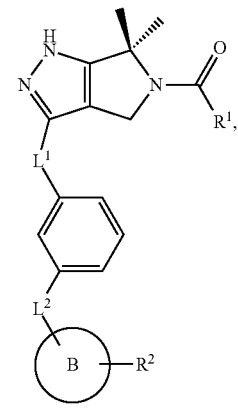

(IV-a)

or a pharmaceutically acceptable salt, solvate, hydrate, polymorph, co-crystal, tautomer, stereoisomer, isotopically labeled derivative, or prodrug thereof, wherein R$^1$, R$^2$, linker L$^1$, linker L$^2$, and Ring B are as defined for Formula (I).

In certain embodiments, a compound of Formula (I) is of Formula (IV-b):

(IV-b)

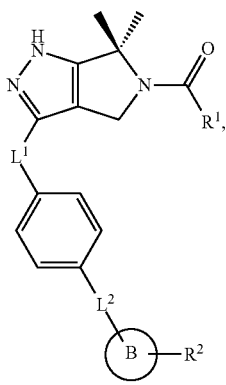

or a pharmaceutically acceptable salt, solvate, hydrate, polymorph, co-crystal, tautomer, stereoisomer, isotopically labeled derivative, or prodrug thereof, wherein $R^1$, $R^2$, linker $L^1$, linker $L^2$, and Ring B are as defined for Formula (I).

In certain embodiments, a compound Formula (I) is of Formula (IV-c):

(IV-c)

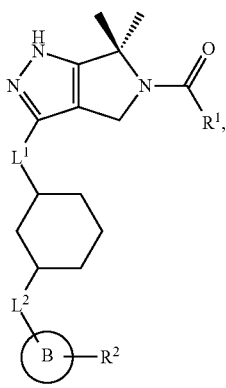

or a pharmaceutically acceptable salt, solvate, hydrate, polymorph, co-crystal, tautomer, stereoisomer, isotopically labeled derivative, or prodrug thereof, wherein $R^1$, $R^2$, linker $L^1$, linker $L^2$, and Ring B are as defined for Formula (I).

In certain embodiments, a compound Formula (I) is of Formula (IV-d):

(IV-d)

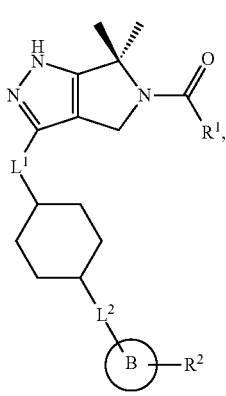

or a pharmaceutically acceptable salt, solvate, hydrate, polymorph, co-crystal, tautomer, stereoisomer, isotopically labeled derivative, or prodrug thereof, wherein $R^1$, $R^2$, linker $L^1$, linker $L^2$, and Ring B are as defined for Formula (I).

In certain embodiments, a compound Formula (I) is of Formula (IV-e):

(IV-e)

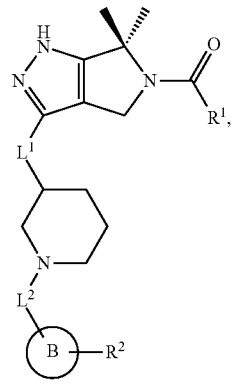

or a pharmaceutically acceptable salt, solvate, hydrate, polymorph, co-crystal, tautomer, stereoisomer, isotopically labeled derivative, or prodrug thereof, wherein $R^1$, $R^2$, linker $L^1$, linker $L^2$, and Ring B are as defined for Formula (I).

In certain embodiments, a compound Formula (I) is of Formula (IV-f):

(IV-f)

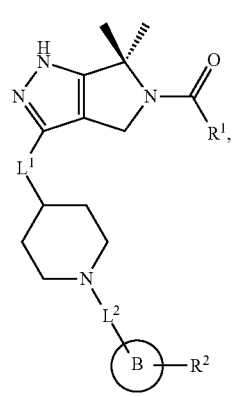

or a pharmaceutically acceptable salt, solvate, hydrate, polymorph, co-crystal, tautomer, stereoisomer, isotopically labeled derivative, or prodrug thereof, wherein $R^1$, $R^2$, linker $L^1$, linker $L^2$, and Ring B are as defined for Formula (I).

In certain embodiments, a compound Formula (I) is of Formula (V-a):

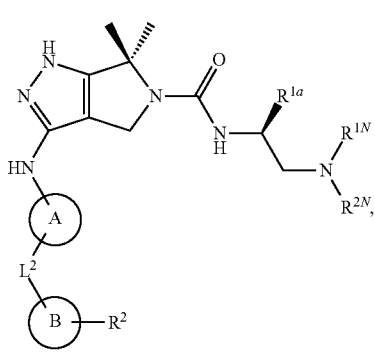

(V-a)

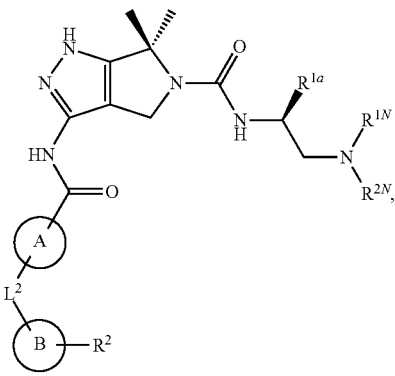

(V-c)

or a pharmaceutically acceptable salt, solvate, hydrate, polymorph, co-crystal, tautomer, stereoisomer, isotopically labeled derivative, or prodrug thereof, wherein:

$R^2$, linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (V-b):

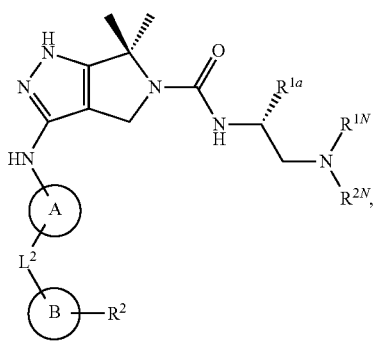

(V-b)

or a pharmaceutically acceptable salt, solvate, hydrate, polymorph, co-crystal, tautomer, stereoisomer, isotopically labeled derivative, or prodrug thereof, wherein:

$R^2$, linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (V-c):

or a pharmaceutically acceptable salt, solvate, hydrate, polymorph, co-crystal, tautomer, stereoisomer, isotopically labeled derivative, or prodrug thereof, wherein:

$R^2$, linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (V-d):

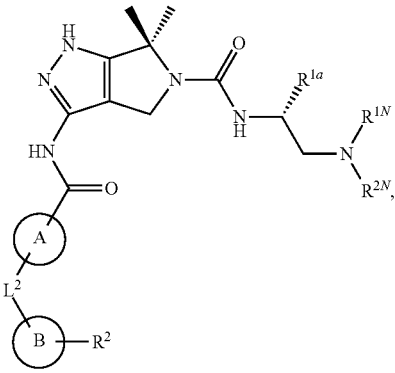

(V-d)

or a pharmaceutically acceptable salt, solvate, hydrate, polymorph, co-crystal, tautomer, stereoisomer, isotopically labeled derivative, or prodrug thereof, wherein:

$R^2$, linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-a):

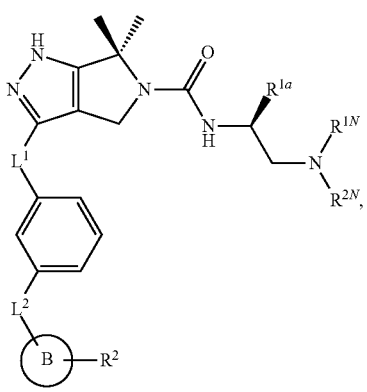

(VI-a)

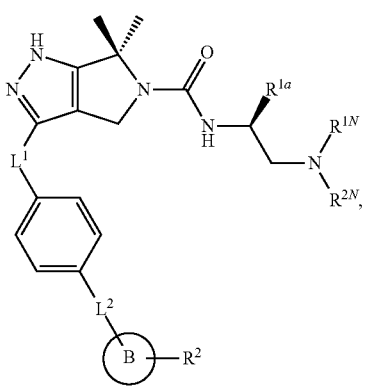

(VI-c)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-b):

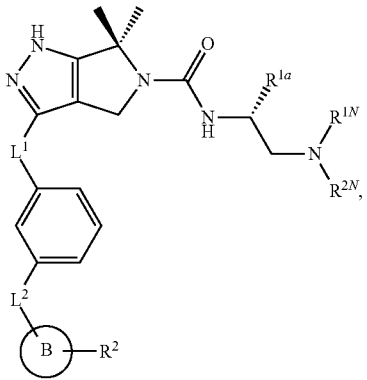

(VI-b)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-c):

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$ $C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-d):

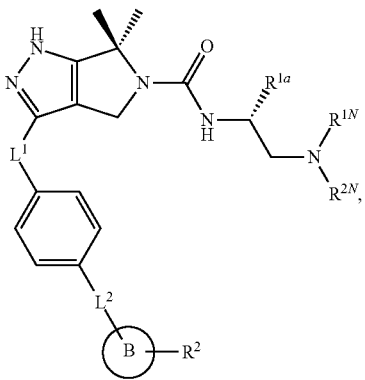

(VI-d)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-e):

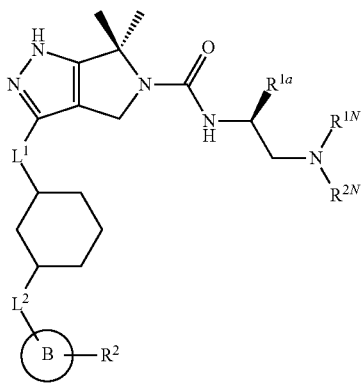

(VI-e)

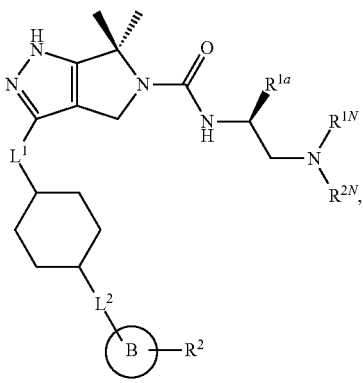

(VI-g)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-f):

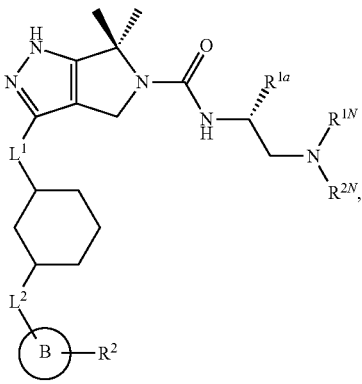

(VI-f)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-g):

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-h):

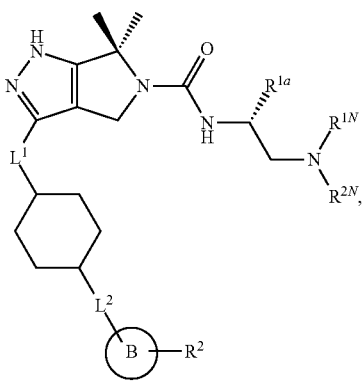

(VI-h)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-i):

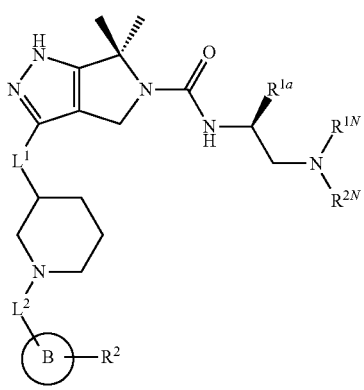

(VI-i)

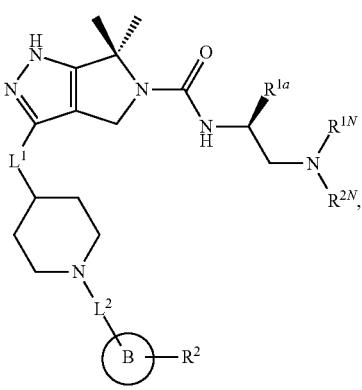

(VI-k)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-j):

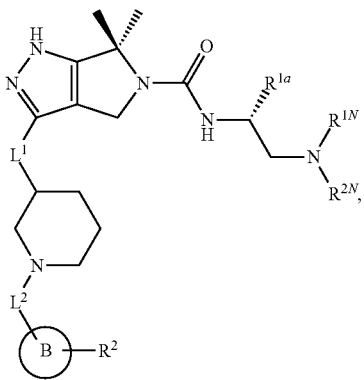

(VI-j)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-k):

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VI-l):

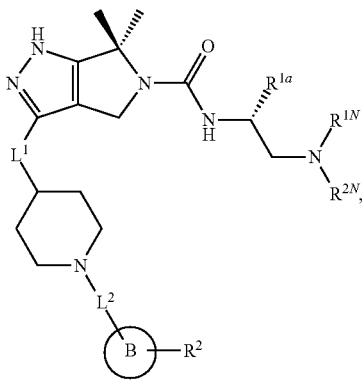

(VI-l)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (VII-a):

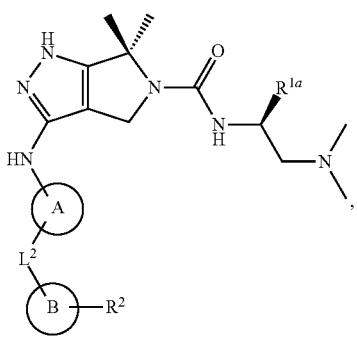

(VII-a)

or a pharmaceutically acceptable salt, solvate, hydrate, polymorph, co-crystal, tautomer, stereoisomer, isotopically labeled derivative, or prodrug thereof, wherein:

$R^2$, linker $L^2$, Ring A, and Ring B are as defined for Formula (I); and $R^{1a}$ is hydrogen, $C_1$-$C_6$ alkyl, or optionally substituted aryl.

In certain embodiments, a compound Formula (I) is of Formula (VII-b):

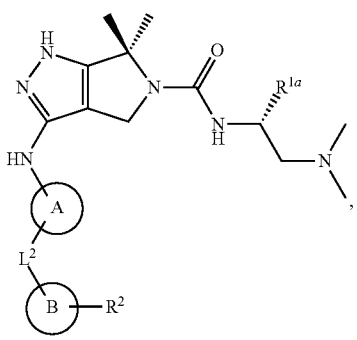

(VII-b)

or a pharmaceutically acceptable salt, solvate, hydrate, polymorph, co-crystal, tautomer, stereoisomer, isotopically labeled derivative, or prodrug thereof, wherein:

$R^2$, linker $L^2$, Ring A, and Ring B are as defined for Formula (I); and $R^{1a}$ is hydrogen, $C_1$-$C_6$ alkyl, or optionally substituted aryl.

In certain embodiments, a compound Formula (I) is of Formula (VII-c):

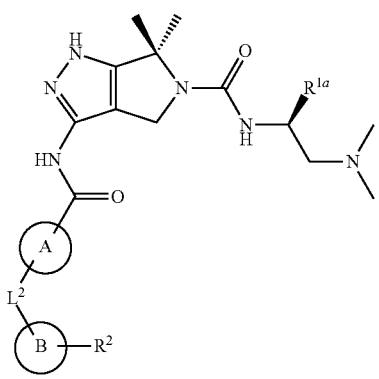

(VII-c)

or a pharmaceutically acceptable salt, solvate, hydrate, polymorph, co-crystal, tautomer, stereoisomer, isotopically labeled derivative, or prodrug thereof, wherein:

$R^2$, linker $L^2$, Ring A, and Ring B are as defined for Formula (I); and $R^{1a}$ is hydrogen, $C_1$-$C_6$ alkyl, or optionally substituted aryl.

In certain embodiments, a compound Formula (I) is of Formula (VII-d):

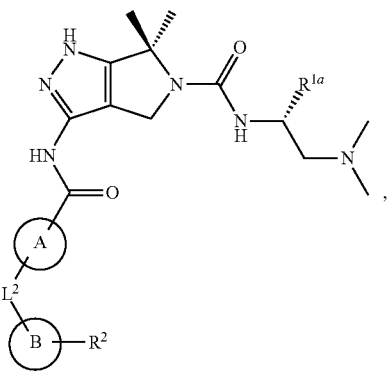

(VII-d)

or a pharmaceutically acceptable salt, solvate, hydrate, polymorph, co-crystal, tautomer, stereoisomer, isotopically labeled derivative, or prodrug thereof, wherein:

$R^2$, linker $L^2$, Ring A, and Ring B are as defined for Formula (I); and $R^{1a}$ is hydrogen, $C_1$-$C_6$ alkyl, or optionally substituted aryl.

In certain embodiments, a compound Formula (I) is of Formula (VIII-a):

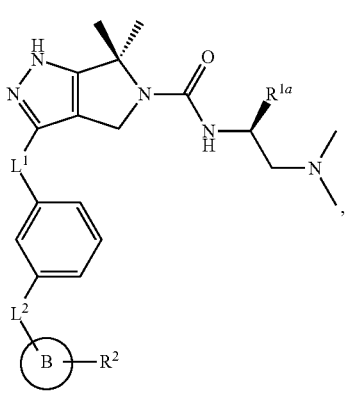

(VIII-a)

or a pharmaceutically acceptable salt, solvate, hydrate, polymorph, co-crystal, tautomer, stereoisomer, isotopically labeled derivative, or prodrug thereof, wherein:

$R^2$, linker $L^1$, linker $L^2$, and Ring B are as defined for Formula (I); and $R^{1a}$ is hydrogen, $C_1$-$C_6$ alkyl, or optionally substituted aryl.

In certain embodiments, a compound Formula (I) is of Formula (VIII-b):

(VIII-b)

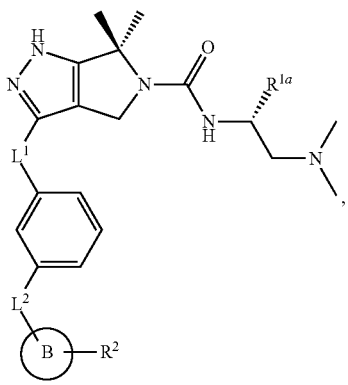

or a pharmaceutically acceptable salt, solvate, hydrate, polymorph, co-crystal, tautomer, stereoisomer, isotopically labeled derivative, or prodrug thereof, wherein:
  $R^2$, linker $L^1$, linker $L^2$, and Ring B are as defined for Formula (I); and
  $R^{1a}$ is hydrogen, $C_1$-$C_6$ alkyl, or optionally substituted aryl.

In certain embodiments, a compound Formula (I) is of Formula (VIII-c):

(VIII-c)

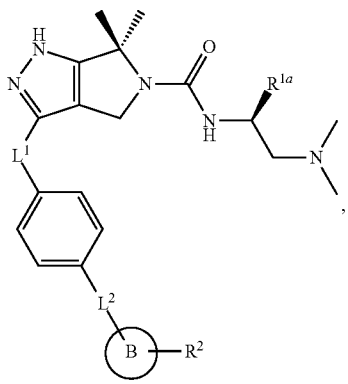

or a pharmaceutically acceptable salt, solvate, hydrate, polymorph, co-crystal, tautomer, stereoisomer, isotopically labeled derivative, or prodrug thereof, wherein:
  $R^2$, linker $L^1$, linker $L^2$, and Ring B are as defined for Formula (I); and
  $R^{1a}$ is hydrogen, $C_1$-$C_6$ alkyl, or optionally substituted aryl.

In certain embodiments, a compound Formula (I) is of Formula (VIII-d):

(VIII-d)

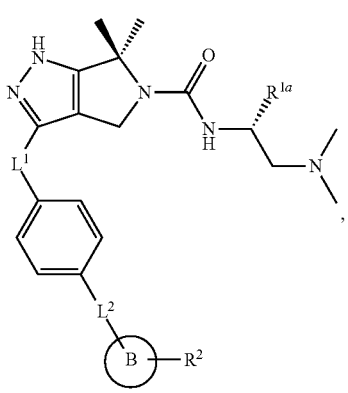

or a pharmaceutically acceptable salt, solvate, hydrate, polymorph, co-crystal, tautomer, stereoisomer, isotopically labeled derivative, or prodrug thereof, wherein:
  $R^2$, linker $L^1$, linker $L^2$, and Ring B are as defined for Formula (I); and
  $R^{1a}$ is hydrogen, $C_1$-$C_6$ alkyl, or optionally substituted aryl.

In certain embodiments, a compound Formula (I) is of Formula (VIII-e):

(VIII-e)

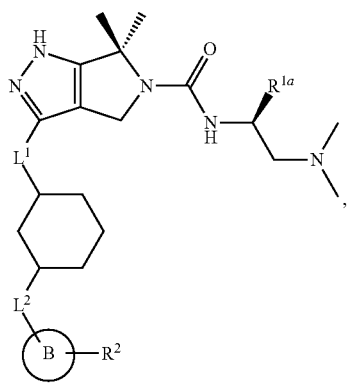

or a pharmaceutically acceptable salt, solvate, hydrate, polymorph, co-crystal, tautomer, stereoisomer, isotopically labeled derivative, or prodrug thereof wherein:
  $R^2$, linker $L^1$, linker $L^2$, and Ring B are as defined for Formula (I); and
  $R^{1a}$ is hydrogen, $C_1$-$C_6$ alkyl, or optionally substituted aryl.

In certain embodiments, a compound Formula (I) is of Formula (VIII-f):

(VIII-f)

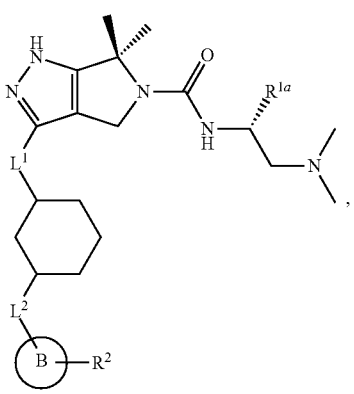

or a pharmaceutically acceptable salt, solvate, hydrate, polymorph, co-crystal, tautomer, stereoisomer, isotopically labeled derivative, or prodrug thereof wherein:
  $R^2$, linker $L^1$, linker $L^2$, and Ring B are as defined for Formula (I); and
  $R^{1a}$ is hydrogen, $C_1$-$C_6$ alkyl, or optionally substituted aryl.

In certain embodiments, a compound Formula (I) is of Formula (VIII-g):

(VIII-g)

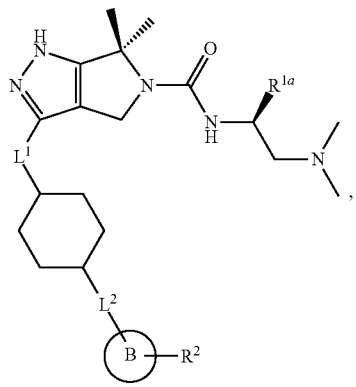

or a pharmaceutically acceptable salt, solvate, hydrate, polymorph, co-crystal, tautomer, stereoisomer, isotopically labeled derivative, or prodrug thereof wherein:

$R^2$, linker $L^1$, linker $L^2$, and Ring B are as defined for Formula (I); and $R^{1a}$ is hydrogen, $C_1$-$C_6$ alkyl, or optionally substituted aryl.

In certain embodiments, a compound Formula (I) is of Formula (VIII-h):

(VIII-h)

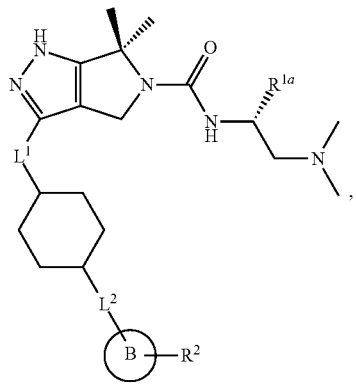

or a pharmaceutically acceptable salt, solvate, hydrate, polymorph, co-crystal, tautomer, stereoisomer, isotopically labeled derivative, or prodrug thereof wherein:

$R^2$, linker $L^1$, linker $L^2$, and Ring B are as defined for Formula (I); and $R^{1a}$ is hydrogen, $C_1$-$C_6$ alkyl, or optionally substituted aryl.

In certain embodiments, a compound Formula (I) is of Formula (VIII-i):

(VIII-i)

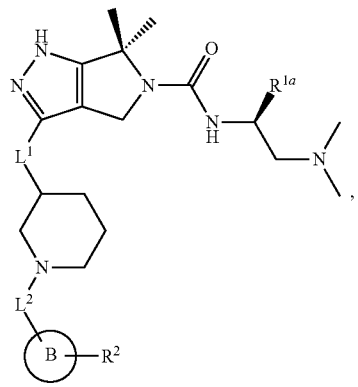

or a pharmaceutically acceptable salt, solvate, hydrate, polymorph, co-crystal, tautomer, stereoisomer, isotopically labeled derivative, or prodrug thereof wherein:

$R^2$, linker $L^1$, linker $L^2$, and Ring B are as defined for Formula (I); and $R^{1a}$ is hydrogen, $C_1$-$C_6$ alkyl, or optionally substituted aryl.

In certain embodiments, a compound Formula (I) is of Formula (VIII-j):

(VIII-j)

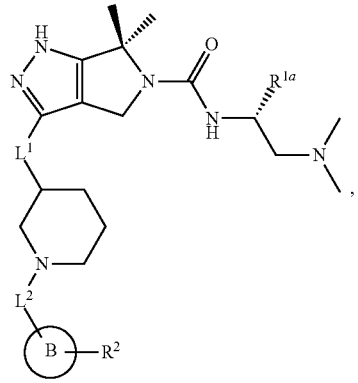

or a pharmaceutically acceptable salt, solvate, hydrate, polymorph, co-crystal, tautomer, stereoisomer, isotopically labeled derivative, or prodrug thereof wherein:

$R^2$, linker $L^1$, linker $L^2$, and Ring B are as defined for Formula (I); and $R^{1a}$ is hydrogen, $C_1$-$C_6$ alkyl, or optionally substituted aryl.

In certain embodiments, a compound Formula (I) is of Formula (VIII-k):

(VIII-k)

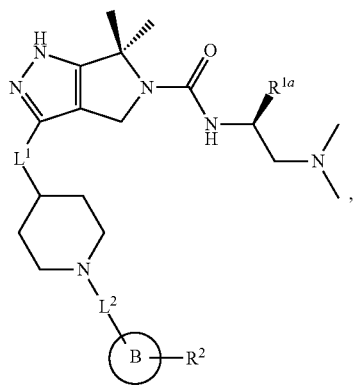

or a pharmaceutically acceptable salt, solvate, hydrate, polymorph, co-crystal, tautomer, stereoisomer, isotopically labeled derivative, or prodrug thereof wherein:

$R^2$, linker $L^1$, linker $L^2$, and Ring B are as defined for Formula (I); and $R^{1a}$ is hydrogen, $C_1$-$C_6$ alkyl, or optionally substituted aryl.

In certain embodiments, a compound Formula (I) is of Formula (VIII-l):

(VIII-l)

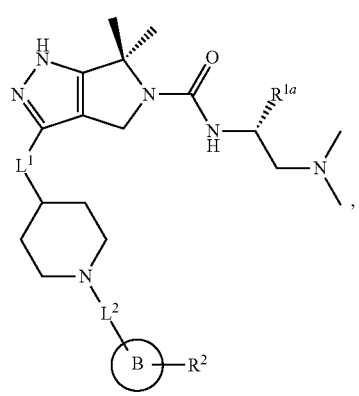

or a pharmaceutically acceptable salt, solvate, hydrate, polymorph, co-crystal, tautomer, stereoisomer, isotopically labeled derivative, or prodrug thereof wherein:

$R^2$, linker $L^1$, linker $L^2$, and Ring B are as defined for Formula (I); and $R^{1a}$ is hydrogen, $C_1$-$C_6$ alkyl, or optionally substituted aryl.

In certain embodiments, a compound Formula (I) is of Formula (IX-a):

(IX-a)

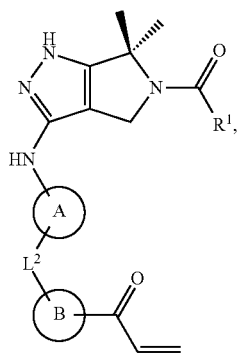

or a pharmaceutically acceptable salt, solvate, hydrate, polymorph, co-crystal, tautomer, stereoisomer, isotopically labeled derivative, or prodrug thereof, wherein $R^1$, linker $L^2$, Ring A, and Ring B are as defined for Formula (I).

In certain embodiments, a compound Formula (I) is of Formula (IX-b):

(IX-b)

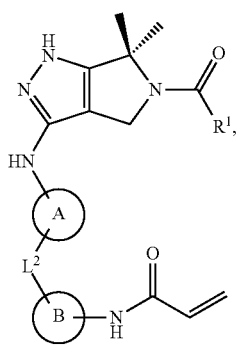

or a pharmaceutically acceptable salt, solvate, hydrate, polymorph, co-crystal, tautomer, stereoisomer, isotopically labeled derivative, or prodrug thereof, wherein $R^1$, linker $L^2$, Ring A, and Ring B are as defined for Formula (I).

In certain embodiments, a compound Formula (I) is of Formula (IX-c):

(IX-c)

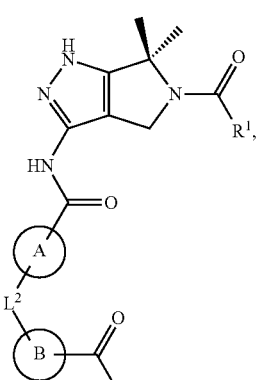

or a pharmaceutically acceptable salt, solvate, hydrate, polymorph, co-crystal, tautomer, stereoisomer, isotopically labeled derivative, or prodrug thereof, wherein $R^1$, linker $L^2$, Ring A, and Ring B are as defined for Formula (I).

In certain embodiments, a compound Formula (I) is of Formula (IX-d):

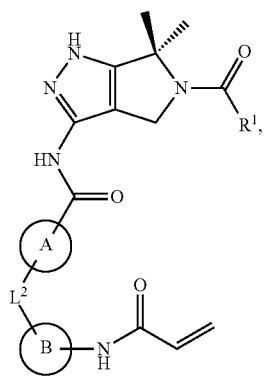

(IX-d)

or a pharmaceutically acceptable salt, solvate, hydrate, polymorph, co-crystal, tautomer, stereoisomer, isotopically labeled derivative, or prodrug thereof, wherein $R^1$, linker $L^2$, Ring A, and Ring B are as defined for Formula (I).

In certain embodiments, a compound Formula (I) is of Formula (X-a):

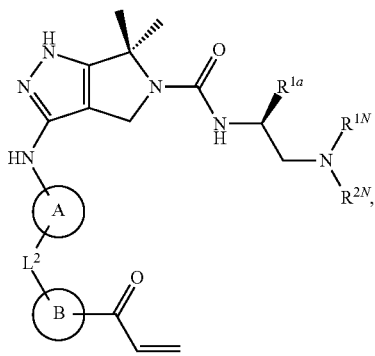

(X-a)

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (X-b):

(X-b)

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (X-c):

(X-c)

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (X-d):

(X-d)

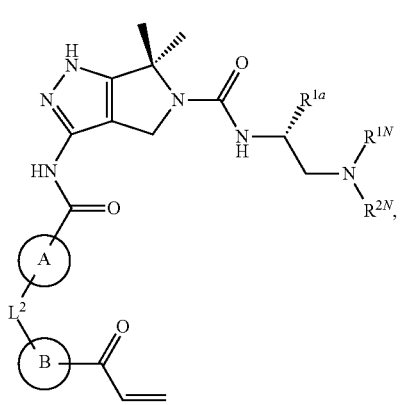

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XI-a):

(XI-a)

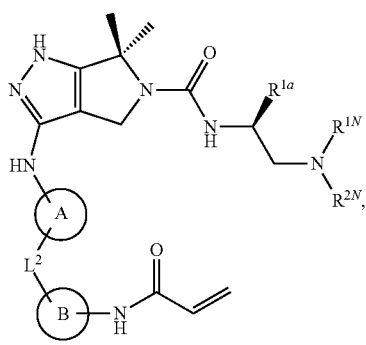

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XI-b):

(XI-b)

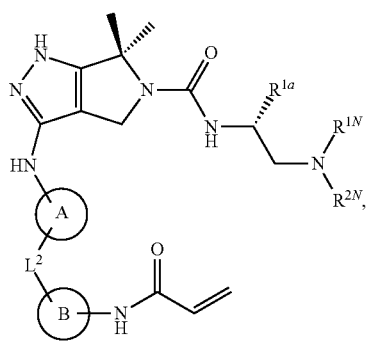

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XI-c):

(XI-c)

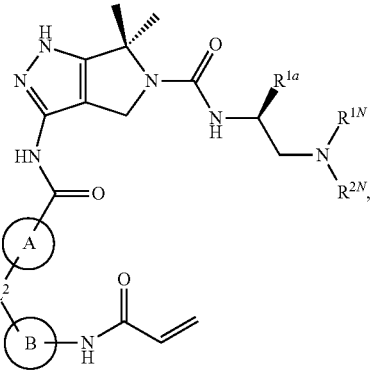

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XI-d):

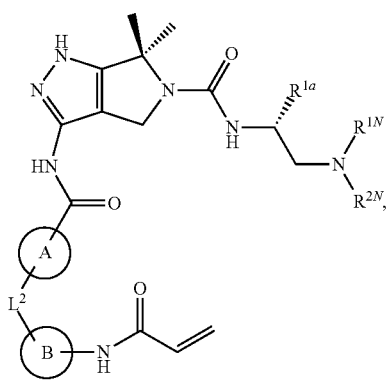

(XI-d)

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XII-a):

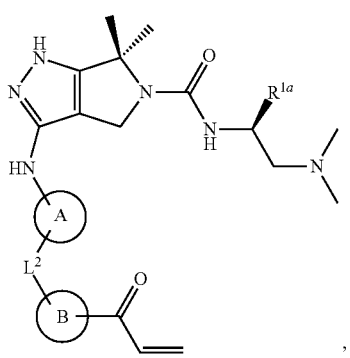

(XII-a)

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XII-b):

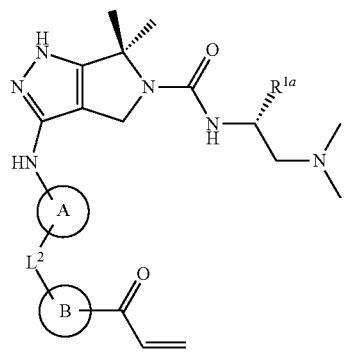

(XII-b)

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XII-c):

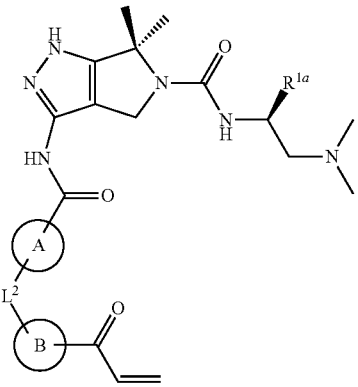

(XII-c)

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XII-d):

(XII-d)

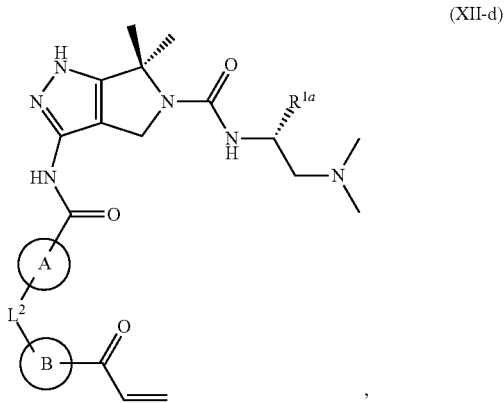

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XIII-a):

(XIII-a)

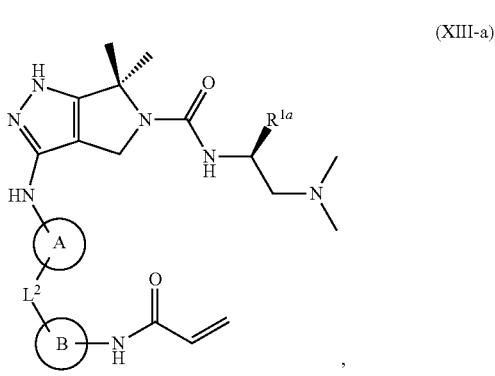

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XIII-b):

(XIII-b)

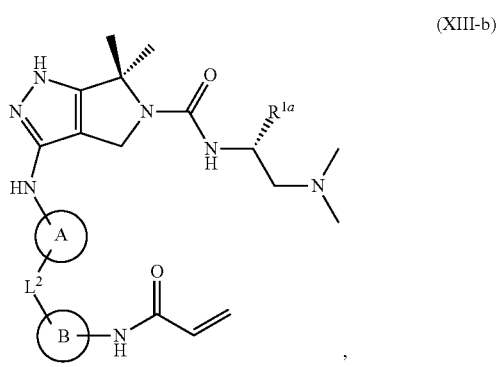

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XIII-c):

(XIII-c)

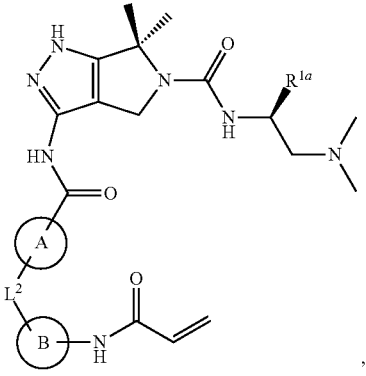

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, a compound Formula (I) is of Formula (XIII-d):

(XIII-d)

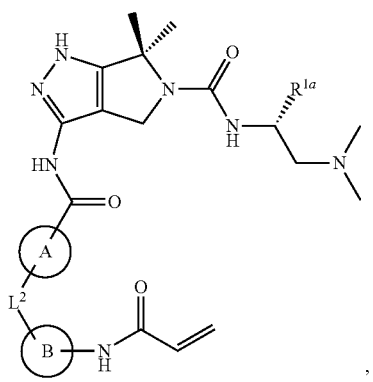

or a pharmaceutically acceptable salt, solvate, hydrate, polymorph, co-crystal, tautomer, stereoisomer, isotopically labeled derivative, or prodrug thereof, wherein:

linker $L^2$, Ring A, and Ring B are as defined for Formula (I);

$R^{1a}$ is hydrogen, $C_1$-$C_6$ alkyl, or optionally substituted aryl; and each of $R^{1N}$ and $R^{2N}$ is independently hydrogen, $C_1$-$C_6$ alkyl, or a nitrogen protecting group, or $R^{1N}$ and $R^{2N}$ are joined to form an optionally substituted carbocyclic, optionally substituted heterocyclic, optionally substituted aryl, or optionally substituted heteroaryl ring.

In certain embodiments, the compound according to Formula (I) is a compound listed in Table 1.

TABLE 1

| Name | Structure | Characterization Data |
|---|---|---|
| Compound 101<br>(S)-3-((3-(4-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide | | $^1$H NMR: 600 MHz (DMSO-$d_6$) δ 10.44 (d, J = 4.2 Hz, 1H), 10.04 (s, 1H), 8.33 (s, 1H), 7.96-7.93 (m, 2H), 7.82-7.80 (m, 2H), 7.34-7.32 (m, 2H), 7.26-7.23 (m, 2H), 7.20-7.10 (m, 3H), 6.52-6.46 (m, 1H), 6.35-6.30 (m, 1H), 6.09 (s, 1H), 5.84-5.81 (m, 1H), 4.89-4.83 (m, 1H), 4.35 (d, J = 19.8 Hz, 2H), 2.64-2.57 (m, 1H), 2.45-2.38 (m, 1H), 2.18 (s, 6H), 1.65 (d, J = 4.2 Hz, 3H), 1.58 (d, J = 4.8 Hz, 3H); MS m/z: 607.4 [M + 1]. |

TABLE 1-continued

Exemplary Compounds of Formula (I).

| Name | Structure | Characterization Data |
| --- | --- | --- |
| Compound 102<br>(S)-3-((4-(4-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide | 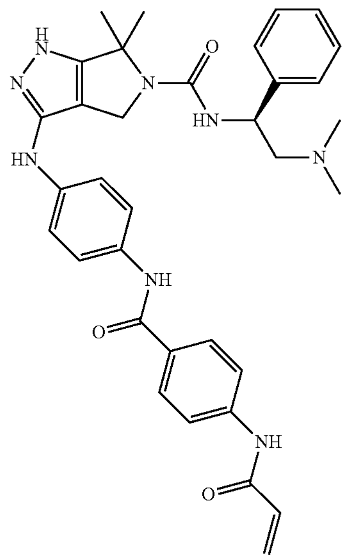 [SMILES: C=CC(=O)Nc1ccc(C(=O)Nc2ccc(Nc3n[nH]c4c3CN(C(=O)N[C@H](CN(C)C)c3ccccc3)C4(C)C)cc2)cc1] | $^1$H NMR (TFA salt): 400 MHz (DMSO-d$_6$) δ 10.46 (s, 1H), 10.01 (s, 1H), 8.98-8.89 (br, 1H), 8.25 (s, 1H), 7.99 (d, J = 8.8 Hz, 2H), 7.85 (d, J = 8.8 Hz, 2H), 7.64 (d, J = 8.8 Hz, 2H), 7.48-7.42 (m, 4H), 7.38-7.34 (m, 1H), 7.00-6.91 (m, 2H), 6.69 (d, J = 8.8 Hz, 1H), 6.53 (dd, J = 17.2, 10.0 Hz, 1H), 6.36 (dd, J = 17.2, 2.0 Hz, 1H), 5.87 (dd, J = 10.0, 2.0 Hz, 1H), 5.40-5.35 (m, 1H), 4.48 (d, J = 10.8 Hz, 1H), 4.33 (d, J = 10.8 Hz, 1H), 3.10-2.95 (m, 2H), 2.93 (d, J = 4.8 Hz, 3H), 2.87 (d, J = 4.8 Hz, 3H), 1.74 (s, 3H), 1.65 (s, 3H); MS m/z: 607.4 [M + 1]. |
| Compound 103<br>(S)-3-((4-(3-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide | 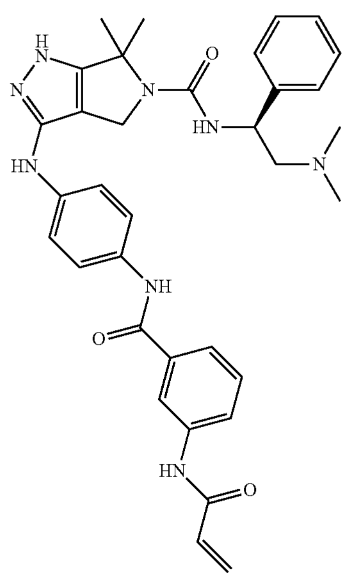 [SMILES: C=CC(=O)Nc1cccc(C(=O)Nc2ccc(Nc3n[nH]c4c3CN(C(=O)N[C@H](CN(C)C)c3ccccc3)C4(C)C)cc2)c1] | $^1$H NMR (TFA salt): 400 MHz (DMSO-d$_6$) δ 11.90-11.70 (br, 1H), 10.26 (s, 1H), 9.98 (s, 1H), 8.22-8.10 (br, 1H), 8.07 (m, 1H), 7.83 (dd, J = 8.0, 1.2 Hz, 1H), 7.57 (d, J = 8.0 Hz, 1H), 7.51 (d, J = 8.8 Hz, 2H), 7.39 (t, J = 8.0 Hz, 1H), 7.27 (d, J = 7.2 Hz, 2H), 7.22 (t, J = 7.2 Hz, 2H), 7.12 (t, J = 7.2 Hz, 1H), 6.39 (dd, J = 17.2, 10.0 Hz, 1H), 6.22 (dd, J = 17.2, 2.0 Hz, 1H), 6.03-5.92 (m, 1H), 5.72 (dd, J = 10.0, 2.0 Hz, 1H), 4.60-4.51 (m, 1H), 4.25-4.14 (m, 2H), 2.52 (dd, J = 12.0, 8.8 Hz, 1H), 2.32-2.27 (m, 1H), 2.10 (s, 6H), 1.57 (s, 3H), 1.50 (s, 3H); MS m/z: 607.4 [M + 1]. |

TABLE 1-continued

Exemplary Compounds of Formula (I).

| Name | Structure | Characterization Data |
|---|---|---|
| Compound 104 (S)-N-(2-(dimethylamino)-1-phenylethyl)-6,6-dimethyl-3-((3-(4-propionamidobenzamido)phenyl)amino)-4,6-dihydropyrrolo[3,4-c]pyrazole-5(1H)-carboxamide | 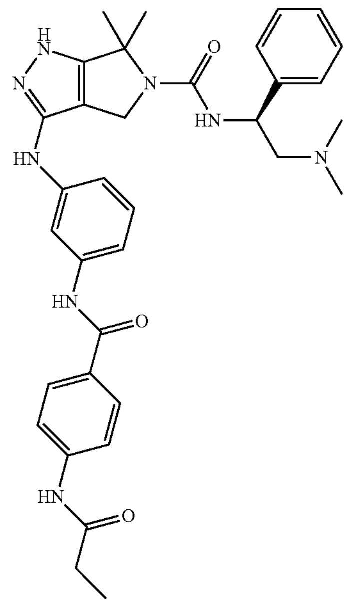 [SMILES: CCC(=O)Nc1ccc(C(=O)Nc2cccc(Nc3n[nH]c4c3CN(C(=O)N[C@H](CN(C)C)c3ccccc3)C4(C)C)c2)cc1] | $^1$H NMR (TFA salt): 400 MHz (DMSO-d$_6$) δ 12.20-11.80 (br, 1H), 10.09 (s, 1H), 9.93 (s, 1H), 8.23 (s, 1H), 7.83 (d, J = 8.0 Hz, 2H), 7.65 (d, J = 8.8 Hz, 2H), 7.50-7.30 (m, 1H), 7.27 (d, J = 6.8 Hz, 2H), 7.18 (t, J = 7.2 Hz, 2H), 7.13-7.09 (m, 3H), 6.59-6.51 (m, 1H), 6.12 (s, 1H), 4.92-4.80 (m, 1H), 4.29 (s, 2H), 2.30 (q, J = 7.6 Hz, 2H), 2.22 (m, 6H), 1.57 (s, 3H), 1.51 (s, 3H), 1.03 (t, J = 7.6 Hz, 3H); MS m/z: 609.4 [M + 1]. |
| Compound 105 (S)-3-((3-(3-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide | 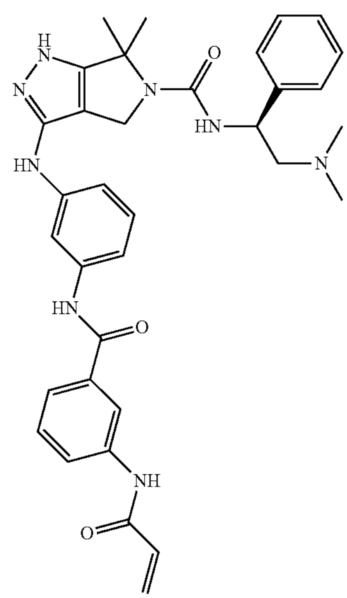 [SMILES: C=CC(=O)Nc1cccc(C(=O)Nc2cccc(Nc3n[nH]c4c3CN(C(=O)N[C@H](CN(C)C)c3ccccc3)C4(C)C)c2)c1] | $^1$H NMR (TFA salt): 400 MHz (DMSO-d$_6$) δ 12.10-11.82 (br, 1H), 10.26 (s, 1H), 10.08 (s, 1H), 8.25 (s, 1H), 8.06 (s, 1H), 7.85 (dd, J = 8.4, 1.2 Hz, 1H), 7.55 (d, J = 7.6 Hz, 1H), 7.39 (t, J = 8.0 Hz, 1H), 7.24 (d, J = 7.2 Hz, 2H), 7.15 (t, J = 12 Hz, 2H), 7.08 (d, J = 6.4 Hz, 1H), 6.39 (dd, J = 17.2, 10.0 Hz, 1H), 6.22 (dd, J = 17.2, 2.0 Hz, 1H), 5.97 (s, 1H), 5.72 (dd, J = 10.0, 2.0 Hz, 1H), 4.76-4.70 (m, 1H), 4.30-4.19 (m, 2H), 2.50-2.44 (m, 1H), 2.29-2.22 (m, 1H), 2.05 (s, 6H), 1.57 (s, 3H), 1.50 (s, 3H); MS m/z: 607.4 [M + 1]. |

TABLE 1-continued

Exemplary Compounds of Formula (I).

| Name | Structure | Characterization Data |
| --- | --- | --- |
| Compound 106<br>3-((3-(4-acrylamidobenzamido)phenyl)amimo)-N-(2-(dimethylamino)ethyl)-6,6-dimethyl-4,6-dihydropyrrolo[3,4-c]pyrazole-5(1H)-carboxamide | | $^1$H NMR (TFA salt): 400 MHz (DMSO-d$_6$) δ 10.49 (s, 1H), 10.07 (s, 1H), 9.41 (s, 1H), 8.37 (s, 1H), 7.99 (d, J = 8.8 Hz, 2H), 7.86 (d, J = 8.8 Hz, 2H), 7.49 (s, 1H), 7.21 (m, 2H), 6.74 (m, 1H), 6.53 (dd, J = 17.2, 10.0 Hz, 1H), 6.38 (m, 1H), 6.36 (dd, J = 17.2, 2.0 Hz, 1H), 5.87 (dd, J = 10.0, 2.0 Hz, 1H), 4.27 (s, 2H), 3.41 (q, J = 5.6 Hz, 2H), 3.18 (q, J = 5.6 Hz, 2H), 2.86 (s, 3H), 2.85 (s, 3H), 1.71 (s, 6H); MS m/z: 531.4 [M + 1]. |
| Compound 107<br>4-acrylamido-N-(3-((6,6-dimethyl-5-(4-methylpiperazine-1-carbonyl)-1,4,5,6-tetrahydropyrrolo[3,4-c]pyrazol-3-yl)amino)phenyl)benzamide | | $^1$H NMR (TFA salt): 400 MHz (DMSO-d$_6$) δ 10.49 (s, 1H), 10.08 (s, 1H), 9.68 (s, 1H), 8.44 (s, 1H), 7.99 (d, J = 8.8 Hz, 2H), 7.86 (d, J = 8.4 Hz, 2H), 7.62 (s, 1H), 7.23-7.13 (m, 2H), 6.84 (d, J = 7.2 Hz, 1H), 6.53 (dd, J = 17.2, 10.0 Hz, 1H), 6.36 (dd, J = 17.2, 2.0 Hz, 1H), 5.87 (dd, J = 10.0, 2.0 Hz, 1H), 4.43 (s, 2H), 3.40-3.33 (m, 4H), 3.15-2.97 (m, 4H), 2.82 (s, 3H), 1.70 (s, 6H); MS m/z: 543.4 [M + 1]. |

TABLE 1-continued

Exemplary Compounds of Formula (I).

| Name | Structure | Characterization Data |
| --- | --- | --- |
| Compound 108<br>3-((3-(4-acrylamidobenzamido)phenyl)amino)-N-(1-(dimethylamino)propan-2-yl)-6,6-dimethyl-4,6-dihydropyrrolo[3,4-c]pyrazole-5(1H)-carboxamide | | $^1$H NMR (TFA salt): 400 MHz (DMSO-d$_6$) δ 10.35 (s, 1H), 9.95 (s, 1H), 8.91 (s, 1H), 8.23 (s, 1H), 7.85 (d, J = 8.4 Hz, 2H), 7.72 (d, J = 8.4 Hz, 2H), 7.32 (s, 1H), 7.11-7.05 (m, 2H), 6.57 (m, 1H), 6.40 (dd, J = 16.8, 10.0 Hz, 1H), 6.23 (dd, J = 16.8, 2.0 Hz, 1H), 5.91 (d, J = 8.4 Hz, 1H), 5.74 (dd, J = 10.0, 2.0 Hz, 1H), 4.18 (s, 2H), 4.14-4.07 (m, 1H), 3.05-2.94 (m, 2H), 2.71 (d, J = 4.8 Hz, 3H), 2.69 (d, J = 4.8 Hz, 3H), 1.59 (s, 6H), 1.01 (d, J = 6.4 Hz, 3H), 0.85-0.76 (m, 1H); MS m/z: 545.3 [M + 1]. |
| Compound 109<br>(S,E)-3-((3-(4-(4-(dimethylamino)but-2-enamido)benzamido)phenyl)amino)-N-(2-hydroxy-1-phenylethyl)-6,6-dimethyl-4,6-dihydropyrrolo[3,4-c]pyrazole-5(1H)-carboxamide | | $^1$H NMR (TFA salt): 400 MHz (DMSO-d$_6$) δ 10.68 (s, 1H), 10.13 (s, 1H), 10.01 (s, 1H), 8.43 (s, 1H), 8.03 (d, J = 8.8 Hz, 2H), 7.88 (d, J = 8.8 Hz, 2H), 7.54 (s, 1H), 7.41-7.39 (m, 2H), 7.34-7.30 (m, 2H), 7.27-7.22 (m, 3H), 6.92-6.82 (m, 2H), 6.58 (d, J = 15.6 Hz, 1H), 6.13 (d, J = 8.0 Hz, 1H), 4.85 (q, J = 6.8 Hz, 1H), 4.48 (q, J = 11.2 Hz, 2H), 4.06 (d, J = 7.2 Hz, 2H), 3.63 (d, J = 6.4 Hz, 2H), 2.91 (s, 6H), 2.64 (t, J = 5.6 Hz, 1H), 1.73 (s, 3H), 1.67 (s, 3H); MS m/z: 637.3 [M + 1]. |

TABLE 1-continued

Exemplary Compounds of Formula (I).

| Name | Structure | Characterization Data |
| --- | --- | --- |
| Compound 110<br>(S)-3-((3-acrylamidophenyl)amino)-N-(2-(dimethylamino)-1-phenylethyl)-6,6-dimethyl-4,6-dihydropyrrolo[3,4-c]pyrazole-5(1H)-carboxamide | | $^1$H NMR (TFA salt): 400 MHz (DMSO-$d_6$) δ 9.94 (s, 1H), 8.90 (s, 1H), 8.24 (s, 1H), 7.35-7.27 (m, 4H), 7.24-7.22 (m, 2H), 7.08-7.02 (m, 2H), 6.56-6.52 (m, 2H), 6.38 (dd, J = 16.8, 10.0 Hz, 1H), 6.16 (dd, J = 16.8, 2.0 Hz, 1H), 5.67 (dd, J = 10.0, 2.0 Hz, 1H), 5.29-5.22 (m, 1H), 4.31 (q, J = 11.2 Hz, 2H), 3.39-3.34 (m, 1H), 3.28-3.22 (m, 1H), 2.80 (d, J = 4.8 Hz, 1H), 2.73 (d, J = 4.8 Hz, 1H), 1.59 (s, 3H), 1.53 (s, 3H); MS m/z: 488.3 [M + 1]. |
| Compound 111<br>(S)-3-((4-acrylamidophenyl)amino)-N-(2-(dimethylamino)-1-phenylethyl)-6,6-dimethyl-4,6-dihydropyrrolo[3,4-c]pyrazole-5(1H)-carboxamide | | $^1$H NMR (TFA salt): 400 MHz (DMSO-$d_6$) δ 9.86 (s, 1H), 8.91 (s, 1H), 8.13 (s, 1H), 7.49-7.43 (m, 2H), 7.40-7.27 (m, 5H), 7.22 (m, 1H), 6.82 (d, J = 9.2 Hz, 1H), 6.55 (d, J = 9.2 Hz, 1H), 6.34 (dd, J = 16.8, 10.0 Hz, 1H), 6.13 (dd, J = 16.8, 2.0 Hz, 1H), 5.62 (dd, J = 10.0, 2.0 Hz, 1H), 5.29-5.22 (m, 1H), 4.33 (d, J = 11.2 Hz, 1H), 4.19 (d, J = 11.2 Hz, 1H), 3.42-3.36 (m, 1H), 3.29-3.23 (m, 1H), 2.81 (d, J = 4.8 Hz, 1H), 2.74 (d, J = 4.8 Hz, 1H), 1.60 (s, 3H), 1.51 (s, 3H); MS m/z: 488.3 [M + 1]. |
| Compound 112<br>(S)-3-(3-(4-acrylamidobenzamido)benzamido)-N-(2-(dimethylamino)-1-phenylethyl)-6,6-dimethyl-4,6-dihydropyrrolo[3,4-c]pyrazole-5(1H)-carboxamide | | $^1$H NMR (TFA salt): 400 MHz (DMSO-$d_6$) δ 10.97 (s, 1H), 10.53 (s, 1H), 10.40 (s, 1H), 9.04 (s, 1H), 8.62 (m, 1H), 8.04 (d, J = 9.2 Hz, 2H), 7.89 (d, J = 9.2 Hz, 2H), 7.83 (d, J = 7.6 Hz, 1H), 7.57-7.44 (m, 4H), 7.36 (t, J = 7.2 Hz, 1H), 6.83 (d, J = 9.2 Hz, 1H), 6.54 (dd, J = 17.2, 10.0 Hz, 1H), 6.37 (dd, J = 17.2, 2.0 Hz, 1H), 5.88 (dd, J = 10.0, 2.0 Hz, 1H), 5.43-5.37 (m, 1H), 4.86 (d, J = 12.4 Hz, 1H), 4.64 (d, J = 11.6 Hz, 1H), 2.95 (d, J = 8.4 Hz, 3H), 2.90 (d, J = 8.4 Hz, 3H), 1.74 (s, 3 H), 1.66 (s, 3 H); MS m/z: 635.3 [M + 1]. |

TABLE 1-continued

Exemplary Compounds of Formula (I).

| Name | Structure | Characterization Data |
| --- | --- | --- |
| Compound 113<br>3-((R)-1-acryloylpiperidine-3-carboxamido)-N-((S)-2-(dimethylamino)-1-phenylethyl)-6,6-dimethyl-4,6-dihydropyrrolo[3,4-c]pyrazole-5(1H)-carboxamide | 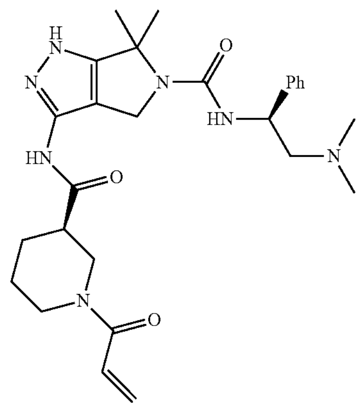 [SMILES: C=CC(=O)N1CCC[C@@H](C(=O)Nc2n[nH]c3c2CN(C(=O)N[C@H](CN(C)C)c2ccccc2)C3(C)C)C1] | $^1$H NMR (TFA salt): 600 MHz (DMSO-$d_6$) δ 10.56 (d, J = 19.8 Hz, 1H), 8.95 (s, 1H), 7.41-7.36 (m, 3H), 7.31-7.27 (m, 1H), 6.87-6.79 (m, 1H), 6.72 (d, J = 9.0 Hz, 1H), 6.08 (d, J = 16.2 Hz, 1H), 5.66 (d, J = 10.2 Hz, 1H), 5.32 (m, 1H), 4.69 (m, 1H), 4.47 (m, 2H), 4.03 (m, 2H), 3.53 (t, J = 12.0 Hz, 2H), 3.35-3.30 (m, 1H), 3.18-3.12 (m, 1H), 2.99 (t, J = 13.2 Hz, 1H), 2.85 (d, J = 5.4 Hz, 3H), 2.82 (d, J = 4.8 Hz, 3H), 2.70 (t, J = 12.0 Hz, 1H), 1.95 (m, 1H), 1.73 (m, 1H), 1.62 (s, 3H), 1.53 (s, 3H), 1.33 (m, 1H); MS m/z: 508.3 [M + 1]. |
| Compound 114<br>3-((S)-1-acryloylpiperidine-3-carboxamido)-N-((S)-2-(dimethylamino)-1-phenylethyl)-6,6-dimethyl-4,6-dihydropyrrolo[3,4-c]pyrazole-5(1H)-carboxamide | 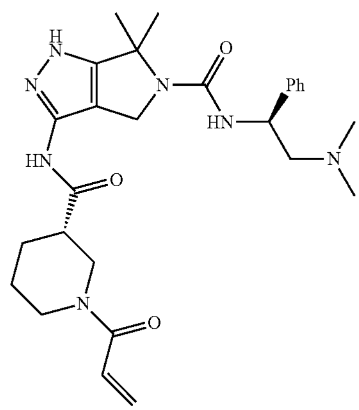 [SMILES: C=CC(=O)N1CCC[C@H](C(=O)Nc2n[nH]c3c2CN(C(=O)N[C@H](CN(C)C)c2ccccc2)C3(C)C)C1] | $^1$H NMR (TFA salt): 400 MHz (DMSO-$d_6$) δ 10.50 (d, J = 15.6 Hz, 1H), 8.90 (s, 1H), 7.37-7.31 (m, 4H), 7.25-7.21 (m, 1H), 6.82-6.72 (m, 1H), 6.66 (d, J = 8.8 Hz, 1H), 6.03 (d, J = 16.4 Hz, 1H), 5.61 (d, J = 10.8 Hz, 1H), 5.27 (m, 1H), 4.62 (m, 1H), 4.43 (m, 2H), 4.07-3.96 (m, 2H), 3.13-3.05 (m, 2H), 2.94 (t, J = 12.0 Hz, 1H), 2.81 (d, J = 5.2 Hz, 3H), 2.77 (d, J = 5.2 Hz, 3H), 2.69-2.57 (m, 1H), 1.89 (m, 1H), 1.67 (m, 1H), 1.57 (s, 3H), 1.49 (s, 3H), 1.29 (m, 1H); MS m/z: 508.3 [M + 1]. |
| Compound 115<br>3-((1-(4-acrylamidobenzoyl)piperidin-3-yl)amino)-N-((S)-2-(dimethylamino)-1-phenylethyl)-6,6-dimethyl-4,6-dihydropyrrolo[3,4-c]pyrazole-5(1H)-carboxamide | 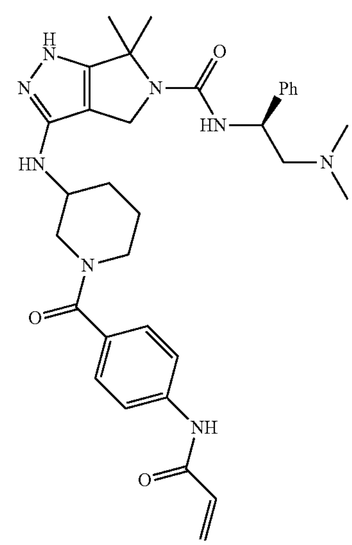 [SMILES: C=CC(=O)Nc1ccc(C(=O)N2CCCC(Nc3n[nH]c4c3CN(C(=O)N[C@H](CN(C)C)c3ccccc3)C4(C)C)C2)cc1] | $^1$H NMR (TFA salt): 600 MHz (DMSO-$d_6$) δ 10.29 (s, 1H), 9.10 (s, 1H), 7.72-7.55 (m, 1H), 7.49-7.26 (m, 7H), 6.73-6.61 (m, 1H), 6.49-6.40 (m, 1H), 6.27-6.24 (m, 1H), 5.77-5.75 (m, 1H), 5.36-5.26 (m, 1H), 4.55-4.50 (m, 1H), 4.30-4.24 (m, 2H), 3.55-3.45 (m, 3H), 3.38-3.32 (m, 2H), 3.28-3.07 (m, 2H), 2.88 (m, 3H), 2.85 (m, 1H), 2.82 (m, 3H), 2.00-1.90 (m, 1H), 1.85-1.70 (m, 1H), 1.65-1.50 (m, 6H), 1.09-1.03 (m, 1H); MS m/z: 599.4 [M + 1]. |

TABLE 1-continued

Exemplary Compounds of Formula (I).

| Name | Structure | Characterization Data |
| --- | --- | --- |
| Compound 116 (S)-3-((1-(4-acrylamidobenzoyl)piperidin-4-yl)amino)-N-(2-(dimethylamino)-1-phenylethyl)-6,6-dimethyl-4,6-dihydropyrrolo[3,4-c]pyrazole-5(1H)-carboxamide | 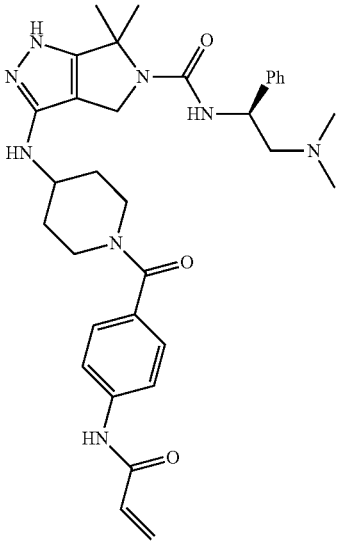 [SMILES: C=CC(=O)Nc1ccc(C(=O)N2CCC(Nc3n[nH]c4c3CN(C(=O)N[C@H](CN(C)C)c3ccccc3)C4(C)C)CC2)cc1] | $^1$H NMR: 600 MHz (DMSO-d$_6$) δ 11.30 (br, 1H), 10.30 (s, 1H), 7.71 (d, J = 9.0 Hz, 2H), 7.36-7.33 (m, 4H), 7.28 (t, J = 7.8 Hz, 2H), 7.18 (t, J = 7.8 Hz, 1H), 6.43 (dd, J = 16.8, 10.2 Hz, 1H), 6.27 (dd, J = 16.8, 2.2 Hz, 1H), 5.95 (d, J = 6.0 Hz, 1H), 5.77 (dd, J = 10.2, 2.2 Hz, 1H), 5.33-5.20 (m, 1H), 4.82 (q, J = 7.2 Hz, 1H), 4.26 (q, J = 12.0 Hz, 2H), 3.72-3.58 (m, 1H), 3.16-3.03 (m, 2H), 2.60 (m, 1H), 2.42 (m, 1H), 2.19 (s, 6H), 1.89 (m, 2H), 1.54 (s, 3H), 1.48 (s, 3H), 1.36 (m, 2H); MS m/z: 599.4 [M + 1]. |
| Compound 117 3-(((1R,3S)-3-(4-acrylamidobenzamido)cyclohexyl)amino)-N-((S)-2-(dimethylamino)-1-phenylethyl)-6,6-dimethyl-4,6-dihydropyrrolo[3,4-c]pyrazole-5(1H)-carboxamide | 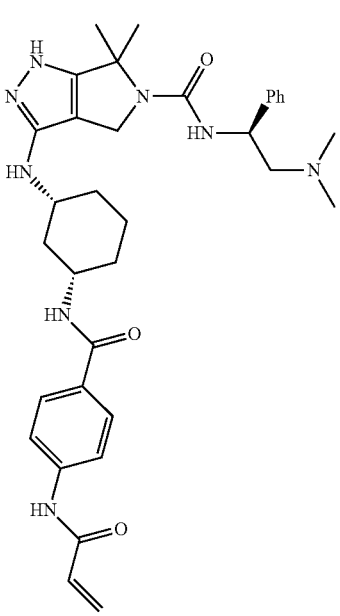 [SMILES: C=CC(=O)Nc1ccc(C(=O)N[C@H]2CCC[C@@H](Nc3n[nH]c4c3CN(C(=O)N[C@H](CN(C)C)c3ccccc3)C4(C)C)C2)cc1] | $^1$H NMR (TFA salt): 600 MHz (DMSO-d$_6$) δ 10.35 (d, J = 3.0 Hz, 1H), 9.11 (s, 1H), 8.09 (d, J = 7.8 Hz, 1H), 7.80 (dd, J = 9.0, 2.0 Hz, 2H), 7.71 (dd, J = 9.0, 1.8 Hz, 2H), 7.46-7.42 (m, 2H), 7.39-7.35 (m, 2H), 7.30-7.28 (m, 1H), 6.68 (t, J = 7.8 Hz, 1H), 6.44 (dd, J = 16.8, 10.2 Hz, 1H), 6.27 (dd, J = 16.8, 2.2 Hz, 1H), 5.78 (dd, J = 10.2, 2.2 Hz, 1H), 5.34-5.30 (m, 1H), 4.52 (t, J = 12.0 Hz, 1H), 4.38 (dd, J = 13.2, 12.0 Hz, 2H), 4.17-4.10 (m, 1H), 3.67 (m, 2H), 3.48 (t, J = 12.0 Hz, 2H), 3.37-3.33 (m, 2H), 2.88 (m, 3H), 2.82 (m, 3H), 1.89-1.80 (m, 2H), 1.71-1.60 (m, 3H), 1.62 (s, 3H), 1.55 (s, 3H), 1.36 (m, 2H); MS m/z: 613.4 [M + 1]. |

TABLE 1-continued

Exemplary Compounds of Formula (I).

| Name | Structure | Characterization Data |
| --- | --- | --- |
| Compound 118<br>3-(((1R,3R)-3-(4-acrylamidobenzamido)cyclohexyl)amino)-N-((S)-2-(dimethylamino)-1-phenylethyl)-6,6-dimethyl-4,6-dihydropyrrolo[3,4-c]pyrazole-5(1H)-carboxamide | | $^1$H NMR: 600 MHz (DMSO-$d_6$) δ 11.22 (br, 1H), 10.32 (s, 1H), 8.19 (dd, J = 7.8, 3.0 Hz, 1H), 7.81 (dd, J = 8.4, 3.0 Hz, 2H), 7.70 (dd, J = 8.4, 5.4 Hz, 2H), 7.35 (d, J = 7.8 Hz, 2H), 7.30-7.26 (m, 2H), 7.20-7.16 (m, 1H), 6.43 (dd, J = 16.8, 10.2 Hz, 1H), 6.27 (dd, J = 16.8, 2.2 Hz, 1H), 6.01 (m, 1H), 5.77 (dd, J = 10.2, 2.2 Hz, 1H), 5.25-5.17 (m, 1H), 4.89-4.82 (m, 1H), 4.36-4.27 (m, 2H), 3.90-3.83 (m, 1H), 3.08-3.01 (m, 1H), 2.68-2.60 (m, 1H), 2.50-2.42 (m, 1H), 2.21 (s, 3H), 2.19 (s, 3H), 2.13-2.08 (m, 1H), 1.92-1.86 (m, 1H), 1.85-1.79 (m, 1H), 1.78-1.73 (m, 1H), 1.54 (s, 3H), 1.48 (d, J = 5.4 Hz, 3H), 1.42-1.35 (m, 1H), 1.28-1.19 (m, 2H), 1.11-1.03 (m, 1H); MS m/z: 613.4 [M + 1]. |
| Compound 119<br>(S)-3-((4-(4-acrylamidobenzamido)cyclohexyl)amino)-N-(2-(dimethylamino)-1-phenylethyl)-6,6-dimethyl-4,6-dihydropyrrolo[3,4-c]pyrazole-5(1H)-carboxamide | | $^1$H NMR: 600 MHz (DMSO-$d_6$) δ 11.30 (br, 1H), 10.32 (s, 1H), 8.11 (d, J = 7.8 Hz, 1H), 7.80 (d, J = 8.4 Hz, 2H), 7.71 (d, J = 8.4 Hz, 2H), 7.37 (m, 2H), 7.32 (m, 2H), 7.22 (m, 1H), 6.43 (dd, J = 16.8, 10.2 Hz, 1H), 6.27 (d, J = 16.8 Hz, 1H), 6.13 (m, 1H), 5.78 (d, J = 10.2, Hz, 1H), 5.13-4.94 (m, 2H), 4.35-4.26 (m, 2H), 3.75-3.49 (m, 1H), 3.47 (t, J = 5.4 Hz, 1H), 3.40 (t, J = 5.4 Hz, 1H), 3.07-2.97 (m, 2H), 2.50-2.32 (m, 4H), 1.98 (d, J = 10.8 Hz, 3H), 1.87 (d, J = 10.2 Hz, 3H), 1.77-1.70 (m, 1H), 1.67-1.60 (m, 1H), 1.56 (s, 3H), 1.49 (s, 3H), 1.47-1.38 (m, 2H), 1.37-1.33 (m, 1H), 1.29-1.17 (m, 4H), 1.15 (t, J = 7.2 Hz, 1H), 0.85-0.76 (m, 1H); MS m/z: 613.4 [M + 1]. |

| Name | Structure | Characterization Data |
|---|---|---|
| Compound 120 | 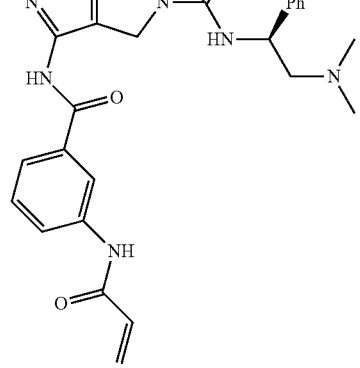 | |
| Compound 121 | 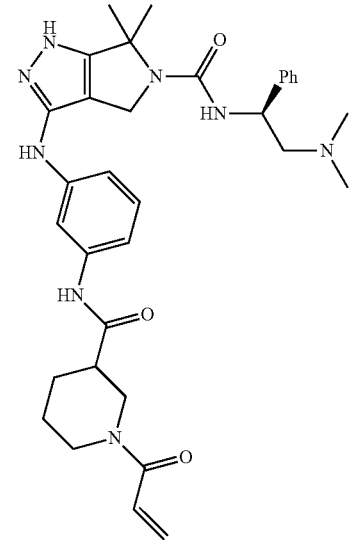 [SMILES: C=CC(=O)N1CCCC(C(=O)Nc2cccc(Nc3n[nH]c4c3CN(C(=O)N[C@H](CN(C)C)c3ccccc3)C4(C)C)c2)C1] | |
| Compound 122 | 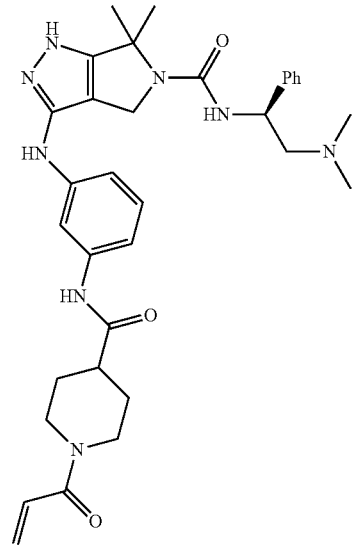 [SMILES: C=CC(=O)N1CCC(C(=O)Nc2cccc(Nc3n[nH]c4c3CN(C(=O)N[C@H](CN(C)C)c3ccccc3)C4(C)C)c2)CC1] | |

TABLE 1-continued

Exemplary Compounds of Formula (I).

| Name | Structure | Characterization Data |
|---|---|---|
| Compound 123 | 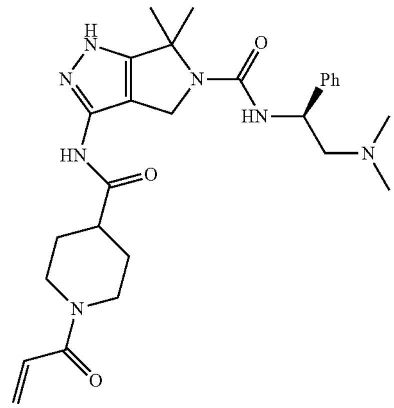 [SMILES: C=CC(=O)N1CCC(C(=O)Nc2n[nH]c3c2CN(C(=O)N[C@H](CN(C)C)c2ccccc2)C3(C)C)CC1] | |
| Compound 124 | 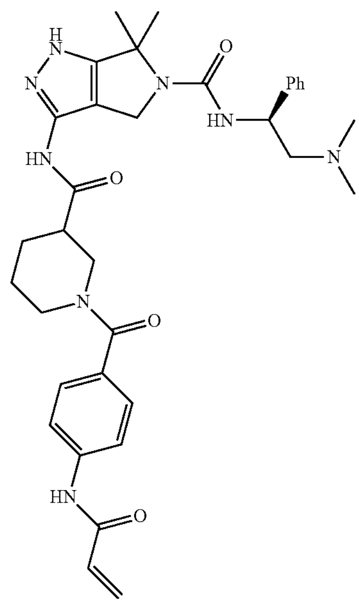 [SMILES: C=CC(=O)Nc1ccc(C(=O)N2CCCC(C(=O)Nc3n[nH]c4c3CN(C(=O)N[C@H](CN(C)C)c3ccccc3)C4(C)C)C2)cc1] | |
| Compound 125 | 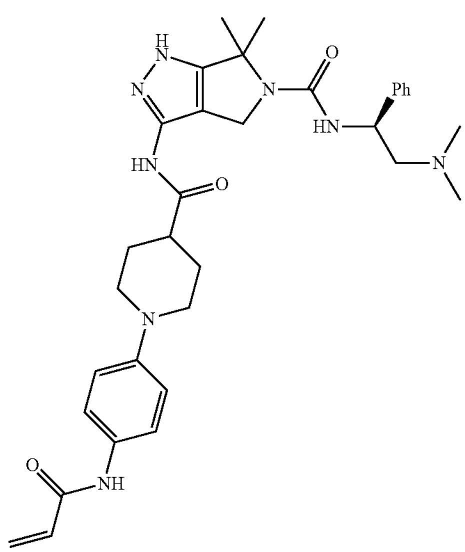 [SMILES: C=CC(=O)Nc1ccc(N2CCC(C(=O)Nc3n[nH]c4c3CN(C(=O)N[C@H](CN(C)C)c3ccccc3)C4(C)C)CC2)cc1] | |

TABLE 1-continued

Exemplary Compounds of Formula (I).

| Name | Structure | Characterization Data |
| --- | --- | --- |
| Compound 126 | 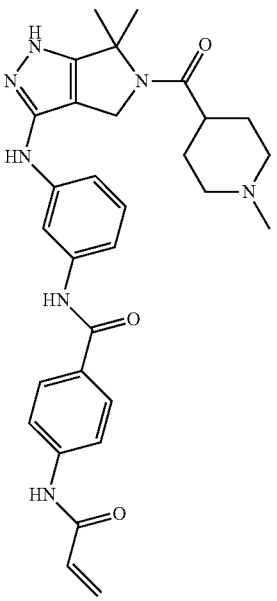 [SMILES: C=CC(=O)Nc1ccc(C(=O)Nc2cccc(Nc3n[nH]c4c3CN(C(=O)C3CCN(C)CC3)C4(C)C)c2)cc1] | |
| Compound 127 | 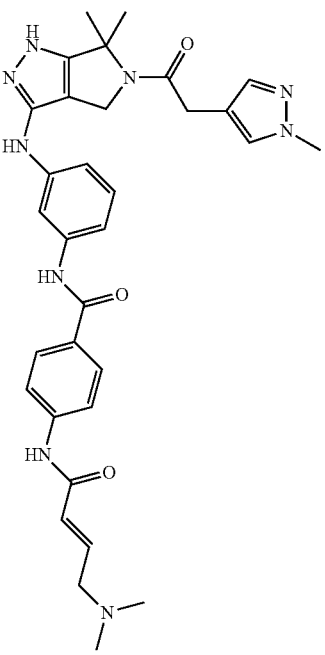 [SMILES: CN(C)C/C=C/C(=O)Nc1ccc(C(=O)Nc2cccc(Nc3n[nH]c4c3CN(C(=O)Cc3cnn(C)c3)C4(C)C)c2)cc1] | |

Pharmaceutical Compositions and Administration

The pharmaceutical compositions described herein may be useful in treating and/or preventing proliferative diseases (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject. The compositions described herein may also be useful for inhibiting the activity of a protein kinase (e.g., CDK (e.g., CDK7)) in a subject, biological sample, tissue, or cell. The compositions described herein may also be useful for inducing apoptosis in a cell.

The present disclosure provides pharmaceutical compositions comprising a compound described herein (e.g., a compound of Formula (I)), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical composition of the invention comprises a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. In certain embodiments, the compound described herein, or a pharmaceutically acceptable salt, solvate, hydrate, polymorph, co-crystal, tautomer, stereoisomer, isotopically labeled derivative, or prodrug thereof, is provided in an effective amount in the pharmaceutical composition.

In certain embodiments, the effective amount is a therapeutically effective amount (e.g., amount effective for treating a proliferative disease in a subject in need thereof). In certain embodiments, the effective amount is an amount effective for inhibiting the activity of a protein kinase (e.g., CDK (e.g., CDK7)) in a subject in need thereof. In certain embodiments, the effective amount is an amount effective for inhibiting the activity of a protein kinase (e.g., CDK (e.g., CDK7)) in a cell. In certain embodiments, the effective amount is an amount effective for inducing apoptosis in a cell. In certain embodiments, the effective amount is a prophylactically effective amount (e.g., amount effective for preventing a proliferative disease in a subject in need thereof and/or for keeping a subject in need thereof in remission of a proliferative disease).

In certain embodiments, a protein kinase described herein is a CDK. In certain embodiments, a protein kinase described herein is CDK1, CDK2, CDK3, CDK4, CDK5, CDK6, CDK7, CDK8, CDK9, CDK10, CDK11, CDK12, CDK13, CDK14, CDK15, CDK16, CDK17, CDK18, CDK19, or CDK20. In certain embodiments, a protein kinase described herein is CDK7. In certain embodiments, a protein kinase described herein is CDK12. In certain embodiments, a protein kinase described herein is CDK13. In certain embodiments, a protein kinase described herein is a Src family kinase. In certain embodiments, a protein kinase described herein is SRC. In certain embodiments, a protein kinase described herein is FGR. In certain embodiments, a protein kinase described herein is BUB1B. In certain embodiments, a protein kinase described herein is CHEK2. In certain embodiments, a protein kinase described herein is HIPK4. In certain embodiments, a protein kinase described herein is PRKCQ. In certain embodiments, a protein kinase described herein is RET. In certain embodiments, a protein kinase described herein is MELK. In certain embodiments, a protein kinase described herein is IRAK1, IRAK4, BMX, or PI3K. In certain embodiments, a protein kinase described herein is ABL, ARG, BLK, CSK, EphB1, EphB2, FGR, FRK, FYN, SRC, YES, LCK, LYN, MAP2K5, NLK, p38a, SNRK, or TEC. In certain embodiments, a protein kinase described herein is ABL1(H396P)-phosphorylated, ABL1-phosphorylated, BLK, EPHA4, EPHB2, EPHB3, EPHB4, FGR, JAK3(JH1domain-catalytic), KIT, KIT(L576P), KIT(V559D), PDGFRB, SRC, YES, ABL1(H396P)-nonphosphorylated, ABL1(Y253F)-phosphorylated, ABL1-nonphosphorylated, FRK, LYN, ABL1(Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1(F317L)-nonphosphorylated, FYN, LCK, EPHA2, ABL1(M351T)-phosphorylated, TXK, EGFR(L858R), EGFR(L861Q), ERBB2, ERBB3, EPHA5, ABL1(F317I)-nonphosphorylated, EGFR(L747-E749del, A750P), CSK, EPHA1, ABL1(F317L)-phosphorylated, BRAF(V600E), EGFR, KIT-autoinhibited, or EGFR(E746-A750del). In certain embodiments, a protein kinase described herein is ABL1(F317L)-nonphosphorylated, ABL1(H396P)-nonphosphorylated, ABL1(H396P)-phosphorylated, ABL1-phosphorylated, BLK, EPHA4, EPHB2, EPHB3, EPHB4, JAK3(JH1domain-catalytic), KIT, KIT(L576P), KIT (V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1(Q252H)-phosphorylated, MEK5, ABL1 (Q252H)-nonphosphorylated, ABL2, FYN, EPHB1, ABL1 (E255K)-phosphorylated, ABL1(F317L)-phosphorylated, EPHA1, ABL1(M351T)-phosphorylated, ERBB4, TXK, LCK, EPHA8, SIK, EPHA5, EGFR(L861Q), CSF1R-autoinhibited, BRAF(V600E), BRK, CSK, KIT(D816V), KIT-autoinhibited, EGFR(L747-T751 del,Sins), EGFR(L858R), EGFR(L747-E749del, A750P), or CSF1R.

In certain embodiments, the effective amount is an amount effective for inhibiting the activity of a protein kinase (e.g., CDK (e.g., CDK7)) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a protein kinase (e.g., CDK (e.g., CDK7)) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a protein kinase (e.g., CDK (e.g., CDK7)) by a range between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents) useful in treating and/or preventing a proliferative disease. The compounds or compositions can be administered in combination with additional pharmaceutical agents that improve their activity (e.g., activity (e.g., potency and/or efficacy) in treating a proliferative disease in a subject in need thereof, in preventing a proliferative disease in a subject in need thereof, and/or in inhibiting the activity of a protein kinase (e.g., CDK (e.g., CDK7) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies in treating and/or preventing a proliferative disease. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease. In certain embodiments, the additional pharmaceutical agent is a pharmaceutical agent useful in preventing a proliferative disease. In certain embodiments, the additional pharmaceutical agent is a pharmaceutical agent useful in inhibiting the activity of a protein kinase (e.g., CDK (e.g., CDK7)) in a subject, biological sample, tissue, or cell. In certain embodiments, the additional pharmaceutical agent is a pharmaceutical agent useful in inducing apoptosis in a cell. In certain embodiments, the additional pharmaceutical agent is a pharmaceutical agent approved by a regulatory agency (e.g., the US FDA) for treating and/or preventing a proliferative disease. Each additional pharmaceutical agent may be administered at a dose and/or on a time schedule determined for that pharmaceutical agent. The additional pharmaceutical agent(s) may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURI-NETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is an anti-myelodysplasia agent. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), or a combination thereof.

In certain embodiments, the additional pharmaceutical agent is an anti-macroglobulinemia agent.

In certain embodiments, the additional pharmaceutical agent is LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZAL- TRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a protein kinase inhibitor (e.g., tyrosine protein kinase inhibitor). In certain embodiments, the additional pharmaceutical agent is an inhibitor of a Src family kinase. In certain embodiments, the additional pharmaceutical agent is a CDK inhibitor. In certain embodiments, the additional pharmaceutical agent is a CDK7 inhibitor. In certain embodiments, the additional pharmaceutical agent is an inhibitor of one or more protein kinases selected from the group consisting of IRAK1, IRAK4, BMX, and PI3K. In certain embodiments, the additional pharmaceutical agent is an inhibitor of one or more protein kinases selected from the group consisting of BUB1B, CDK2, CDK9, CHEK2, FGR, HIPK4, PRKCQ, RET, SRC, or MELK. In certain embodiments, the additional pharmaceutical agent is an inhibitor of one or more protein kinases selected from the group consisting of ABL, ARG, BLK, CSK, EphB1, EphB2, FGR, FRK, FYN, SRC, YES, LCK, LYN, MAP2K5, NLK, p38a, SNRK, and TEC. In certain embodiments, the additional pharmaceutical agent is an inhibitor of one or more protein kinases selected from the group consisting of ABL1(H396P)-phosphorylated, ABL1-phosphorylated, BLK, EPHA4, EPHB2, EPHB3, EPHB4, FGR, JAK3(JH1domain-catalytic), KIT, KIT(L576P), KIT (V559D), PDGFRB, SRC, YES, ABL1(H396P)-nonphosphorylated, ABL1(Y253F)-phosphorylated, ABL1-nonphosphorylated, FRK, LYN, ABL1(Q252H)-nonphosphorylated, DDR1, EPHB1, ERBB4, p38-alpha, ABL2, ABL1(Q252H)-phosphorylated, SIK, EPHA8, MEK5, ABL1(E255K)-phosphorylated, ABL1(F317L)-nonphosphorylated, FYN, LCK, EPHA2, ABL1(M351T)-phosphorylated, TXK, EGFR(L858R), EGFR(L861Q), ERBB2, ERBB3, EPHA5, ABL1(F317I)-nonphosphorylated, EGFR(L747-E749del, A750P), CSK, EPHA1, ABL1 (F317L)-phosphorylated, BRAF(V600E), EGFR, KIT-autoinhibited, and EGFR(E746-A750del). In certain embodiments, the additional pharmaceutical agent is an inhibitor of one or more protein kinases selected from the group consisting of ABL1(F317L)-nonphosphorylated, ABL1(H396P)-nonphosphorylated, ABL1(H396P)-phosphorylated, ABL1-phosphorylated, BLK, EPHA4, EPHB2, EPHB3, EPHB4, JAK3(JH1domain-catalytic), KIT, KIT (L576P), KIT(V559D), LYN, PDGFRB, SRC, YES, ABL1-nonphosphorylated, ABL1(Y253F)-phosphorylated, ERBB3, FGR, FRK, p38-alpha, ABL1(F317I)-nonphosphorylated, DDR1, EPHA2, ABL1(Q252H)-phosphorylated, MEK5, ABL1(Q252H)-nonphosphorylated, ABL2, FYN, EPHB1, ABL1(E255K)-phosphorylated, ABL1(F317L)-phosphorylated, EPHA1, ABL1(M351T)-phosphorylated, ERBB4, TXK, LCK, EPHA8, SIK, EPHA5, EGFR(L861Q), CSF1R-autoinhibited, BRAF(V600E), BRK, CSK, KIT (D816V), KIT-autoinhibited, EGFR(L747-T751del,Sins), EGFR(L858R), EGFR(L747-E749del, A750P), and CSF1R. In certain embodiments, the additional pharmaceutical agent is an anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered in combination with an anti-cancer therapy including, but not limited to, transplantation (e.g., bone marrow transplantation, stem cell transplantation), surgery, radiation therapy, immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Methods of Treatment and Uses

The present invention also provides methods for the treatment or prevention of a proliferative disease (e.g., cancers (e.g., leukemia, acute lymphoblastic leukemia, lymphoma, Burkitt's lymphoma, melanoma, multiple myeloma, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases).

The compounds described herein may:

exhibit kinase inhibitory activity, exhibit the ability to inhibit cyclin-dependent kinase (CDK), exhibit the ability to inhibit cyclin-dependent kinase 7 (CDK7), exhibit the ability to inhibit cyclin-dependent kinase 7 (CDK7), without inhibiting another cyclin-dependent kinase (CDK), exhibit a therapeutic effect and/or preventative effect in the treatment of cancers, exhibit a therapeutic effect and/or preventative effect in the treatment of Myc-dependent cancers, and/or exhibit a therapeutic profile (e.g., optimum safety and curative effect) that is superior to existing chemotherapeutic agents.

Without wishing to be bound by any particular theory, the compounds described herein may be able to bind (e.g., covalently modify) a protein kinase described herein. In certain embodiments, the $R^2$ group of a compound described herein may be able to bind (e.g., covalently modify) to the protein kinase. In certain embodiments, the $R^2$ group of a compound described herein may be able to covalently bind a cysteine residue of the protein kinase. In certain embodiments, the $R^2$ group of a compound described herein may be able to covalently bind Cys312 residue of CDK7.

In another aspect, the present disclosure provides methods of inhibiting the activity of a protein kinase in a subject, the methods comprising administering to the subject an effective amount (e.g., therapeutically effective amount) of a compound, or pharmaceutical composition thereof, as described herein.

In another aspect, the present disclosure provides methods of inhibiting the activity of a protein kinase in a biological sample, the methods comprising contacting the biological sample with an effective amount of a compound, or pharmaceutical composition thereof, as described herein.

In another aspect, the present disclosure provides methods of inhibiting the activity of a protein kinase in a tissue, the methods comprising contacting the tissue with an effective amount of a compound, or pharmaceutical composition thereof, as described herein.

In another aspect, the present disclosure provides methods of inhibiting the activity of a protein kinase in a cell, the methods comprising contacting the cell with an effective amount of a compound, or pharmaceutical composition thereof, as described herein.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, a biological sample described herein is bone marrow, lymph node, spleen, or blood.

In certain embodiments, a cell described herein is in vitro. In certain embodiments, a cell described herein is ex vivo. In certain embodiments, a cell described herein is in vivo. In certain embodiments, a cell described herein is a malignant cell (e.g., malignant blood cell). In certain embodiments, a cell described herein is a malignant hematopoietic stem cell (e.g., malignant myeloid cell or malignant lymphoid cell). In certain embodiments, a cell described herein is a malignant lymphocyte (e.g., malignant T-cell or malignant B-cell). In certain embodiments, a cell described herein is a malignant red blood cell, malignant white blood cell, or malignant platelet. In certain embodiments, a cell described herein is a malignant neutrophil, malignant macrophage, or malignant plasma cell.

The proliferative disease to be treated or prevented using the compounds described herein may be associated with overexpression of a kinase, such as cyclin-dependent kinase (CDK). The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are CDC2 (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins.

Modulation of the expression levels, degradation rates, protein levels, and activity levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the prerequisite biochemical criteria at a given cell cycle checkpoint, i.e., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

CDK7, a member of the CDK family, was originally isolated as the catalytic subunit of the trimeric CDK-activating kinase (CAK) complex. This complex, consisting of CDK7, cyclin H, and MAT 1, is responsible for activation of the mitotic promoting factor in vitro. The discovery that CDK7 was also a component of the basal transcription repair factor IIH (TFIIH) implicated a dual role for CDK7 in transcription as part of TFIIH and in the control of the cell cycle as the trimeric CAK complex. TFIIH is a multi-subunit protein complex identified as a factor required for RNA polymerase II (RNAP II)-catalyzed transcription, and subsequently this complex was found to play a key role in nucleotide excision repair. CDK7 is a component of at least three complexes, i.e., the trimeric CAK complex, the quaternary complex with the XPD (or ERCC2, a protein involved in transcription-coupled nucleotide excision repair), and the nine-subunit TFIIH complex. The two functions of CDK7 in CAK and CTD phosphorylation support critical facets of cellular proliferation, cell cycling, and transcription. Overexpression of CDK7 may inhibit apoptosis, promote transcription and cell proliferation, and/or disrupt DNA repair, and therefore, cause proliferative diseases. In certain embodiments, the proliferative disease to be treated or prevented using the compounds described herein may be associated with overexpression of a CDK (e.g., CDK7).

A proliferative disease may be associated with aberrant activity of a CDK (e.g., CDK7). Aberrant activity of a CDK (e.g., CDK7) may be an elevated and/or an inappropriate activity of the CDK. Deregulation of cell cycle progression is a characteristic of a proliferative disease, and a majority of proliferative diseases have abnormalities in some component of CDK (e.g., CDK7) activity, frequently through elevated and/or inappropriate CDK activation. Inhibition of the catalytic activity of CDK7 would be expected to inhibit cell cycle progression by blocking the phosphorylation of cell cycle CDKs, and would additionally inhibit transcription of effectors of cell division. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of CDK7 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Apoptosis is the process of programmed cell death. Inhibition of apoptosis may result in uncontrolled cell proliferation and, therefore, may cause proliferative diseases. The cell cycle CDKs (CDK1, 2, 4, and 6) are activated by phosphorylation by CDK7/cyclin H (also called CAK). Inhibition of CDK7 would therefore result in cell-cycle arrest at multiple points in the cell cycle due to failure to activate the cell cycle CDKs. CDK 7 activates transcription by phosphorylating the CTD of RNAP II. Inhibition of CTD phosphorylation has been shown to inhibit transcription and reduce expression of short lived proteins, including those involved in apoptosis regulation. It is appreciated in the art that stalling of RNA polymerase may activate p53 (also known as protein 53 or tumor protein 53, a tumor suppressor protein that is encoded in humans by the TP53 gene), leading to apoptosis. Thus, inhibition of the activity of CDK7 are expected to cause cytotoxicity by inducing apoptosis. The compounds described herein, and pharmaceutically acceptable salts, solvates, hydrates, polymorphs, co-crystals, tautomers, stereoisomers, isotopically labeled derivatives, prodrugs, and compositions thereof, may induce apoptosis, and therefore, be useful in treating and/or preventing proliferative diseases.

In certain embodiments, the proliferative disease to be treated or prevented using the compounds described herein is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of MYC (a gene that codes for a transcription factor). In certain embodiments, the cancer is a MYC-dependent cancer. In certain embodiments, the proliferative disease is a hematological malignancy. In certain embodiments, the proliferative disease is a blood cancer. In certain embodiments, the proliferative disease is a hematological malignancy. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is colorectal cancer. In certain embodiments, the proliferative disease is breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

Another aspect of the invention relates to methods of inhibiting the activity of a kinase in a biological sample or subject. In certain embodiments, the kinase is CDK. In certain embodiments, the kinase is CDK7. In certain embodiments, the activity of the kinase is aberrant activity of the kinase. In certain embodiments, the inhibition of the activity of the kinase is irreversible. In other embodiments, the inhibition of the activity of the kinase is reversible. In certain embodiments, the methods of inhibiting the activity of the kinase include attaching a compound described herein to the kinase.

Also provided in the present invention are methods of inhibiting transcription of genes in a biological sample or subject. Genes which may have their transcription inhibited by the compounds herein include MYC, KLF2, E2F2, CDK6, CCND3, E2F3, HNRPDL, TET1, and IL7R.

The present invention also provides methods of inhibiting cell growth in a biological sample or subject.

In still another aspect, the present invention provides methods of inducing apoptosis of a cell in a biological sample or a subject.

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of a CDK. In certain embodiments, the additional pharmaceutical agent is an inhibitor of CDK7. In certain embodiments, the additional pharmaceutical agent is a selective inhibitor of CDK7. In certain embodiments, the additional pharmaceutical agent is a nonselective inhibitor of CDK7. In certain embodiments, the additional pharmaceutical agent is an inhibitor of another CDK. In certain embodiments, the additional pharmaceutical agent is a selective inhibitor of another CDK. In certain embodiments, the additional pharmaceutical agent is a nonselective inhibitor of another CDK. In certain embodiments, the additional pharmaceutical agent is flavopiridol, triptolide, SNS-032 (BMS-387032), PHA-767491, PHA-793887, BS-181, (S)-CR8, (R)-CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a calmodulin-dependent kinase (CaM Kinase). In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase.

In some embodiments, the additional pharmaceutical agent is a topoisomerase inhibitor, a MCL1 inhibitor, a BCL-2 inhibitor, a BCL-xL inhibitor, a BRD4 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In some embodiments, the additional pharmaceutical agent is etoposide, obatoclax, or navitoclax, and the disease to be treated is breast cancer, e.g., triple-negative breast cancer, HER2 positive breast cancer, ER-positive breast cancer, or ER/PR-positive breast cancer. In some embodiments, the additional pharmaceutical agent is etoposide, JIB04, or cisplatin, and the disease to be treated is Ewing's sarcoma. In some embodiments, the additional pharmaceutical agent is JQ1 or NVP2, and the disease to be treated is leukemia, e.g., acute myelogenous leukemia, myeloblastic leukemia, promyelocytic leukemia, myelomonocytic leukemia, monocytic leukemia, monoblastic leukemia, or megakaryoblastic leukemia. In certain embodiments, a pharmaceutical composition described herein further comprises a combination of the additional pharmaceutical agents described herein.

The inventive compounds or compositions may synergistically augment inhibition of CDK7 induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In some embodiments, the activity of a protein kinase is non-selectively inhibited by the compounds or pharmaceutical compositions described herein. In some embodiments, the activity of a protein kinase described herein is selectively inhibited by the compounds or pharmaceutical compositions described herein, compared to the activity of a different protein (e.g., a different protein kinase). In certain embodiments, the activity of CDK (e.g., CDK7) is selectively inhibited by a compound or pharmaceutical composition described herein, compared to the activity of a different protein. In certain embodiments, the activity of CDK7 is selectively inhibited by a compound or pharmaceutical composition described herein, compared to the activity of a different CDK protein. In certain embodiments, the activity of CDK7 is selectively inhibited by a compound or pharmaceutical composition described herein, compared to the activity of CDK12. In certain embodiments, the activity of CDK7 is selectively inhibited by a compound or pharmaceutical composition described herein, compared to the activity of CDK13. In certain embodiments, the activity of CDK7 is selectively inhibited by a compound or pharmaceutical composition described herein, compared to the activity of CDK12 and the activity of CDK13.

The selectivity of a compound or pharmaceutical composition described herein in inhibiting the activity of a protein kinase over a different protein (e.g., a different protein kinase) may be measured by the quotient of the $IC_{50}$ value of the compound or pharmaceutical composition in inhibiting the activity of the different protein over the $IC_{50}$ value of the compound or pharmaceutical composition in inhibiting the activity of the protein kinase. The selectivity of a compound or pharmaceutical composition described herein for a protein kinase over a different protein may also be measured by the quotient of the $K_d$ value of an adduct of the compound or pharmaceutical composition and the different protein over the $K_d$ value of an adduct of the compound or pharmaceutical composition and the protein kinase. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

In certain embodiments, a kit described herein includes a first container comprising a compound or pharmaceutical composition described herein. In certain embodiments, a kit described herein is useful in treating a proliferative disease (e.g., cancers (e.g., leukemia, acute lymphoblastic leukemia, lymphoma, Burkitt's lymphoma, melanoma, multiple myelomia, breast cancer, Ewing's sarcoma, osteosarcoma, brain cancer, neuroblastoma, lung cancer, colorectal cancer), benign neoplasms, diseases associated with angiogenesis, inflammatory diseases, autoinflammatory diseases, and autoimmune diseases) in a subject in need thereof, preventing a proliferative disease in a subject in need thereof, inhibiting the activity of a protein kinase (e.g., CDK (e.g., CDK7)) in a subject, biological sample, tissue, or cell, and/or inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, preventing a proliferative disease in a subject in need thereof, inhibiting the activity of a protein kinase (e.g., CDK (e.g., CDK7)) in a subject, biological sample, tissue, or cell, and/or inducing apoptosis in a cell. A kit described herein may include one or more additional pharmaceutical agents described herein as a separate composition.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthesis of the Compounds

The compounds provided herein can be prepared from readily available starting materials using the following general methods and procedures. Reactions were monitored by thin layer chromatography (TLC) with 0.25 mm E. Merck pre-coated silica gel plates (60 $F_{254}$) and Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ C18 column (4.6×50 mm, 5 μm particle size): solvent gradient=95% A at 0 min, 0% A at 5 min; solvent A=0.5% TFA in Water; solvent B=Methanol; flow rate: 1.5 mL/min. Purification of reaction products was carried out by flash chromatography using CombiFlash® Rf with Teledyne Isco RediSep® Rf High Performance Gold or Silicycle SiliaSep™ High Performance columns (4 g, 12 g, 24 g, 40 g, 80 g or 120 g) or by Waters preparative HPLC system with a C18 column: solvent gradient—100% A at 0 min, 0% A at 15 min; solvent A—0.5% TFA in Water; solvent B=Methanol; flow rate: 20 mL/min. The purity of all compounds was over 95% and was analyzed with Waters LCMS system. $^{1}H$ NMR and $^{13}C$ NMR spectra were obtained using a Varian Inova-600 or 400 MHz spectrometer. Chemical shifts are reported relative to chloroform ($\delta$=7.24) for $^{1}H$ NMR or dimethyl sulfoxide ($\delta$=2.50) for $^{1}H$ NMR and dimethyl sulfoxide ($\delta$=39.51) for $^{13}C$ NMR. Data are reported as (br=broad, s=singlet, d=doublet, t=triplet, q=quartet, m=multiplet).

Example 1. (S)-3-((3-(4-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide (Compound 101)

The synthesis of Compound 101 follows Synthetic Scheme 1. The syntheses of Compounds 102 to 111 (presented in Table 2) follow a corresponding method.

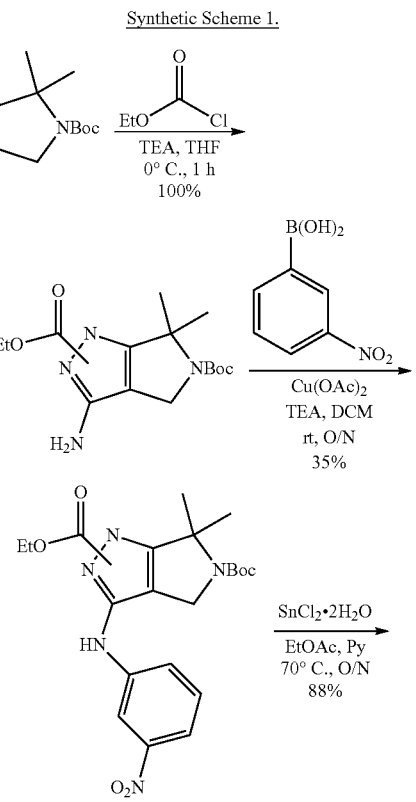

Synthetic Scheme 1.

151
-continued
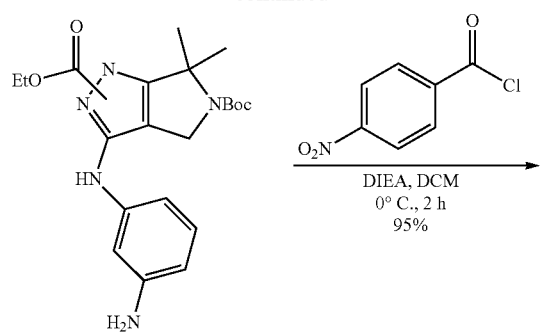
152
-continued
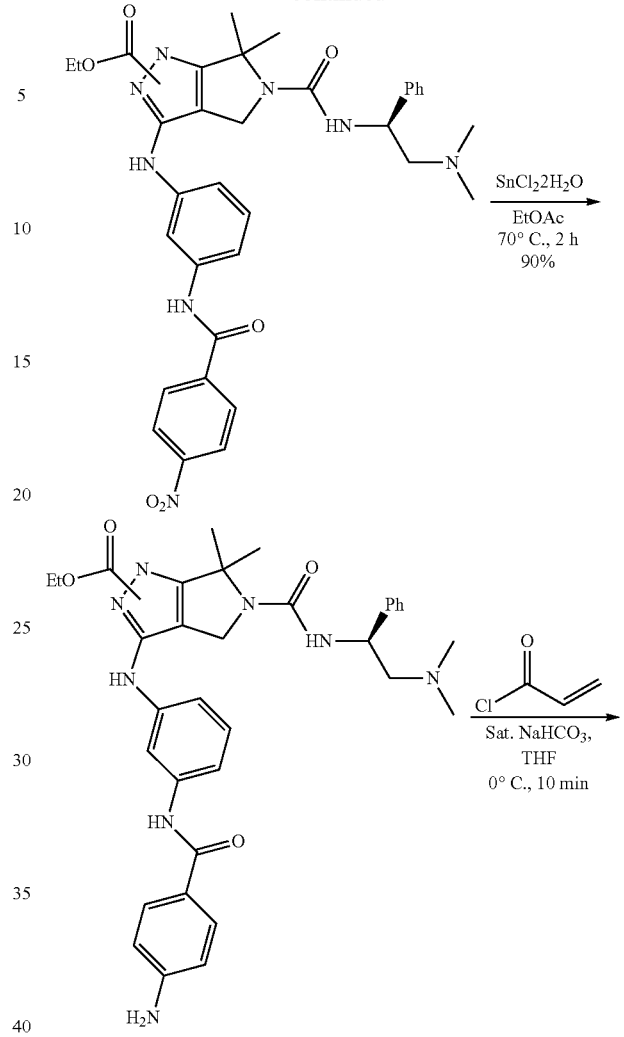
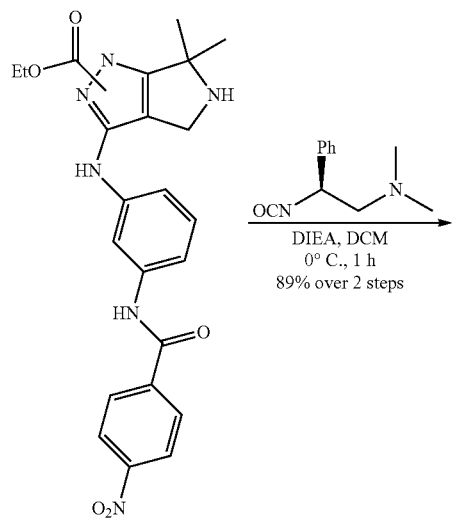
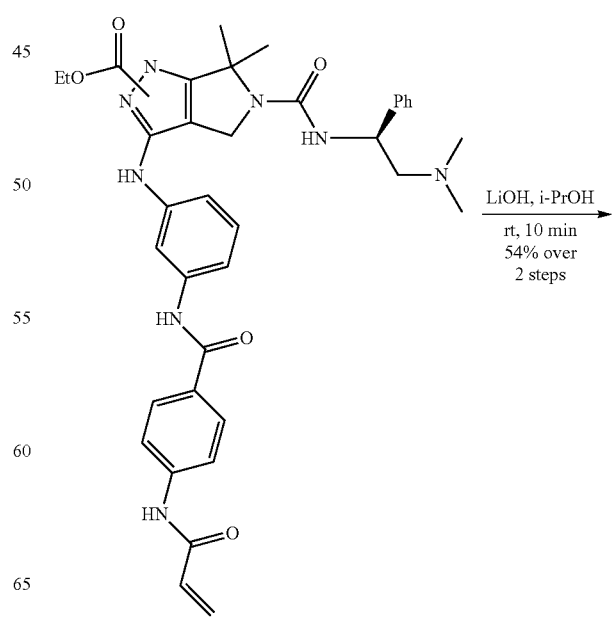

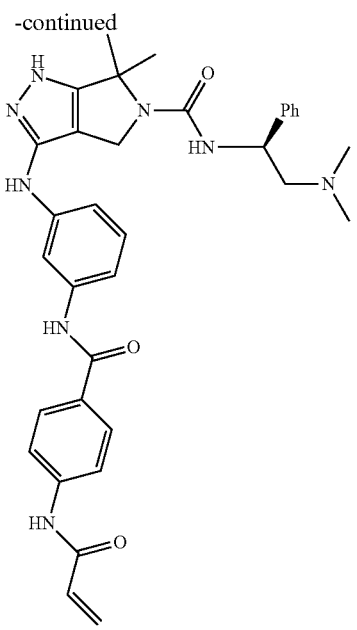

5-(tert-Butyl) Ethyl 3-amino-6,6-dimethyl-4,6-dihydropyrrolo[3,4-c]pyrazole-1,5-dicarboxylate

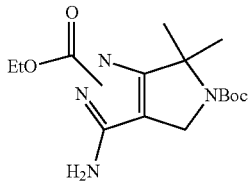

To a solution of tert-butyl 3-amino-6,6-dimethyl-4,6-dihydropyrrolo[3,4-c]pyrazole-5(1H)-carboxylate (1.0 g, 3.95 mmol) and TEA (0.6 g, 0.82 mL, 5.93 mmol) in THF (10 mL) was added ethyl chloroformate (0.43 g, 0.38 mL, 3.95 mmol) dropwise at 0° C. The mixture was stirred at 0° C. for 1 h. The solvent was evaporated and the residue was partitioned with EtOAc and sat. NaHCO₃. The organic layer was washed with water and brine, dried (Na₂SO₄). This was concentrated to give 5-(tert-butyl) ethyl 3-amino-6,6-dimethyl-4,6-dihydropyrrolo[3,4-c]pyrazole-1,5-dicarboxylate as an off white solid (1.28 g, 100%). LC/MS (ESI) m/z=325.3 (M+H)⁺.

5-(tert-Butyl) Ethyl 6,6-dimethyl-3-((3-nitrophenyl)amino)-4,6-dihydropyrrolo[3,4-c]pyrazole-1,5-dicarboxylate

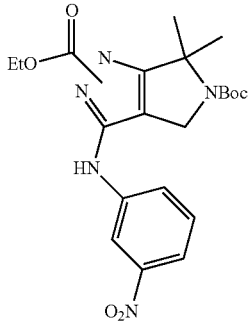

To a suspension of 5-(tert-butyl) ethyl 3-amino-6,6-dimethyl-4,6-dihydropyrrolo[3,4-c]pyrazole-1,5-dicarboxylate (500 mg, 1.54 mmol), (3-nitrophenyl)boronic acid (514 mg, 3.08 mmol), and Cu(OAc)₂ (420 mg, 2.31 mmol) in DCM (10 mL) was added TEA (311 mg, 0.43 mL, 3.08 mmol). The mixture was stirred at room temperature overnight. Solvent was evaporated and the crude was purified by flash column chromatography on silica gel (EtOAc/hexane, 0-70%) to give 5-(tert-butyl) ethyl 6,6-dimethyl-3-((3-nitrophenyl)amino)-4,6-dihydropyrrolo[3,4-c]pyrazole-1,5-dicarboxylate as a yellow solid (240 mg, 35%). LC/MS (ESI) m/z=446.4 (M+H)⁺.

5-(tert-Butyl) Ethyl 3-((3-aminophenyl)amino)-6,6-dimethyl-4,6-dihydropyrrolo[3,4-c]pyrazole-1,5-dicarboxylate

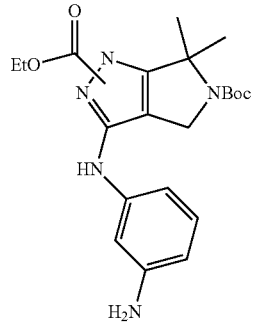

To a solution of 5-(tert-butyl) ethyl 6,6-dimethyl-3-((3-nitrophenyl)amino)-4,6-dihydropyrrolo[3,4-c]pyrazole-1,5-dicarboxylate (120 mg, 0.27 mmol) in EtOAc (2 mL) and pyridine (0.2 mL) was added SnCl₂.2H₂O (305 mg, 1.35 mmol). The mixture was stirred at 70° C. overnight. The mixture was diluted with CHCl₃/i-PrOH (v/v 4:1) and washed with sat. NaHCO₃ and brine, dried (Na₂SO₄), and concentrated. The crude was purified by flash column chromatography on silica gel (MeOH/DCM, 0-10%) to give 5-(tert-butyl) ethyl 3-((3-aminophenyl)amino)-6,6-dimethyl-4,6-dihydropyrrolo[3,4-c]pyrazole-1,5-dicarboxylate as a yellow solid (99 mg, 88%). LC/MS (ESI) m/z=416.4 (M+H)⁺.

5-(tert-Butyl) Ethyl 6,6-dimethyl-3-((3-(4-nitrobenzamido)phenyl)amino)-4,6-dihydropyrrolo[3,4-c]pyrazole-1,5-dicarboxylate

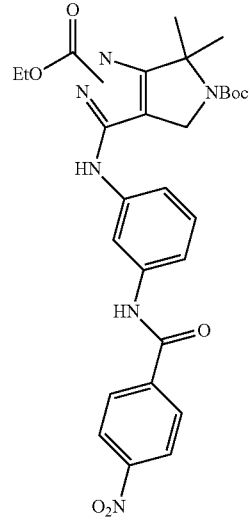

To a solution of 5-(tert-butyl) ethyl 3-((3-aminophenyl)amino)-6,6-dimethyl-4,6-dihydropyrrolo[3,4-c]pyrazole-1, 5-dicarboxylate (99 mg, 0.24 mmol) and DIEA (62 mg, 84 µL, 0.48 mmol) in DCM (2 mL) was added 4-nitrobenzoyl chloride (53 mg, 0.29 mmol) at 0° C. The reaction was stirred at room temperature for 2 h and concentrated. The crude was purified by flash column chromatography on silica gel (MeOH/DCM, 0-5%) to give 5-(tert-butyl) ethyl 6,6-dimethyl-3-((3-(4-nitrobenzamido)phenyl)amino)-4,6-dihydropyrrolo[3,4-c]pyrazole-1,5-dicarboxylate as a yellow solid (129 mg, 95%). LC/MS (ESI) m/z=565.4 (M+H)+.

Ethyl 6,6-dimethyl-3-((3-(4-nitrobenzamido)phenyl)amino)-5,6-dihydropyrrolo[3,4-c]pyrazole-1 (4H)-carboxylate

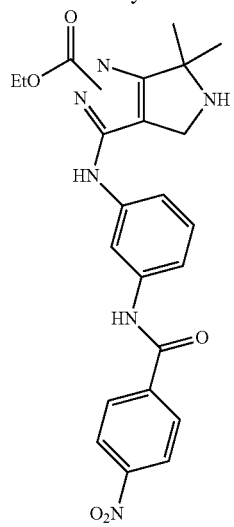

To a solution of 5-(tert-butyl) 1- or 2-ethyl 6,6-dimethyl-3-((3-(4-nitrobenzamido)phenyl)amino)-4,6-dihydropyrrolo[3,4-c]pyrazole-1,5-dicarboxylate (129 mg, 0.23 mmol) in DCM (1 mL) was added TFA (1 mL). The reaction was stirred at room temperature for 1 h and concentrated to give ethyl 6,6-dimethyl-3-((3-(4-nitrobenzamido)phenyl)amino)-5,6-dihydropyrrolo[3,4-c]pyrazole-1(4H)-carboxylate as a TFA salt, which was used directly without further purification. LC/MS (ESI) m/z=464.4 (M+H)−.

Ethyl (S)-5-((2-(dimethylamino)-1-phenylethyl)carbamoyl)-6,6-dimethyl-3-((3-(4-nitrobenzamido)phenyl)amino)-5,6-dihydropyrrolo[3,4-c]pyrazole-1 (4H)-carboxylate

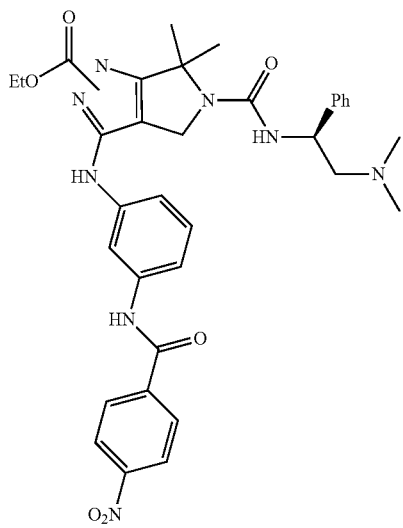

To a mixture of ethyl 6,6-dimethyl-3-((3-(4-nitrobenzamido)phenyl)amino)-5,6-dihydropyrrolo[3,4-c]pyrazole-1(4H)-carboxylate (TFA salt, 0.23 mmol) in DCM (2 mL) was added DIEA (148 mg, 0.2 mL, 1.15 mmol) at 0° C., followed by (S)-2-isocyanato-N,N-dimethyl-2-phenylethan-1-amine HCl salt (62 mg, 0.27 mmol). The solution was stirred at 0° C. for 1 h and diluted with CHCl3/i-PrOH (v/v 4:1) and washed with sat. NaHCO3 and brine, dried (Na2SO4), and concentrated. The crude was purified by flash column chromatography on silica gel (1.75 M NH3 in MeOH/DCM, 0-10%) to give ethyl (S)-5-((2-(dimethylamino)-1-phenylethyl)carbamoyl)-6,6-dimethyl-3-((3-(4-nitrobenzamido)phenyl)amino)-5,6-dihydropyrrolo[3,4-c]pyrazole-1(4H)-carboxylate as a yellow solid (134 mg, 89% over 2 steps). LC/MS (ESI) m/z=655.4 (M+H)+.

Ethyl (S)-3-((3-(4-aminobenzamido)phenyl)amino)-5-((2-(dimethylamino)-1-phenylethyl)carbamoyl)-6,6-dimethyl-5,6-dihydropyrrolo[3,4-c]pyrazole-1 (4H)-carboxylate

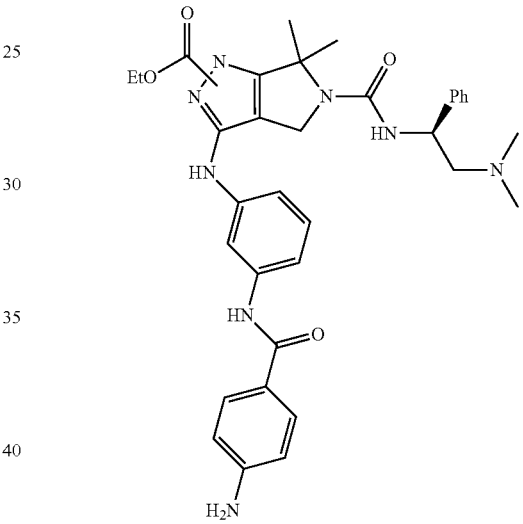

To a solution of ethyl (S)-5-((2-(dimethylamino)-1-phenylethyl)carbamoyl)-6,6-dimethyl-3-((3-(4-nitrobenzamido)phenyl)amino)-5,6-dihydropyrrolo[3,4-c]pyrazole-1(4H)-carboxylate (134 mg, 0.20 mmol) in EtOAc (2 mL) was added SnCl2.2H2O (226 mg, 1.0 mmol). The mixture was stirred at 70° C. for 2 h and diluted with CHCl3/i-PrOH (v/v 4:1) and washed with sat. NaHCO3 and brine, dried (Na2SO4), and concentrated. The crude was purified by flash column chromatography on silica gel (1.75 M NH3 in MeOH/DCM, 0-10%) to give ethyl (S)-3-((3-(4-aminobenzamido)phenyl)amino)-5-((2-(dimethylamino)-1-phenylethyl)carbamoyl)-6,6-dimethyl-5,6-dihydropyrrolo[3,4-c]pyrazole-1(4H)-carboxylate as a yellow solid (112 mg, 90%). LC/MS (ESI) m/z=625.4 (M+H)+.

Compound 101. (S)-3-((3-(4-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide

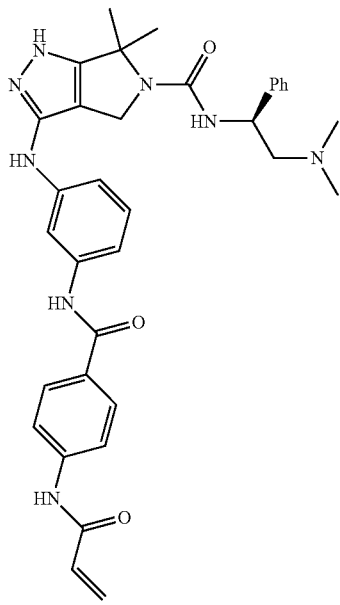 [SMILES: C=CC(=O)Nc1ccc(C(=O)Nc2cccc(Nc3n[nH]c4c3CN(C(=O)N[C@H](CN(C)C)c3ccccc3)C4(C)C)c2)cc1]

To a mixture of ethyl (S)-3-((3-(4-aminobenzamido)phenyl)amino)-5-((2-(dimethylamino)-1-phenylethyl)carbamoyl)-6,6-dimethyl-5,6-dihydropyrrolo[3,4-c]pyrazole-1(4H)-carboxylate (20 mg, 0.032 mmol) in THF (1 mL) and sat. NaHCO$_3$ (1 mL) was added acryloyl chloride (5.8 mg, 0.064 mmol) dropwise at 0° C. The mixture was stirred at 0° C. for 10 min and diluted with CHCl$_3$/i-PrOH (v/v 4:1) and washed with sat. NaHCO$_3$ and brine, dried (Na$_2$SO$_4$), and concentrated. The crude ethyl (S)-3-((3-(4-acrylamidobenzamido)phenyl)amino)-5-((2-(dimethylamino)-1-phenylethyl)carbamoyl)-6,6-dimethyl-5,6-dihydropyrrolo[3,4-c]pyrazole-1(4H)-carboxylate was dissolved in i-PrOH (1 mL) and LiOH (1 M, 1 mL) was added. After stirred at room temperature for 10 min, the mixture was diluted with CHCl$_3$/i-PrOH (v/v 4:1) and washed with sat. NaHCO$_3$ and brine, dried (Na$_2$SO$_4$), and concentrated. The crude was purified by reverse phase preparative HPLC (MeOH/H$_2$O, 0-100%) to give (S)-3-((3-(4-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide as a white solid (10.5 mg, 54%). $^1$H NMR: 600 MHz (DMSO-d$_6$) δ 10.44 (d, J=4.2 Hz, 1H), 10.04 (s, 1H), 8.33 (s, 1H), 7.96-7.93 (m, 2H), 7.82-7.80 (m, 2H), 7.34-7.32 (m, 2H), 7.26-7.23 (m, 2H), 7.20-7.10 (m, 3H), 6.52-6.46 (m, 1H), 6.35-6.30 (m, 1H), 6.09 (s, 1H), 5.84-5.81 (m, 1H), 4.89-4.83 (m, 1H), 4.35 (d, J=19.8 Hz, 2H), 2.64-2.57 (m, 1H), 2.45-2.38 (m, 1H), 2.18 (s, 6H), 1.65 (d, J=4.2 Hz, 3H), 1.58 (d, J=4.8 Hz, 3H); MS m/z: 607.4 [M+1].

TABLE 2

The following compounds were produced by using the corresponding starting compounds according to a method similar to that described in Example 1:

| Name | Structure | Characterization Data |
|---|---|---|
| Compound 102 (S)-3-((4-(4-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide | (structure) | $^1$H NMR (TFA salt): 400 MHz (DMSO-d$_6$) δ 10.46 (s, 1H), 10.01 (s, 1H), 8.98-8.89 (br, 1H), 8.25 (s, 1H), 7.99 (d, J = 8.8 Hz, 2H), 7.85 (d, J = 8.8 Hz, 2H), 7.64 (d, J = 8.8 Hz, 2H), 7.48-7.42 (m, 4H), 7.38-7.34 (m, 1H), 7.00-6.91 (m, 2H), 6.69 (d, J = 8.8 Hz, 1H), 6.53 (dd, J = 17.2, 10.0 Hz, 1H), 6.36 (dd, J = 17.2, 2.0 Hz, 1H), 5.87 (dd, J = 10.0, 2.0 Hz, 1H), 5.40-5.35 (m, 1H), 4.48 (d, J = 10.8 Hz, 1H), 4.33 (d, J = 10.8 Hz, 1H), 3.10-2.95 (m, 2H), 2.93 (d, J = 4.8 Hz, 3H), 2.87 (d, J = 4.8 Hz, 3H), 1.74 (s, 3H), 1.65 (s, 3H); MS m/z: 607.4 [M + 1]. |

TABLE 2-continued

The following compounds were produced by using the corresponding starting compounds according to a method similar to that described in Example 1:

| Name | Structure | Characterization Data |
| --- | --- | --- |
| Compound 103 (S)-3-((4-(3-acrylamidobenzamido) phenyl)amino)-N-(2-(dimethylamino)-1-phenylethyl)-6,6-dimethyl-4,6-dihydropyrrolo[3,4-c]pyrazole-5(1H)-carboxamide | 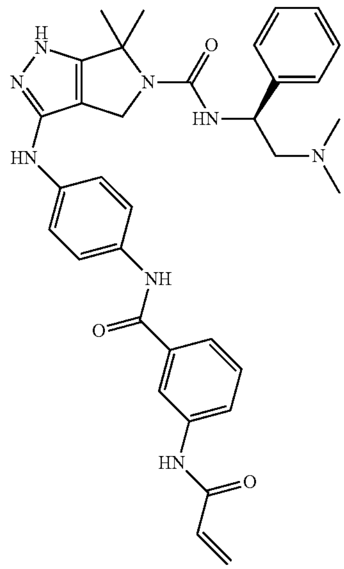 [SMILES: C=CC(=O)Nc1cccc(C(=O)Nc2ccc(Nc3n[nH]c4c3CN(C(=O)N[C@H](CN(C)C)c3ccccc3)C4(C)C)cc2)c1] | $^1$H NMR (TFA salt): 400 MHz (DMSO-$d_6$) δ 11.90-11.70 (br, 1H), 10.26 (s, 1H), 9.98 (s, 1H), 8.22-8.10 (br, 1H), 8.07 (m, 1H), 7.83 (dd, J = 8.0, 1.2 Hz, 1H), 7.57 (d, J = 8.0 Hz, 1H), 7.51 (d, J = 8.8 Hz, 2H), 7.39 (t, J = 8.0 Hz, 1H), 7.27 (d, J = 7.2 Hz, 2H), 7.22 (t, J = 7.2 Hz, 2H), 7.12 (t, J = 7.2 Hz, 1H), 6.39 (dd, J = 17.2, 10.0 Hz, 1H), 6.22 (dd, J = 17.2, 2.0 Hz, 1H), 6.03-5.92 (m, 1H), 5.72 (dd, J = 10.0, 2.0 Hz, 1H), 4.60-4.51 (m, 1H), 4.25-4.14 (m, 2H), 2.52 (dd, J = 12.0, 8.8 Hz, 1H), 2.32-2.27 (m, 1H), 2.10 (s, 6H), 1.57 (s, 3H), 1.50 (s, 3H); MS m/z: 607.4 [M + 1]. |
| Compound 104 (S)-N-(2-(dimethylamino)-1-phenylethyl)-6,6-dimethyl-3-((3-(4-propionamidobenzamido) phenyl)amino)-4,6-dihydropyrrolo[3,4-c]pyrazole-5(1H)-carboxamide | 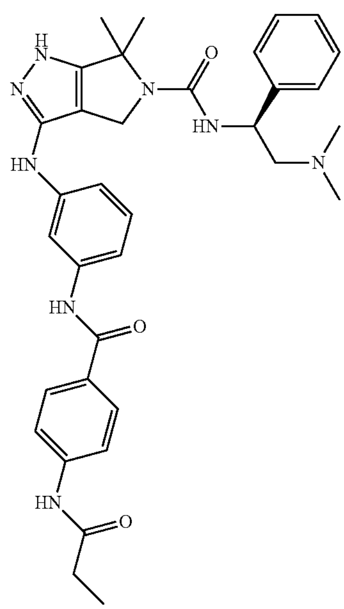 [SMILES: CCC(=O)Nc1ccc(C(=O)Nc2cccc(Nc3n[nH]c4c3CN(C(=O)N[C@H](CN(C)C)c3ccccc3)C4(C)C)c2)cc1] | $^1$H NMR (TFA salt): 400 MHz (DMSO-$d_6$) δ 12.20-11.80 (br, 1H), 10.09 (s, 1H), 9.93 (s, 1H), 8.23 (s, 1H), 7.83 (d, J = 8.0 Hz, 2H), 7.65 (d, J = 8.8 Hz, 2H), 7.50-7.30 (m, 1H), 7.27 (d, J = 6.8 Hz, 2H), 7.18 (t, J = 7.2 Hz, 2H), 7.13-7.09 (m, 3H), 6.59-6.51 (m, 1H), 6.12 (s, 1H), 4.92-4.80 (m, 1H), 4.29 (s, 2H), 2.30 (q, J = 7.6 Hz, 2H), 2.22 (m, 6H), 1.57 (s, 3H), 1.51 (s, 3H), 1.03 (t, J = 7.6 Hz, 3H); MS m/z: 609.4 [M + 1]. |

TABLE 2-continued

The following compounds were produced by using the corresponding starting compounds according to a method similar to that described in Example 1:

| Name | Structure | Characterization Data |
|---|---|---|
| Compound 105 (S)-3-((3-(3-acrylamidobenzamido)phenyl)amino)-N-(2-(dimethylamino)-1-phenylethyl)-6,6-dimethyl-4,6-dihydropyrrolo[3,4-c]pyrazole-5(1H)-carboxamide | | $^1$H NMR (TFA salt): 400 MHz (DMSO-$d_6$) δ 12.10-11.82 (br, 1H), 10.26 (s, 1H), 10.08 (s, 1H), 8.25 (s, 1H), 8.06 (s, 1H), 7.85 (dd, J = 8.4, 1.2 Hz, 1H), 7.55 (d, J = 7.6 Hz, 1H), 7.39 (t, J = 8.0 Hz, 1H), 7.24 (d, J = 7.2 Hz, 2H), 7.15 (t, J = 7.2 Hz, 2H), 7.08 (d, J = 6.4 Hz, 1H), 6.39 (dd, J = 17.2, 10.0 Hz, 1H), 6.22 (dd, J = 17.2, 2.0 Hz, 1H), 5.97 (s, 1H), 5.72 (dd, J = 10.0, 2.0 Hz, 1H), 4.76-4.70 (m, 1H), 4.30-4.19 (m, 2H), 2.50-2.44 (m, 1H), 2.29-2.22 (m, 1H), 2.05 (s, 6H), 1.57 (s, 3H), 1.50 (s, 3H); MS m/z: 607.4 [M +1]. |
| Compound 106 3-((3-(4-acrylamidobenzamido)phenyl)amino)-N-(2-(dimethylamino)ethyl)-6,6-dimethyl-4,6-dihydropyrrolo[3,4-c]pyrazole-5(1H)-carboxamide | 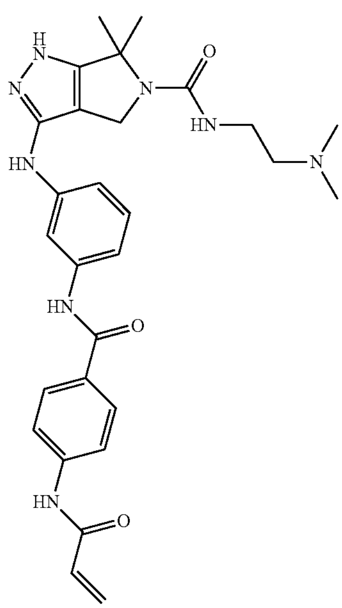 [SMILES: C=CC(=O)Nc1ccc(C(=O)Nc2cccc(Nc3n[nH]c4c3CN(C(=O)NCCN(C)C)C4(C)C)c2)cc1] | $^1$H NMR (TFA salt): 400 MHz (DMSO-$d_6$) δ 10.49 (s, 1H), 10.07 (s, 1H), 9.41 (s, 1H), 8.37 (s, 1H), 7.99 (d, J = 8.8 Hz, 2H), 7.86 (d, J = 8.8 Hz, 2H), 7.49 (s, 1H), 7.21 (m, 2H), 6.74 (m, 1H), 6.53 (dd, J = 17.2, 10.0 Hz, 1H), 6.38 (m, 1H), 6.36 (dd, J = 17.2, 2.0 Hz, 1H), 5.87 (dd, J = 10.0, 2.0 Hz, 1H), 4.27 (s, 2H), 3.41 (q, J = 5.6 Hz, 2H), 3.18 (q, J = 5.6 Hz, 2H), 2.86 (s, 3H), 2.85 (s, 3H), 1.71 (s, 6H); MS m/z: 531.4 [M + 1]. |

TABLE 2-continued

The following compounds were produced by using the corresponding starting compounds according to a method similar to that described in Example 1:

| Name | Structure | Characterization Data |
|---|---|---|
| Compound 107 4-acrylamido-N-(3-((6,6-dimethyl-5-(4-methylpiperazine-1-carbonyl)-1,4,5,6-tetrahydropyrrolo[3,4-c]pyrazol-3-yl)amino)phenyl)benzamide | 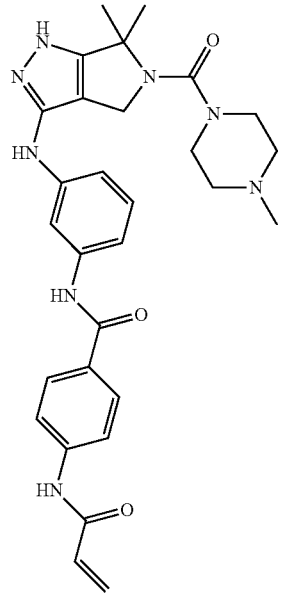 | $^1$H NMR (TFA salt): 400 MHz (DMSO-$d_6$) δ 10.49 (s, 1H), 10.08 (s, 1H), 9.68 (s, 1H), 8.44 (s, 1H), 7.99 (d, J = 8.8 Hz, 2H), 7.86 (d, J = 8.4 Hz, 2H), 7.62 (s, 1H), 7.23-7.13 (m, 2H), 6.84 (d, J = 12 Hz, 1H), 6.53 (dd, J = 17.2, 10.0 Hz, 1H), 6.36 (dd, J = 17.2, 2.0 Hz, 1H), 5.87 (dd, J = 10.0, 2.0 Hz, 1H), 4.43 (s, 2H), 3.40-3.33 (m, 4H), 3.15-2.97 (m, 4H), 2.82 (s, 3H), 1.70 (s, 6H); MS m/z: 543.4 [M + 1]. |
| Compound 108 3-((3-(4-acrylamidobenzamido)phenyl)amino)-N-(1-(dimethylamino)propan-2-yl)-6,6-dimethyl-4,6-dihydropyrrolo[3,4-c]pyrazole-5(1H)-carboxamide | 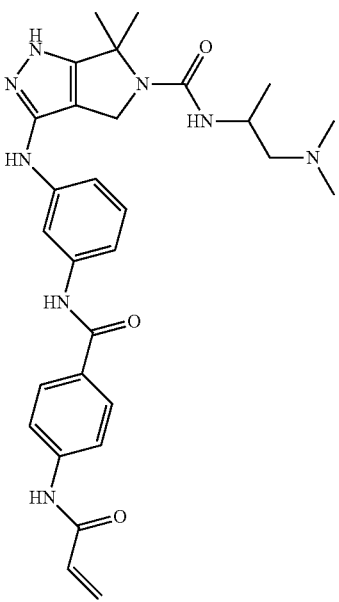 [SMILES: C=CC(=O)Nc1ccc(C(=O)Nc2cccc(Nc3n[nH]c4c3CN(C(=O)NC(C)CN(C)C)C4(C)C)c2)cc1] | $^1$H NMR (TFA salt): 400 MHz (DMSO-$d_6$) δ 10.35 (s, 1H), 9.95 (s, 1H), 8.91 (s, 1H), 8.23 (s, 1H), 7.85 (d, J = 8.4 Hz, 2H), 7.72 (d, J = 8.4 Hz, 2H), 7.32 (s, 1H), 7.11-7.05 (m, 2H), 6.57 (m, 1H), 6.40 (dd, J = 16.8, 10.0 Hz, 1H), 6.23 (dd, J = 16.8, 2.0 Hz, 1H), 5.91 (d, J = 8.4 Hz, 1H), 5.74 (dd, J = 10.0, 2.0 Hz, 1H), 4.18 (s, 2H), 4.14-4.07 (m, 1H), 3.05-2.94 (m, 2H), 2.71 (d, J = 4.8 Hz, 3H), 2.69 (d, J = 4.8 Hz, 3H), 1.59 (s, 6H), 1.01 (d, J = 6.4 Hz, 3H), 0.85-0.76 (m, 1H); MS m/z: 545.3 [M + 1]. |

TABLE 2-continued

The following compounds were produced by using the corresponding starting compounds according to a method similar to that described in Example 1:

| Name | Structure | Characterization Data |
| --- | --- | --- |
| Compound 109 (S,E)-3-((3-(4-(4-(dimethylamino)but-2-enamido)benzamido)phenyl)amino)-N-(2-hydroxy-1-phenylethyl)-6,6-dimethyl-4,6-dihydropyrrolo[3,4-c]pyrazole-5(1H)-carboxamide | 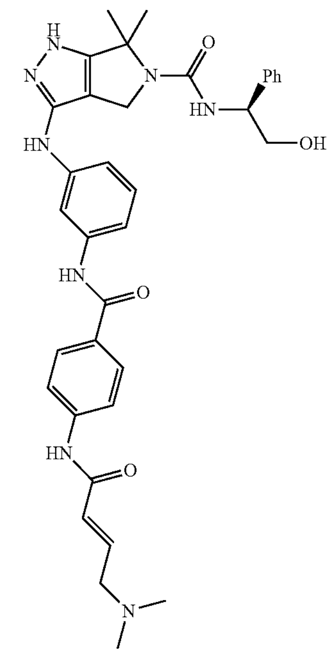 [SMILES: CN(C)C/C=C/C(=O)Nc1ccc(C(=O)Nc2cccc(Nc3n[nH]c4c3CN(C(=O)N[C@H](CO)c3ccccc3)C4(C)C)c2)cc1] | $^1$H NMR (TFA salt): 400 MHz (DMSO-$d_6$) δ 10.68 (s, 1H), 10.13 (s, 1H), 10.01 (s, 1H), 8.43 (s, 1H), 8.03 (d, J = 8.8 Hz, 2H), 7.88 (d, J = 8.8 Hz, 2H), 7.54 (s, 1H), 7.41-7.39 (m, 2H), 7.34-7.30 (m, 2H), 7.27-7.22 (m, 3H), 6.92-6.82 (m, 2H), 6.58 (d, J = 15.6 Hz, 1H), 6.13 (d, J = 8.0 Hz, 1H), 4.85 (q, J = 6.8 Hz, 1H), 4.48 (q, J = 11.2 Hz, 2H), 4.06 (d, J = 7.2 Hz, 2H), 3.63 (d, J = 6.4 Hz, 2H), 2.91 (s, 6H), 2.64 (t, J = 5.6 Hz, 1H), 1.73 (s, 3H), 1.67 (s, 3H); MS m/z: 637.3 [M + 1]. |
| Compound 110 (S)-3-((3-acrylamidophenyl)amino)-N-(2-(dimethylamino)-1-phenylethyl)-6,6-dimethyl-4,6-dihydropyrrolo[3,4-c]pyrazole-5(1H)-carboxamide | 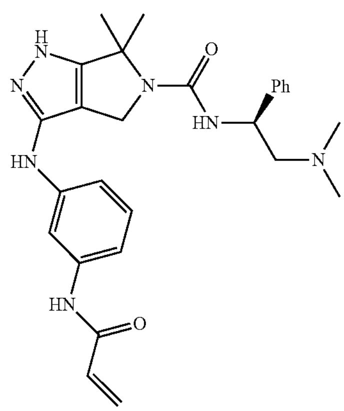 [SMILES: C=CC(=O)Nc1cccc(Nc2n[nH]c3c2CN(C(=O)N[C@H](CN(C)C)c2ccccc2)C3(C)C)c1] | $^1$H NMR (TFA salt): 400 MHz (DMSO-$d_6$) δ 9.94 (s, 1H), 8.90 (s, 1H), 8.24 (s, 1H), 7.35-7.27 (m, 4H), 7.24-7.22 (m, 2H), 7.08-7.02 (m, 2H), 6.56-6.52 (m, 2H), 6.38 (dd, J = 16.8, 10.0 Hz, 1H), 6.16 (dd, J = 16.8, 2.0 Hz, 1H), 5.67 (dd, 10.0, 2.0 Hz, 1H), 5.29-5.22 (m, 1H), 4.31 (q, J = 11.2 Hz, 2H), 3.39-3.34 (m, 1H), 3.28-3.22 (m, 1H), 2.80 (d, J = 4.8 Hz, 1H), 2.73 (d, J = 4.8 Hz, 1H), 1.59 (s, 3H), 1.53 (s, 3H); MS m/z: 488.3 [M + 1]. |
| Compound 111 (S)-3-((4-acrylamidophenyl)amino)-N-(2-(dimethylamino)-1-phenylethyl)-6,6-dimethyl-4,6-dihydropyrrolo[3,4-c]pyrazole-5(1H)-carboxamide | | $^1$H NMR (TFA salt): 400 MHz (DMSO-$d_6$) δ 9.86 (s, 1H), 8.91 (s, 1H), 8.13 (s, 1H), 7.49-7.43 (m, 2H), 7.40-7.27 (m, 5H), 7.22 (m, 1H), 6.82 (d, J = 9.2 Hz, 1H), 6.55 (d, J = 9.2 Hz, 1H), 6.34 (dd, J = 16.8, 10.0 Hz, 1H), 6.13 (dd, J = 16.8, 2.0 Hz, 1H), 5.62 (dd, J = 10.0, 2.0 Hz, 1H), 5.29-5.22 (m, 1H), 4.33 (d, J = 11.2 Hz, 1H), 4.19 (d, J = 11.2 Hz, 1H), 3.42-3.36 (m, 1H), 3.29-3.23 (m, 1H), 2.81 (d, J = 4.8 Hz, 1H), 2.74 (d, J = 4.8 Hz, 1H), 1.60 (s, 3H), 1.51 (s, 3H); MS m/z: 488.3 [M + 1]. |

Example 2. (S)-3-(3-(4-acrylamidobenzamido)benzamido)-N-(2-(dimethylamino)-1-phenylethyl)-6,6-dimethyl-4,6-dihydropyrrolo[3,4-c]pyrazole-5(1H)-carboxamide (Compound 112)
The synthesis of Compound 112 follows Synthetic Scheme 2. The syntheses of Compounds 120, and 214 to 217 (presented in Table 3) follow a corresponding method.
Synthetic Scheme 2.
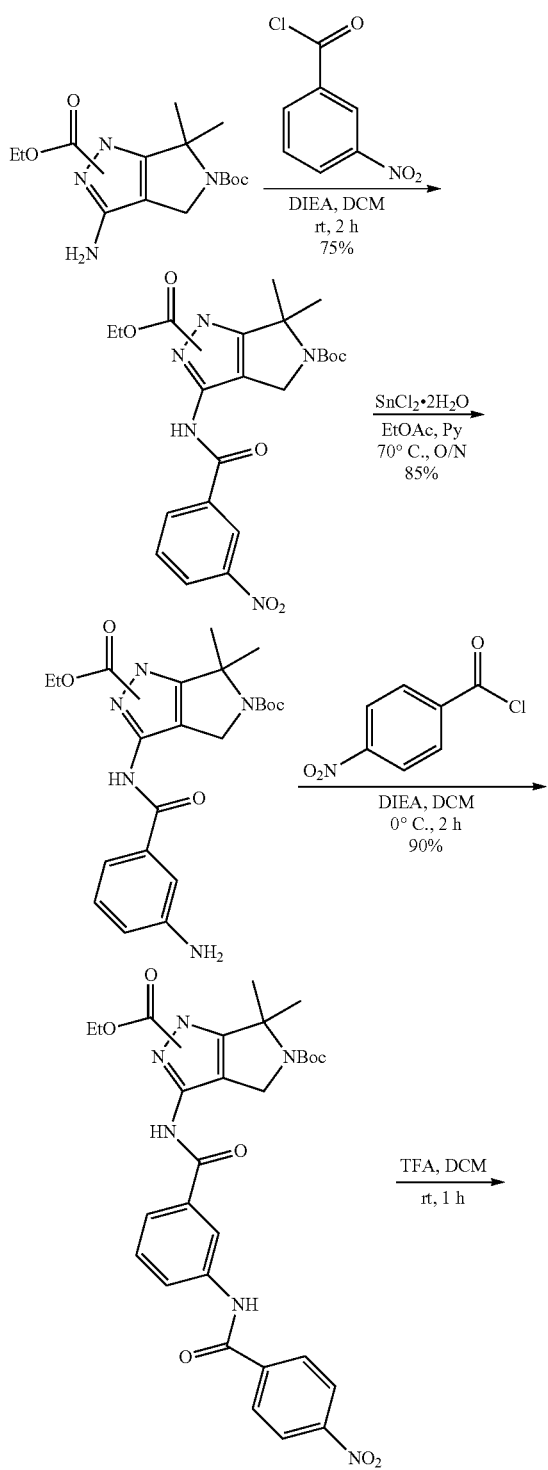
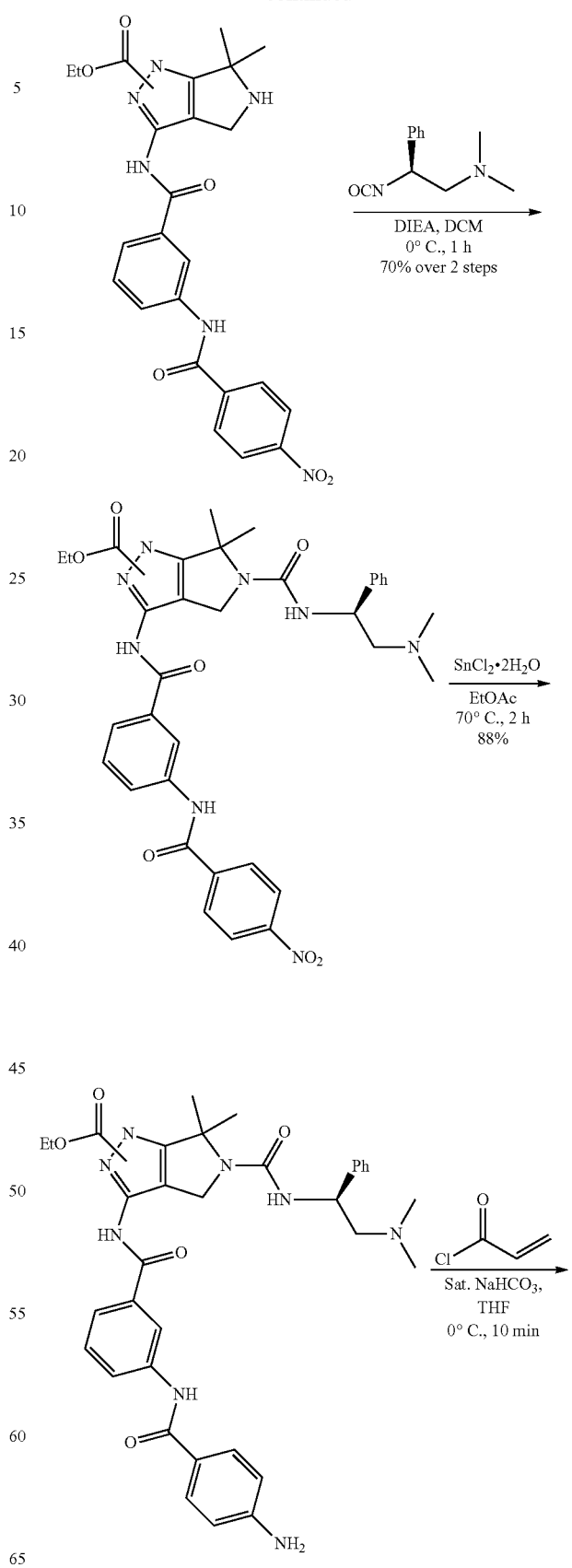

-continued

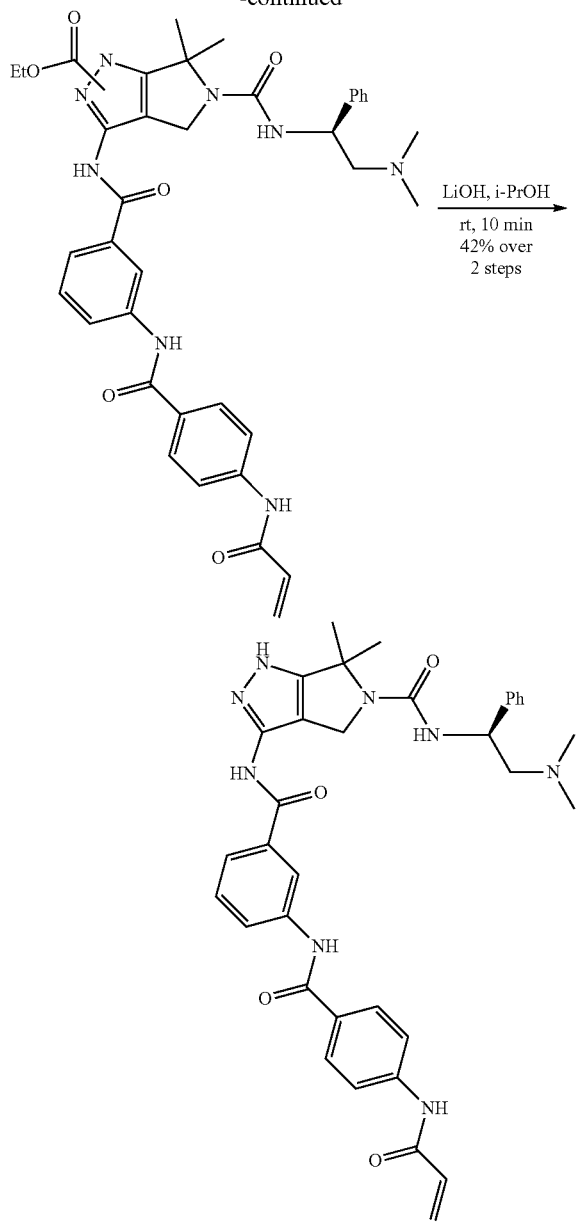

LiOH, i-PrOH
rt, 10 min
42% over 2 steps 5-(tert-Butyl) Ethyl 6,6-dimethyl-3-(3-nitrobenzamido)-4,6-dihydropyrrolo[3,4-c]pyrazole-1,5-dicarboxylate

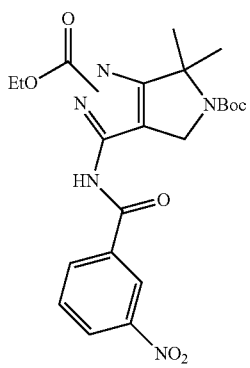

To a solution of 5-(tert-butyl) ethyl 3-amino-6,6-dimethyl-4,6-dihydropyrrolo[3,4-c]pyrazole-1,5-dicarboxylate (100 mg, 0.31 mmol) and DIEA (79 mg, 0.11 mL, 0.62 mmol) in DCM (2 mL) was added 3-nitrobenzoyl chloride (87 mg, 0.47 mmol). The reaction was stirred at room temperature for 2 h and concentrated. The crude was purified by flash column chromatography on silica gel (EtOAc/hexanes, 0-70%) to give 5-(tert-Butyl) ethyl 6,6-dimethyl-3-(3-nitrobenzamido)-4,6-dihydropyrrolo[3,4-c]pyrazole-1,5-dicarboxylate as a yellow solid (110 mg, 75%). LC/MS (ESI) m/z=474.4 (M+H)⁺.

Compound 112. (S)-3-(3-(4-acrylamidobenzamido)benzamido)-N-(2-(dimethylamino)-1-phenylethyl)-6,6-dimethyl-4,6-dihydropyrrolo[3,4-c]pyrazole-5(1H)-carboxamide

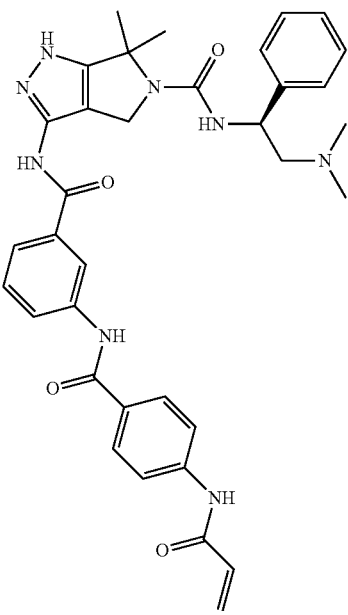 [SMILES: C=CC(=O)Nc1ccc(C(=O)Nc2cccc(C(=O)Nc3n[nH]c4c3CN(C(=O)N[C@H](CN(C)C)c3ccccc3)C4(C)C)c2)cc1]

Following the previously described synthetic procedure of Compound 101 from 5-(tert-butyl) ethyl 6,6-dimethyl-3-(3-nitrobenzamido)-4,6-dihydropyrrolo[3,4-c]pyrazole-1,5-dicarboxylate, (S)-3-(3-(4-acrylamidobenzamido)benzamido)-N-(2-(dimethylamino)-1-phenylethyl)-6,6-dimethyl-4,6-dihydropyrrolo[3,4-c]pyrazole-5(1H)-carboxamide was obtained as a white solid. ¹H NMR (TFA salt): 400 MHz (DMSO-$d_6$) δ 10.97 (s, 1H), 10.53 (s, 1H), 10.40 (s, 1H), 9.04 (s, 1H), 8.62 (m, 1H), 8.04 (d, J=9.2 Hz, 2H), 7.89 (d, J=9.2 Hz, 2H), 7.83 (d, J=7.6 Hz, 1H), 7.57-7.44 (m, 4H), 7.36 (t, J=7.2 Hz, 1H), 6.83 (d, J=9.2 Hz, 1H), 6.54 (dd, J=17.2, 10.0 Hz, 1H), 6.37 (dd, J=17.2, 2.0 Hz, 1H), 5.88 (dd, J=10.0, 2.0 Hz, 1H), 5.43-5.37 (m, 1H), 4.86 (d, J=12.4 Hz, 1H), 4.64 (d, J=11.6 Hz, 1H), 2.95 (d, J=8.4 Hz, 3H), 2.90 (d, J=8.4 Hz, 3H), 1.74 (s, 3H), 1.66 (s, 3H); MS m/z: 635.3 [M+1].

TABLE 3

The following compounds were produced using the corresponding starting compounds according to a method similar to that described for synthesis of Compound 112:

| Name | Structure | Characterization Data |
|---|---|---|
| Compound 120. (S)-3-(3-acrylamidobenzamido)-N-(2-(dimethylamino)-1-phenylethyl)-6,6-dimethyl-4,6-dihydropyrrolo[3,4-c]pyrazole-5(1H)-carboxamide | 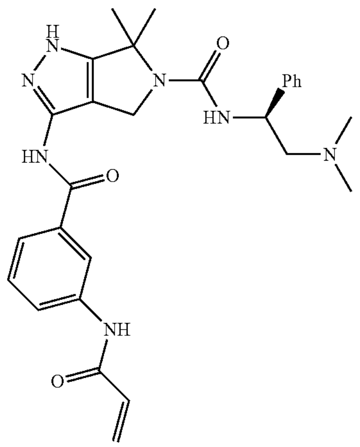 [SMILES: C=CC(=O)Nc1cccc(C(=O)Nc2n[nH]c3c2CN(C(=O)N[C@H](CN(C)C)c2ccccc2)C3(C)C)c1] | $^1$H NMR (TFA salt): 600 MHz (DMSO-d$_6$) δ 10.77 (s, 1H), 10.19 (s, 1H), 8.86 (s, 1H), 8.32 (s, 1H), 7.60 (m, 1H), 7.54 (m, 1H), 7.28 (m, 4H), 7.15 (m, 1H), 6.62 (m, 1H), 6.31 (m, 1H), 6.14 (m, 1H), 5.64 (m, 1H), 5.19 (m, 1H), 4.64 (m, 1H), 4.42 (m, 1H), 3.41 (m, 1H), 3.19 (m, 1H), 2.73 (m, 3H), 2.69 (m, 3H), 1.53 (s, 3H), 1.44 (s, 3H); MS m/z: 516.3 [M + 1]. |
| Compound 214. (S)-3-(4-acrylamidobenzamido)-N-(2-(dimethylamino)-1-phenylethyl)-6,6-dimethyl-4,6-dihydropyrrolo[3,4-c]pyrazole-5(1H)-carboxamide | 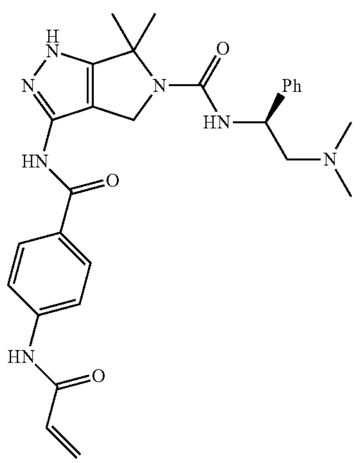 [SMILES: C=CC(=O)Nc1ccc(C(=O)Nc2n[nH]c3c2CN(C(=O)N[C@H](CN(C)C)c2ccccc2)C3(C)C)cc1] | $^1$H NMR: 600 MHz (DMSO-d$_6$) δ 10.80 (s, 1H), 10.43 (s, 1H), 8.98 (s, 1H), 7.99 (d, J = 8.8 Hz, 2H), 7.78 (d, J = 8.8 Hz, 2H), 7.71 (d, J = 7.6 Hz, 2H), 7.38 (t, J = 7.0 Hz, 2H), 7.28 (t, J = 7.0 Hz, 1H), 6.75 (d, J = 9.4 Hz, 1H), 6.45 (dd, J = 17.0, 10.0 Hz, 1H), 6.29 (dd, J = 16.4, 2.4 Hz, 1H), 5.80 (dd, J = 10.0, 1.8 Hz, 1H), 5.33 (m, 1H), 4.75 (d, J = 11.7 Hz, 1H), 4.53 (d, J = 11.7 Hz, 1H), 3.53 (m, 1H), 3.33 (m, 1H), 2.86 (d, J = 4.7 Hz, 3H), 2.82 (d, J = 5.3 Hz, 3H), 1.65 (s, 3H), 1.57 (s, 3H); MS m/z: 516.3 [M + 1]. |
| Compound 215. (S)-N-(2-(dimethylamino)-1-phenylethyl)-6,6-dimethyl-3-(4-propionamidobenzamido)-4,6-dihydropyrrolo[3,4-c]pyrazole-5(1H)-carboxamide | 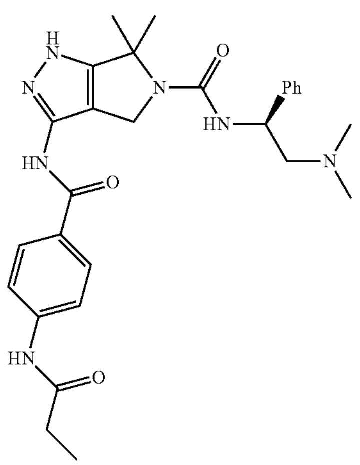 [SMILES: CCC(=O)Nc1ccc(C(=O)Nc2n[nH]c3c2CN(C(=O)N[C@H](CN(C)C)c2ccccc2)C3(C)C)cc1] | $^1$H NMR: 600 MHz (DMSO-d$_6$) δ 12.38 (s, 1H), 10.71 (s, 1H), 10.12 (s, 1H), 7.95 (m, 2H), 7.69 (m, 2H), 7.35 (d, J = 7.0 Hz, 2H), 7.28 (t, J = 7.6 Hz, 2H), 7.18 (d, J = 7.6 Hz, 1H), 6.25 (m, 1H), 4.87 (m, 1H), 4.52 (m, 2H), 2.68 (m, 1H), 2.41 (m, 1H), 2.34 (q, J = 7.6 Hz, 2H), 2.20 (m, 6H), 1.62 (m, 3H), 1.55 (s, 3H), 1.08 (t, J = 7.6 Hz, 1H); MS m/z: 518.3 [M + 1]. |

TABLE 3-continued

The following compounds were produced using the corresponding starting compounds according to a method similar to that described for synthesis of Compound 112:

| Name | Structure | Characterization Data |
|---|---|---|
| Compound 216. (S)-3-(4-acrylamido-2-methoxybenzamido)-N-(2-(dimethylamino)-1-phenylethyl)-6,6-dimethyl-4,6-dihydropyrrolo[3,4-c]pyrazole-5(1H)-carboxamide | 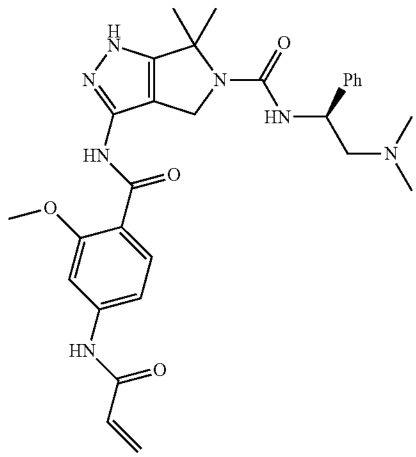 | $^1$H NMR (a mixture of rotamers): 600 MHz (DMSO-$d_6$) δ 12.41, 12.32 (s, 1H), 10.49, 10.45 (s, 1H), 10.29, 10.09 (s, 1H), 8.97 (br, 1H), 7.86 (m, 1H), 7.63 (m, 1H), 7.38 (m, 2H), 7.32 (m, 2H), 7.22 (m, 1H), 6.44 (dd, J = 17.0, 10.0 Hz, 1H), 6.30 (dd, J = 17.0, 1.2 Hz, 1H), 5.81 (d, J = 11.7 Hz, 1H), 5.05 (br, 1H), 4.63 (m, 1H), 4.57 (m, 1H), 3.95 (m, 3H), 2.70-2.20 (m, 6H), 1.64, 1.60 (s, 3H), 1.56, 1.52 (s, 3H); MS m/z: 546.3 [M + 1]. |
| Compound 217. (S)-3-(4-acrylamido-3-methoxybenzamido)-N-(2-(dimethylamino)-1-phenylethyl)-6,6-dimethyl-4,6-dihydropyrrolo[3,4-c]pyrazole-5(1H)-carboxamide | 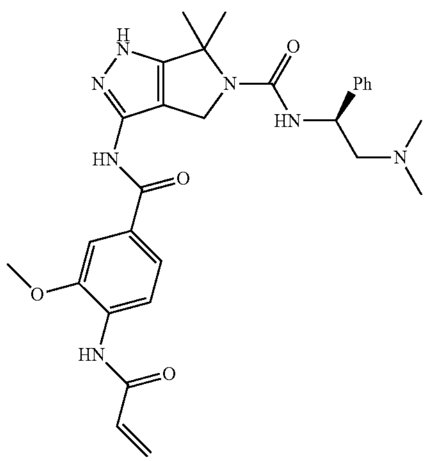 | $^1$H NMR: 600 MHz (DMSO-$d_6$) δ 12.44 (s, 1H), 10.87 (s, 1H), 9.55 (s, 1H), 8.26 (m, 1H), 7.72 (s, 1H), 7.65 (m, 1H), 7.38 (m, 2H), 7.32 (m, 2H), 7.23 (m, 1H), 6.76 (dd, J = 17.0, 10.0 Hz, 1H), 6.46 (br, 1H), 6.25 (dd, J = 17.0, 1.8 Hz, 1H), 5.75 (d, J = 10.0 Hz, 1H), 5.07 (br, 1H), 4.63 (m, 1H), 4.56 (m, 1H), 3.94 (s, 3H), 2.79-2.06 (m, 6H), 1.64 (s, 3H), 1.57 (s, 3H); MS m/z: 546.3 [M + 1]. |

Example 3. 3-(1-acryloylpiperidine-3-carboxamido)-N—((S)-2-(dimethylamino)-1-phenylethyl)-6,6-dimethyl-4,6-dihydropyrrolo[3,4-c]pyrazole-5(1H)-carboxamide (Compounds 113 & 114)

The synthesis of Compounds 113 follows Synthetic Scheme 3. The synthesis of Compounds 114, 123, 221, and 222 (presented in Table 4) follows a corresponding method.

Synthetic Scheme 3.

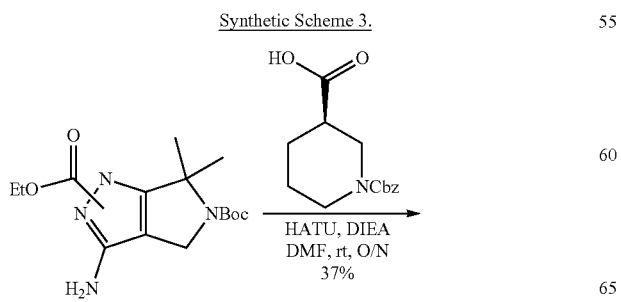

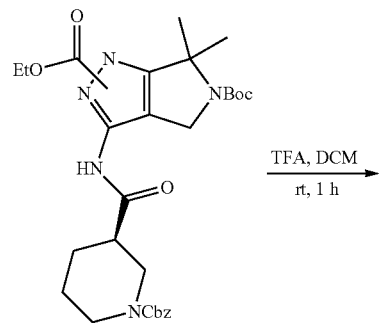

-continued

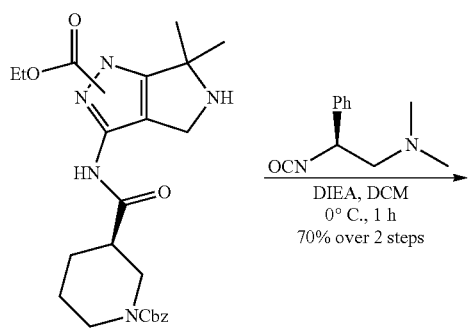

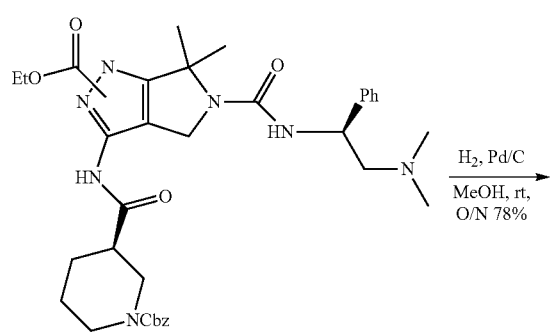

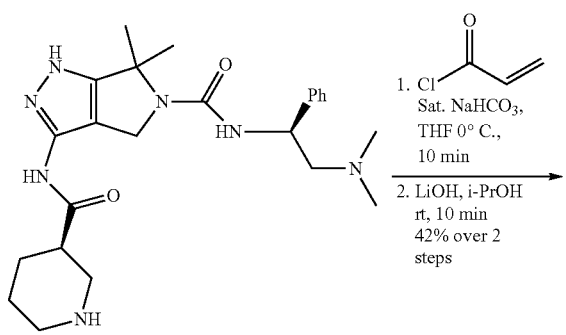

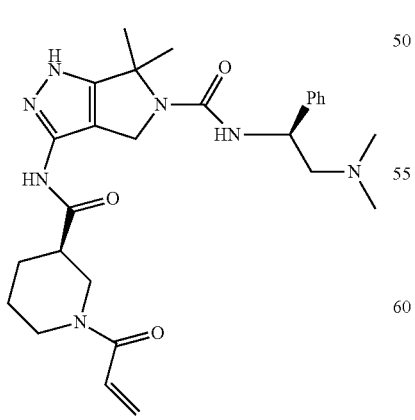

5-(tert-Butyl) Ethyl (R)-3-(1-((benzyloxy)carbonyl) piperidine-3-carboxamido)-6,6-dimethyl-4,6-dihydropyrrolo[3,4-c]pyrazole-1,5-dicarboxylate

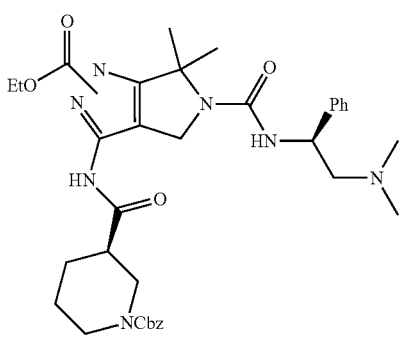

To a solution of 5-(tert-butyl) ethyl 3-amino-6,6-dimethyl-4,6-dihydropyrrolo[3,4-c]pyrazole-1,5-dicarboxylate (100 mg, 0.31 mmol), (R)-1-((benzyloxy)carbonyl)piperidine-3-carboxylic acid (122 mg, 0.47 mmol), and DIEA (120 mg, 0.16 mL, 0.93 mmol) in DMF (2 mL) was HATU (236 mg, 0.62 mmol). The mixture was stirred at room temperature overnight and diluted with ethyl acetate and sat. NaHCO₃. The organic layer was washed with water and brine, dried (Na₂SO₄), and concentrated. The crude was purified by flash column chromatography on silica gel (EtOAc/hexanes, 0-70%) to give 5-(tert-butyl) ethyl (R)-3-(1-((benzyloxy)carbonyl)piperidine-3-carboxamido)-6,6-dimethyl-4,6-dihydropyrrolo[3,4-c]pyrazole-1,5-dicarboxylate as a yellow solid (65 mg, 37%). LC/MS (ESI) m/z=570.4 (M+H)⁺.

Ethyl 3-((R)-1-((benzyloxy)carbonyl)piperidine-3-carboxamido)-5-(((S)-2-(dimethylamino)-1-phenylethyl)carbamoyl)-6,6-dimethyl-5,6-dihydropyrrolo [3,4-c]pyrazole-1(4H)-carboxylate To a solution of 5-(tert-butyl) ethyl (R)-3-(1-((benzyloxy)carbonyl)piperidine-3-carboxamido)-6,6-dimethyl-4,6-dihydropyrrolo[3,4-c]pyrazole-1,5-dicarboxylate (65 mg, 0.115 mmol) in DCM (1 mL) was added TFA (1 mL). The reaction was stirred at room temperature for 1 h and concentrated to give ethyl (R)-3-(1-((benzyloxy)carbonyl)piperidine-3-carboxamido)-6,6-dimethyl-5,6-dihydropyrrolo [3,4-c]pyrazole-1 (4H)-carboxylate as a TFA salt, which was used directly without further purification. LC/MS (ESI) m/z=470.4 (M+H)⁺.

To a mixture of (R)-3-(1-((benzyloxy)carbonyl)piperidine-3-carboxamido)-6,6-dimethyl-5,6-dihydropyrrolo[3,4-c]pyrazole-1 (4H)-carboxylate (TFA salt, 0.115 mmol) in DCM (1 mL) was added DIEA (74 mg, 0.1 mL, 0.57 mmol) at 0° C., followed by (S)-2-isocyanato-N,N-dimethyl-2-phenylethan-1-amine HCl salt (31 mg, 0.14 mmol). The solution was stirred at 0° C. for 1 h and diluted with CHCl₃/i-PrOH (v/v 4:1) and washed with sat. NaHCO₃ and brine, dried (Na₂SO₄), and concentrated. The crude was purified by flash column chromatography on silica gel (1.75 M NH₃ in MeOH/DCM, 0-10%) to give ethyl 3-((R)-1-((benzyloxy)carbonyl)piperidine-3-carboxamido)-5-(((S)-2-(dimethylamino)-1-phenylethyl)carbamoyl)-6,6-dimethyl-5,6-dihydropyrrolo[3,4-c]pyrazole-1 (4H)-carboxylate as a yellow solid (53 mg, 70% over 2 steps). LC/MS (ESI) m/z=660.4 (M+H)⁺.

N—((S)-2-(dimethylamino)-1-phenylethyl)-6,6-dimethyl-3-((R)-piperidine-3-carboxamido)-4,6-dihydropyrrolo[3,4-c]pyrazole-5(1H)-carboxamide

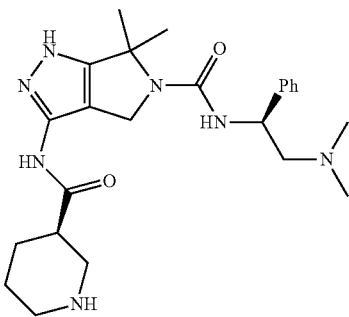 [SMILES: CN(C)C[C@@H](NC(=O)N1Cc2c(NC(=O)[C@@H]3CCCNC3)n[nH]c2C1(C)C)c1ccccc1]

A mixture of ethyl 3-((R)-1-((benzyloxy)carbonyl)piperidine-3-carboxamido)-5-(((S)-2-(dimethylamino)-1-phenylethyl)carbamoyl)-6,6-dimethyl-5,6-dihydropyrrolo[3,4-c]pyrazole-1(4H)-carboxylate (53 mg, 0.081 mmol) and 10% Pd/C (10 mg) in MeOH (5 mL) was degassed. The mixture was stirred under H₂ (1 atm) at room temperature overnight. The reaction was filtered through Celite® and concentrated to give N—((S)-2-(dimethylamino)-1-phenylethyl)-6,6-dimethyl-3-((R)-piperidine-3-carboxamido)-4,6-dihydropyrrolo[3,4-c]pyrazole-5(1H)-carboxamide as a clear wax (28 mg, 78%). LC/MS (ESI) m/z: 454.4 (M+H)⁺.

Compound 113: 3-((R)-1-acryloylpiperidine-3-carboxamido)-N—((S)-2-(dimethylamino)-1-phenylethyl)-6,6-dimethyl-4,6-dihydropyrrolo[3,4-c]pyrazole-5(1H)-carboxamide

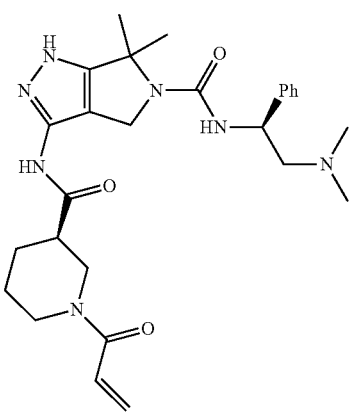 [SMILES: C=CC(=O)N1CCC[C@@H](C(=O)Nc2n[nH]c3c2CN(C(=O)N[C@H](CN(C)C)c2ccccc2)C3(C)C)C1]

To a mixture of N—((S)-2-(dimethylamino)-1-phenylethyl)-6,6-dimethyl-3-((R)-piperidine-3-carboxamido)-4,6-dihydropyrrolo[3,4-c]pyrazole-5(1H)-carboxamide (20 mg, 0.044 mmol) in THF (1 mL) and sat. NaHCO₃ (1 mL) was added acryloyl chloride (12 mg, 0.13 mmol) dropwise at 0° C. The mixture was stirred at 0° C. for 10 min and diluted with CHCl₃/i-PrOH (v/v 4:1) and washed with sat. NaHCO₃ and brine, dried (Na₂SO₄), and concentrated. The crude was dissolved in i-PrOH (1 mL) and LiOH (1 M, 1 mL) was added. After stirred at room temperature for 10 min, the mixture was diluted with CHCl₃/i-PrOH (v/v 4:1) and washed with sat. NaHCO₃ and brine, dried (Na₂SO₄), and concentrated. The crude was purified by reverse phase preparative HPLC (MeOH/H₂O, 0-100%) to give 3-((R)-1-acryloylpiperidine-3-carboxamido)-N—((S)-2-(dimethylamino)-1-phenylethyl)-6,6-dimethyl-4,6-dihydropyrrolo[3,4-c]pyrazole-5(1H)-carboxamide TFA salt as a white solid (11 mg, 42%). ¹H NMR (TFA salt): 600 MHz (DMSO-d₆) δ 10.56 (d, J=19.8 Hz, 1H), 8.95 (s, 1H), 7.41-7.36 (m, 3H), 7.31-7.27 (m, 1H), 6.87-6.79 (m, 1H), 6.72 (d, J=9.0 Hz, 1H), 6.08 (d, J=16.2 Hz, 1H), 5.66 (d, J=10.2 Hz, 1H), 5.32 (m, 1H), 4.69 (m, 1H), 4.47 (m, 2H), 4.03 (m, 2H), 3.53 (t, J=12.0 Hz, 2H), 3.35-3.30 (m, 1H), 3.18-3.12 (m, 1H), 2.99 (t, J=13.2 Hz, 1H), 2.85 (d, J=5.4 Hz, 3H), 2.82 (d, J=4.8 Hz, 3H), 2.70 (t, J=12.0 Hz, 1H), 1.95 (m, 1H), 1.73 (m, 1H), 1.62 (s, 3H), 1.53 (s, 3H), 1.33 (m, 1H); MS m/z: 508.3 [M+1].

Compound 114. 3-((S)-1-acryloylpiperidine-3-carboxamido)-N—((S)-2-(dimethylamino)-1-phenylethyl)-6,6-dimethyl-4,6-dihydropyrrolo[3,4-c]pyrazole-5(1H)-carboxamide

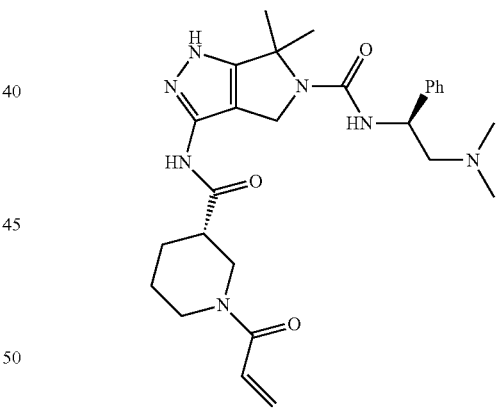

3-((S)-1-Acryloylpiperidine-3-carboxamido)-N—((S)-2-(dimethylamino)-1-phenylethyl)-6,6-dimethyl-4,6-dihydropyrrolo[3,4-c]pyrazole-5 (1H)-carboxamide was prepared by using the corresponding starting compounds according to a method similar to that described for Compound 113. ¹H NMR (TFA salt): 400 MHz (DMSO-d₆) δ 10.50 (d, J=15.6 Hz, 1H), 8.90 (s, 1H), 7.37-7.31 (m, 4H), 7.25-7.21 (m, 1H), 6.82-6.72 (m, 1H), 6.66 (d, J=8.8 Hz, 1H), 6.03 (d, J=16.4 Hz, 1H), 5.61 (d, J=10.8 Hz, 1H), 5.27 (m, 1H), 4.62 (m, 1H), 4.43 (m, 2H), 4.07-3.96 (m, 2H), 3.13-3.05 (m, 2H), 2.94 (t, J=12.0 Hz, 1H), 2.81 (d, J=5.2 Hz, 3H), 2.77 (d, J=5.2 Hz, 3H), 2.69-2.57 (m, 1H), 1.89 (m, 1H), 1.67 (m, 1H), 1.57 (s, 3H), 1.49 (s, 3H), 1.29 (m, 1H); MS m/z: 508.3 [M+1].

TABLE 4

The following compounds were produced using the corresponding starting compounds according to a method similar to that described for the synthesis of Compound 113:

| Name | Structure | Characterization Data |
| --- | --- | --- |
| Compound 123 (S)-3-(1-acryloylpiperidine-4-carboxamido)-N-(2-(dimethylamino)-1-phenylethyl)-6,6-dimethyl-4,6-dihydropyrrolo[3,4-c]pyrazole-5(1H)-carboxamide | 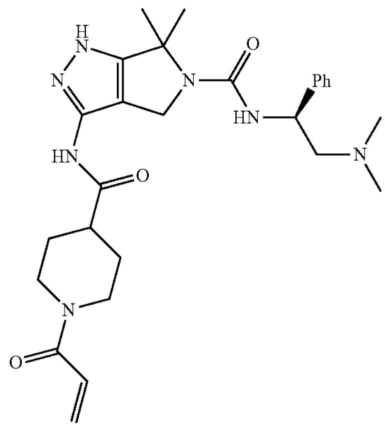 [SMILES: C=CC(=O)N1CCC(C(=O)Nc2n[nH]c3c2CN(C(=O)N[C@H](CN(C)C)c2ccccc2)C3(C)C)CC1] | $^1$H NMR (TFA salt): 600 MHz (DMSO-$d_6$) δ 10.45 (s, 1H), 8.93 (s, 1H), 7.35 (m, 3H), 7.25 (t, J = 7.0 Hz, 1H), 6.76 (dd, J = 16.4, 10.6 Hz, 1H), 6.67 (d, J = 9.4 Hz, 1H), 6.04 (dd, J = 16.4, 2.4 Hz, 1H), 5.62 (dd, J = 10.6, 2.4 Hz, 1H), 5.28 (td, J = 12.3, 3.5 Hz, 1H), 4.64 (d, J = 11.7 Hz, 1H), 4.43 (d, J = 12.3 Hz, 1H), 4.39 (d, J = 12.3 Hz, 1H), 4.05 (d, J = 14.1 Hz, 1H), 3.49 (t, J = 12.3 Hz, 1H), 3.29 (m, 1H), 3.04 (t, J = 12.9 Hz, 1H), 2.81 (d, J = 4.7 Hz, 3H), 2.79 (d, J = 4.7 Hz, 3H), 2.82 (m, 2H), 1.77 (m, 2H), 1.58 (s, 3H), 1.50 (s, 3H), 1.42 (m, 2H); MS m/z: 508.3 [M + 1]. |
| Compound 221. 3-((1s,4R)-4-acrylamidocyclohexane-1-carboxamido)-N-((S)-2-(dimethylamino)-1-phenylethyl)-6,6-dimethyl-4,6-dihydropyrrolo(3,4-c]pyrazole-5(1H)-carboxamide | 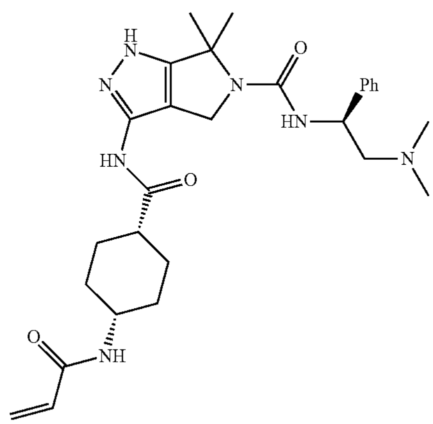 [SMILES: C=CC(=O)N[C@H]1CC[C@@H](C(=O)Nc2n[nH]c3c2CN(C(=O)N[C@H](CN(C)C)c2ccccc2)C3(C)C)CC1] | $^1$H NMR: 600 MHz (DMSO-$d_6$) δ 12.26 (s, 1H), 10.27 (s, 1H), 7.92 (s, 1H), 7.37 (m, 2H), 7.32 (m, 2H), 7.23 (m, 1H), 6.32 (dd, J = 17.0, 10.6 Hz, 1H), 6.06 (dd, J = 17.0, 2.4 Hz, 1H), 5.54 (dd, J = 10.0, 2.4 Hz, 1H), 4.56 (m, 1H), 4.48 (m, 1H), 3.86 (m, 1H), 2.43 (m, 2H), 1.76 (m, 4H), 1.60 (s, 3H), 1.57 (m, 2H), 1.53 (s, 3H); MS m/z: 522.3 [M + 1]. |
| Compound 222 3-((1r,4S)-4-acrylamidocyclohexane-1-carboxamido)-N-((S)-2-(dimethylamino)-1-phenylethyl)-6,6-dimethyl-4,6-dihydropyrrolo[3,4-c]pyrazole-5(1H)-carboxamide | 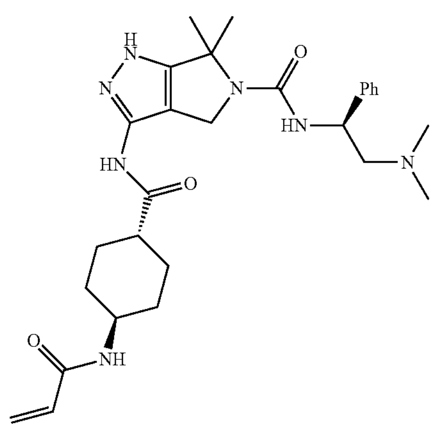 [SMILES: C=CC(=O)N[C@H]1CC[C@H](C(=O)Nc2n[nH]c3c2CN(C(=O)N[C@H](CN(C)C)c2ccccc2)C3(C)C)CC1] | $^1$H NMR: 600 MHz (DMSO-$d_6$) δ 12.24 (s, 1H), 10.31 (s, 1H), 7.97 (d, J = 7.6 Hz, 1H), 7.36 (d, J = 7.0 Hz, 2H), 7.29 (t, J = 7.6 Hz, 2H), 7.20 (t, J = 7.6 Hz, 1H), 6.34 (m, 1H), 6.16 (dd, J = 17.2, 10.0 Hz, 1H), 6.05 (dd, J = 17.0, 2.4 Hz, 1H), 5.55 (dd, J = 10.0, 2.4 Hz, 1H), 4.94 (m, 1H), 4.48 (m, 2H), 3.55 (m, 1H), 2.32 (m, 6H), 1.84 (m, 4H), 1.59 (s, 3H), 1.51 (s, 3H), 1.48 (m, 2H), 1.21 (m, 2H); MS m/z: 522.3 [M + 1]. |

Example 4. 3-((1-(4-acrylamidobenzoyl)piperidin-3-yl)amino)-N—((S)-2-(dimethylamino)-1-phenyl-ethyl)-6,6-dimethyl-4,6-dihydropyrrolo[3,4-c]pyrazole-5(1H)-carboxamide (Compound 115)
The synthesis of Compounds 115 follows Synthetic Scheme 4. The syntheses of Compounds 116 to 119, and Compounds 228 to 232 (presented in Table 5) follow a corresponding method.
Synthetic Scheme 4.
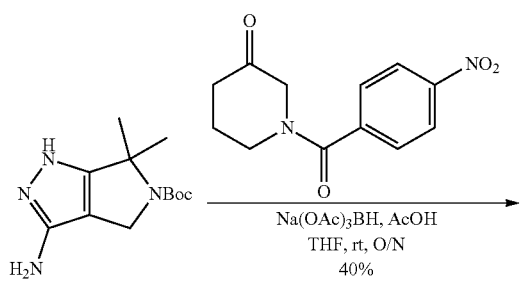
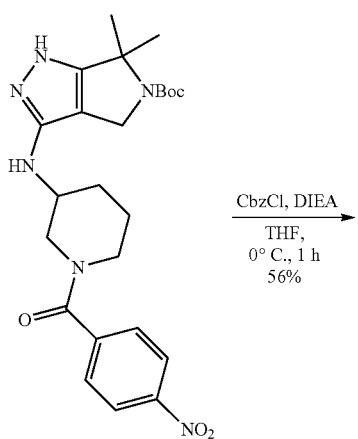
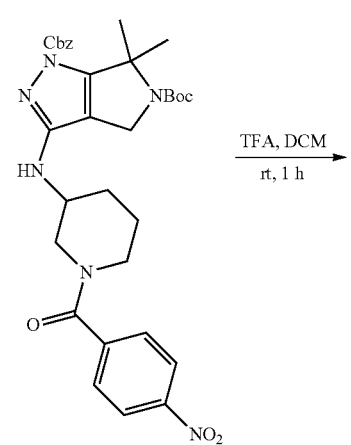
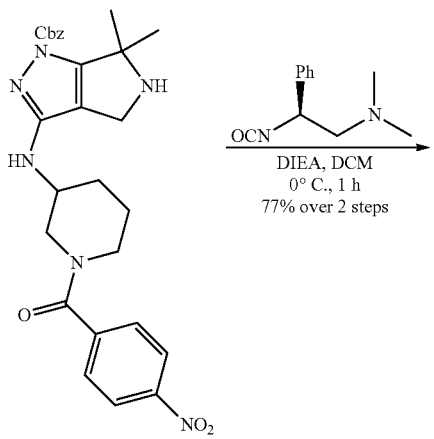
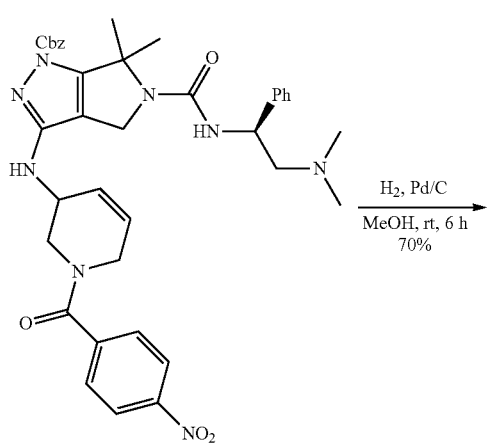
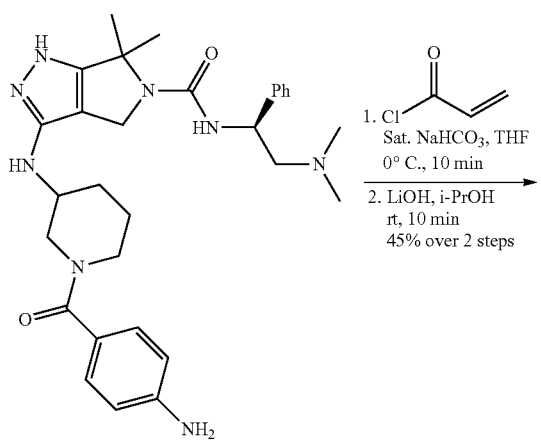

183

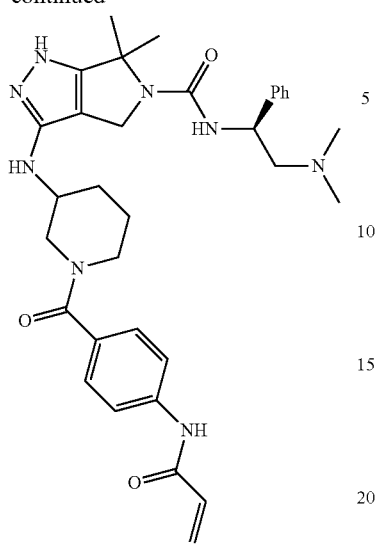

Tert-Butyl 6,6-dimethyl-3-((1-(4-nitrobenzoyl)piperidin-3-yl)amino)-4,6-dihydropyrrolo[3,4-c]pyrazole-5(1H)-carboxylate

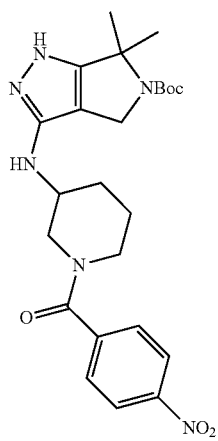 [SMILES: CC(C)(C)OC(=O)N1Cc2c(NC3CCCN(C(=O)c4ccc([N+](=O)[O-])cc4)C3)n[nH]c2C1(C)C]

To a solution of tert-butyl 3-amino-6,6-dimethyl-4,6-dihydropyrrolo[3,4-c]pyrazole-5(1H)-carboxylate (50 mg, 0.20 mmol) in THF (1 mL) was added 1-(4-nitrobenzoyl)piperidin-3-one (49 mg, 0.20 mmol), followed by AcOH (5 drops) and Na(OAc)$_3$BH (127 mg, 0.60 mmol). The mixture was stirred at room temperature O/N and diluted with EtOAc and sat. NaHCO$_3$. The organic layer was washed with water and brine, dried (Na$_2$SO$_4$), and concentrated. The crude was purified by reverse phase preparative HPLC (MeOH/H$_2$O, 0-100%) to give tert-butyl 6,6-dimethyl-3-((1-(4-nitrobenzoyl)piperidin-3-yl)amino)-4,6-dihydropyrrolo[3,4-c]pyrazole-5(1H)-carboxylate as a TFA salt (48 mg, 40%). LC/MS (ESI) m/z: 485.4 (M+H)$^+$.

184

1-Benzyl 5-(tert-butyl) 6,6-dimethyl-3-((1-(4-nitrobenzoyl)piperidin-3-yl)amino)-4,6-dihydropyrrolo[3,4-c]pyrazole-1,5-dicarboxylate

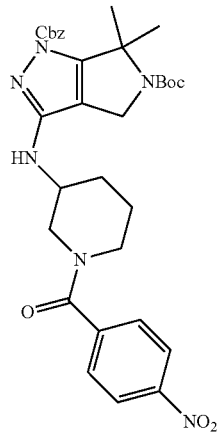 [SMILES: CC(C)(C)OC(=O)N1Cc2c(NC3CCCN(C(=O)c4ccc([N+](=O)[O-])cc4)C3)nn(C(=O)OCc3ccccc3)c2C1(C)C]

To a solution of tert-butyl 6,6-dimethyl-3-((1-(4-nitrobenzoyl)piperidin-3-yl)amino)-4,6-dihydropyrrolo[3,4-c]pyrazole-5(1H)-carboxylate TFA salt (48 mg, 0.08 mmol) in THF (2 mL) was added DIEA (31 mg, 42 μL, 0.24 mmol) at 0° C. Benzyl chloroformate (14 mg, 0.08 mmol) was added dropwise and stirred at 0° C. for 1 h. The reaction was diluted with EtOAc and sat. NaHCO$_3$. The organic layer was washed with water and brine, dried (Na$_2$SO$_4$), and concentrated. The crude was purified by flash column chromatography on silica gel (EtOAc/hexanes, 0-70%) to give 1-benzyl 5-(tert-butyl) 6,6-dimethyl-3-((1-(4-nitrobenzoyl)piperidin-3-yl)amino)-4,6-dihydropyrrolo[3,4-c]pyrazole-1,5-dicarboxylate as a yellow solid (28 mg, 56%). LC/MS (ESI) m/z: 619.4 (M+H)$^+$.

Benzyl 5-(((S)-2-(dimethylamino)-1-phenylethyl)carbamoyl)-6,6-dimethyl-3-((1-(4-nitrobenzoyl)piperidin-3-yl)amino)-5,6-dihydropyrrolo[3,4-c]pyrazole-1 (4H)-carboxylate

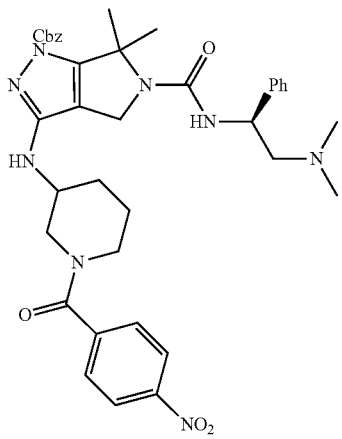 [SMILES: CN(C)C[C@@H](NC(=O)N1Cc2c(NC3CCCN(C(=O)c4ccc([N+](=O)[O-])cc4)C3)nn(C(=O)OCc3ccccc3)c2C1(C)C)c1ccccc1]

To a solution of 1-benzyl 5-(tert-butyl) 6,6-dimethyl-3-((1-(4-nitrobenzoyl)piperidin-3-yl)amino)-4,6-dihydropyrrolo[3,4-c]pyrazole-1,5-dicarboxylate (28 mg, 0.045 mmol)

in DCM (1 mL) was added TFA (1 mL). The reaction was stirred at room temperature for 1 h and concentrated to give benzyl 6,6-dimethyl-3-((1-(4-nitrobenzoyl)piperidin-3-yl)amino)-5,6-dihydropyrrolo[3,4-c]pyrazole-1(4H)-carboxylate as a TFA salt, which was used directly without further purification. LC/MS (ESI) m/z=519.4 (M+H)+.

To a mixture of benzyl 6,6-dimethyl-3-((1-(4-nitrobenzoyl)piperidin-3-yl)amino)-5,6-dihydropyrrolo[3,4-c]pyrazole-1(4H)-carboxylate (TFA salt, 0.045 mmol) in DCM (1 mL) was added DIEA (29 mg, 39 µL, 0.22 mmol) at 0° C., followed by (S)-2-isocyanato-N,N-dimethyl-2-phenylethan-1-amine HCl salt (12 mg, 0.054 mmol). The solution was stirred at 0° C. for 1 h and diluted with CHCl₃/i-PrOH (v/v 4:1) and washed with sat. NaHCO₃ and brine, dried (Na₂SO₄), and concentrated. The crude was purified by flash column chromatography on silica gel (1.75 M NH₃ in MeOH/DCM, 0-10%) to give benzyl 5-(((S)-2-(dimethylamino)-1-phenylethyl)carbamoyl)-6,6-dimethyl-3-((1-(4-nitrobenzoyl)piperidin-3-yl)amino)-5,6-dihydropyrrolo[3,4-c]pyrazole-1 (4H)-carboxylate (24 mg, 77% over 2 steps). LC/MS (ESI) m/z=709.4 (M+H)+.

3-((1-(4-Aminobenzoyl)piperidin-3-yl)amino)-N—((S)-2-(dimethylamino)-1-phenylethyl)-6,6-dimethyl-4,6-dihydropyrrolo[3,4-c]pyrazole-5(1H)-carboxamide

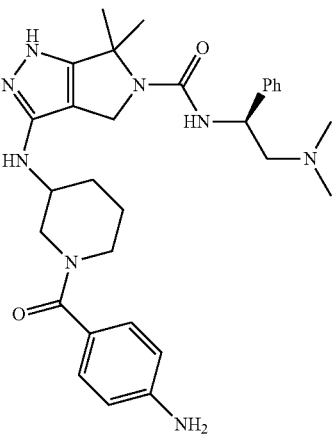 [SMILES: CN(C)C[C@@H](NC(=O)N1Cc2c(NC3CCCN(C(=O)c4ccc(N)cc4)C3)n[nH]c2C1(C)C)c1ccccc1]

A mixture of benzyl 5-(((S)-2-(dimethylamino)-1-phenylethyl)carbamoyl)-6,6-dimethyl-3-((1-(4-nitrobenzoyl)piperidin-3-yl)amino)-5,6-dihydropyrrolo[3,4-c]pyrazole-1 (4H)-carboxylate (24 mg, 0.034 mmol) and 10% Pd/C (5 mg) in MeOH (5 mL) was degassed. The mixture was stirred under H₂ (1 atm) at room temperature for 6 h. The reaction was filtered through Celite® and concentrated to give 3-((1-(4-aminobenzoyl)piperidin-3-yl)amino)-N—((S)-2-(dimethylamino)-1-phenylethyl)-6,6-dimethyl-4,6-dihydropyrrolo[3,4-c]pyrazole-5(1H)-carboxamide as a clear wax (18 mg, 70%). LC/MS (ESI) m/z: 545.4 (M+H)+.

Compound 115. 3-((1-(4-acrylamidobenzoyl)piperidin-3-yl)amino)-N—((S)-2-(dimethylamino)-1-phenylethyl)-6,6-dimethyl-4,6-dihydropyrrolo[3,4-c]pyrazole-5(1H)-carboxamide

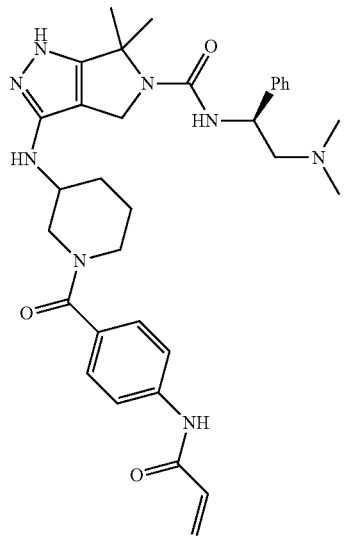 [SMILES: C=CC(=O)Nc1ccc(C(=O)N2CCCC(Nc3n[nH]c4c3CN(C(=O)N[C@H](CN(C)C)c3ccccc3)C4(C)C)C2)cc1]

To a mixture of 3-((1-(4-aminobenzoyl)piperidin-3-yl)amino)-N—((S)-2-(dimethylamino)-1-phenylethyl)-6,6-dimethyl-4,6-dihydropyrrolo[3,4-c]pyrazole-5(1H)-carboxamide (18 mg, 0.033 mmol) in THF (1 mL) and sat. NaHCO₃ (1 mL) was added acryloyl chloride (9.0 mg, 0.099 mmol) dropwise at 0° C. The mixture was stirred at 0° C. for 10 min and diluted with CHCl₃/i-PrOH (v/v 4:1) and washed with sat. NaHCO₃ and brine, dried (Na₂SO₄), and concentrated. The crude was dissolved in i-PrOH (1 mL) and LiOH (1 M, 1 mL) was added. After stirred at room temperature for 10 min, the mixture was diluted with CHCl₃/i-PrOH (v/v 4:1) and washed with sat. NaHCO₃ and brine, dried (Na₂SO₄), and concentrated. The crude was purified by reverse phase preparative HPLC (MeOH/H₂O, 0-100%) to give 3-((1-(4-acrylamidobenzoyl)piperidin-3-yl)amino)-N—((S)-2-(dimethylamino)-1-phenylethyl)-6,6-dimethyl-4,6-dihydropyrrolo[3,4-c]pyrazole-5(1H)-carboxamide TFA salt as a white solid (10.5 mg, 45%). ¹H NMR (TFA salt): 600 MHz (DMSO-d₆) δ 10.29 (s, 1H), 9.10 (s, 1H), 7.72-7.55 (m, 1H), 7.49-7.26 (m, 7H), 6.73-6.61 (m, 1H), 6.49-6.40 (m, 1H), 6.27-6.24 (m, 1H), 5.77-5.75 (m, 1H), 5.36-5.26 (m, 1H), 4.55-4.50 (m, 1H), 4.30-4.24 (m, 2H), 3.55-3.45 (m, 3H), 3.38-3.32 (m, 2H), 3.28-3.07 (m, 2H), 2.88 (m, 3H), 2.85 (m, 1H), 2.82 (m, 3H), 2.00-1.90 (m, 1H), 1.85-1.70 (m, 1H), 1.65-1.50 (m, 6H), 1.09-1.03 (m, 1H); MS m/z: 599.4 [M+1].

TABLE 5

The following compounds were produced using the corresponding starting compounds according to a method similar to that described for the synthesis of Compound 115:

| Name | Structure | Characterization Data |
| --- | --- | --- |
| Compound 116 (S)-3-((1-(4-acrylamidobenzoyl)piperidin-4-yl)amino)-N-(2-(dimethylamino)-1-phenylethyl)-6,6-dimethyl-4,6-dihydropyrrolo[3,4-c]pyrazole-5(1H)-carboxamide | 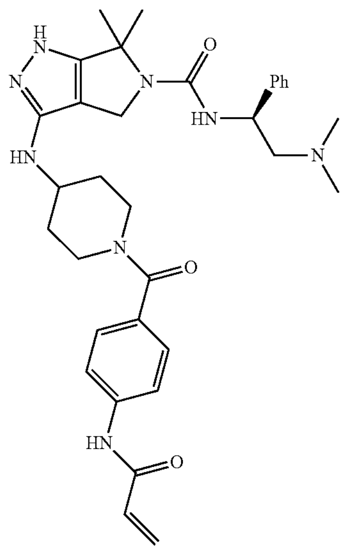 [SMILES: C=CC(=O)Nc1ccc(C(=O)N2CCC(Nc3n[nH]c4c3CN(C(=O)N[C@H](CN(C)C)c3ccccc3)C4(C)C)CC2)cc1] | $^1$H NMR: 600 MHz (DMSO-$d_6$) δ 11.30 (br, 1H), 10.30 (s, 1H), 7.71 (d, J = 9.0 Hz, 2H), 7.36-7.33 (m, 4H), 7.28 (t, J = 7.8 Hz, 2H), 7.18 (t, J = 7.8 Hz, 1H), 6.43 (dd, J = 16.8, 10.2 Hz, 1H), 6.27 (dd, J = 16.8, 2.2 Hz, 1H), 5.95 (d, J = 6.0 Hz, 1H), 5.77 (dd, J = 10.2, 2.2 Hz, 1H), 5.33-5.20 (m, 1H), 4.82 (q, J = 7.2 Hz, 1H), 4.26 (q, J = 12.0 Hz, 2H), 3.72-3.58 (m, 1H), 3.16-3.03 (m, 2H), 2.60 (m, 1H), 2.42 (m, 1H), 2.19 (s, 6H), 1.89 (m, 2H), 1.54 (s, 3H), 1.48 (s, 3H), 1.36 (m, 2H); MS m/z: 599.4 [M + 1]. |
| Compound 117 3-(((1R,3S)-3-(4-acrylamidobenzamido)cyclohexyl)amino)-N-((S)-2-(dimethylamino)-1-phenylethyl)-6,6-dimethyl-4,6-dihydropyrrolo[3,4-c]pyrazole-5(1H)-carboxamide | 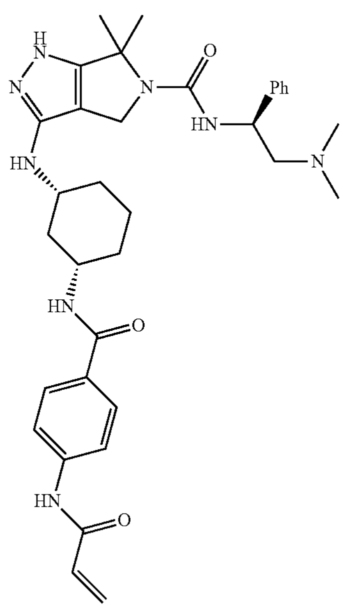 [SMILES: C=CC(=O)Nc1ccc(C(=O)N[C@H]2CCC[C@@H](Nc3n[nH]c4c3CN(C(=O)N[C@H](CN(C)C)c3ccccc3)C4(C)C)C2)cc1] | $^1$H NMR (TFA salt): 600 MHz (DMSO-$d_6$) δ 10.35 (d, J = 3.0 Hz, 1H), 9.11 (s, 1H), 8.09 (d, J = 7.8 Hz, 1H), 7.80 (dd, J = 9.0, 2.0 Hz, 2H), 7.71 (dd, J = 9.0, 1.8 Hz, 2H), 7.46-7.42 (m, 2H), 7.39-7.35 (m, 2H), 7.30-7.28 (m, 1H), 6.68 (t, J = 7.8 Hz, 1H), 6.44 (dd, J = 16.8, 10.2 Hz, 1H), 6.27 (dd, J = 16.8, 2.2 Hz, 1H), 5.78 (dd, J = 10.2, 2.2 Hz, 1H), 5.34-5.30 (m, 1H), 4.52 (t, J = 12.0 Hz, 1H), 4.38 (dd, J = 13.2, 12.0 Hz, 2H), 4.17-4.10 (m, 1H), 3.67 (m, 2H), 3.48 (t, J = 12.0 Hz, 2H), 3.37-3.33 (m, 2H), 2.88 (m, 3H), 2.82 (m, 3H), 1.89-1.80 (m, 2H), 1.71-1.60 (m, 3H), 1.62 (s, 3H), 1.55 (s, 3H), 1.36 (m, 2H); MS m/z: 613.4 [M + 1]. |

TABLE 5-continued

The following compounds were produced using the corresponding starting compounds according to a method similar to that described for the synthesis of Compound 115:

| Name | Structure | Characterization Data |
|---|---|---|
| Compound 118<br>3-(((1R,3R)-3-(4-acrylamidobenzamido)cyclohexyl)amino)-N-((S)-2-(dimethylamino)-1-phenylethyl)-6,6-dimethyl-4,6-dihydropyrrolo[3,4-c]pyrazole-5(1H)-carboxamide | | $^1$H NMR: 600 MHz (DMSO-$d_6$) δ 11.22 (br, 1H), 10.32 (s, 1H), 8.19 (dd, J = 7.8, 3.0 Hz, 1H), 7.81 (dd, J = 8.4, 3.0 Hz, 2H), 7.70 (dd, J = 8.4, 5.4 Hz, 2H), 7.35 (d, J = 7.8 Hz, 2H), 7.30-7.26 (m, 2H), 7.20-7.16 (m, 1H), 6.43 (dd, J = 16.8, 10.2 Hz, 1H), 6.27 (dd, J = 16.8, 2.2 Hz, 1H), 6.01 (m, 1H), 5.77 (dd, J = 10.2, 2.2 Hz, 1H), 5.25-5.17 (m, 1H), 4.89-4.82 (m, 1H), 4.36-4.27 (m, 2H), 3.90-3.83 (m, 1H), 3.08-3.01 (m, 1H), 2.68-2.60 (m, 1H), 2.50-2.42 (m, 1H), 2.21 (s, 3H), 2.19 (s, 3H), 2.13-2.08 (m, 1H), 1.92-1.86 (m, 1H), 1.85-1.79 (m, 1H), 1.78-1.73 (m, 1H), 1.54 (s, 3H), 1.48 (d, J = 5.4 Hz, 3H), 1.42-1.35 (m, 1H), 1.28-1.19 (m, 2H), 1.11-1.03 (m, 1H); MS m/z: 613.4 [M + 1]. |
| Compound 119<br>(S)-3-((4-(4-acrylamidobenzamido)cyclohexyl)amino)-N-(2-(dimethylamino)-1-phenylethyl)-6,6-dimethyl-4,6-dihydropyrrolo[3,4-c]pyrazole-5(1H)-carboxamide | | $^1$H NMR: 600 MHz (DMSO-$d_6$) δ 11.30 (br, 1H), 10.32 (s, 1H), 8.11 (d, J = 7.8 Hz, 1H), 7.80 (d, J = 8.4 Hz, 2H), 7.71 (d, J = 8.4 Hz, 2H), 7.37 (m, 2H), 7.32 (m, 2H), 7.22 (m, 1H), 6.43 (dd, J = 16.8, 10.2 Hz, 1H), 6.27 (d, J = 16.8 Hz, 1H), 6.13 (m, 1H), 5.78 (d, J = 10.2, Hz, 1H), 5.13-4.94 (m, 2H), 4.35-4.26 (m, 2H), 3.75-3.49 (m, 1H), 3.47 (t, J = 5.4 Hz, 1H), 3.40 (t, J = 5.4 Hz, 1H), 3.07-2.97 (m, 2H), 2.50-2.32 (m, 4H), 1.98 (d, J = 10.8 Hz, 3H), 1.87 (d, J = 10.2 Hz, 3H), 1.77-1.70 (m, 1H), 1.67-1.60 (m, 1H), 1.56 (s, 3H), 1.49 (s, 3H), 1.47-1.38 (m, 2H), 1.37-1.33 (m, 1H), 1.29-1.17 (m, 4H), 1.15 (t, J = 7.2 Hz, 1H), 0.85-0.76 (m, 1H); MS m/z: 613.4 [M + 1]. |
| Compound 228.<br>3-(((1R,3S)-3-acrylamidocyclohexyl)amino)-N-((S)-2-(dimethylamino)-1-phenylethyl)-6,6-dimethyl-4,6-dihydropyrrolo[3,4-c]pyrazole-5(1H)-carboxamide | | $^1$H NMR: 600 MHz (DMSO-$d_6$) δ 11.24 (br, 1H), 9.01 (br, 1H), 8.07 (m, 1H), 7.40 (m, 2H), 7.35 (m, 2H), 7.26 (m, 1H), 6.52 (br, 1H), 6.17 (ddd, J = 17.0, 10.0, 1.2 Hz, 1H), 6.05 (ddd, J = 17.0, 7.0, 1.8 Hz, 1H), 5.55 (ddd, J = 10.0, 7.6, 2.4 Hz, 1H), 5.20 (m, 1H), 4.42 (m, 1H), 4.31 (m, 1H), 3.69 (m, 1H), 2.98 (m, 1H), 2.76 (m, 6H), 2.03 (m, 1H), 1.87 (m, 1H), 1.76 (m, 2H), 1.56 (s, 3H), 1.48 (s, 3H), 1.32 (m, 1H), 1.08 (m, 2H); MS m/z: 494.4 [M + 1]. |

TABLE 5-continued

The following compounds were produced using the corresponding starting compounds according to a method similar to that described for the synthesis of Compound 115:

| Name | Structure | Characterization Data |
| --- | --- | --- |
| Compound 229. 3-(((1R,3R)-3-acrylamidocyclohexyl)amino)-N-((S)-2-(dimethylamino)-1-phenylethyl)-6,6-dimethyl-4,6-dihydropyrrolo[3,4-c]pyrazole-5(1H)-carboxamide | 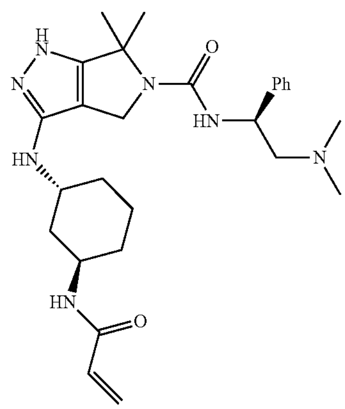 [SMILES: C=CC(=O)N[C@@H]1CCC[C@@H](Nc2n[nH]c3c2CN(C(=O)N[C@H](CN(C)C)c2ccccc2)C3(C)C)C1] | $^1$H NMR: 600 MHz (DMSO-$d_6$) δ 11.13 (br, 1H), 9.00 (br, 1H), 7.96 (m, 1H), 7.40 (t, J = 7.6 Hz, 2H), 7.36 (t, J = 7.0 Hz, 2H), 7.27 (t, J = 7.0 Hz, 1H), 6.52 (br, 1H), 6.25 (ddd, J = 17.0, 10.6, 7.0 Hz, 1H), 6.04 (ddd, J = 17.0, 3.5, 2.4 Hz, 1H), 5.53 (ddd, J = 10.0, 10.0, 2.4 Hz, 1H), 5.27 (m, 1H), 4.43 (m, 1H), 4.30 (t, J = 11.2 Hz, 1H), 4.01 (m, 1H), 3.50 (m, 1H), 2.78 (m, 6H), 1.74 (m, 2H), 1.61 (m, 1H), 1.57 (s, 3H), 1.52 (m, 3H), 1.48 (s, 3H), 1.22 (m, 2H); MS m/z: 494.4 [M + 1]. |
| Compound 230. (S)-3-((4-acrylamidocyclohexyl)amino)-N-(2-(dimethylamino)-1-phenylethyl)-6,6-dimethyl-4,6-dihydropyrrolo[3,4-c]pyrazole-5(1H)-carboxamide | 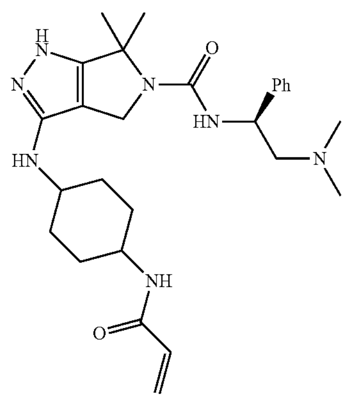 [SMILES: C=CC(=O)NC1CCC(Nc2n[nH]c3c2CN(C(=O)N[C@H](CN(C)C)c2ccccc2)C3(C)C)CC1] | $^1$H NMR (mixture of diastereomers): 600 MHz (DMSO-$d_6$) δ 11.28 (br, 1H), 9.04 (s, 1H), 7.94 (dd, J = 18.8, 7.6 Hz, 1H), 7.41 (d, J = 7.6 Hz, 2H), 7.36 (t, J = 7.0 Hz, 2H), 7.27 (t, J = 7.6 Hz, 1H), 6.58 (br, 1H), 6.28 (dd, J = 17.0, 10.6 Hz, 1H for one isomer), 6.20 (dd, J = 17.0, 10.0 Hz, 1H for another isomer), 6.05 (ddd, J = 17.0, 4.7, 2.4 Hz, 1H), 5.54 (dd, J = 10.0, 2.4 Hz, 1H), 5.29 (br, 1H), 4.42 (dd, J = 23.5, 10.0 Hz, 1H), 4.29 (dd, J = 27.0, 11.2 Hz, 1H), 3.72 (m, 1H), 3.55 (m, 1H), 3.20 (m, 1H), 2.97 (m, 1H), 2.81 (m, 6H), 1.94 (m, 1H), 1.83 (m, 1H), 1.61 (m, 2H), 1.57 (s, 3H), 1.49 (s, 3H for one isomer), 1.48 (s, 3H for another isomer), 1.23 (m, 2H); MS m/z: 494.4 [M + 1]. |
| Compound 231. (S)-3-((1-acryloylpiperidin-4-yl)amino)-N-(2-(dimethylamino)-1-phenylethyl)-6,6-dimethyl-4,6-dihydropyrrolo[3,4-c]pyrazole-5(1H)-carboxamide | | $^1$H NMR: 600 MHz (DMSO-$d_6$) δ 11.30 (br, 1H), 7.34 (d, J = 7.6 Hz, 2H), 7.29 (t, J = 7.0 Hz, 2H), 7.19 (t, J = 7.0 Hz, 1H), 6.81 (dd, J = 17.0, 10.6 Hz, 1H), 6.08 (dd, J = 17.0, 2.9 Hz, 1H), 5.98 (br, 1H), 5.65 (dd, J = 10.0, 2.4 Hz, 1H), 4.86 (m, 1H), 4.27 (m, 2H), 4.20 (d, J = 13.0 Hz, 1H), 3.95 (d, J = 13.5 Hz, 1H), 3.19 (t, J = 12.3 Hz, 1H), 2.91 (t, J = 11.2 Hz, 1H), 2.22 (m, 6H), 1.88 (m, 2H), 1.55 (s, 3H), 1.48 (s, 3H), 1.28 (m, 2H); MS m/z: 480.3 [M + 1]. |

TABLE 5-continued

The following compounds were produced using the corresponding starting compounds according to a method similar to that described for the synthesis of Compound 115:

| Name | Structure | Characterization Data |
|---|---|---|
| Compound 232. 3-((1-acryloylpiperidin-3-yl)amino)-N-((S)-2-(dimethylamino)-1-phenylethyl)-6,6-dimethyl-4,6-dihydropyrrolo[3,4-c]pyrazole-5(1H)-carboxamide | 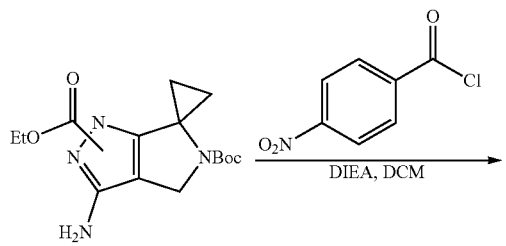 | $^1$H NMR: 600 MHz (DMSO-$d_6$) δ 11.29 (br, 1H), 7.33 (m, 2H), 7.28 (m, 2H), 7.19 (m, 1H), 6.81 (m, 1H), 6.63 (dd, J = 16.4, 10.6 Hz, 1H), 6.10 (dd, J = 15.9, 5.9 Hz, 1H), 6.02 (d, J = 17.0 Hz, 1H), 5.96 (m, 1H), 5.66 (d, J = 9.4 Hz, 1H), 5.56 (dd, J = 18.8, 12.3 Hz, 1H), 5.31 (m, 1H), 4.84 (m, 1H), 4.36 (m, 1H), 4.25 (m, 2H), 4.01 (m, 1H), 3.86 (m, 2H), 3.19 (m, 1H), 3.06 (m, 1H), 2.64 (m, 2H), 2.20 (m, 6H), 1.95 (m, 1H), 1.73 (m, 1H), 1.55 (s, 3H), 1.48 (d, J = 5.9 Hz, 3H), 1.43 (m, 2H); MS m/z: 480.3 [M + 1]. |

Example 5. (S)-3'-(4-acrylamidobenzamido)-N-(2-(dimethylamino)-1-phenylethyl)-1',4'-dihydro-5'H-spiro[cyclopropane-1,6'-pyrrolo[3,4-c]pyrazole]-5'-carboxamide (Compound 233)

The synthesis of Compound 233 follows Synthetic Scheme 5. The syntheses of Compounds 234-240 (presented in Table 6) follow a corresponding method.

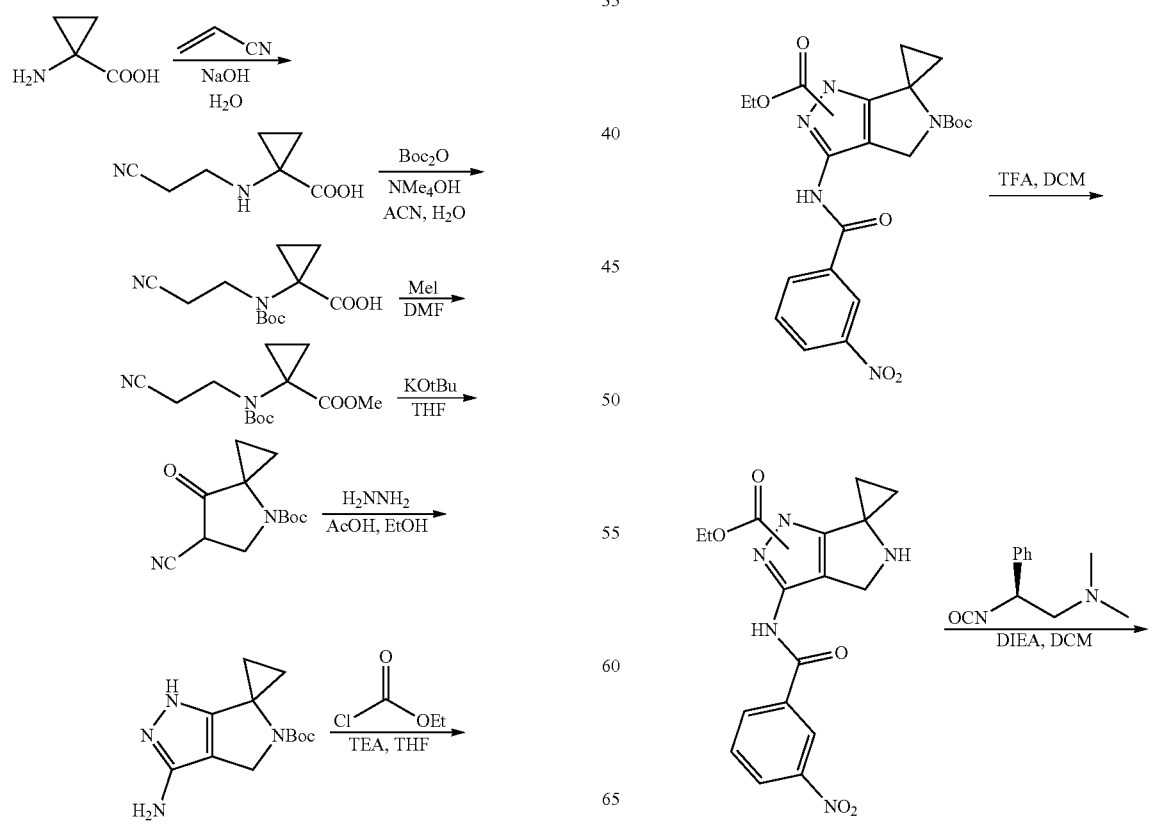

Synthetic Scheme 5.

195
-continued

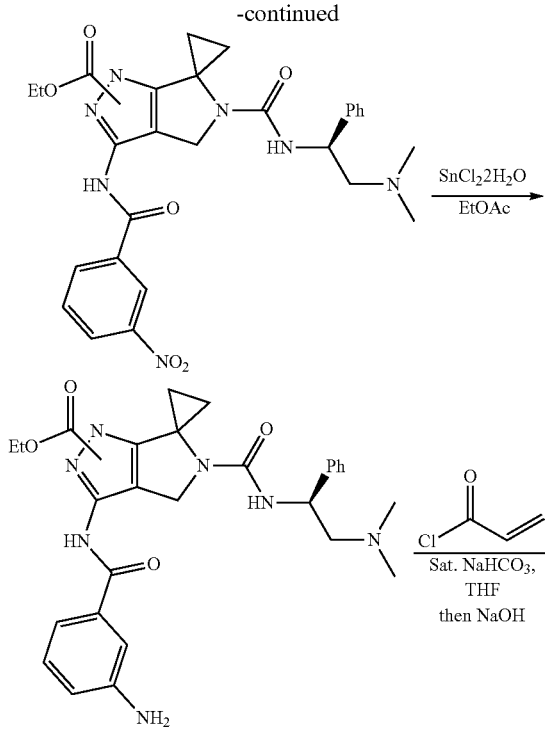

SnCl₂2H₂O / EtOAc

Cl / Sat. NaHCO₃, THF then NaOH

196
-continued

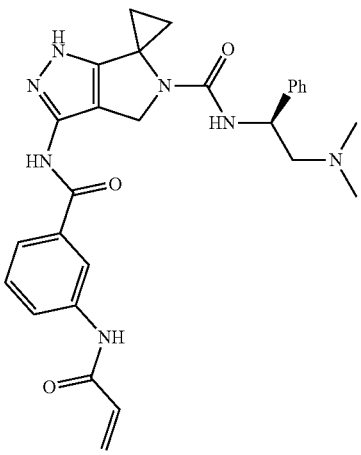

TABLE 6

The following compounds were produced using the corresponding starting compounds according to a method similar to that described for the synthesis of Compound 233.

| Name | Structure | Characterization Data |
|---|---|---|
| Compound 233. (S)-3'-(4-acrylamidobenzamido)-N-(2-(dimethylamino)-1-phenylethyl)-1',4'-dihydro-5'H-spiro[cyclopropane-1,6'-pyrrolo[3,4-c]pyrazole]-5'-carboxamide | 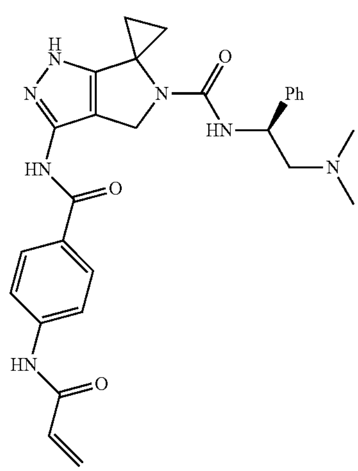 [SMILES: C=CC(=O)Nc1ccc(C(=O)Nc2n[nH]c3c2CN(C(=O)N[C@H](CN(C)C)c2ccccc2)C32CC2)cc1] | $^1$H NMR: 600 MHz (DMSO-$d_6$) δ 12.16 (br, 1H), 10.79 (s, 1H), 10.44 (s, 1H), 8.00 (m, 2H), 7.79 (m, 2H), 7.36 (m, 2H), 7.30 (m, 2H), 7.21 (m, 1H), 6.46 (dd, J = 17.0, 10.0 Hz, 1H), 6.29 (dd, J = 17.0, 1.8 Hz, 1H), 5.80 (dd, J = 10.0, 1.8 Hz, 1H), 4.89 (m, 1H), 4.70 (m, 2H), 2.27 (m, 6H), 2.05 (m, 1H), 1.99 (m, 1H), 0.82 (m, 4H); MS m/z: 514.3 [M + 1]. |

TABLE 6-continued

The following compounds were produced using the corresponding starting compounds according to a method similar to that described for the synthesis of Compound 233.

| Name | Structure | Characterization Data |
|---|---|---|
| Compound 234. (R)-3-(4-acrylamidobenzamido)-N-((S)-2-(dimethylamino)-1-phenylethyl)-6-isopropyl-4,6-dihydropyrrolo[3,4-c]pyrazole-5(1H)-carboxamide | 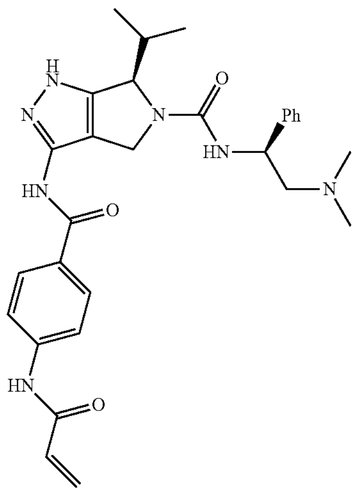 [SMILES: C=CC(=O)Nc1ccc(C(=O)Nc2n[nH]c3c2CN(C(=O)N[C@H](CN(C)C)c2ccccc2)[C@@H]3C(C)C)cc1] | $^1$H NMR: 600 MHz (DMSO-$d_6$) δ 12.42 (br, 1H), 10.77 (s, 1H), 10.45 (s, 1H), 8.00 (d, J = 8.2 Hz, 2H), 7.79 (d, J = 8.2 Hz, 2H), 7.38 (m, 2H), 7.32 (m, 2H), 7.22 (m, 1H), 6.60 (br, 1H), 6.47 (dd, J = 17.0, 10.0 Hz, 1H), 6.29 (dd, J = 17.0, 2.4 Hz, 1H), 5.79 (dd, J = 10.6, 1.8 Hz, 1H), 1.83 (m, 1H), 4.54 (m, 2H), 2.33 (m, 6H), 0.98 (d, J = 5.3 Hz, 3H), 0.84 (m, 1H), 0.49 (d, J = 6.5 Hz, 3H); MS m/z: 530.3 [M + 1]. |
| Compound 235. (S)-3-(4-acrylamidobenzamido)-N-((S)-2-(dimethylamino)-1-phenylethyl)-6-isopropyl-4,6-dihydropyrrolo[3,4-c]pyrazole-5(1H)-carboxamide | 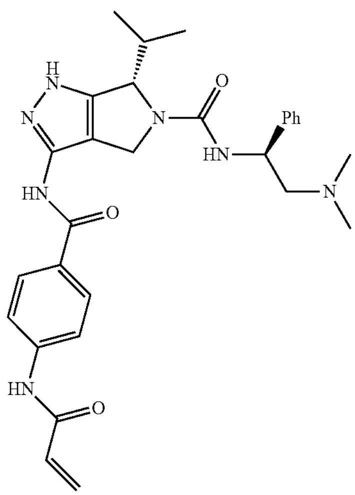 [SMILES: C=CC(=O)Nc1ccc(C(=O)Nc2n[nH]c3c2CN(C(=O)N[C@H](CN(C)C)c2ccccc2)[C@H]3C(C)C)cc1] | $^1$H NMR: 600 MHz (DMSO-$d_6$) δ 12.40 (br, 1H), 10.76 (s, 1H), 10.44 (s, 1H), 8.00 (d, J = 7.6 Hz, 2H), 7.78 (d, J = 7.6 Hz, 2H), 7.35 (m, 2H), 7.30 (m, 2H), 7.20 (m, 1H), 6.56 (br, 1H), 6.47 (dd, J = 17.0, 10.0 Hz, 1H), 6.29 (dd, J = 17.0, 1.8 Hz, 1H), 5.80 (dd, J = 10.0, 1.8 Hz, 1H), 4.97 (m, 1H), 4.79 (m, 1H), 4.53 (m, 2H), 2.37 (m, 6H), 1.00 (m, 3H), 0.84 (m, 1H), 0.55 (d, J = 7.0 Hz, 3H); MS m/z: 530.3 [M + 1]. |
| Compound 236. (S)-3'-(4-acrylamidobenzamido)-N-(2-(dimethylamino)-1-phenylethyl)-1',4'-dihydro-5'H-spiro(cyclohexane-1,6'-pyrrolo[3,4-c]pyrazole]-5'-carboxamide | 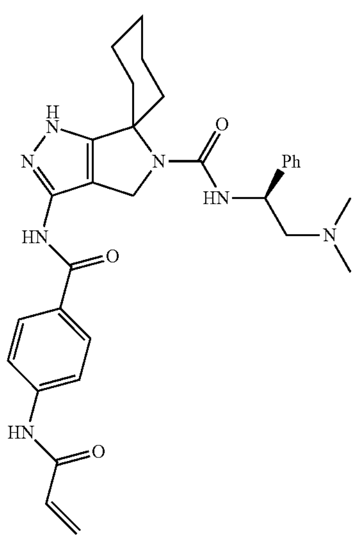 [SMILES: C=CC(=O)Nc1ccc(C(=O)Nc2n[nH]c3c2CN(C(=O)N[C@H](CN(C)C)c2ccccc2)C32CCCCC2)cc1] | $^1$H NMR: 500 MHz (DMSO-$d_6$) δ 12.40 (br, 1H), 10.83 (s, 1H), 10.48 (s, 1H), 8.06 (d, J = 8.5 Hz, 2H), 7.86 (d, J = 8.5 Hz, 2H), 7.42 (d, J = 7.3 Hz, 2H), 7.35 (t, J = 7.3 Hz, 2H), 7.25 (t, J = 7.3 Hz, 1H), 6.53 (dd, J = 17.0, 10.0 Hz, 1H), 6.37 (dd, J = 17.0, 1.8 Hz, 1H), 6.27 (m, 1H), 5.88 (dd, J = 10.0, 1.8 Hz, 1H), 4.92 (m, 1H), 4.59 (m, 2H), 2.87 (m, 1H), 2.74 (m, 2H), 2.46 (m, 1H), 2.25 (s, 6H), 1.69 (m, 4H), 1.53 (m, 2H), 1.42 (m, 2H), 1.29 (s, 6H), 1.21 (m, 2H), 0.91 (m, 2H); MS m/z: 556.3 [M + 1]. |

TABLE 6-continued

The following compounds were produced using the corresponding starting compounds according to a method similar to that described for the synthesis of Compound 233.

| Name | Structure | Characterization Data |
| --- | --- | --- |
| Compound 237. (R)-3-(4-acrylamidobenzamido)-N-((S)-2-(dimethylamino)-1-phenylethyl)-6-phenyl-4,6-dihydropyrrolo[3,4-c]pyrazole-5(1H)-carboxamide | 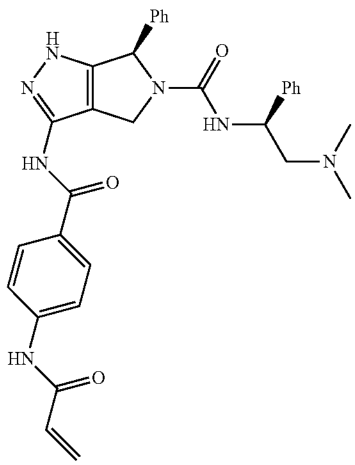 [SMILES: C=CC(=O)Nc1ccc(C(=O)Nc2n[nH]c3c2CN(C(=O)N[C@H](CN(C)C)c2ccccc2)[C@@H]3c2ccccc2)cc1] | ¹H NMR (a mixture of two rotamers): 500 MHz (DMSO-d₆) δ 12.33, 12.14 (s, 1H), 10.84, 10.73 (s, 1H), 10.35 (s, 1H), 7.95 (m, 2H), 7.73 (m, 2H), 7.23 (m, 9H), 7.10 (t, J = 7.3 Hz, 1H), 6.40 (dd, J = 17.1, 10.1 Hz, 1H), 6.24 (dd, J = 16.8, 1.8 Hz, 1H), 5.93 (m, 1H), 5.74 (dd, J = 10.1, 1.8 Hz, 1H), 4.73 (m, 1H), 4.61 (m, 2H), 2.21 (m, 1H), 1.99 (m, 6H); MS m/z: 564.3 [M + 1]. |
| Compound 238. (R)-3-(4-acrylamidobenzamido)-N-((S)-2-(dimethylamino)-1-phenylethyl)-6-phenyl-4,6-dihydropyrrolo[3,4-c]pyrazole-5(1H)-carboxamide | 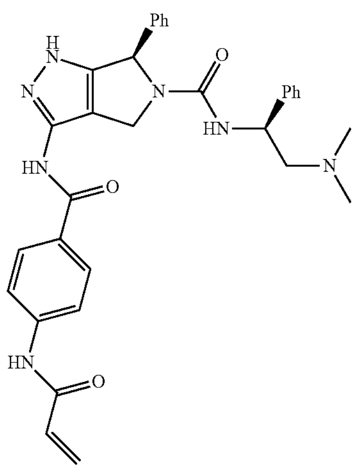 [SMILES: C=CC(=O)Nc1ccc(C(=O)Nc2n[nH]c3c2CN(C(=O)N[C@H](CN(C)C)c2ccccc2)[C@@H]3c2ccccc2)cc1] | ¹H NMR: 500 MHz (DMSO-d₆) δ 12.33 (s, 1H), 10.75 (s, 1H), 10.35 (s, 1H), 7.95 (m, 2H), 7.73 (m, 2H), 7.21 (m, 10H), 6.40 (dd, J = 17.1, 10.0 Hz, 1H), 6.24 (dd, J = 17.1, 1.8 Hz, 1H), 5.87 (m, 1H), 5.75 (dd, J = 10.1, 1.8 Hz, 1H), 4.72 (m, 2H), 4.61 (m, 1H), 2.57 (m, 1H), 2.31 (m, 1H), 2.11 (s, 6H); MS m/z: 564.3 [M + 1]. |
| Compound 239. (S)-3-(4-acrylamidobenzamido)-N-((S)-2-(dimethylamino)-1-phenylethyl)-6-phenyl-4,6-dihydropyrrolo[3,4-c]pyrazole-5(1H)-carboxamide | 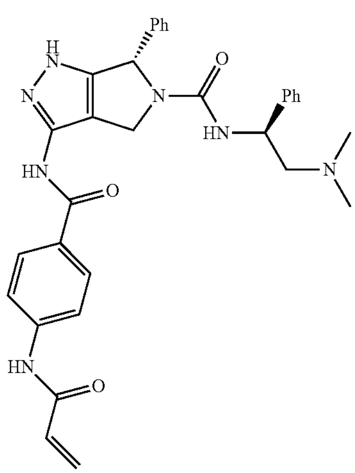 [SMILES: C=CC(=O)Nc1ccc(C(=O)Nc2n[nH]c3c2CN(C(=O)N[C@H](CN(C)C)c2ccccc2)[C@H]3c2ccccc2)cc1] | ¹H NMR (a mixture of two rotamers): 500 MHz (DMSO-d₆) δ 12.34, 12.10 (s, 1H), 10.74 (s, 1H), 10.35 (s, 1H), 7.95 (m, 2H), 7.73 (m, 2H), 7.20 (m, 10H), 6.40 (dd, J = 17.1, 10.1 Hz, 1H), 6.24 (dd, J = 17.1, 1.8 Hz, 1H), 5.93 (m, 1H), 5.74 (dd, J = 10.1, 1.8 Hz, 1H), 4.73 (m, 1H), 4.61 (m, 2H), 2.23 (m, 1H), 2.00 (m, 6H); MS m/z: 564.3 [M + 1]. |

TABLE 6-continued

The following compounds were produced using the corresponding starting compounds according to a method similar to that described for the synthesis of Compound 233.

| Name | Structure | Characterization Data |
|---|---|---|
| Compound 240. (S)-3-(4-acrylamidobenzamido)-N-((S)-2-(dimethylamino)-1-phenylethyl)-6-phenyl-4,6-dihydropyrrolo[3,4-c]pyrazole-5(1H)-carboxamide | 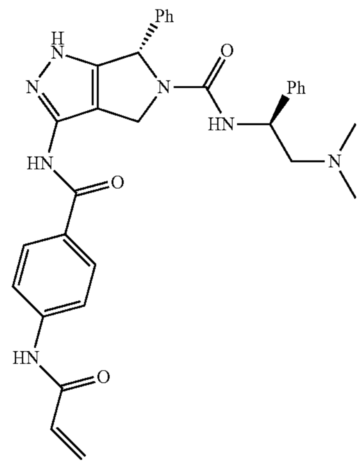 [SMILES: C=CC(=O)Nc1ccc(C(=O)Nc2n[nH]c3c2CN(C(=O)N[C@H](CN(C)C)c2ccccc2)[C@H]3c2ccccc2)cc1] | $^1$H NMR: 500 MHz (DMSO-$d_6$) δ 12.37 (s, 1H), 10.77 (s, 1H), 10.42 (s, 1H), 7.96 (m, 2H), 7.75 (m, 2H), 7.20 (m, 10H), 6.43 (dd, J = 17.1, 10.1 Hz, 1H), 6.24 (dd, J = 17.1, 1.8 Hz, 1H), 5.90 (m, 1H), 5.75 (dd, J = 10.1, 1.8 Hz, 1H), 4.42 (m, 6H), 1.19 (m, 1H); MS m/z: 564.3 [M + 1]. |

The synthesis of Compound 241 follows Synthetic Scheme 6. The syntheses of Compounds 242-247 (presented in Table 7) follow a corresponding method.

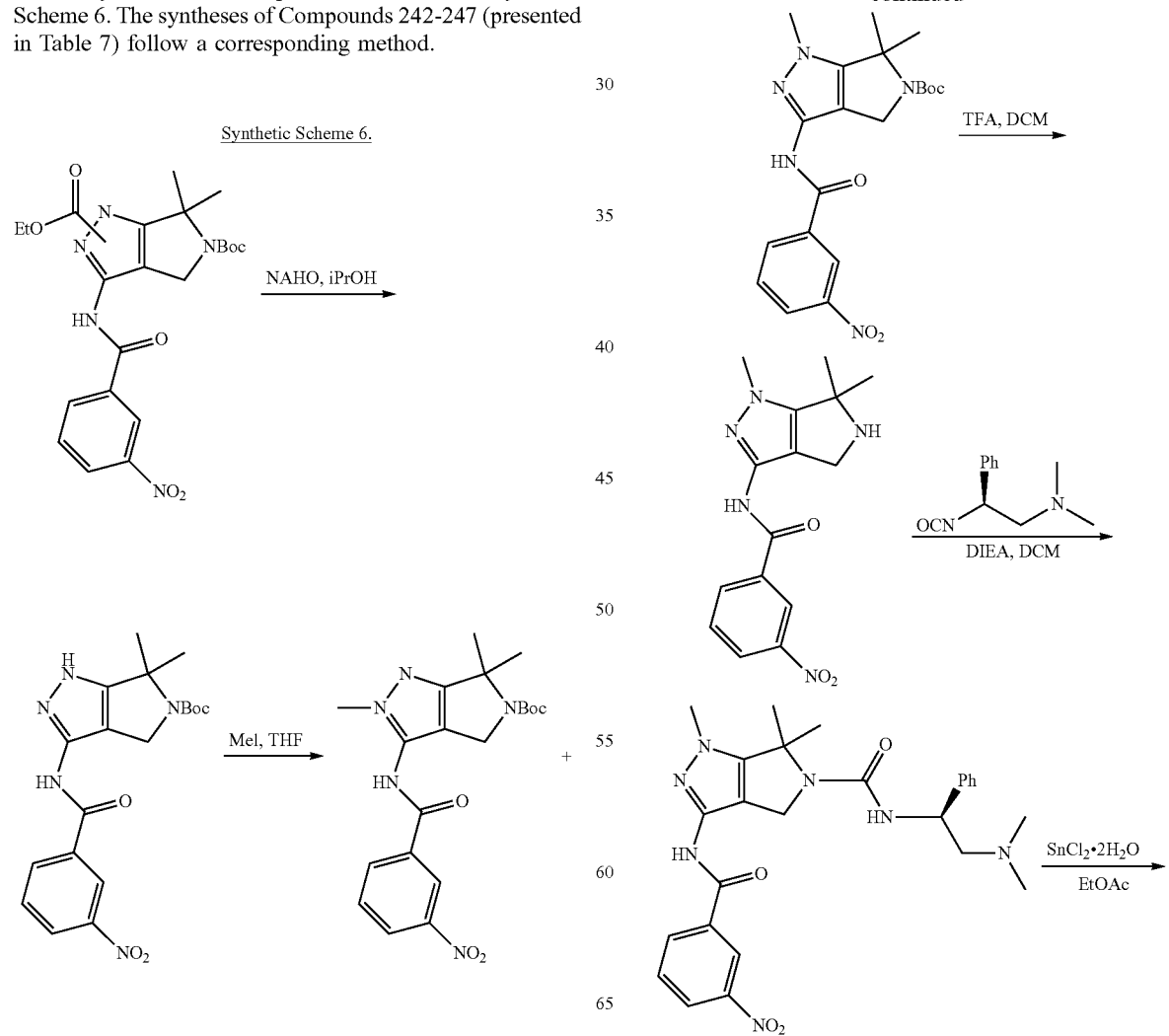

Synthetic Scheme 6.

203
-continued

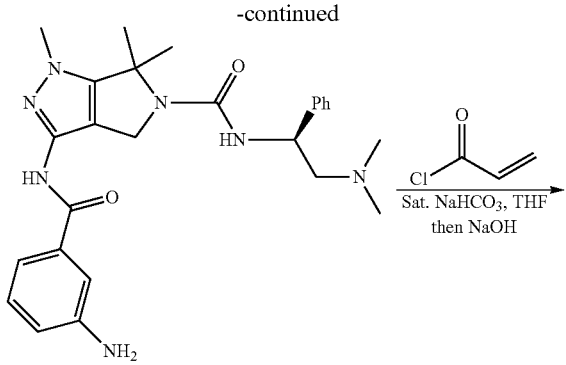

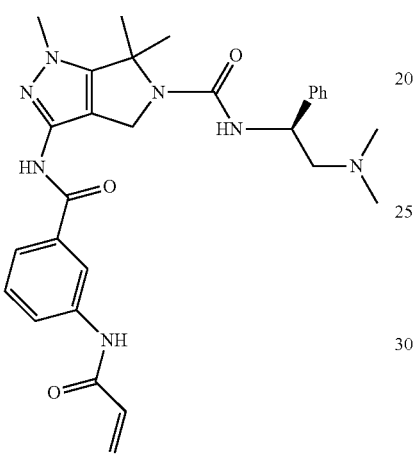

t-Butyl 6,6-dimethyl-3-(3-nitrobenzamido)-4,6-dihydropyrrolo[3,4-c]pyrazole-5(1H)-carboxylate

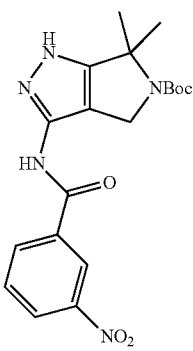 [SMILES: CC(C)(C)OC(=O)N1Cc2c(NC(=O)c3cccc([N+](=O)[O-])c3)n[nH]c2C1(C)C]

To a solution of 5-(tert-butyl) ethyl 6,6-dimethyl-3-((3-nitrophenyl)amino)-4,6-dihydropyrrolo[3,4-c]pyrazole-1,5-dicarboxylate (500 mg, 1.05 mmol) in i-PrOH (5 mL) was added 1 M NaOH aqueous solution (5 mL). The mixture was stirred at rt for 30 min and extracted with CHCl₃/i-PrOH (v:v 4:1). The crude was purified by flash column chromatography on silica gel (1.75 M NH₃ in MeOH/DCM, 0-15%) to give t-butyl 6,6-dimethyl-3-(3-nitrobenzamido)-4,6-dihydropyrrolo[3,4-c]pyrazole-5(1H)-carboxylate as a yellow solid (394 mg, 93%). LC/MS (ESI) m/z: 402.4 (M+H)⁺.

204 t-Butyl 1,6,6-trimethyl-3-(3-nitrobenzamido)-4,6-dihydropyrrolo[3,4-c]pyrazole-5(1H)-carboxylate

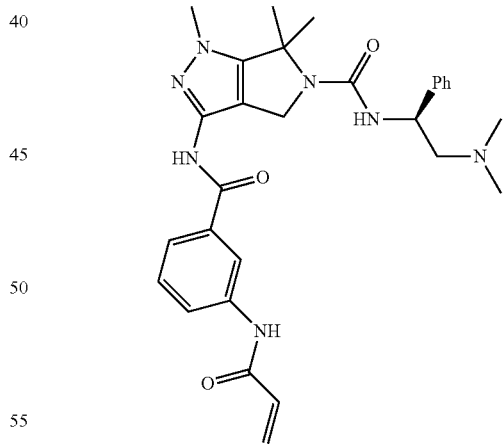

A solution of t-butyl 6,6-dimethyl-3-(3-nitrobenzamido)-4,6-dihydropyrrolo[3,4-c]pyrazole-5(1H)-carboxylate (394 mg, 0.98 mmol) and methyl iodide (697 mg, 0.31 mL, 4.91 mmol) in THF (5 mL) was stirred at 80° C. overnight. The mixture was cooled and extracted with EtOAc and washed with sat. NaHCO₃ and brine. The crude was purified by reverse phase preparative HPLC (MeOH/H₂O, 0-100%) to give t-butyl 1,6,6-trimethyl-3-(3-nitrobenzamido)-4,6-dihydropyrrolo[3,4-c]pyrazole-5(1H)-carboxylate (123 mg, 30%) and t-butyl 2,6,6-trimethyl-3-(3-nitrobenzamido)-2,6-dihydropyrrolo[3,4-c]pyrazole-5(4H)-carboxylate (108 mg, 26%) as white solids. LC/MS (ESI) m/z: 416.4 (M+H)⁺.

Example 41. (S)-3-(3-acrylamidobenzamido)-N-(2-(dimethylamino)-1-phenylethyl)-1,6,6-trimethyl-4,6-dihydropyrrolo[3,4-c]pyrazole-5(1H)-carboxamide Following the previous described procedure starting with t-butyl 1,6,6-trimethyl-3-(3-nitrobenzamido)-4,6-dihydropyrrolo[3,4-c]pyrazole-5(1H)-carboxylate, (S)-3-(3-acrylamidobenzamido)-N-(2-(dimethylamino)-1-phenylethyl)-1,6,6-trimethyl-4,6-dihydropyrrolo[3,4-c]pyrazole-5(1H)-carboxamide was obtained as a white solid. ¹H NMR: 500 MHz (DMSO-d₆) δ 10.70 (s, 1H), 10.34 (s, 1H), 7.94 (d, J=8.9 Hz, 2H), 7.71 (d, J=8.9 Hz, 2H), 7.31 (d, J=7.3 Hz, 2H), 7.23 (t, J=7.6 Hz, 2H), 7.13 (t, J=7.3 Hz, 1H), 6.40 (dd, J=17.1, 10.1 Hz, 1H), 6.24 (dd, J=17.1, 1.8 Hz, 1H), 6.21 (m, 1H), 5.74 (dd, J=10.1, 1.8 Hz, 1H), 4.81 (q, J=7.3 Hz, 1H), 4.45 (dd, J=15.9, 11.9 Hz, 1H), 3.65 (s, 3H), 2.60 (m, 1H), 2.33 (m, 1H), 2.13 (s, 6H), 1.64 (s, 3H), 1.56 (s, 3H); MS m/z: 530.3 [M+1].

TABLE 7

The following compounds were produced using the corresponding starting compounds according to a method similar to that described for the synthesis of Compound 241:

| Name | Structure | Characterization Data |
| --- | --- | --- |
| Compound 242. (S)-3-(4-acrylamidobenzamido)-N-(2-(dimethylamino)-1-phenylethyl)-2,6,6-trimethyl-2,6-dihydropyrrolo[3,4-c]pyrazole-5(4H)-carboxamide | 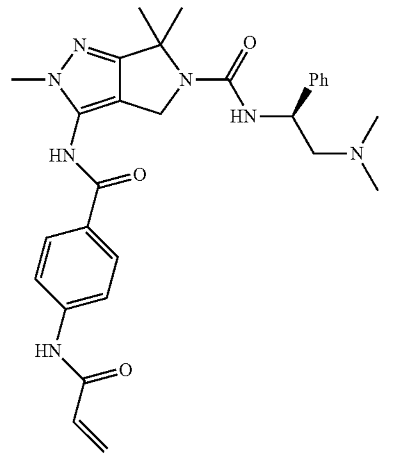 | ¹H NMR: 500 MHz (DMSO-d₆) δ 10.40 (s, 1H), 10.22 (s, 1H), 7.93 (d, J = 8.9 Hz, 2H), 7.77 (d, J = 8.9 Hz, 2H), 7.28 (d, J = 7.3 Hz, 2H), 7.22 (t, J = 7.6 Hz, 2H), 7.12 (t, J = 7.3 Hz, 1H), 6.41 (dd, J = 17.1, 10.1 Hz, 1H), 6.24 (dd, J = 17.1, 1.8 Hz, 1H), 6.14 (d, J = 7.3 Hz, 1H), 5.75 (dd, J = 10.1, 1.8 Hz, 1H), 4.81 (q, J = 7.9 Hz, 1H), 4.34 (dd, J = 15.3, 12.5 Hz, 1H), 3.67 (s, 3H), 2.57 (m, 1H), 2.30 (m, 1H), 2.12 (s, 6H), 1.53 (s, 3H), 1.46 (s, 3H); MS m/z: 530.3 [M + 1]. |
| Compound 243. (S)-3-(4-acrylamido-2-methoxybenzamido)-N-(2-(dimethylamino)-1-phenylethyl)-1,6,6-trimethyl-4,6-dihydropyrrolo[3,4-c]pyrazole-5(1H)-carboxamide | 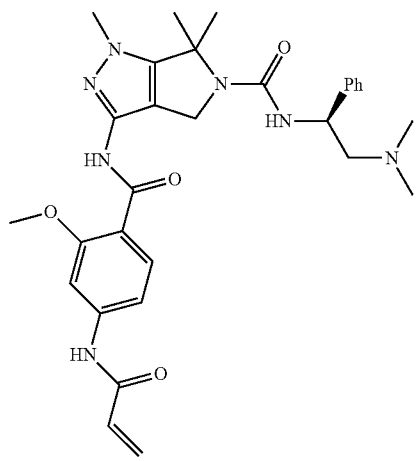 | ¹H NMR: 500 MHz (DMSO-d₆) δ 10.40 (s, 1H), 10.01 (s, 1H), 7.79 (d, J = 8.5 Hz, 1H), 7.58 (dd, J = 1.5 Hz, 1H), 7.32 (m, 2H), 7.25 (t, J = 7.3 Hz, 2H), 7.16 (t, J = 7.3 Hz, 1H), 6.40 (dd, J = 17.1, 10.1 Hz, 1H), 6.37 (br, 1H), 6.25 (dd, J = 16.8, 1.8 Hz, 1H), 5.76 (dd, J = 10.1, 1.8 Hz, 1H), 4.92 (m, 1H), 4.49 (m, 2H), 3.89 (s, 3H), 3.64 (s, 3H), 2.30 (m, 6H), 1.64 (s, 3H), 1.57 (s, 3H); MS m/z: 560.3 [M + 1]. |
| Compound 244. (S)-3-(4-acrylamido-2-methoxybenzamido)-N-(2-(dimethylamino)-1-phenylethyl)-2,6,6-trimethyl-2,6-dihydropyrrolo[3,4-c]pyrazole-5(4H)-carboxamide | 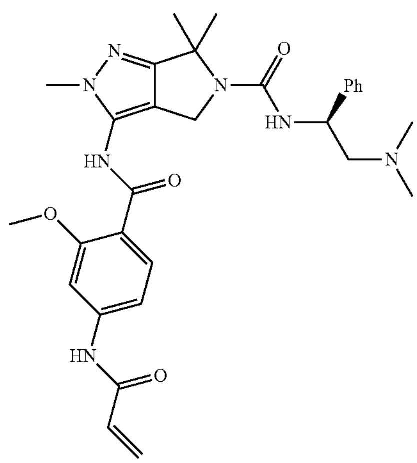 | ¹H NMR: 500 MHz (DMSO-d₆) δ 10.52 (s, 1H), 10.01 (s, 1H), 7.79 (d, J = 8.5 Hz, 1H), 7.65 (dd, J = 1.8 Hz, 1H), 7.31 (d, J = 8.5 Hz, 2H), 7.24 (t, J = 7.6 Hz, 2H), 7.14 (t, J = 7.3 Hz, 1H), 6.43 (dd, J = 16.8, 10.1 Hz, 1H), 6.25 (br, 1H), 6.25 (dd, J = 16.8, 1.8 Hz, 1H), 5.76 (dd, J = 10.1, 1.8 Hz, 1H), 4.89 (m, 1H), 4.41 (m, 2H), 3.90 (s, 3H), 3.67 (s, 3H), 2.23 (m, 6H), 1.54 (s, 3H), 1.46 (s, 3H); MS m/z: 560.3 [M + 1]. |

TABLE 7-continued

The following compounds were produced using the corresponding starting compounds according to a method similar to that described for the synthesis of Compound 241:

| Name | Structure | Characterization Data |
|---|---|---|
| Compound 245. 3-(4-acrylamidobenzamido)-N-(1-(dimethylamino)propan-2-yl)-1,6,6-trimethyl-4,6-dihydropyrrolo[3,4-c]pyrazole-5(1H)-carboxamide | 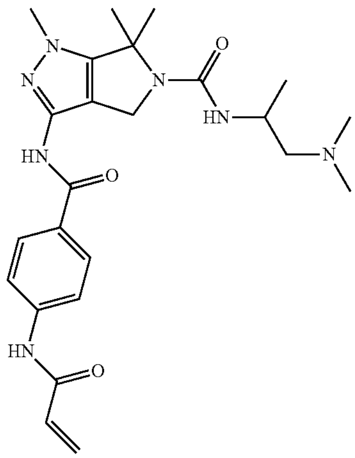 | $^1$H NMR: 500 MHz (DMSO-$d_6$) δ 10.68 (s, 1H), 10.33 (s, 1H), 7.93 (d, J = 8.9 Hz, 2H), 7.71 (d, J = 8.9 Hz, 2H), 6.39 (dd, J = 17.1, 10.1 Hz, 1H), 6.23 (dd, J = 17.1, 1.8 Hz, 1H), 5.74 (dd, J = 10.1, 1.8 Hz, 1H), 5.64 (d, J = 7.9 Hz, 1H), 4.33 (dd, J = 21.7, 11.9 Hz, 2H), 3.74 (m, 1H), 3.66 (s, 3H), 2.20 (dd, J = 11.9, 7.0 Hz, 1H), 2.10 (m, 1H), 2.08 (s, 6H), 1.64 (s, 6H), 1.00 (d, J = 6.4 Hz, 3H); MS m/z: 530.3 [M + 1]. |
| Compound 246. (S)-2-(dimethylamino)-1-phenylethyl 3-(4-acrylamidobenzamido)-1,6,6-trimethyl-4,6-dihydropyrrolo[3,4-c]pyrazole-5(1H)-carboxylate | 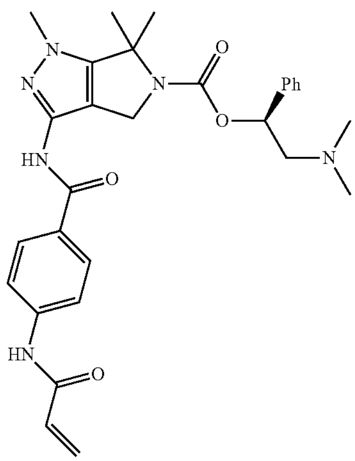 [SMILES: C=CC(=O)Nc1ccc(C(=O)Nc2nn(C)c3c2CN(C(=O)O[C@H](CN(C)C)c2ccccc2)C3(C)C)cc1] | $^1$H NMR (a mixture of two rotamers): 500 MHz (DMSO-$d_6$) δ 10.74, 10.70 (s, 1H), 10.33, 10.32 (s, 1H), 7.93 (m, 2H), 7.69 (m, 2H), 7.32 (m, 4H), 7.23 (m, 1H), 6.39 (m, 1H), 6.23 (m, 1H), 5.75 (m, 1H), 4.56 (dd, J = 15.3, 13.4 Hz, 2H), 4.40, 4.31 (d, J = 13.4 Hz, 1H), 3.68, 3.67 (s, 3H), 2.73 (m, 1H), 2.45 (m, 1H), 2.17, 2.15 (s, 6H), 1.73, 1.55 (s, 3H), 1.64 (s, 3H); MS m/z: 531.3 [M + 1]. |
| Compound 247. (S)-N-(2-(dimethylamino)-1-phenylethyl)-1,6,6-trimethyl-3-(4-propionamidobenzamido)-4,6-dihydropyrrolo[3,4-c]pyrazole-5(1H)-carboxamide | 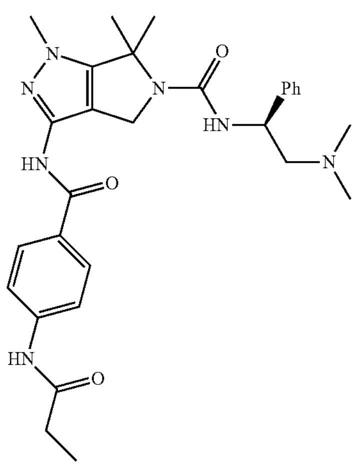 [SMILES: CCC(=O)Nc1ccc(C(=O)Nc2nn(C)c3c2CN(C(=O)N[C@H](CN(C)C)c2ccccc2)C3(C)C)cc1] | $^1$H NMR: 500 MHz (DMSO-$d_6$) δ 10.79 (s, 1H), 10.18 (s, 1H), 8.03 (d, J = 8.9 Hz, 2H), 7.76 (d, J = 8.9 Hz, 2H), 7.43 (d, J = 7.3 Hz, 2H), 7.35 (t, J = 7.3 Hz, 2H), 7.25 (t, J = 7.3 Hz, 1H), 6.34 (d, J = 7.3 Hz, 1H), 4.93 (q, J = 7.9 Hz, 1H), 4.56 (dd, J = 16.5, 11.9 Hz, 2H), 3.78 (s, 3H), 2.72 (m, 1H), 2.45 (m, 1H), 2.42 (q, J = 7.6 Hz, 2H), 2.25 (s, 6H), 1.77 (s, 3H), 1.69 (s, 3H), 1.16 (t, J = 7.3 Hz, 3H); MS m/z: 532.4 [M + 1]. |

Biological Assays of the Compounds

Example 5. Inhibition of Kinase Activity

Compounds of the invention were assayed for activity against a variety of different kinases. Exemplary results are presented as calculated IC$_{50}$ values (Table A1 & A2). In Table A1 and A2 "A" represents a calculated IC$_{50}$ value of less than 100 nM; "B" represents a calculated IC$_{50}$ value of greater than or equal to 100 nM and less than 1 μM; and "C" represents a calculated IC$_{50}$ value of 1 μM or greater. The co-factors used for each kinase in the assays were as follows: CDK7: cyclin H and MNAT1; CDK2: cyclin A; CDK9: cyclin K.

TABLE A1

Calculated $IC_{50}$ values of exemplary compounds of the invention against CDK7.

| Compound No. | CDK7 $IC_{50}$ |
|---|---|
| 101 | A |
| 102 | A |
| 103 | A |
| 104 | A |
| 105 | A |
| 106 | B |
| 107 | A |
| 108 | A |
| 109 | A |
| 110 | A |
| 111 | B |
| 112 | A |
| 113 | A |
| 114 | A |
| 115 | A |
| 116 | A |
| 117 | A |
| 118 | A |
| 119 | A |
| 120 | A |
| 123 | A |
| 214 | A |
| 215 | A |
| 216 | A |
| 217 | A |
| 222 | A |
| 231 | A |
| 232 | A |
| 233 | A |
| 234 | A |
| 235 | C |
| 236 | B |
| 237 | C |
| 238 | C |
| 239 | C |
| 240 | C |
| 241 | A |
| 242 | C |
| 243 | C |
| 244 | C |
| 245 | C |
| 246 | B |

TABLE A2

Calculated $IC_{50}$ values of exemplary compounds of the invention against various kinases.

| Kinase | Compound No. 101 | Compound No. 106 |
|---|---|---|
| CDK2 | C | |
| CDK9 | C | |
| CHEK2 | A | |
| FGR | A | |
| HIPK4 | B | |
| PRKCQ | A | |
| RET | A | |
| SRC | A | |
| MELK | B | B |

Example 6. Inhibition of Cell Proliferation

Exemplary compounds of the invention were tested at different concentrations. Cells were plated in 96-well plates at the following seeding densities: Jurkat T-cell acute lymphoblastic leukemia 25,000 cells/well; HCT116 colorectal carcinoma 8,000 cells/well; Kelly neuroblastoma 4,000 cells/well. The cells were treated with various concentration of compounds (ranging from 1 nM to 10 μM). DMSO solvent with no compound served as a control. Following incubation for 72 hours, cell survival following treatment with exemplary compounds described herein was assessed by CellTiter-Glo® Luminescent cell viability assay (Promega). $IC_{50}$ values were determined using GRAPHPAD PRISM 6 software. Exemplary results are shown in Table A3, wherein "A" represents a calculated $IC_{50}$ value of less than 500 nM; "B" represents a calculated $IC_{50}$ value of greater than or equal to 500 nM and less than 5000 μM; and "C" represents a calculated $IC_{50}$ value of 5000 μM or greater

TABLE A3

Calculated $IC_{50}$ values of exemplary compounds of the invention against cancer cells.

| Compound No. | Jurkat T-cell acute lymphoblastic leukemia | HCT116 colorectal carcinoma | Kelly neuroblastoma |
|---|---|---|---|
| 101 | A | A | B |
| 102 | | | C |
| 104 | B | B | |
| 106 | | | C |
| 107 | B | | |
| 112 | | | B |

Example 7. Labeling of CDK7 with an Inhibitor

Figure 2:
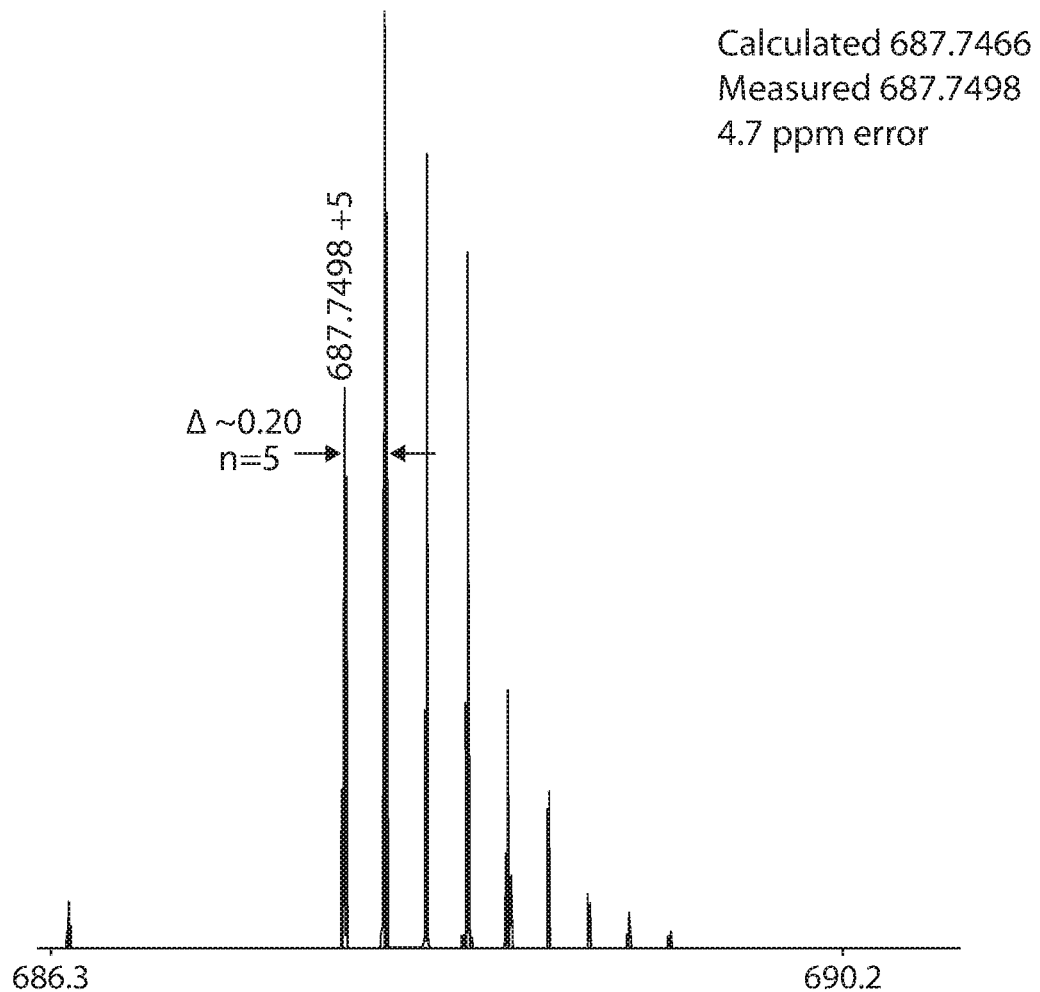
FIG. 2 shows an MS spectrum (m/z 686-690) recorded during analysis of peptides derived from CDK7 treated with Compound 101. Signal at m/z 687.7498 corresponds to YFSNRPGPTPGCQLPRPNCPVETLK (SEQ ID NO: 3), with Cys312 labeled with Compound 101.

CAK complex (Millipore cat#14-476) in 40 mM Hepes pH 7.4, 150 mM NaCl, 5% glycerol and 1 mM DTT with protease and phosphatase inhibitors was incubated with a 10-fold molar excess of Compound 101 for 6 hrs at 37° C. Proteins were resolved by SDS-PAGE, bands corresponding to CDK7 were digested in-gel with trypsin, and peptides analyzed by nano LC-MS using an Orbitrap XL mass spectrometer (ThermoFisher Scientific, San Jose, Calif.). Efficiency of labeling was estimated from the reduction in signal of the Cys312 containing peptide YFSNRPGPTPGCQLPRPNCPVETLK (SEQ ID NO: 3) compared to DMSO control. Signals from CDK7 peptides VPFLPGDSDLDQLTR (SEQ ID NO: 1) and LDFLGEGQFATVYK were used for normalization. See FIG. 1 for the total ion chromatograms (TIC) and extracted ion chromatograms (EIC) of the CDK7 peptides treated with DMSO (A-D) or Compound 101 (E-H). The labeled peptide was detected by mass spectrometry, as shown in the spectrum of FIG. 2. The signal at m/z 687.7498 corresponds to YFSNRPGPTPGCQLPRPNCPVETLK (SEQ ID NO: 3 ), labeled with Compound 101 at Cys312.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of the formula:

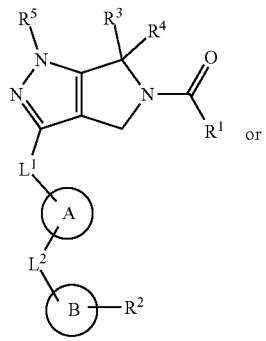 (I-a)

or

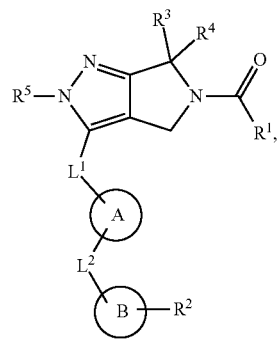 (I-b)

or a pharmaceutically acceptable salt, solvate, hydrate, tautomer, stereoisomer, isotopically labeled derivative, or prodrug thereof, wherein:

$R^1$ is —$NR^aR^b$, —$CHR^aR^b$, or —$OR^a$, wherein each of $R^a$ and $R^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or $R^a$ and $R^b$ are joined to form an optionally substituted carbocyclic, optionally substituted heterocyclic, optionally substituted aryl, or optionally substituted heteroaryl ring;

each of $R^3$ and $R^4$ is independently hydrogen, halogen, optionally substituted $C_1$-$C_6$ alkyl, or optionally substituted aryl, or $R^3$ and $R^4$ are joined to form an optionally substituted $C_3$-$C_6$ carbocyclyl ring;

$R^5$ is hydrogen, optionally substituted $C_1$-$C_6$ alkyl, or a nitrogen protecting group;

$L^1$ is —$NR^{L1}$—, —$NR^{L1}C(=O)$—, —$C(=O)NR^{L1}$—, —O—, or —S—, wherein $R^{L1}$ is hydrogen, optionally substituted $C_1$-$C_6$ alkyl, or a nitrogen protecting group;

is Ring A, wherein Ring A is optionally substituted carbocyclyl, optionally substituted heterocyclyl, optionally substituted aryl, or optionally substituted heteroaryl;

$L^2$ is a bond, —C(=O)—, —$NR^{L2}$—, —C(=O)$NR^{L2}$—, —$NR^{L2}$C(=O)—, —O—, or —S—, wherein $R^{L2}$ is hydrogen, optionally substituted $C_1$-$C_6$ alkyl, or a nitrogen protection group;

B is Ring B, wherein Ring B is absent, optionally substituted carbocyclyl, optionally substituted heterocyclyl, optionally substituted aryl, or optionally substituted heteroaryl; and $R^2$ is of the formula:

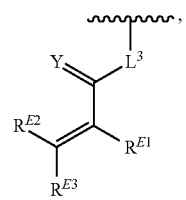 (i-1)

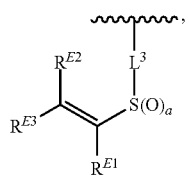 (i-2)

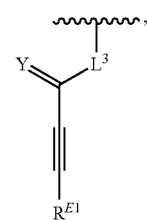 (i-3)

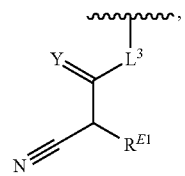 (i-4)

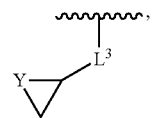 (i-6)

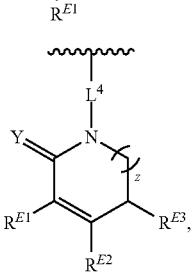 (i-7)

(i-8) 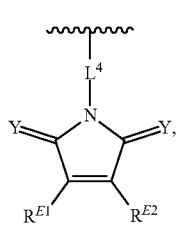
(i-10) 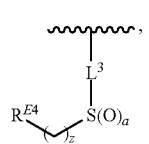
(i-12) 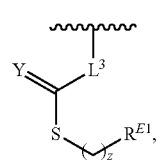
(i-13) 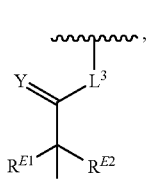
(i-14) 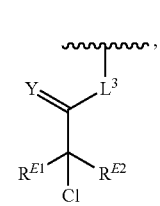
(i-15) 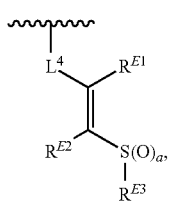
(i-16) 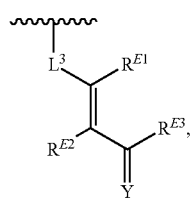
(i-17) 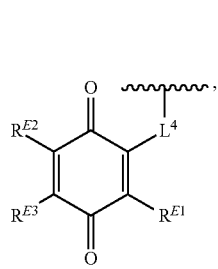
(i-19) 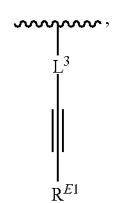
(i-20) 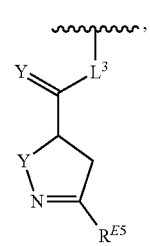
(i-21) 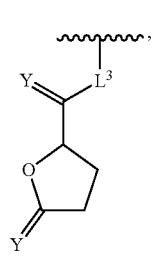
(i-22) 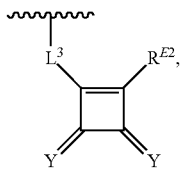
(i-23) 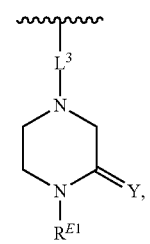
(i-24) 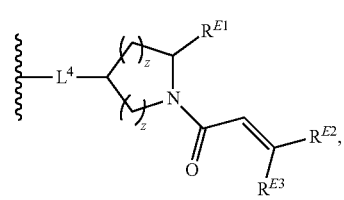
(i-25) 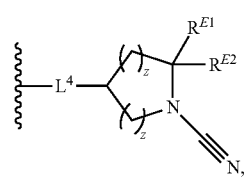

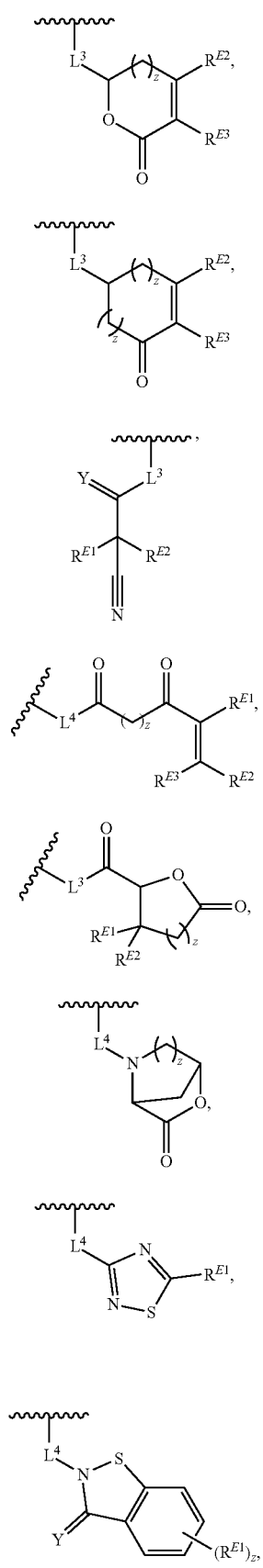

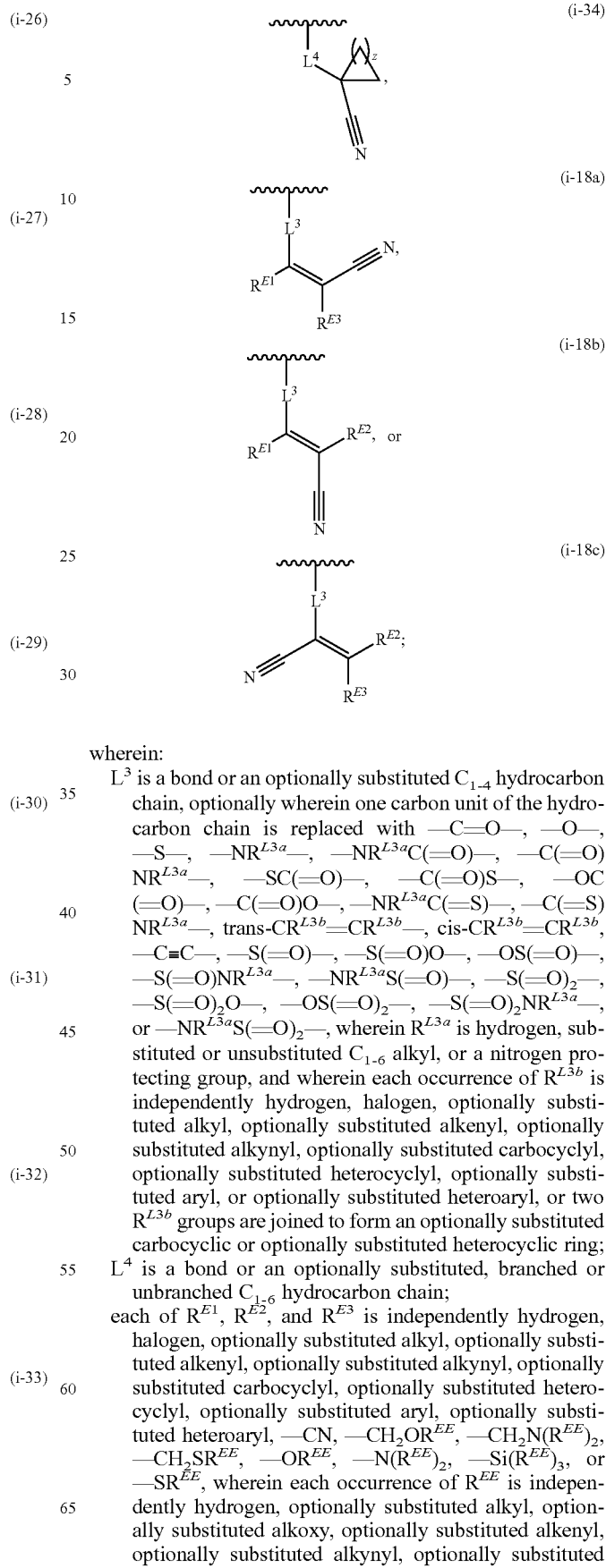

wherein:

$L^3$ is a bond or an optionally substituted $C_{1-4}$ hydrocarbon chain, optionally wherein one carbon unit of the hydrocarbon chain is replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two $R^{EE}$ groups are joined to form an optionally substituted heterocyclic ring;

or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring;

$R^{E4}$ is a leaving group;

$R^{E5}$ is halogen;

each instance of Y is independently O, S, or $NR^{E7}$, wherein $R^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits;

each nitrogen protecting group, together with the nitrogen atom to which the nitrogen protecting group is attached, is independently selected from the group consisting of formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, phenacylsulfonamide, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{2-10}$ alkenyl, C$_{2-10}$ alkynyl, C$_3$-10 carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups, or two instances of the nitrogen protecting group together with the nitrogen atoms to which the nitrogen protecting groups are attached are N,N'-isopropylidenediamine;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(NR$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{cc}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, and 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents are joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, or 5-10 membered heteroaryl; or two geminal R$^{gg}$ substituents are joined to form =O or =S;

X$^-$ is a counterion; and each oxygen protecting group, together with the oxygen atom to which the nitrogen protecting group is attached, is independently selected from the group consisting of methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-l-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, tosylate (Ts), —$R^{aa}$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3^+$X$^-$, —P(O$R^{cc}$)$_2$, —P(O$R^{cc}$)$_3^+$X$^-$, —P(=O)($R^{aa}$)$_2$, —P(=O)(O$R^{cc}$)$_2$, and —P(=O)(N($R^{bb}$)$_2$)$_2$.

2. The compound of claim 1, or a pharmaceutically acceptable salt, solvate, hydrate, tautomer, stereoisomer, isotopically labeled derivative, or prodrug thereof, wherein:
each of $R^3$ and $R^4$ is independently hydrogen, halogen, or optionally substituted $C_1$-$C_6$ alkyl, or $R^3$ and $R^4$ are joined to form an optionally substituted $C_3$-$C_6$ carbocyclyl ring.

3. The compound of claim 2, or a pharmaceutically acceptable salt, solvate, hydrate, tautomer, stereoisomer, isotopically labeled derivative, or prodrug thereof, wherein the compound is of Formula (II) or (III):

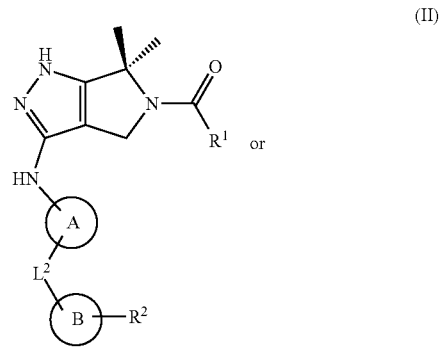

(II)

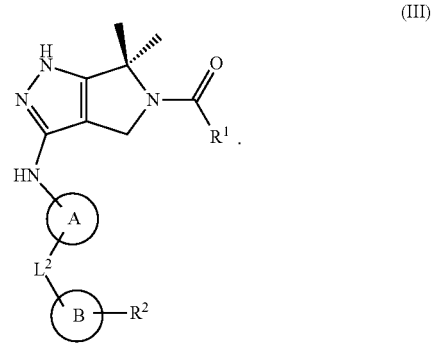

(III)

4. The compound of claim 2, or a pharmaceutically acceptable salt, solvate, hydrate, tautomer, stereoisomer, isotopically labeled derivative, or prodrug thereof, wherein the compound is of formula:

(IV-a)
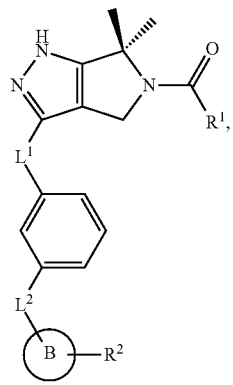
(IV-c)
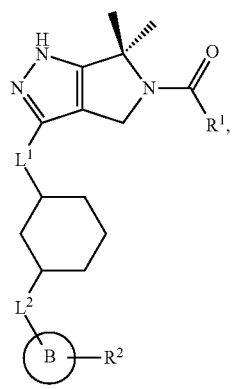
(IV-d)
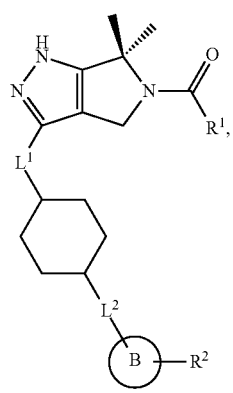
(IV-e)
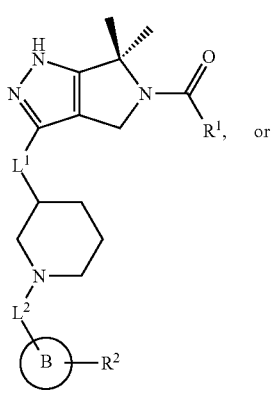
(IV-f)
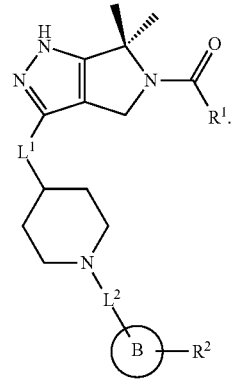
5. The compound of claim 2, or a pharmaceutically acceptable salt, solvate, hydrate, tautomer, stereoisomer, isotopically labeled derivative, or prodrug thereof, wherein the compound is of formula:
(V-a)
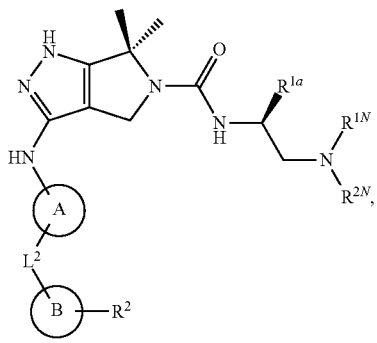
(V-b)
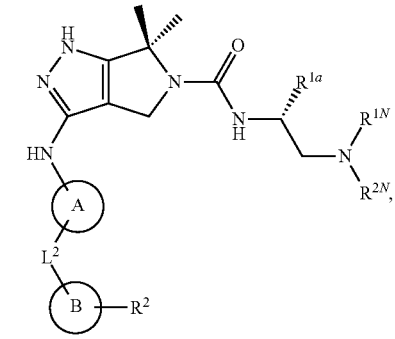
(V-c)
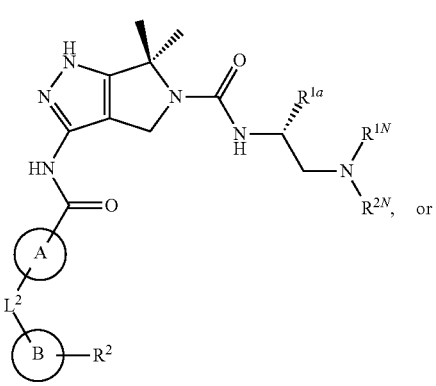

(V-d)

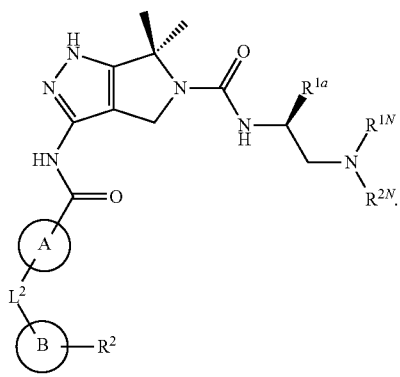

wherein:

R$^{1a}$ is hydrogen, optionally substituted C$_1$-C$_6$ alkyl, or optionally substituted aryl; and each of R$^{1N}$ and R$^{2N}$ is independently hydrogen, optionally substituted C$_1$-C$_6$ alkyl, or a nitrogen protecting group, or R$^{1N}$ and R$^{2N}$ are joined to form an optionally substituted heterocyclic or optionally substituted heteroaryl ring.

6. The compound of claim 2, or a pharmaceutically acceptable salt, solvate, hydrate, tautomer, stereoisomer, isotopically labeled derivative, or prodrug thereof, wherein the compound is of formula:

(VI-a)

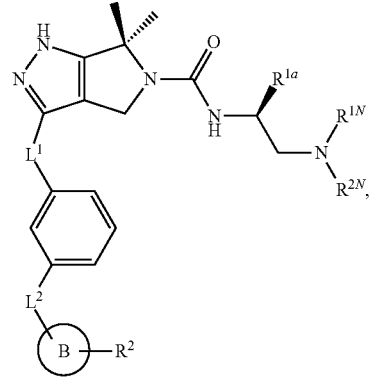

(VI-b)

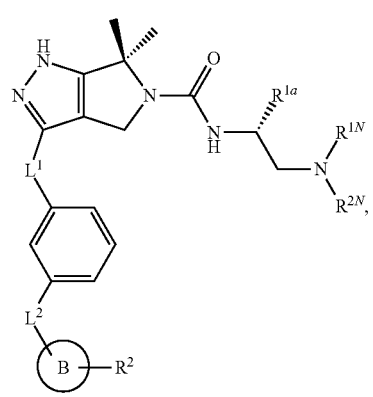

(VI-d)

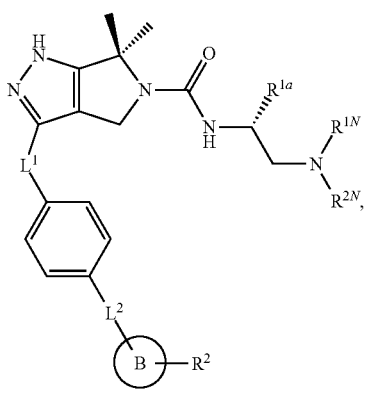

(VI-e)

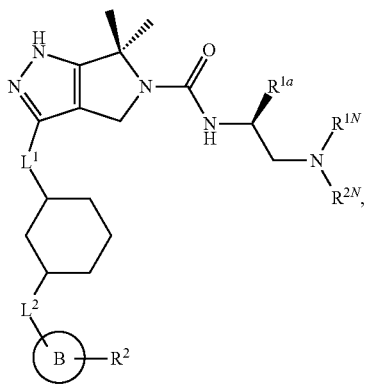

(VI-f)

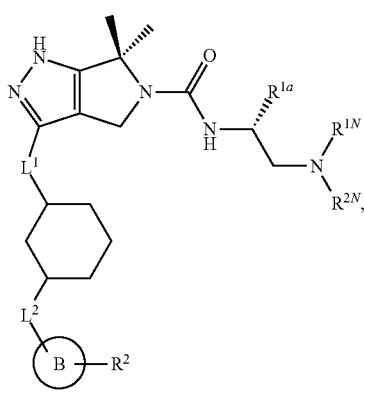

(VI-g)

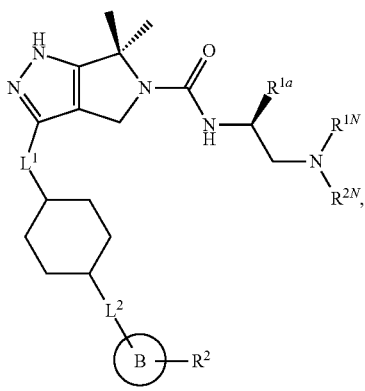

(VI-h)
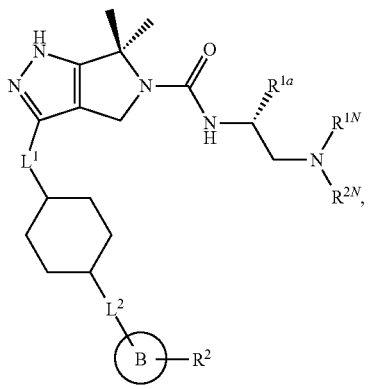

(VI-i)
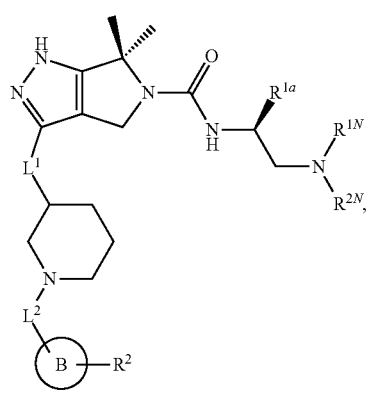

(VI-j)
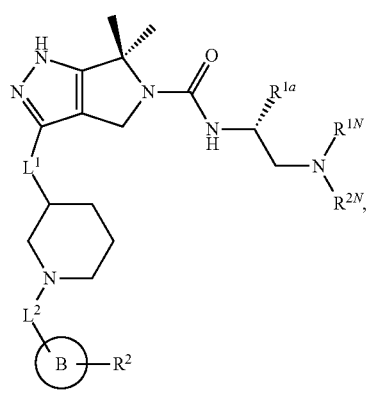

(VI-k)
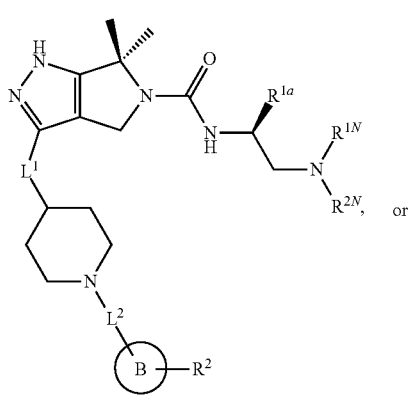

or (VI-l)
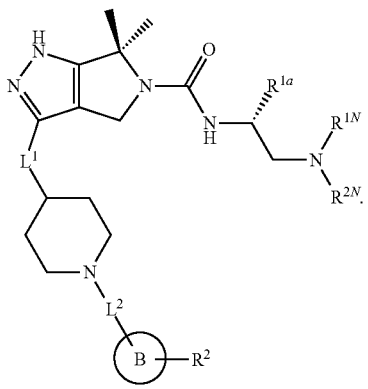

wherein:
  $R^{1a}$ is hydrogen, optionally substituted $C_1$-$C_6$ alkyl, or optionally substituted aryl; and
  each of $R^{1N}$ and $R^{2N}$ is independently hydrogen, optionally substituted $C_1$-$C_6$ alkyl, or a nitrogen protecting group, or $R^{1N}$ and $R^{2N}$ are joined to form an optionally substituted heterocyclic or optionally substituted heteroaryl ring.

7. The compound of claim 2, or a pharmaceutically acceptable salt, solvate, hydrate, tautomer, stereoisomer, isotopically labeled derivative, or prodrug thereof, wherein the compound is of formula:

(VII-a)
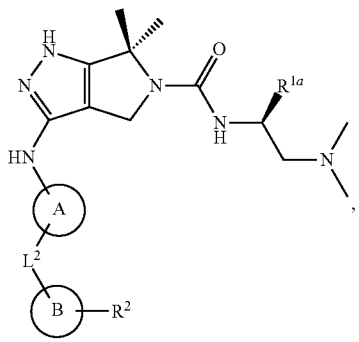

(VII-b)
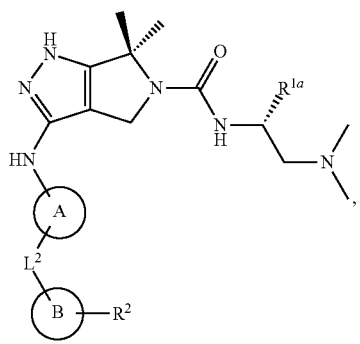

(VII-c)
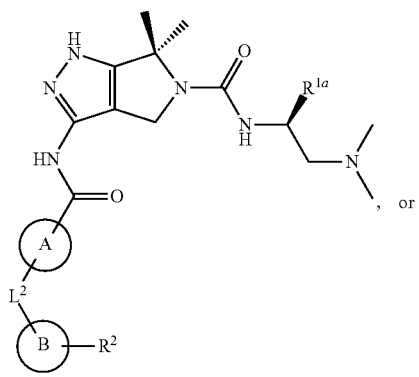
, or
(VII-d)
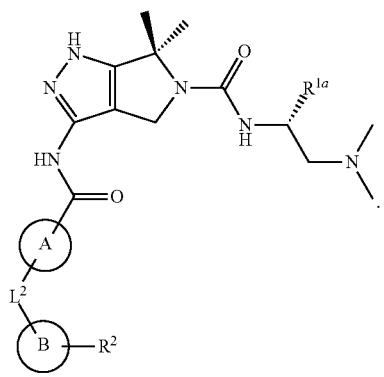
wherein $R^{1a}$ is hydrogen, optionally substituted $C_1$-$C_6$ alkyl, or optionally substituted aryl.
8. The compound of claim 2, or a pharmaceutically acceptable salt, solvate, hydrate, tautomer, stereoisomer, isotopically labeled derivative, or prodrug thereof, wherein the compound is of formula:
(VIII-a)
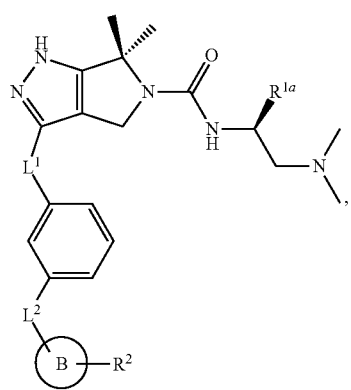
(VIII-b)
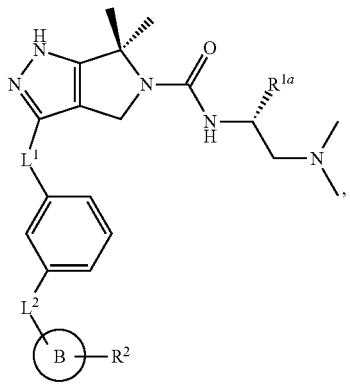
(VIII-d)
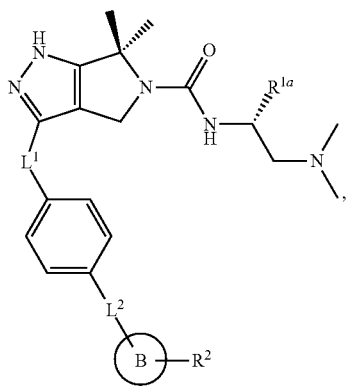
(VIII-e)
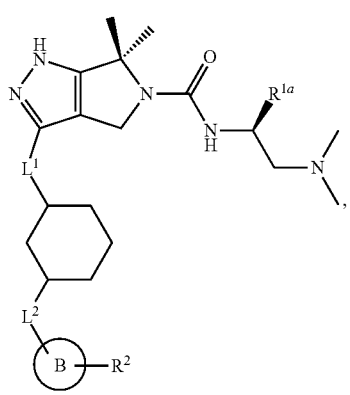
(VIII-f)
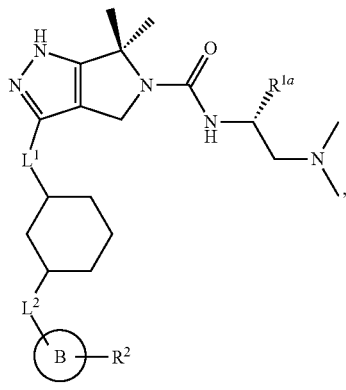

(VIII-g)
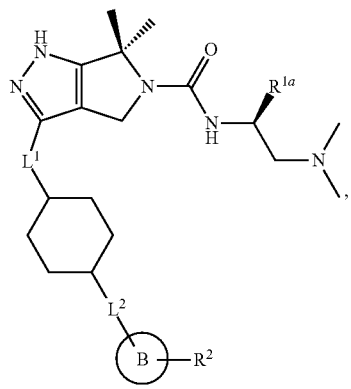
(VIII-h)
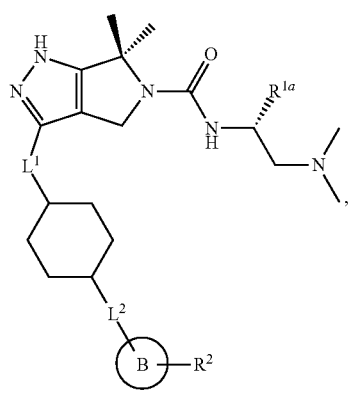
(VIII-i)
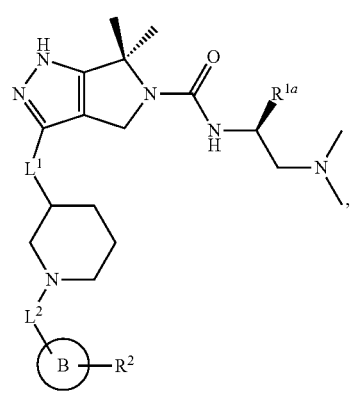
(VIII-j)
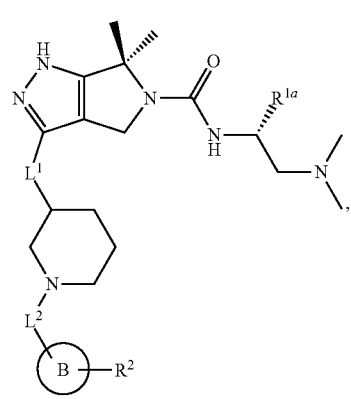
(VIII-k)
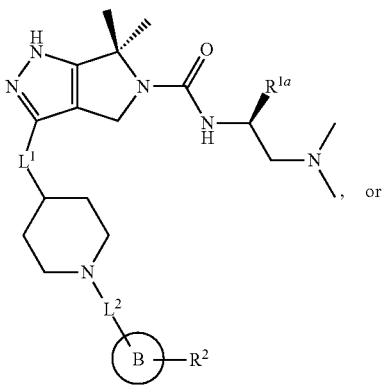
, or
(VIII-l)
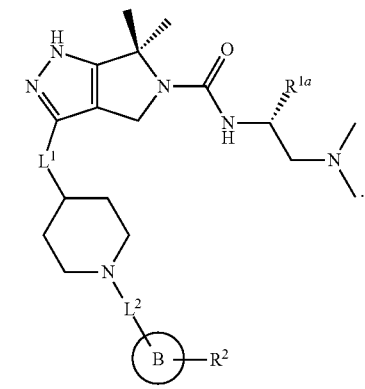
wherein $R^{1a}$ is hydrogen, optionally substituted $C_1$-$C_6$ alkyl, or optionally substituted aryl.
9. The compound of claim 2, or a pharmaceutically acceptable salt, solvate, hydrate, tautomer, stereoisomer, isotopically labeled derivative, or prodrug thereof, wherein the compound is of formula:
(IX-a)
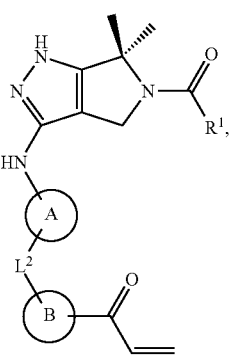

-continued (IX-b)

(IX-c)

(IX-d)

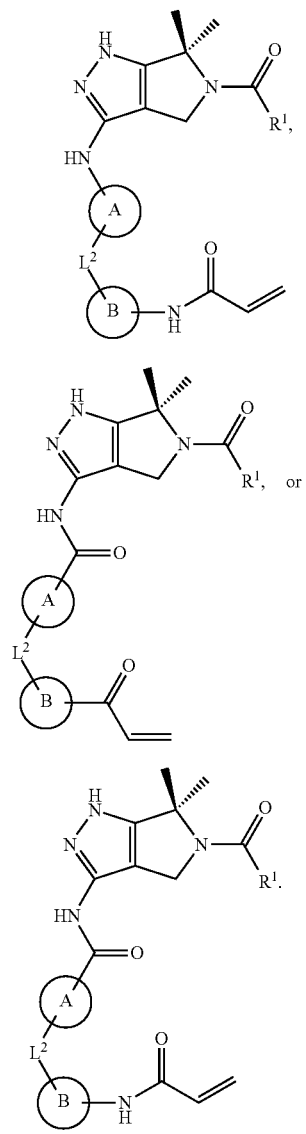

10. The compound of claim 2, or a pharmaceutically acceptable salt, solvate, hydrate, tautomer, stereoisomer, isotopically labeled derivative, or prodrug thereof, wherein the compound is of formula:

(X-a)

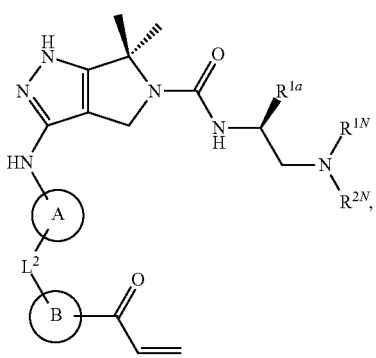

-continued (X-b)

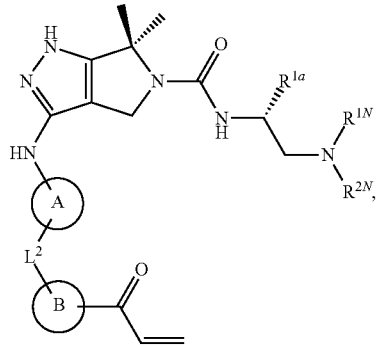

(X-c)

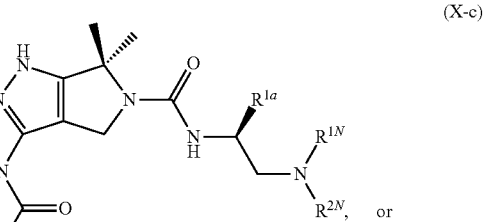

(X-d)

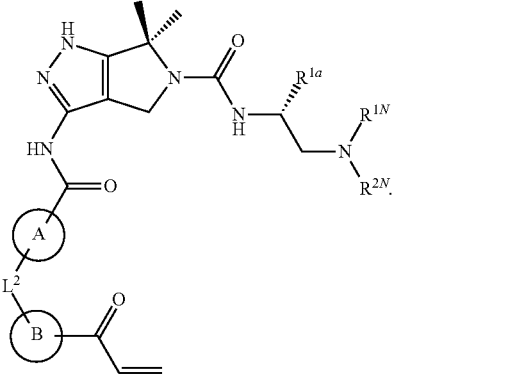

wherein:
R$^{1a}$ is hydrogen, optionally substituted C$_1$-C$_6$ alkyl, or optionally substituted aryl; and
each of R$^{1N}$ and R$^{2N}$ is independently hydrogen, optionally substituted C$_1$-C$_6$ alkyl, or a nitrogen protecting group, or R$^{1N}$ and R$^{2N}$ are joined to form an optionally substituted heterocyclic or optionally substituted heteroaryl ring.

11. The compound of claim 2, or a pharmaceutically acceptable salt, solvate, hydrate, tautomer, stereoisomer, isotopically labeled derivative, or prodrug thereof, wherein the compound is of formula:

(XI-a)

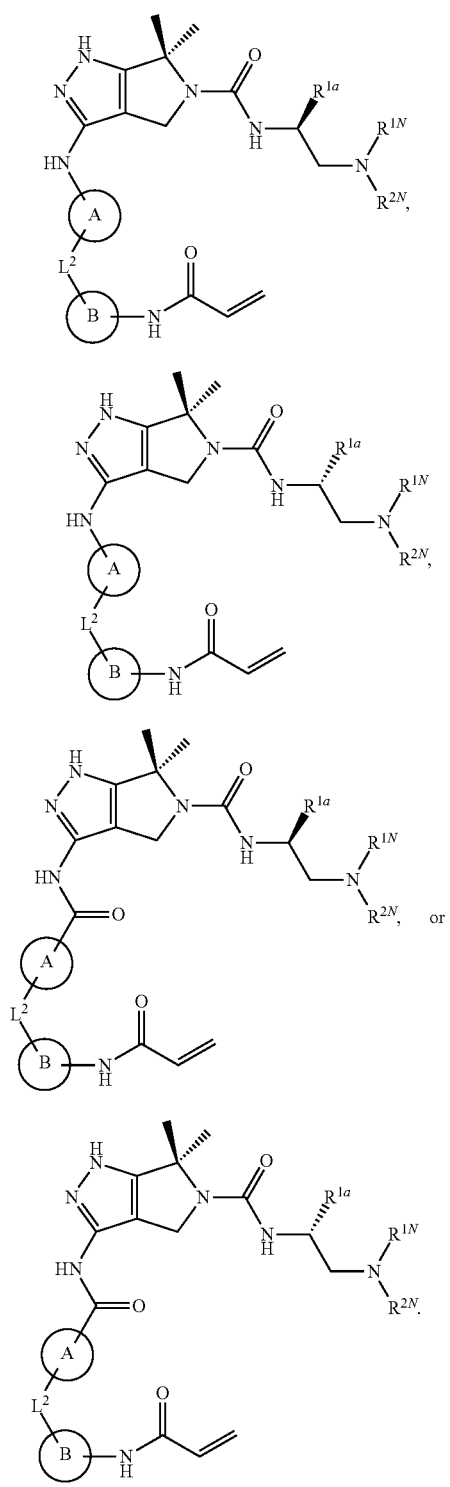

(XI-b)

(XI-c)

(XI-d)

wherein:
R$^{1a}$ is hydrogen, optionally substituted C$_1$-C$_6$ alkyl, or optionally substituted aryl; and
each of R$^{1N}$ and R$^{2N}$ is independently hydrogen, optionally substituted C$_1$-C$_6$ alkyl, or a nitrogen protecting group, or R$^{1N}$ and R$^{2N}$ are joined to form an optionally substituted heterocyclic or optionally substituted heteroaryl ring.

12. The compound of claim 2, or a pharmaceutically acceptable salt, solvate, hydrate, tautomer, stereoisomer, isotopically labeled derivative, or prodrug thereof, wherein the compound is of formula:

(XII-a)

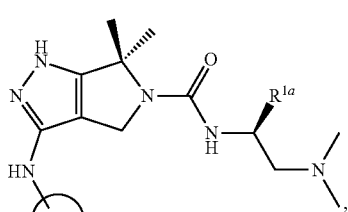

(XII-b)

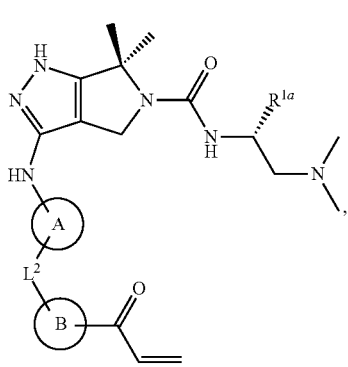

(XII-c)

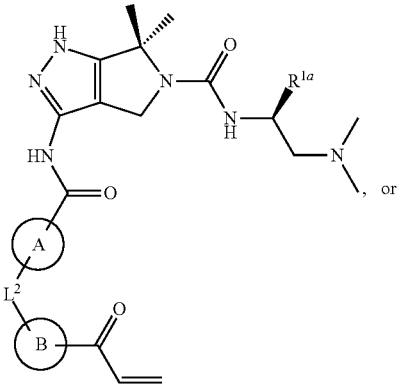, or (XII-d)

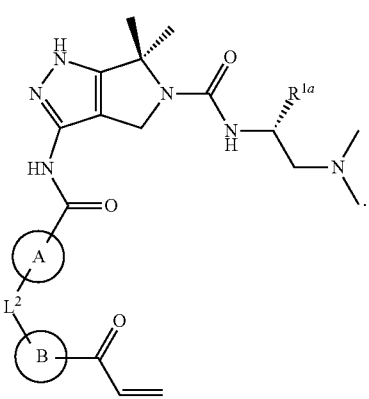

wherein R$^{1a}$ is hydrogen, optionally substituted C$_1$-C$_6$ alkyl, or optionally substituted aryl.

13. The compound of claim 2, or a pharmaceutically acceptable salt, solvate, hydrate, tautomer, stereoisomer, isotopically labeled derivative, or prodrug thereof, wherein the compound is of formula:

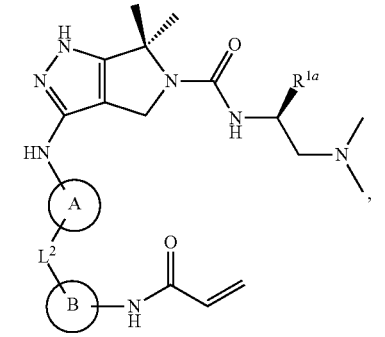

(XIII-a)

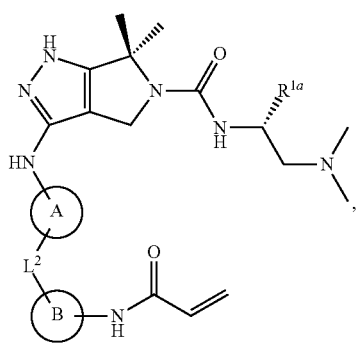

(XIII-b)

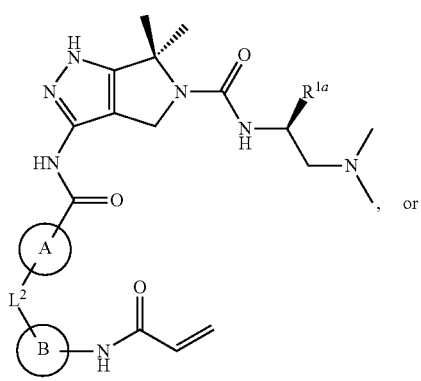

(XIII-c)

, or

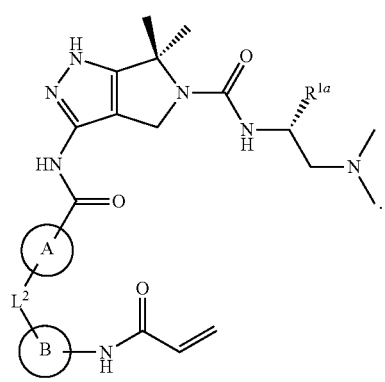

(XIII-d)

wherein R$^{1a}$ is hydrogen, optionally substituted C$_1$-C$_6$ alkyl, or optionally substituted aryl.

14. The compound of claim 1, wherein the compound is of formula:

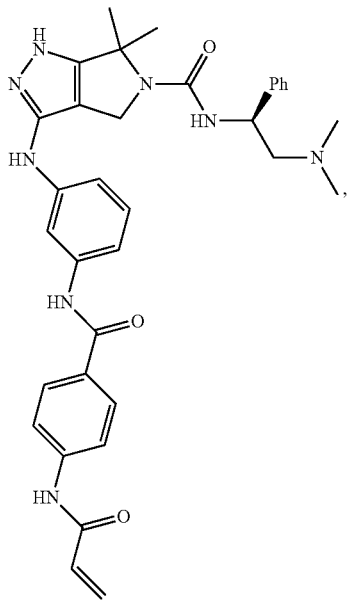

,

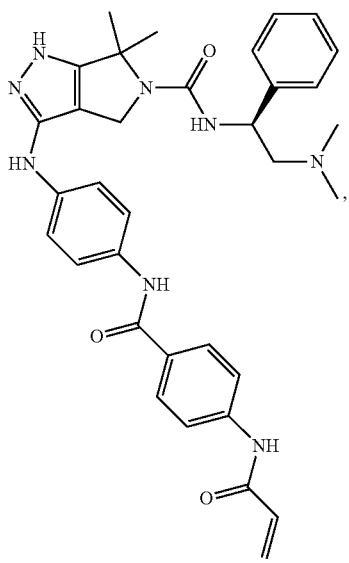

,

243
-continued
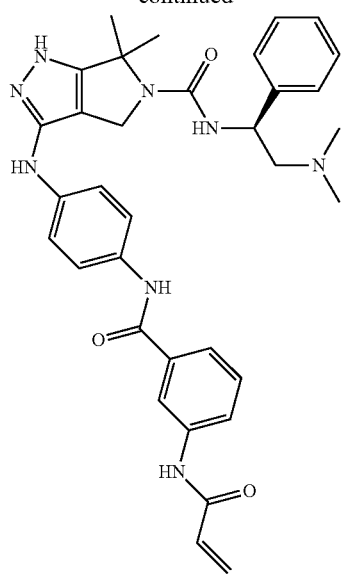
244
-continued
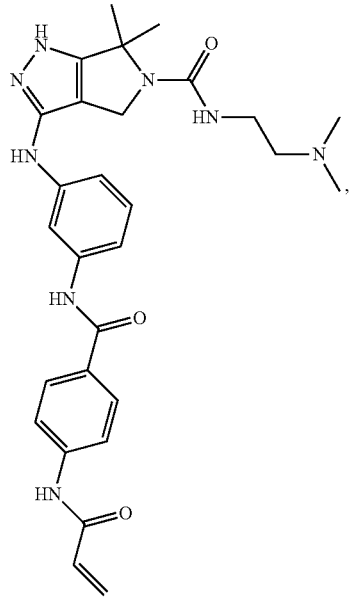
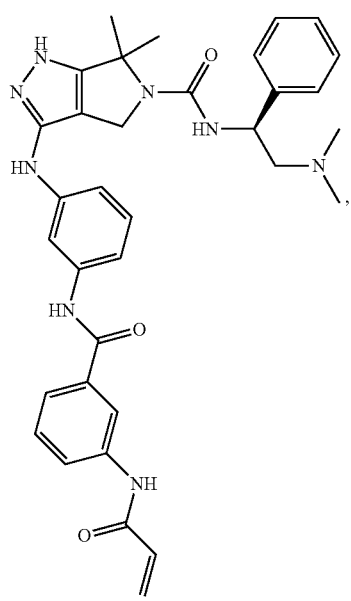
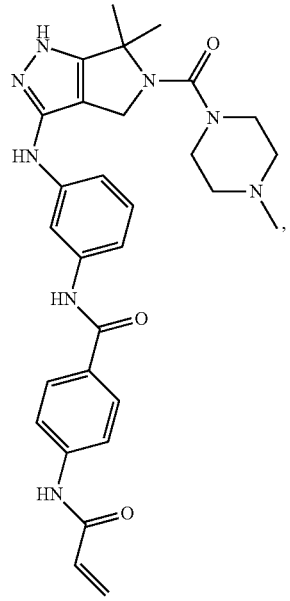

245
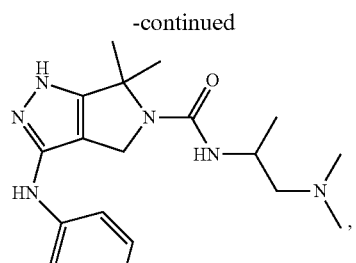
246
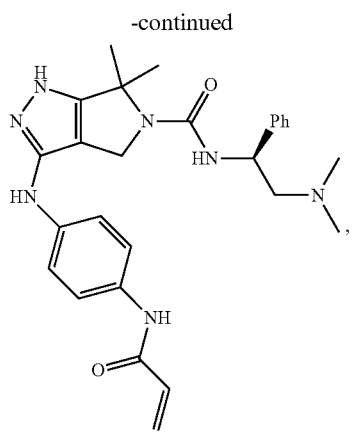
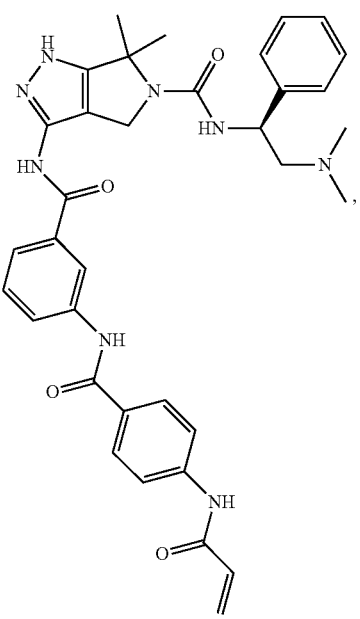
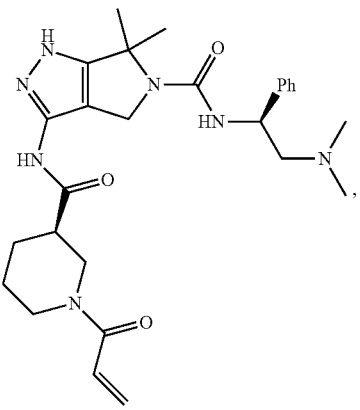

247
-continued
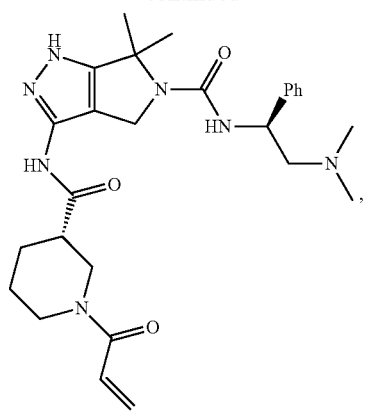
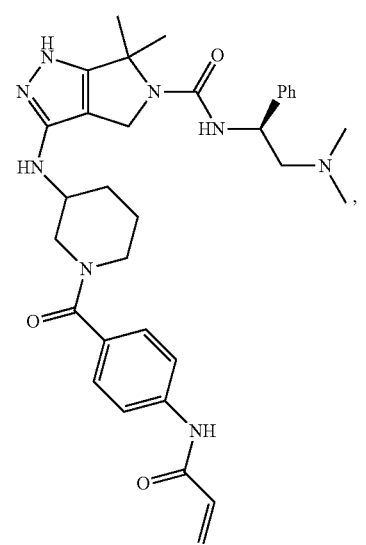
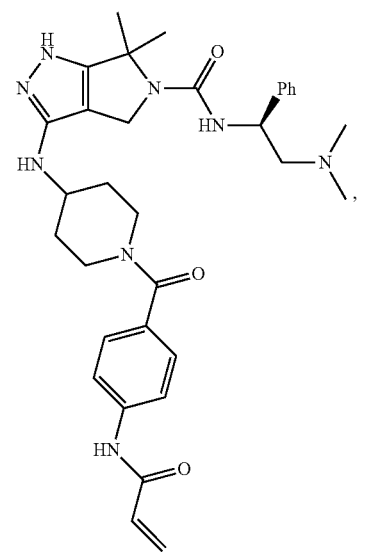
248
-continued
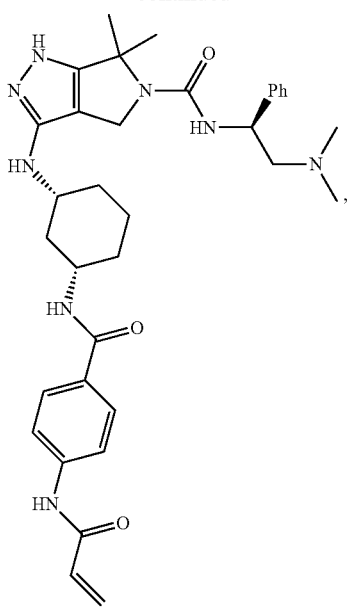
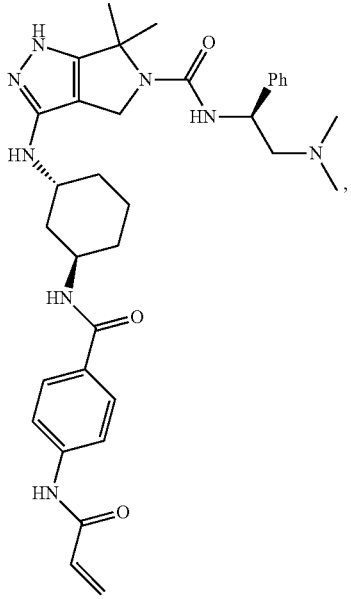

249
-continued
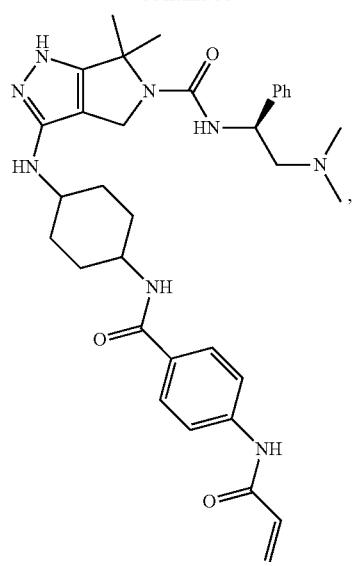
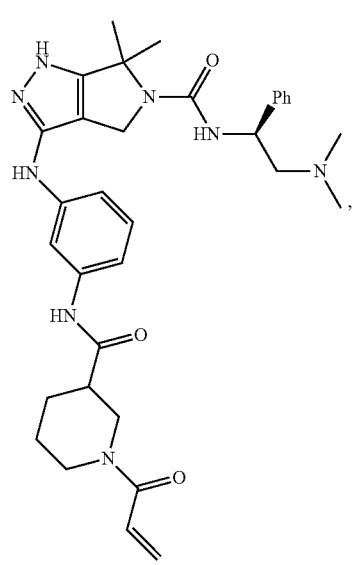
250
-continued
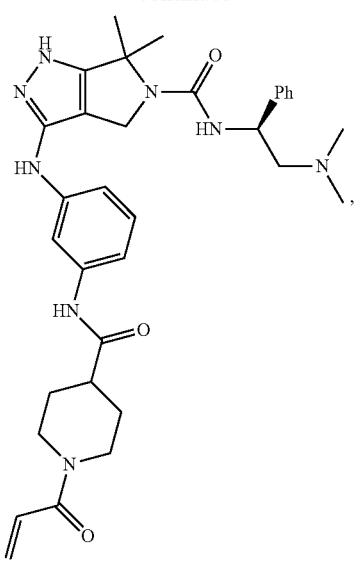
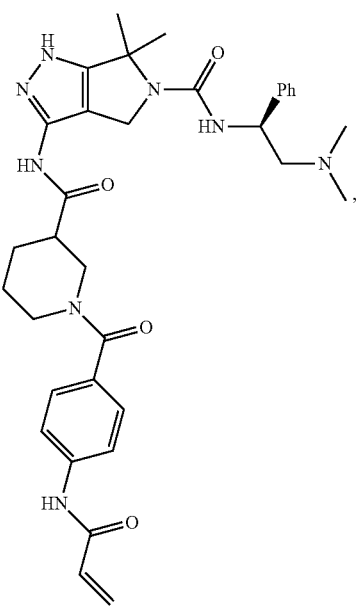

251
-continued
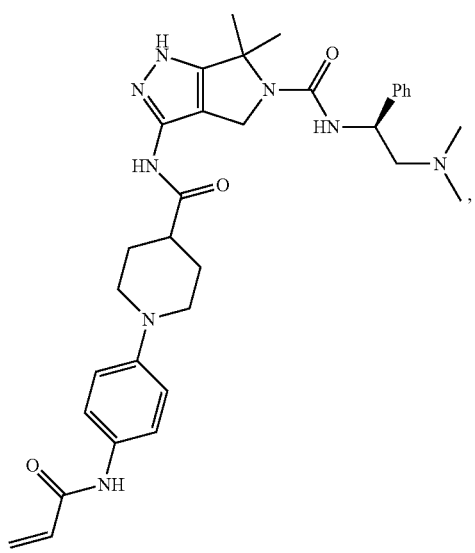
252
-continued
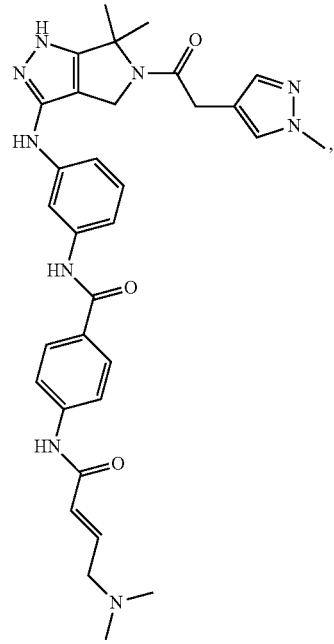 [SMILES: CN(C)C/C=C/C(=O)Nc1ccc(C(=O)Nc2cccc(Nc3n[nH]c4c3CN(C(=O)Cc3cnn(C)c3)C4(C)C)c2)cc1]
or a pharmaceutically acceptable salt, solvate, hydrate, stereoisomer, tautomer, isotopically labeled derivative, or prodrug thereof.
15. The compound of claim 1, wherein the compound is of formula:

253
-continued
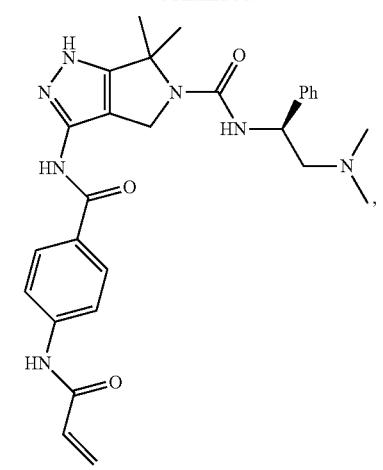
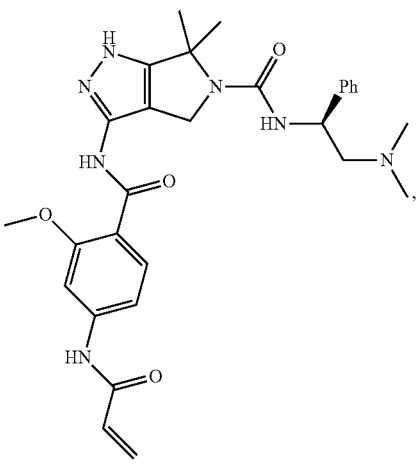
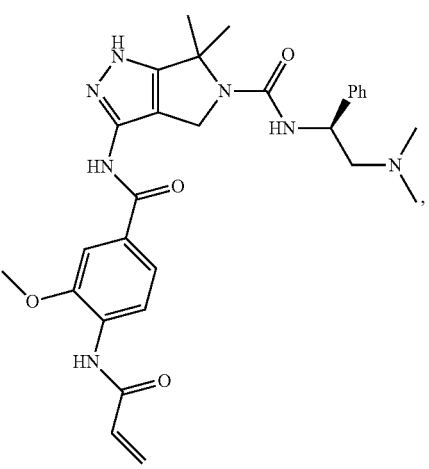
254
-continued
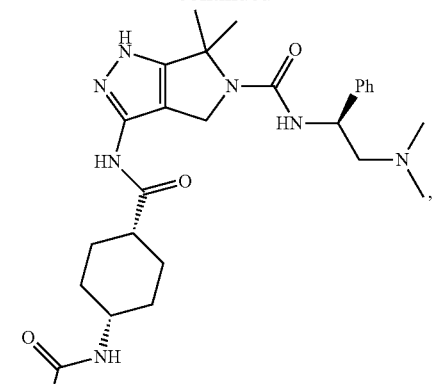
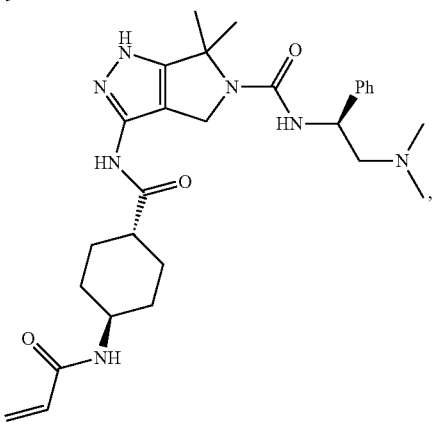
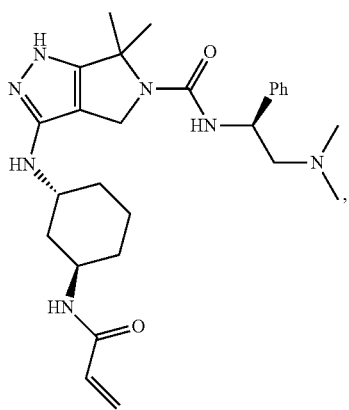

255
-continued
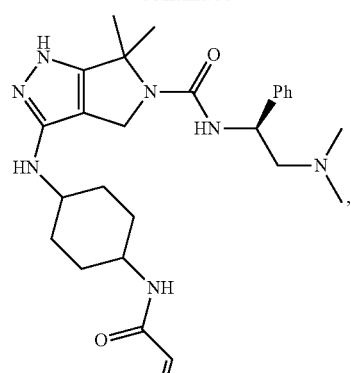
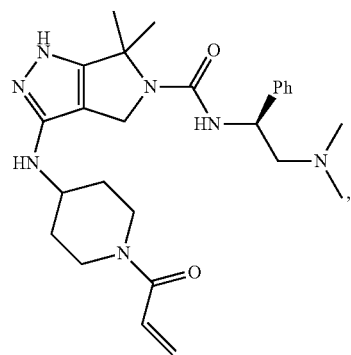
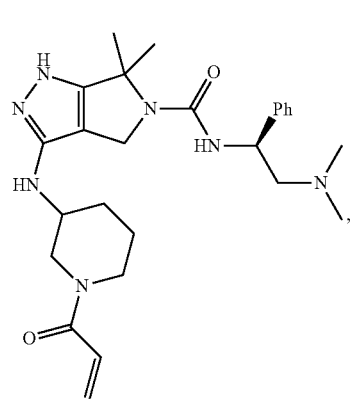
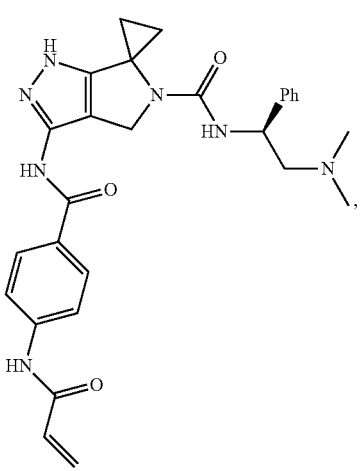
256
-continued
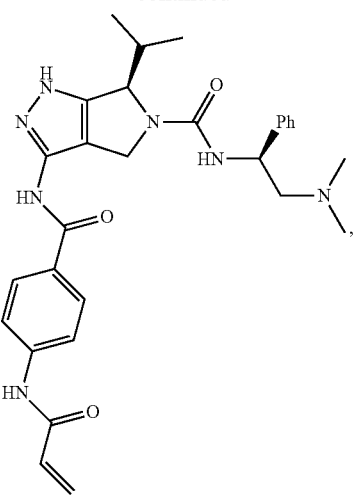
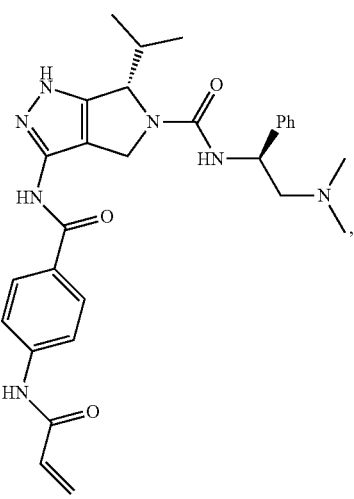
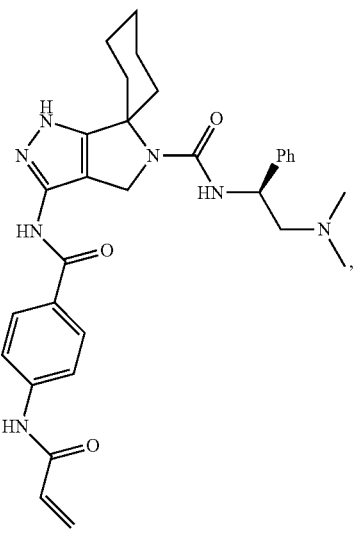

257
-continued
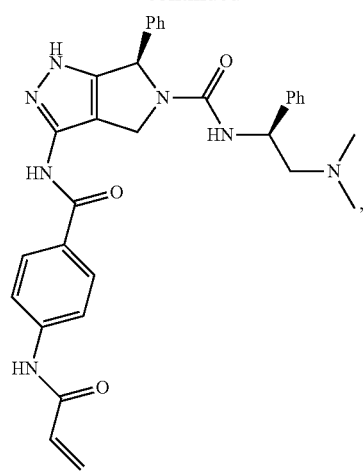
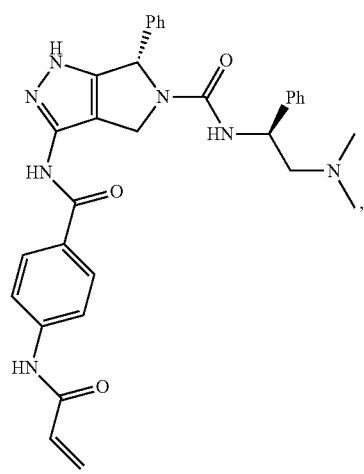
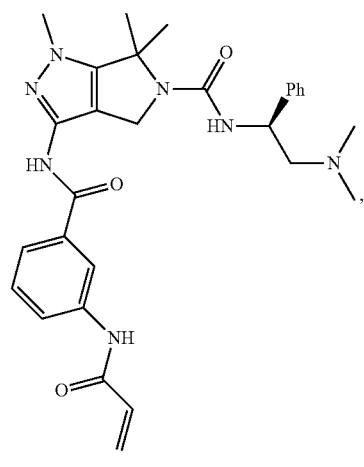
258
-continued
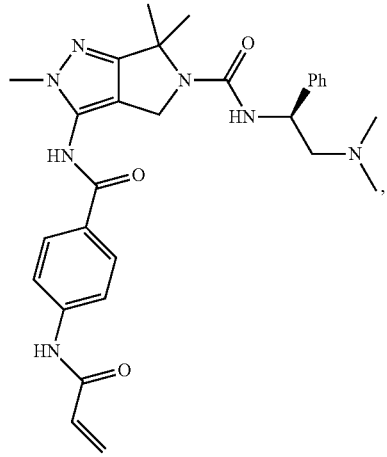
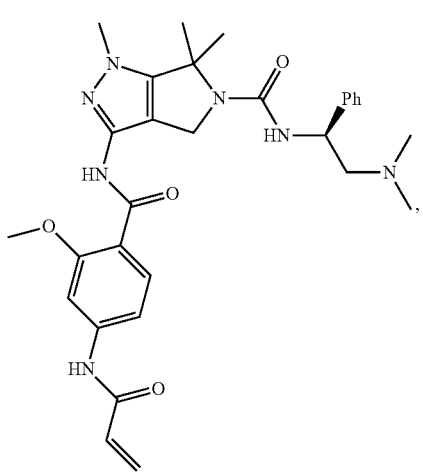
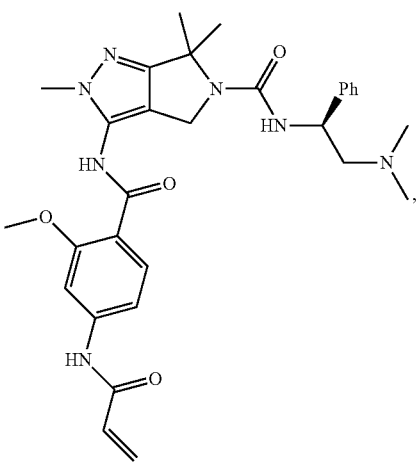

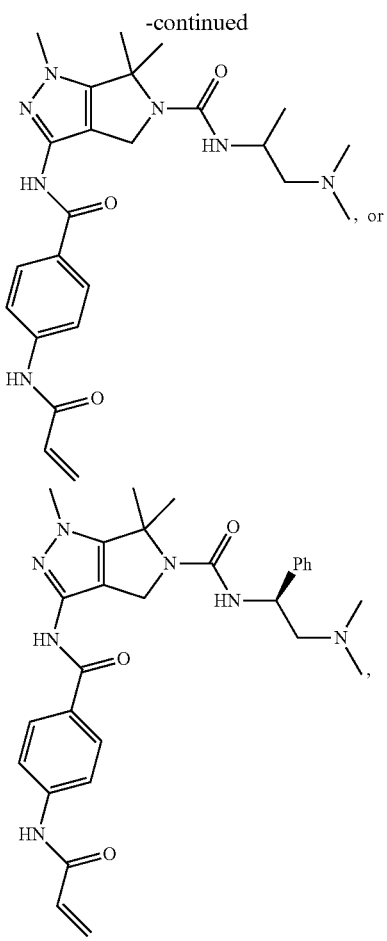

, or

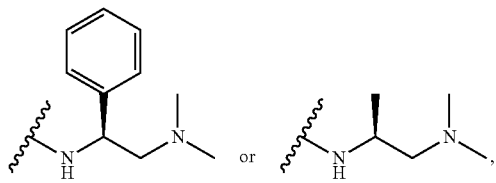

or a pharmaceutically acceptable salt, solvate, hydrate, stereoisomer, tautomer, isotopically labeled derivative, or prodrug thereof.

16. A pharmaceutical composition comprising a compound of claim 1, or a pharmaceutically acceptable salt, solvate, hydrate, tautomer, stereoisomer, isotopically labeled derivative, or prodrug thereof, and a pharmaceutically acceptable excipient.

17. The compound of claim 2, or a pharmaceutically acceptable salt, solvate, hydrate, tautomer, stereoisomer, isotopically labeled derivative, or prodrug thereof, wherein $R^1$ is

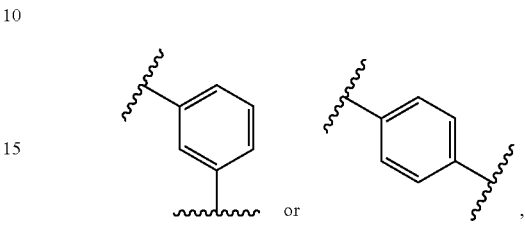

18. The compound of claim 2, or a pharmaceutically acceptable salt, solvate, hydrate, tautomer, stereoisomer, isotopically labeled derivative, or prodrug thereof, wherein $R^3$ and $R^4$ are both —$CH_3$.

19. The compound of claim 2, or a pharmaceutically acceptable salt, solvate, hydrate, tautomer, stereoisomer, isotopically labeled derivative, or prodrug thereof, wherein $R^5$ is hydrogen.

20. The compound of claim 2, or a pharmaceutically acceptable salt, solvate, hydrate, tautomer, stereoisomer, isotopically labeled derivative, or prodrug thereof, wherein $L^1$ is —NH(C=O)—.

21. The compound of claim 2, or a pharmaceutically acceptable salt, solvate, hydrate, tautomer, stereoisomer, isotopically labeled derivative, or prodrug thereof, wherein Ring A is

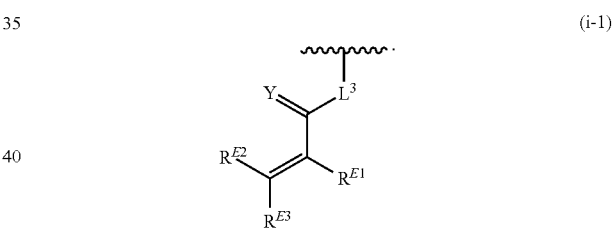

wherein each ring atom is optionally substituted, as valency permits.

22. The compound of claim 2, or a pharmaceutically acceptable salt, solvate, hydrate, tautomer, stereoisomer, isotopically labeled derivative, or prodrug thereof, wherein:
$L^2$ is a bond; and
Ring B is absent.

23. The compound of claim 2, or a pharmaceutically acceptable salt, solvate, hydrate, tautomer, stereoisomer, isotopically labeled derivative, or prodrug thereof, wherein $R^2$ is of Formula (i-1):

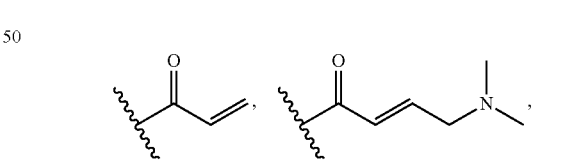

(i-1)

24. The compound of claim 2, or a pharmaceutically acceptable salt, solvate, hydrate, tautomer, stereoisomer, isotopically labeled derivative, or prodrug thereof, wherein $R^2$ is:

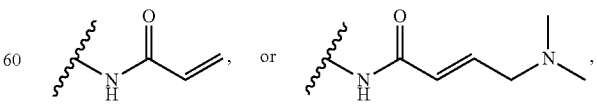

25. The compound of claim 2, or a pharmaceutically acceptable salt, solvate, hydrate, tautomer, stereoisomer, isotopically labeled derivative, or prodrug thereof, wherein the compound is of the formula:

(IV-b)

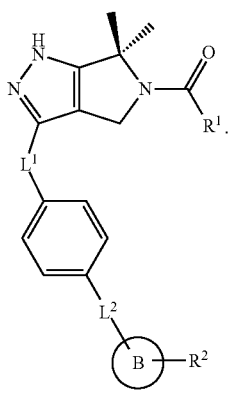

26. The compound of claim 2, or a pharmaceutically acceptable salt, solvate, hydrate, tautomer, stereoisomer, isotopically labeled derivative, or prodrug thereof, wherein the compound is of the formula:

(VI-c)

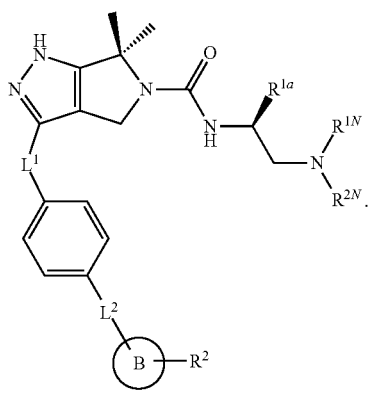

wherein:
  $R^{1a}$ is hydrogen, opitionally substituted $C_1$-$C_6$ alkyl, or optionally substituted aryl; and
  each of $R^{1N}$ and $R^{2N}$ is independently hydrogen, optionally substituted $C_1$-$C_6$ alkyl, or a nitrogen protecting group, or $R^{1N}$ and $R^{2N}$ are joined to form an optionally substituted heterocyclic or optionally substituted heteroaryl ring.

27. The compound of claim 2, or a pharmaceutically acceptable salt, solvate, hydrate, tautomer, stereoisomer, isotopically labeled derivative, or prodrug thereof, wherein the compound is of the formula:

(VIII-c)

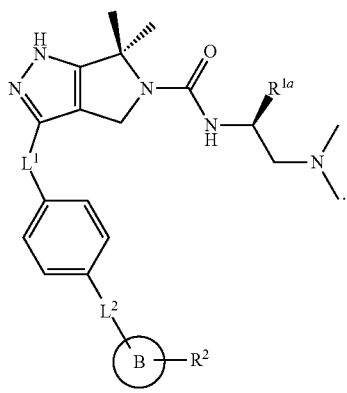

wherein $R^{1a}$ is hydrogen, optionally substituted $C_1$-$C_6$ alkyl, or optionally substituted aryl.

28. The compound of claim 2, or a pharmaceutically acceptable salt, tautomer, or stereoisomer thereof.

29. The compound of claim 2, or a pharmaceutically acceptable salt or tautomer thereof, wherein the compound is of the formula:

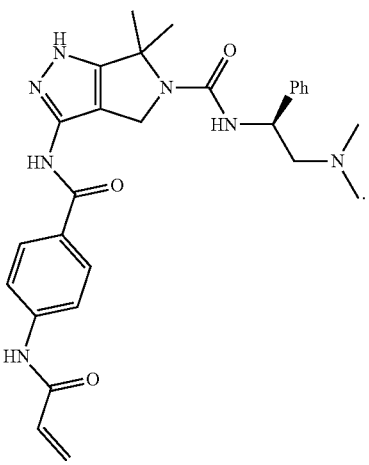 [SMILES: C=CC(=O)Nc1ccc(C(=O)Nc2n[nH]c3c2CN(C(=O)N[C@H](CN(C)C)c2ccccc2)C3(C)C)cc1]

30. The pharmaceutical composition of claim 16 comprising a compound of the formula:

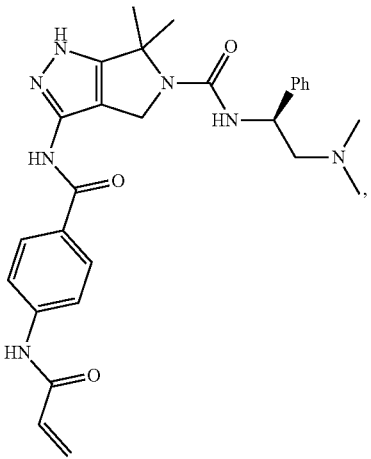 [SMILES: C=CC(=O)Nc1ccc(C(=O)Nc2n[nH]c3c2CN(C(=O)N[C@H](CN(C)C)c2ccccc2)C3(C)C)cc1]

or a pharmaceutically acceptable salt or tautomer thereof, and a pharmaceutically acceptable excipient.

31. The compound of claim 2, or a pharmaceutically acceptable salt, solvate, hydrate, tautomer, stereoisomer, isotopically labeled derivative, or prodrug thereof, wherein $R^5$ is optionally substituted $C_1$-$C_6$ alkyl.

32. The compound of claim 2, or a pharmaceutically acceptable salt, solvate, hydrate, tautomer, stereoisomer, isotopically labeled derivative, or prodrug thereof, wherein $R^5$ is —$CH_3$.

33. A compound of the formula:

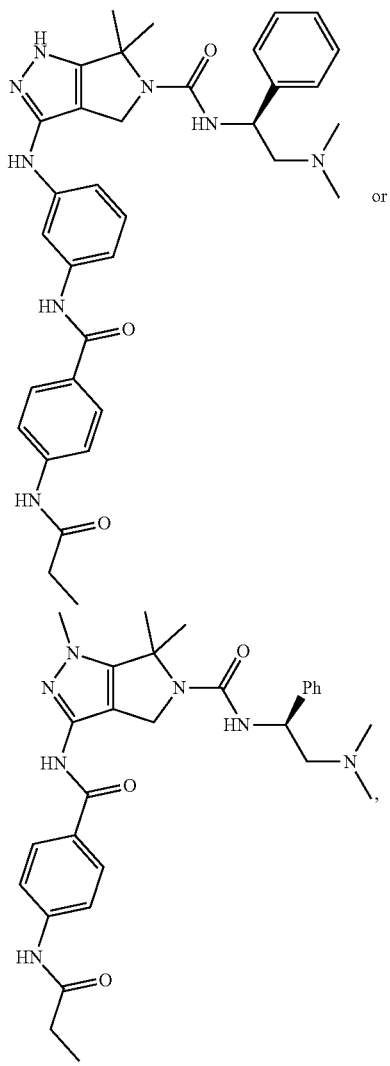

or

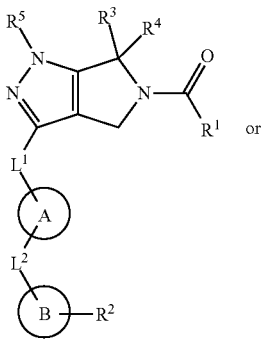

or a pharmaceutically acceptable salt, solvate, hydrate, stereoisomer, tautomer, isotopically labeled derivative, or prodrug thereof.

34. The compound of claim 33, or a pharmaceutically acceptable salt or tautomer thereof.

35. A pharmaceutical composition comprising a compound of claim 33, or a pharmaceutically acceptable salt, solvate, hydrate, tautomer, stereoisomer, isotopically labeled derivative, or prodrug thereof, and a pharmaceutically acceptable excipient.

36. The compound of claim 1, wherein the compound is of the formula:

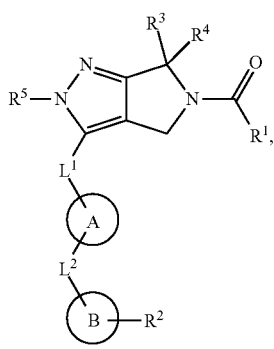

or a pharmaceutically acceptable salt thereof.

* * * * *

UNITED STATES PATENT AND TRADEMARK OFFICE
CERTIFICATE OF CORRECTION

Page 1 of 2

PATENT NO. : 10,870,651 B2
APPLICATION NO. : 15/538763
DATED : December 22, 2020
INVENTOR(S) : Nathanael S. Gray et al.

It is certified that error appears in the above-identified patent and that said Letters Patent is hereby corrected as shown below:

In the Claims

In Claim 3, in Column 226, Lines 45-60, the formula: " 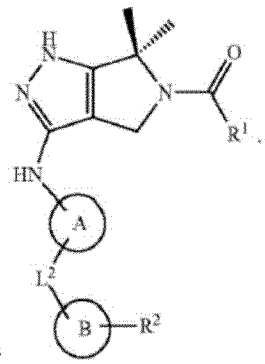 "

Should be replaced with the formula: -- 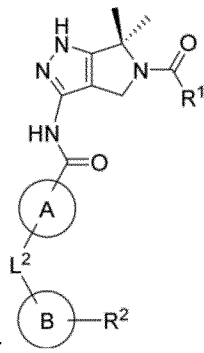 --.

Signed and Sealed this
Twenty-fifth Day of October, 2022

Katherine Kelly Vidal
*Director of the United States Patent and Trademark Office*

CERTIFICATE OF CORRECTION (continued)
U.S. Pat. No. 10,870,651 B2

In Claim 15, in Column 259, Lines 18-35, the formula: " 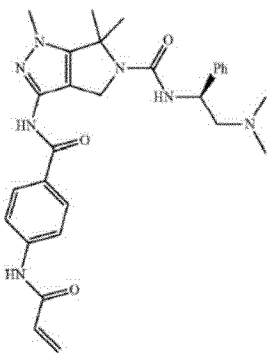 "

Should be replaced with the formula: -- 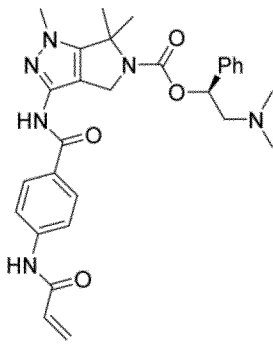 --.

In Claim 26, in Column 261, Line 39, the text "opitionally" should be replaced with the text --optionally--.

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Val Pro Phe Leu Pro Gly Asp Ser Asp Leu Asp Gln Leu Thr Arg
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Leu Asp Phe Leu Gly Glu Gly Gln Phe Ala Thr Val Tyr Lys
1               5                   10

<210> SEQ ID NO 3
<211> LENGTH: 25
<212> TYPE: PRT
<213> ORGANISM: Artificial Sequence
<220> FEATURE:
<223> OTHER INFORMATION: Synthetic

<400> SEQUENCE: 3

Tyr Phe Ser Asn Arg Pro Gly Pro Thr Pro Gly Cys Gln Leu Pro Arg
1               5                   10                  15

Pro Asn Cys Pro Val Glu Thr Leu Lys
                20                  25
```

-continued

```
<210> SEQ ID NO 4
<211> LENGTH: 346
<212> TYPE: PRT
<213> ORGANISM: Homo sapiens

<400> SEQUENCE: 4
```

Met Ala Leu Asp Val Lys Ser Arg Ala Lys Arg Tyr Glu Lys Leu Asp
1               5                   10                  15

Phe Leu Gly Glu Gly Gln Phe Ala Thr Val Tyr Lys Ala Arg Asp Lys
            20                  25                  30

Asn Thr Asn Gln Ile Val Ala Ile Lys Lys Ile Lys Leu Gly His Arg
        35                  40                  45

Ser Glu Ala Lys Asp Gly Ile Asn Arg Thr Ala Leu Arg Glu Ile Lys
    50                  55                  60

Leu Leu Gln Glu Leu Ser His Pro Asn Ile Ile Gly Leu Leu Asp Ala
65                  70                  75                  80

Phe Gly His Lys Ser Asn Ile Ser Leu Val Phe Asp Phe Met Glu Thr
                85                  90                  95

Asp Leu Glu Val Ile Ile Lys Asp Asn Ser Leu Val Leu Thr Pro Ser
            100                 105                 110

His Ile Lys Ala Tyr Met Leu Met Thr Leu Gln Gly Leu Glu Tyr Leu
        115                 120                 125

His Gln His Trp Ile Leu His Arg Asp Leu Lys Pro Asn Asn Leu Leu
    130                 135                 140

Leu Asp Glu Asn Gly Val Leu Lys Leu Ala Asp Phe Gly Leu Ala Lys
145                 150                 155                 160

Ser Phe Gly Ser Pro Asn Arg Ala Tyr Thr His Gln Val Val Thr Arg
                165                 170                 175

Trp Tyr Arg Ala Pro Glu Leu Leu Phe Gly Ala Arg Met Tyr Gly Val
            180                 185                 190

Gly Val Asp Met Trp Ala Val Gly Cys Ile Leu Ala Glu Leu Leu Leu
        195                 200                 205

Arg Val Pro Phe Leu Pro Gly Asp Ser Asp Leu Asp Gln Leu Thr Arg
    210                 215                 220

Ile Phe Glu Thr Leu Gly Thr Pro Thr Glu Glu Gln Trp Pro Asp Met
225                 230                 235                 240

Cys Ser Leu Pro Asp Tyr Val Thr Phe Lys Ser Phe Pro Gly Ile Pro
                245                 250                 255

Leu His His Ile Phe Ser Ala Ala Gly Asp Asp Leu Leu Asp Leu Ile
            260                 265                 270

Gln Gly Leu Phe Leu Phe Asn Pro Cys Ala Arg Ile Thr Ala Thr Gln
        275                 280                 285

Ala Leu Lys Met Lys Tyr Phe Ser Asn Arg Pro Gly Pro Thr Pro Gly
    290                 295                 300

Cys Gln Leu Pro Arg Pro Asn Cys Pro Val Glu Thr Leu Lys Glu Gln
305                 310                 315                 320

Ser Asn Pro Ala Leu Ala Ile Lys Arg Lys Arg Thr Glu Ala Leu Glu
                325                 330                 335

Gln Gly Gly Leu Pro Lys Lys Leu Ile Phe
            340                 345